US008053440B2

(12) United States Patent
Hansen

(10) Patent No.: US 8,053,440 B2
(45) Date of Patent: Nov. 8, 2011

(54) COMPOUNDS FOR THE PREVENTION AND TREATMENT OF CARDIOVASCULAR DISEASES

(75) Inventor: Henrik C. Hansen, Calgary (CA)

(73) Assignee: Resverlogix Corporation, Calgary, Alberta (CA)

( * ) Notice: Subject to any disclaimer, the term of this patent is extended or adjusted under 35 U.S.C. 154(b) by 1267 days.

(21) Appl. No.: 11/670,238

(22) Filed: Feb. 1, 2007

(65) Prior Publication Data
US 2008/0188467 A1 Aug. 7, 2008

(51) Int. Cl.
A01N 43/54 (2006.01)
A61K 31/517 (2006.01)
C07D 239/72 (2006.01)

(52) U.S. Cl. .................... 514/266.1; 544/283
(58) Field of Classification Search .................. 544/283; 514/266.1
See application file for complete search history.

(56) References Cited

U.S. PATENT DOCUMENTS

| 2,065,593 A | 12/1936 | Lubs |
| 2,065,900 A | 12/1936 | Laska et al. |
| 2,071,329 A | 2/1937 | Brown |
| 3,251,837 A | 5/1966 | Holland et al. |
| 3,600,394 A | 8/1971 | Coyne et al. |
| 3,773,946 A | 11/1973 | Creger |
| 3,930,024 A | 12/1975 | Creger |
| 3,965,128 A | 6/1976 | Fürst et al. |
| 4,613,593 A | 9/1986 | Yamatsu et al. |
| 4,689,344 A | 8/1987 | Bar-Tana |
| 4,711,896 A | 12/1987 | Bar-Tana et al. |
| 4,825,005 A | 4/1989 | Frey et al. |
| 5,124,337 A | 6/1992 | Dugar et al. |
| 5,126,351 A | 6/1992 | Luzzio et al. |
| 5,244,904 A | 9/1993 | Nagase et al. |
| 5,354,749 A | 10/1994 | Dressel et al. |
| 5,407,942 A | 4/1995 | Dressel et al. |
| 5,409,930 A * | 4/1995 | Spada et al. .................. 514/248 |
| 5,446,071 A | 8/1995 | Grese |
| 5,480,883 A | 1/1996 | Spada et al. |
| 5,539,119 A | 7/1996 | Nagase et al. |
| 5,576,322 A | 11/1996 | Takase et al. |
| 5,595,974 A | 1/1997 | Tomaru |
| 5,693,652 A | 12/1997 | Takase et al. |
| 5,707,987 A | 1/1998 | Nakagawa et al. |
| 5,733,913 A | 3/1998 | Blankley et al. |
| 5,756,344 A | 5/1998 | Onda et al. |
| 5,756,544 A | 5/1998 | Bisgaier et al. |
| 5,756,736 A | 5/1998 | Arzeno et al. |
| 5,756,763 A | 5/1998 | Takeuchi et al. |
| 5,763,414 A | 6/1998 | Bok et al. |
| 5,783,577 A | 7/1998 | Houghten et al. |
| 5,792,461 A | 8/1998 | Bok et al. |
| 5,792,902 A | 8/1998 | Benoit et al. |
| 5,798,344 A | 8/1998 | Kuroki et al. |
| 5,801,180 A | 9/1998 | Takase et al. |
| 5,854,264 A | 12/1998 | Anthony et al. |
| 5,877,208 A | 3/1999 | Bok et al. |
| 5,922,866 A | 7/1999 | Miyata et al. |
| 5,965,556 A | 10/1999 | Takeuchi et al. |
| 6,022,901 A | 2/2000 | Goodman |
| 6,048,903 A | 4/2000 | Toppo |
| 6,054,435 A | 4/2000 | Or et al. |
| 6,133,241 A | 10/2000 | Bok et al. |
| 6,165,984 A | 12/2000 | Bok et al. |
| 6,168,776 B1 | 1/2001 | Klunk et al. |
| 6,239,114 B1 | 5/2001 | Guthrie et al. |
| 6,291,456 B1 | 9/2001 | Stein et al. |
| 6,303,629 B1 | 10/2001 | Kun |
| 6,414,037 B1 | 7/2002 | Pezzuto et al. |
| 6,455,577 B2 | 9/2002 | Bok et al. |
| 6,482,479 B1 | 11/2002 | Dübal et al. |
| 6,512,161 B1 | 1/2003 | Rouy et al. |
| 6,541,045 B1 | 4/2003 | Charters et al. |
| 6,541,522 B2 | 4/2003 | Inman et al. |
| 6,548,548 B2 | 4/2003 | Campbell et al. |
| 6,613,772 B1 * | 9/2003 | Schindler et al. .......... 514/266.2 |
| 6,635,642 B1 | 10/2003 | Jackson et al. |
| 6,673,780 B2 | 1/2004 | Dasseux et al. |
| 6,703,422 B2 | 3/2004 | Dasseux et al. |
| 7,087,612 B2 | 8/2006 | Rodriguez Sarmiento et al. |
| 7,173,128 B2 | 2/2007 | Ravichandran et al. |
| 7,244,776 B2 | 7/2007 | Ravichandran et al. |
| 2002/0004608 A1 | 1/2002 | Alig et al. |
| 2002/0091263 A1 | 7/2002 | Trova |
| 2003/0064967 A1 | 4/2003 | Luchoomun |

(Continued)

FOREIGN PATENT DOCUMENTS

AU 719140 7/1998

(Continued)

OTHER PUBLICATIONS

Kurata, H. et al. "A Candidate High Density Lipoprotein (HDL) Receptor, HB$_2$, with Possible Multiple Functions Shows Sequence Homology with Adhesion Molecules" *J Atheroscler Thromb* 4(3):112-117 (1998).

Kurowska, E.M. "Essential Amino Acids in Relation to Hypercholesterolemia Induced in Rabbits by Dietary Casein" *J Nutr* 120:831-836 (1990).

Kuzuya, M. et al. "Probucol Prevents Oxidative Injury to Endothelial Cells" *J Lipid Res* 32:197-204 (1991).

Laarhoven, W.H. et al. "Syntheses, infrared spectra and molecular refractions of some sterically hindered p,p'-dimethoxystilbenes. The influence of non-planarity in styrene and stilbene derivatives IV" *Recueil des Travaux Chimiques des Pays-Bas* 80:775-791 (1961).

(Continued)

Primary Examiner — Paul V. Ward
(74) Attorney, Agent, or Firm — Finnegan, Henderson, Farabow, Garrett & Dunner, LLP

(57) ABSTRACT

The present disclosure relates to compounds, which are useful for regulating the expression of apolipoprotein A-I (ApoA-I), and their use for treatment and prevention of cardiovascular disease and related disease states, including cholesterol- or lipid-related disorders, such as, for example, atherosclerosis.

34 Claims, 7 Drawing Sheets

U.S. PATENT DOCUMENTS

| | | | |
|---|---|---|---|
| 2003/0068526 A1 | 4/2003 | Kamatani et al. | |
| 2003/0072964 A1 | 4/2003 | Kwong et al. | |
| 2003/0171429 A1 | 9/2003 | Chen et al. | |
| 2004/0001834 A1 | 1/2004 | Kim et al. | |
| 2004/0033480 A1 | 2/2004 | Wong et al. | |
| 2004/0058903 A1 | 3/2004 | Takasugi et al. | |
| 2004/0097493 A1 | 5/2004 | Chen et al. | |
| 2004/0198750 A1 | 10/2004 | Green et al. | |
| 2004/0235888 A1 | 11/2004 | Yamamori et al. | |
| 2004/0242615 A1 | 12/2004 | Yamamori et al. | |
| 2004/0248950 A1 | 12/2004 | Ishizuka et al. | |
| 2005/0043300 A1 | 2/2005 | Middleton et al. | |
| 2005/0080021 A1 | 4/2005 | Tucker et al. | |
| 2005/0080024 A1 | 4/2005 | Tucker et al. | |
| 2005/0261319 A1 | 11/2005 | Deuschle et al. | |
| 2006/0116364 A1 | 6/2006 | Hamaoka et al. | |
| 2006/0205767 A1 | 9/2006 | Wong et al. | |
| 2007/0218155 A1 | 9/2007 | Kuhrts | |
| 2008/0275069 A1* | 11/2008 | Mizutani et al. | 514/264.1 |
| 2010/0004448 A1 | 1/2010 | Hansen et al. | |

FOREIGN PATENT DOCUMENTS

| | | |
|---|---|---|
| CA | 2104981 | 3/1994 |
| CA | 2345406 | 4/2000 |
| CN | 1067070 C | 6/2001 |
| DE | 637259 | 10/1936 |
| DE | 652772 | 11/1937 |
| DE | 36 01 417 | 7/1987 |
| DE | 42 15 588 | 11/1993 |
| DE | 196 51 099 | 6/1998 |
| DE | 197 56 388 A1 | 6/1999 |
| DE | 199 34 799 | 2/2001 |
| EP | 0210342 A2 | 2/1987 |
| EP | 0258190 A2 | 3/1988 |
| EP | 0343499 B1 | 11/1989 |
| EP | 0182213 B1 | 9/1990 |
| EP | 0407217 A1 | 1/1991 |
| EP | 0488602 A1 | 6/1992 |
| EP | 0272455 B1 | 2/1993 |
| EP | 0 564 350 | 10/1993 |
| EP | 0375404 B1 | 2/1994 |
| EP | 0333175 B1 | 6/1994 |
| EP | 0409413 B1 | 8/1994 |
| EP | 0420511 B1 | 8/1994 |
| EP | 0 633 022 | 1/1995 |
| EP | 569 795 | 4/1995 |
| EP | 0330108 B1 | 12/1995 |
| EP | 0 747 051 | 12/1996 |
| EP | 643 119 | 4/2000 |
| EP | 1125908 A1 | 8/2001 |
| EP | 0498723 B1 | 9/2001 |
| EP | 0607439 B1 | 1/2002 |
| EP | 0776893 B1 | 2/2002 |
| EP | 1 195 378 | 4/2002 |
| EP | 1398032 A1 | 3/2004 |
| EP | 1 418 164 | 5/2004 |
| EP | 1 426 046 | 6/2004 |
| EP | 1477481 A1 | 11/2004 |
| EP | 1637523 A1 | 3/2006 |
| EP | 2005941 A2 | 12/2008 |
| FR | 803201 | 9/1936 |
| FR | 803619 | 10/1936 |
| FR | 2 244 493 | 4/1975 |
| FR | 2244492 | 4/1975 |
| GB | 472489 | 9/1937 |
| GB | 1 175 808 | 12/1969 |
| GB | 1 179 019 | 1/1970 |
| GB | 2292149 | 2/1996 |
| JP | 680656 | 3/1994 |
| JP | 7-041442 | 2/1995 |
| JP | 7-061942 | 3/1995 |
| JP | 7-118241 | 5/1995 |
| JP | 7-179380 | 7/1995 |
| JP | 7-233109 | 9/1995 |
| JP | 7247289 | 9/1995 |
| JP | 10287678 | 10/1998 |
| JP | 2001/131151 | 5/2001 |
| JP | 2001/139550 | 5/2001 |
| JP | 2001/335476 | 12/2001 |
| JP | 2002/249483 | 9/2002 |
| JP | 2004203751 | 7/2004 |
| JP | 2004307440 | 11/2004 |
| KR | 10-0707532 | 4/2007 |
| WO | WO 91/18901 A1 | 12/1991 |
| WO | WO 92/09374 A1 | 6/1992 |
| WO | WO 92/18123 | 10/1992 |
| WO | WO 92/20642 | 11/1992 |
| WO | WO 92/21661 | 12/1992 |
| WO | WO 93/07124 A1 | 4/1993 |
| WO | WO 93/08174 A1 | 4/1993 |
| WO | WO 94/14763 A1 | 7/1994 |
| WO | WO 95/03277 A1 | 2/1995 |
| WO | WO 95/23150 A1 | 8/1995 |
| WO | WO 96/15128 | 5/1996 |
| WO | WO 96/31206 | 10/1996 |
| WO | WO 97/10221 A1 | 3/1997 |
| WO | WO 97/15308 | 5/1997 |
| WO | WO 97/28118 A1 | 8/1997 |
| WO | WO 97/28132 A1 | 8/1997 |
| WO | WO 97/28134 A1 | 8/1997 |
| WO | WO 97/29106 | 8/1997 |
| WO | WO 97/48694 | 12/1997 |
| WO | WO 98/11438 A1 | 3/1998 |
| WO | WO 98/26127 | 6/1998 |
| WO | WO 98/30530 A1 | 7/1998 |
| WO | WO 98/50370 A1 | 11/1998 |
| WO | WO 98/51307 | 11/1998 |
| WO | WO 98/51308 | 11/1998 |
| WO | WO 98/55124 | 12/1998 |
| WO | WO 99/00116 A2 | 1/1999 |
| WO | WO 99/11634 A1 | 3/1999 |
| WO | WO 99/18077 | 4/1999 |
| WO | WO 99/29667 A1 | 6/1999 |
| WO | WO 00/23075 | 4/2000 |
| WO | WO 00/35865 | 6/2000 |
| WO | WO 00/44362 | 8/2000 |
| WO | WO 00/55168 A1 | 9/2000 |
| WO | WO 00/64888 A1 | 11/2000 |
| WO | WO 01/00554 | 1/2001 |
| WO | WO 01/60775 A1 | 8/2001 |
| WO | WO 01/82916 A2 | 11/2001 |
| WO | WO 01/83456 A1 | 11/2001 |
| WO | WO 02/074307 | 9/2002 |
| WO | WO 02/087556 | 11/2002 |
| WO | WO 02/096426 A1 | 12/2002 |
| WO | WO 03/007959 | 1/2003 |
| WO | WO 03/016292 A1 | 2/2003 |
| WO | WO 03/018008 A1 | 3/2003 |
| WO | WO 03/040256 A2 | 5/2003 |
| WO | WO 03/040257 | 5/2003 |
| WO | WO 03/070236 A2 | 8/2003 |
| WO | WO 03/099274 | 12/2003 |
| WO | WO 03/106435 A1 | 12/2003 |
| WO | WO 2004/017920 A2 | 3/2004 |
| WO | WO 2004/032846 A2 | 4/2004 |
| WO | WO 2004/037176 A2 | 5/2004 |
| WO | WO 2004/039795 | 5/2004 |
| WO | WO 2004/047755 | 6/2004 |
| WO | WO 2004/056355 | 7/2004 |
| WO | WO 2004/058717 | 7/2004 |
| WO | WO 2004/065392 A1 | 8/2004 |
| WO | WO 2004/072042 | 8/2004 |
| WO | WO 2004/092196 A2 | 10/2004 |
| WO | WO 2004/092196 A3 | 10/2004 |
| WO | WO 2004/094452 A2 | 11/2004 |
| WO | WO 2004/094452 A3 | 11/2004 |
| WO | WO 2004/112710 | 12/2004 |
| WO | WO 2005/034960 | 4/2005 |
| WO | WO 2005/065183 A2 | 7/2005 |
| WO | WO 2005/066162 A1 | 7/2005 |
| WO | WO 2005/075431 A1 | 8/2005 |
| WO | WO 2005115993 * | 12/2005 |
| WO | WO 2006/012577 A2 | 2/2006 |
| WO | WO 2006/045096 A2 | 4/2006 |
| WO | WO 2006/045096 A3 | 4/2006 |
| WO | WO 2006/071095 A1 | 7/2006 |

| | | | |
|---|---|---|---|
| WO | WO 2006/105081 A2 | 10/2006 | |
| WO | WO 2006/105081 A3 | 10/2006 | |
| WO | WO 2007/071055 A1 | 6/2007 | |
| WO | WO 2010/079431 A2 | 7/2010 | |

OTHER PUBLICATIONS

Lagrost, L. et al. "Opposite Effects of Cholesteryl Ester Transfer Protein and Phospholipid Transfer Protein on the Size Distribution of Plasma High Density Lipoproteins" *J Biol Chem* 271(32):19058-19065 (Aug. 9, 1996).

Landshulz, K.T. et al. "Regulation of Scavenger Receptor, Class B, Type I, a High Density Lipoprotein Receptor, in Liver and Steroidogenic Tissues of the Rat" *J Clin Invest* 98(4):984-995 (Aug. 1996).

Lin, J-K. et al. "Chemoprevention of Cancer and Cardiovascular Disease by Resveratrol" *Proc Natl Sci Counc ROC(B)* 23(3):99-106 (1999).

Linnell, W.H. "Isomers of stilbœstrol. II." *Q J Pharm Pharmacol* 15:384-388 (1942).

Maher, V.M.G. et al. "Lipoprotein (a) and coronary heart disease" *Curr Opin Lipidol* 6:229-235 (1995).

Manach, C. et al. "Polyphenols and prevention of cardiovascular diseases" *Curr Opin Lipidol* 16:77-84 (2005).

Marks, F. "Epidermal Growth Control Mechanisms, Hyperplasia, and Tumor Promotion in the Skin" *Cancer Res* 36:2636-2343 (1976).

Melani, F. et al. "Tricyclic heterocyclic systems: pyrazolo[5',4':4,5]- and pyrazolo-[3',4':4,5]pyrano[2,3-*b*]pyridine derivatives" *J Heterocyclic Chem* 25:1367 (Sep.-Oct. 1988).

Mondal, S. et al. "Two-Stage Chemical Oncogenesis in Cultures of C3H/10T1/2 Cells" *Cancer Res* 36:2254-2260 (Jul. 1976).

Nourooz-Zadeh, J. "Ferrous Ion Oxidation in Presence of Xylenol Orange for Detection of Lipid Hydroperoxides in Plasma" *Methods Enzymol* 300:58-62 (1999).

Office Action in pending U.S. Appl. No. 11/254,420 mailed Mar. 3, 2009.

Ohtomo, T. et al. "Comparative activities of daidzein metabolites, equol and *O*-desmethylangolensin, on bone mineral density and lipid metabolism in ovariectomixed mice and in osteoclast cell cultures" *Eur J Nutr* 47(5):273-279 (2008).

Ordovas, J.M. "Gene-diet interaction and plasma lipid responses to dietary intervention" *Biochem Soc Trans* 30(2):68-73 (2002).

Parra, H.J. et al. "A Case-Control Study of Lipoprotein Particles in Two Populations at Contrasting Risk for Coronary Heart Disease. The ECTIM Study" *Arterioscler Thromb* 12:701-707 (1992).

Pearson, D.E. et al. "The *ortho* Bromination of Phenols" *J Org Chem* 32:2358-2360 (1967).

Pettit, G.R. et al. "Antineoplastic Agents. 465. Structural Modification of Resveratrol: Sodium Resverastatin Phosphate" *J Med Chem* 45:2534-2542 (2002).

Rajakumar, P. et al. "TiCl4-dioxane. A facile and efficient system for de-O-benzylation, de-O-allylation, and de-O-xylylation of phenolic ethers" *Synthetic Communications* 33(22):3891-3896 (2003).

Richtzenhain, H. "Estrogenic stilbene and diphenylethane derivatives. II." *Chemische Berichte* 82:405-407 (1949) (German) (No English abstract available).

Rigotti, A. et al. "Regulation by Adrenocorticotropic Hormone of the in Vivo Expression of Scavenger Receptor Class B Type I (SR-BI), a High Density Lipoprotein Receptor, in Steroidogenic Cells of the Murine Adrenal Gland" *J Biol Chem* 271(52):33545-33549 (1996).

Rodriguez, A. et al. "Novel effects of the Acyl-Coenzyme A: Cholesterol Acyltransferase Inhibitor 58-035 on Foam Cell Development in Primary Human Monocyte-Derived Macrophages" *Arterioscler Thromb Vasc Biol* 19:2199-2206 (1999).

Rubin, E.M. et al. "Expression of Human Apolipoprotein A-I in Transgenic Mice Results in Reduced Plasma Levels of Murine Apolipoprotein A-I and the Appearance of Two New High Density Lipoprotein Size Subclasses" *Proc Natl Acad Sci USA* 88:434-438 (Jan. 1991).

Rubin, E.M. et al. "Inhibition of Early Atherogenesis in Transgenic Mice by Human Apolipoprotein AI" *Nature* 353:265-267 (Sep. 19, 1991).

Schultz, T.P. et al. "Role of stilbenes in the natural durability of wood: fungicidal structure-activity relationships" *Phytochemistry* 29(5):1501-1507 (1990).

Shapiro, D.J. et al. "Micro Assay for 3-Hydroxy-3-Methylglutaryl-CoA Reductase in Rat Liver and L-Cell Fibroblasts" *Biochem Biophys Acta* 370:369-377 (1974).

Sieber, R.H. "Reactions of chloroacetaldehyde with aromatic hydrocarbons, phenols, and phenol ethers" *Justus Liebigs Annalen der Chemie* 730:31-46 (1969) (German), Abstract p. 31.

Sliwa, H. et al. "Tautomerie entre structures a-enaminocetone et b-ceto iminoether presentee par les piperidines resultant de la semihydrogenation d'alcoxy-2-acyl-3 pyridines" *J Heterocyclic Chem* 16:969 (1979) (French), Summary p. 944.

Slowing, K. et al. "Anti-Inflammatory Activity of Leaf Extracts of *Eugenia jambos* in Rats" *J Ethnopharmacol* 43:9-11 (1994).

Smyth, M.S. et al. "Non-amine based analogues of lavendustin A as protein-tyrosine kinase inhibitors" *J Med Chem* 36(20):3010-3014 (1993).

Sun, D. et al. "In Vitro Testing of Drug Absorption for Drug 'Developability' Assessment: Forming an Interface Between in Vitro Preclinical Data and Clinical Outcome" *Curr Opin Drug Discov Devel* 7(1):75-85 (2004).

Suryadevara, V. et al. "Association of Abnormal Serum Liquids in Elderly Persons With Artherosclerotic Vascular Disease and Demetia, Artheroslerotic Vascular Disease Without Demetia, Demetia Without Artherosclerotic Vascular Disease, and No Dementia or Artherosclerotic Vascular Disease" *J Gerontol Med Sci* 58(9):859-861 (2003).

Tardif, J-C. et al. "Probucol and Multivitamins in the Prevention of Restenosis After Coronary Angioplasty" *N. Engl J Med* 337(6):365-367 (1997).

Toth, P.P. et al. "Therapeutic Interventions Targeted at the Augmentation of Reserve Cholesterol Transport" *Curr Opin Cardiol* 19:374-379 (2004).

Tudan, C. et al. "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-Phenylalanine, and Phorbol Ester by O-(Chloroacetylcarbamoyl) Fumagillol (AGM-01470; TNP-470)" *Biochem Pharmacol* 58:1869-1880 (1999).

U.S. Appl. No. 11/990,162, entitled "Pharmaceutical Compositions for the Prevention and Treatment of Complex Diseases and Delivery by Insertable Medical Devices", filed Feb. 7, 2008.

Utermann, G. "The Mysteries of Lipoprotein(a)" *Science* 246:904-910 (1999).

Vippagunta, S.R. et al. "Crystalline solids" *Adv Drug Delivery Rev* 48:3-26 (2001).

Webster Ninth New Collegiate Dictionary, Definition of 'Prevent', 1 page (2000).

Yamakoshi, J. et al. "Isoflavone aglycone-rich extract without soy protein attenuates atherosclerosis development in cholesterol-fed rabbits" *J Nutr* 130(8):1887-1893 (2000).

Yoshioka, N. et al. "Semiempirical Investigation of Stilbene-Linked Diradicals and Magnetic Study of Their Bis(*N-tert*-butylnitroxide) Variants" *J Org Chem* 59(15):4272-4280 (1994).

Abdul-Rahman, A. et al. "Dinuclear molybdenum complexes derived from diphenols: electrochemical interactions and reduced species" *Polyhedron* 16(24):4353-4362 (1997).

Acton, S. et al. "Identification of Scavenger Receptor SR-BI as a High Density Lipoprotein Receptor" *Science, New Series* 271(5248):518-520 (Jan. 26, 1996).

Asztalos, B.F. "High-Density Lipoprotein Metabolism and Progression of Atherosclerosis: New Insights from the HDL Atherosclerosis Treatment Study" *Curr Opin Cardiol* 19:385-391 (2004).

Baba, S. et al. "Continuous intake of polyphenolic compounds containing cocoa powder reduces LDL oxidative susceptibility and has beneficial effects on plasma HDL-cholesterol concentrations in humans" *Am J Clin Nutr* 85:709-717 (2007).

Badimon, J.J. et al. "Role of High Density Lipoproteins in the Regression of Atherosclerosis" *Circulation* 86(Suppl. III):III-86-III-94 (1992).

Barrans, A. et al. "Pre-β HDL: Structure and Metabolism" *Biochem Biophys Acta* 1300:73-85 (1996).

Barter, P.J. et al. "High Density Lipoproteins and Coronary Heart Disease" *Atherosclerosis* 121:1-12 (1996).

Bayly, S.R. et al. "Electronic and magnetic metal-metal interactions in dinuclear oxomolybdenum(V) complexes across bis-phenolate bridging ligands with different spacers between the pholate termini: ligand-centered vs. metal-centered redox activity" *J. Chem. Soc., Dalton Transactions* 9:1401-1414 (2001).

Bertele, V. et al. "Platelet Thromboxane Synthetase Inhibitors with Low Doses of Aspirin: Possible Resolution of the 'Aspirin Dilemma'" *Science* 220:517-519 (Apr. 29, 1983).

Bhilare, S.V. et al. "Ionic-Liquid-Influenced Expeditious and Stereoselective Synthesis of Olefins" *Synthetic Communications* 37(18):3111-3117 (2007).

Bisgaier, C.L. et al. "A Novel Compound That Elevates High Density Lipoprotein and Activates the Peroxisome Proliferator Activated Receptor" *J Lipid Res* 39:17-30 (1998).

Buhle, E.L. et al. "Trivalent carbon. II. Unsymmetrical hexaaryldimethyl peroxides" *J Am Chem Soc* 65:584-586 (1943).

Chyu, K.-Y. et al. "Differential Effects of Green Tea-Derived Catechin on Developing Versus Established Atherosclerosis in Apolipoprotein E-Null Mice" *Circulation* 109:2448-2453 (2004).

Clarkson, T.B. et al. "Inhibition of Postmenopausal Atherosclerosis Progression: A Comparison of the Effects of Conjugated Equine Estrogens and Soy Phytoestrogens" *J Clin Endocrinol Metab* 86(1):41-47 (2001).

Cooper, K.A. et al. "Wine polyphenols and promotion of cardiac health" *Nutr Res Rev* 17:111-129 (2004).

Cramer, R. et al. "New Syntheses of Aryl Fluorides and Aryl Fluorosulfonates from Oxyflourides of Sulfur" *J Org Chem* 26:4164-4165 (1961).

Dansky, H.M. et al. "High-Density Lipoprotein and Plaque Regression: The Good Cholesterol Gets Even Better" *Circulation* 100:1762-1763 (1999).

Decossin,C. et al. "Subclasses of LpA-I In Coronary Artery Disease: Distribution and Cholesterol Efflux Ability" *Eur J Clin Invest* 27:299-307 (1997).

Eiden, F. et al. "1,2-Bisbenzopyranyl-ethane" *Archiv der Pharmazie* 313(2):120-128 (1980) (German), Abstract p. 120.

English language Derwent abstract for CN 1067070, 4 pages (1997).
English language Derwent abstract for EP 0210342, 2 pages (1986).
English language Derwent abstract for EP 2005941, 4 pages (2009).
English language Derwent abstract for JP 7247289, 1 page (1995).
English language Derwent abstract for JP 2004203751, 3 pages (2004).
English language Derwent abstract for JP 2004307440, 3 pages (2004).
English language Derwent abstract for JP 10287678, 1 page (1999).
English language Derwent abstract for JP 680656, 2 pages (1994).

Esterbauer, H. et al. "Continuous Monitoring of In Vitro Oxidation of Human Low Density Lipoprotein" *Free Radical Res Commun* 6(1):67-75 (1989).

Fielding, C.J. et al. "Molecular Physiology of Reverse Cholesterol Transport" *J Lipid Res* 36:211-228 (1995).

Fieser, L.F. "Potentials of some unstable oxidation-reduction systems" *J. Am. Chem. Soc.* 52:4915-4940 (1930).

Gidez, L.I. et al. "Separation and Quantitation of Subclasses of Human Plasma High Density Lipoproteins by a Simple Precipitation Procedure" *J Lipid Res* 23:1206-1223 (1982).

Gordon, T. et al. "High Density Lipoprotein As a Protective Factor Against Coronary Heart Disease" *Am J Med* 62(5):707-714 (May 1977).

Hakamata, H. et al. "Differential effects of an acyl-coenzyme A: cholesterol acyltransferase inhibitor on HDL-induced cholesterol efflux from rat macrophage foam cells" *FEBS Letters* 363:29-32 (1995).

Heeg, J.F. et al. "Plasma Levels of Probucol in Man After Single and Repeated Oral Doses" *La Nouvelle Presse Medicale* 9:2990-2994 (1980).

Hemingway, R.W. et al. "Gas-liquid chromatographic examination of stilbene derivatives" *J. Chromatography* 50(3):391-399 (1970).

Hidaka, H. et al. "Affinity Purification of the Hepatic High-Density Lipoprotein Receptor Identifies Two Acidic Glycoproteins and Enables Further Characterization of Their Binding Properties" *Biochem J* 284:161-167 (1992).

Hirano, K-i et al. "Genetic Cholesteryl Ester Transfer Protein Deficiency Is Extremely Frequent in the Omagari Area of Japan. Marked Hyperalphalipoproteinemia Caused by CETP Gene Mutation Is Not Associated With Longevity" *Arterioscler Thromb Vasc Biol* 17:1053-1059 (1997).

International Search Report and Written Opinion issued in Application No. PCT/CA2007/000146, mailed on Oct. 29, 2007.

Ishibashi, S. et al. "Hypercholesterolemia in Low Density Lipoprotein Receptor Knockout Mice and its Reversal by Adenovirus-Mediated Gene Delivery" *J Clin Invest* 92:883-893 (1993).

Ishibashi, S. et al. "Massive Xanthomatosis and Atherosclerosis in Cholesterol-Fed Low Density Lipoprotein Receptor-Negative Mice" *J Clin Invest* 93:1885-1893 (1994).

Jayatilake, G.S. et al. "Kinase Inhibitors From *Polygonum cuspidatum*" *J Nat Prod* 56(10):1805-1810 (Oct. 1993).

Kilbourne, E.J. et al. "Involvement of Early Growth Response Factor Egr-1 in Apolipoprotein AI Gene Transcription" *J Biol Chem* 270(12):7004-7010 (1995).

Kulkarni, K.R. et al. "Quantification of $HDL_2$ and $HDL_3$ Cholesterol by the Vertical Auto Profile-II (VAP-II) Methodology" *J Lipid Res* 38:2353-2364 (1997).

Chakrabarty et al., "Induction of apoptosis in human cancer cell lines by diospyrin, a plant-derived bisnaphthoquinonoid, and its synthetic derivatives," *Cancer Letters* 188(1-2):85-93 (2002).

Co-pending U.S. Appl. No. 11/254,420, filed Oct. 20, 2005, Inventors: Norman C.W. Wong et al.

Co-pending U.S. Appl. No. 11/990,162, filed Feb. 7, 2008, Inventors: Norman C.W. Wong et al.

English Language Derwent Abstract of DE 36 01 417.
English Language Derwent Abstract of EP 0 564 350.
English Language Derwent Abstract of FR 2 244 493.

Gerritsen et al., "Flavenoids inhibit cytokine-induced endothelial cell adhesion protein gene expression," *Am. J. Pathol.* 147(2):278-292 (1995).

Hazra et al., "New diospyrin derivatives with improved tumour inhibitory activity towards ehrlich ascites carcinoma," *Medical Science Research* 22(5):351-353 (1994).

Hazra et al., "Synthesis of an antitumor derivative of diospyrin," *IRCS Medical Science* 14(1):35-36 (1986).

International Search Report and Written Opinion as issued in International Application No. PCT/US2006/029827 mailed on Apr. 16, 2007.

International Search Report and Written Opinion as issued in International Application No. PCT/US2005/037719 mailed on Mar. 9, 2007.

International Search Report and Written Opinion as issued in International Application No. PCT/US2005/038048 mailed on Mar. 7, 2007.

International Search Report and Written Opinion as issued in International Application No. PCT/CA2004/001818 mailed on Feb. 28, 2005.

Jin et al., "Antiplatelet and antithrombotic activities of CP201, a newly synthesized 1,4-naphthoquinone derivative," *Vasc. Pharmacol.* 41(1):35-41 (2004).

Kawamatsu et al., "2-Amino-4-phenylthiazole derivatives as anit-atherogenic agents," *Eur. J. Med. Chem.* 16(4):355-362 (1981).

Kublak et al., "The preparation of the aza-spirobicyclic system of discorhabdin c via an intramolecular phenolate alkylation," *Tetrahedron Lett.* 31(27):3845-3848 (1990).

Lin et al. "Potential bioreductive alkylating agents. 7. Antitumor effects of phenyl-substituted 2-chloromethyl-3-phenyl-1,4-naphthoquinones," *J. Med. Chem.* 19(11):1336-1338 (1976).

Meckes et al., "The effects of chrysin and pinostrobin, 2 flavonoids isolated from teloxys graveolens leaves, on isolated guinea-pig ileum," *Phytomedicine* 5(6):459-463 (1998).

Middleton et al., "Quercetin inhibits lipopolysaccharide-induced expression of endothelial cell intracellular adhesion molecule-1," *Int. Archives of Allergy and Immunology* 107(1/3):435-436 (1995).

Quinones et al., "The EGR-1 gene is induced by DNA-damaging agents and non-genotoxic drugs in both normal and neoplastic human cells," *Life Sciences* 72(26):2975-2992 (2003).
Ragione et al., "Antioxidants induce different phenotypes by a distinct modulation of signal transduction," *FEBS Letters* 523:289-294 (2002).
Ragione et al., "p21cip1 Gene expression is modulated by Egr1," *J. Biol. Chem.* 278(26):23360-23368 (2003).
Rimando et al., "Pterostilbene, a new agonist for the peroxisome proliferator-activated receptor alpha-isoform, lowers plasma lipoproteins and cholesterol in hyercholesterolemic hamsters," *J. Agri. Food Chem.* 53(9):3403-3407 (2005).
Woelle et al., "Selective inhibition of tumor necrosis factor-induced vascular cell adhesion molecule-1 gene expression by a novel flavonoid: lack of effect on transcription factor NF-kappa-B," *Arterioscler. Thromb. Vasc. Biol.* 16(12):1501-1508 (1996).
Wurm et al., "1,4-Naphthoquinones, XXVI: Phenyl-1,4-naphthoquinone derivatives with the hydroxylation patterns of bioflavonoids," *Pharmazie* 52(10):739 (1997).
Wurm, "2-(3,5-Di-*tert*-butyl-4-hydroxyphenyl)-1,4-Naphthochinone Als 5-Lipoxygenasehemmer," *Archiv der Pharmazie* 324:491-495 (1991).
Yardley et al., "In vitro activity of diospyrin and derivatives against leishmania donovani, trypanosoma cruzi and trypanosoma brucei brucei," *Phytotherapy Research* 10(7):559-562 (1996).
English language Derwent abstract for DE 196 51 099.
English language Derwent abstract for DE 197 56 388.
English language Derwent abstract for DE 199 34 799.
English language Derwent abstract for DE 42 15 588.
English language Derwent abstract for EP 569 795.
English language Derwent abstract for JP 2002/249483.
English language Derwent abstract for JP 7041442.
English language Derwent abstract for JP 7061942.
English language Derwent abstract for JP 7118241.
English language Derwent abstract for JP 7179380.
English language Derwent abstract for JP 7233109.
Patent Abstracts of Japan English language abstract of JP 2001/131151.
Patent Abstracts of Japan English language abstract of JP 2001/139550.
Patent Abstracts of Japan English language abstract of JP 2001/335476.
Co-pending U.S. Appl. No. 11/255,103, filed Oct. 20, 2005, Inventors: Norman C.W. Wong et al.
Dai et al., "Synthesis of 3,4-Disubstitute Isoquinolines via Palladium-Catalyzed Cross-Coupling of 2-(1-Alkynyl)benzaldimines and Organic Halides," *J. Org. Chem.* 68:920-928 (2002).
Dai et al., "Synthesis of 3-Substituted 4-Aroylisoquinolines via Pd-Catalyzed Carbonylative Cydization of 2-(1-Alkynyl)benzaldimines," *J. Org. Chem.* 67:7042-7047 (2002).
Ferreira et al., "Diversity of Structure and Function in Oligomeric Flavanoids," *Tetrahedron* 48:1743-1803 (1992).
Flammang et al., "2,3-Benzodiazepines: 2-Aminoisoquinolinones From Ring Contraction of 1-oxo-2,3-Benzodiazepines," *C R Acad. Sci. Paris, Series C* 290:361-363 (1980).
Fokialakis et al., "A New Class of Phytoestrogens: Evaluation of the Estrogenic Activity of Deoxybenzoins," *Chem. & Biol.* 11:397-406 (2004).
Gugler et al., "Disposition of Quercetin in Man After Single Oral and Intravenous Doses," *Eur. J. Clin. Pharmacol.* 9:229-234 (1975), Abstract.
Hertog et al., "Dietary Antioxidant Flavonoids and Risk of Coronary Heart Disease: The Zutphen Elderly Study," *Lancet* 342:1007-1011 (1993).
Huang et al., "Synthesis of Isoquinolines by Palladium-Catalyzed Cyclization, Followed by a Heck Reaction," *Tetrahedron Lett.* 43:3557-3560 (2002).
Jeong et al., "Hypocholesterolemic Activity of Hesperetin Derivatives," *Bioorg. & Med. Chem. Lett.* 13:2663-2665 (2003).
Kim et al., "Hypothetical Drug Binding Receptor Site Analysis Using CoMFA Method for 3-Arylisoquinolines Active Against SK-OV-3 Tumor Cell Line," *Yakhak Hoechi* 46(4):219-225 (2002).

Lamon-Fava, "Genistein Activates Apolipoprotein A-1 Gene Expression in the Human Hepatoma Cell Line Hep G2," *J. Nutrition* 130:2489-2492 (2000).
Lin et al., "Solvent Effects on Aza-anionic Cycloaromatization of 2-(2-Substituted-ethynyl)benzonitriles," *J. Chinese Chem. Soc.* 48:211-214 (2001).
Lin et al., "The Role of Absorption, Distribution, Metabolism, Excretion and Toxicity in Drug Recovery," *Curr. Top. Med. Chem.* 3:1125-1154 (2003).
Lopez et al., "The Synthesis of Substituted 2-Aryl-4(3*H*)-quinazolinones using NaHSO$_3$/DMA. Steric Effect Upon the Cyclisation-Dehydrogenation Step" *J. Chem. Research (S)* pp. 258-259 (2000).
Mahto et al., "Synthesis of 3-Aryl-7-hydroxy Isochromenes" *Asian J. Chem.* 11(2):431-435 (1999).
McKee et al., "Some Basically Substituted Quinazolines" *J. Am. Chem. Soc.* 68(10):1902-1903 (1946).
Rice-Evans, "Flavonoids and Isoflavones (Phytoestrogens): Absorption, Metabolism, and Bioactivity," *Free Rad. Bio. & Med.* 36:827-828 (2004).
Rose et al., "Oxygen Heterocycles. XIII. From 3-Arylisocoumarins to 3-Arylisoquinolines and 4-Aryl-5H-2,3-benzodiazepines," *J. Chem. Soc. (Section C: Organic)* 17:2205-2208 (1968).
Sarkhel et al., "3-Arylisocoumarin: Synthesis of 3-(4-Methoxyphenyl)isocoumarin," *J. Indian Chem. Soc.* 53:915-916 (1976).
Schiess et al., "Thermolytic Ring Opening of Acyloxybenzocyclobutenes: An Efficient Route to 3-Substituted Isoquinolines," *Tetrahedron Lett.* 26:3959-3962 (1985).
Tait et al., "Synthesis and Free Radical Scavenging Activity of 4-(2H-1,2,4-Benzothiadiazine-1,1-dioxide-3-yl)-2,6-bis(1,1-dimethylethyl)phenols," *Tetrahedron* 52(38):12587-12596 (1996).
Talbert, "Current Recommendations for the Treatment of Dyslipidemia," *Pharm. Ther.* 29:104 (2004).
Theriault et al., "Modulation of Hepatic Lipoprotein Synthesis and Secretion by Taxifolin, a Plant Flavonoid," *Journal of Lipid Research* 41:1969-1979 (2000).
Tovar et al., "Pyrylium Salts via Electrophilic Cyclization: Applications for Novel 3-Arylisoquinoline Syntheses," *J. Org. Chem.* 64:6499-6504 (1999).
Van Der Goot et al., "The Growth-Inhibitory Action of Some 1-Aminoisoquinolines and Related Compounds on Mycoplasma Gallisepticum," *Eur. J. Med. Chem.* 10:603-606 (1975).
Varin et al., "Enzymatic Assay for Flavonoid Sulfotransferase," *Anal. Biochem.* 161:176-180 (1987).
Walle, "Absorption and Metabolism of Flavonoids," *Free Rad. Biol. & Med.* 36(7):829-837 (2004).
"Trans-Resveratrol [501-36-0]. Review of Toxicological Literature." Mar. 2002.
Abdel-Jalil et al., "Synthesis and Antitumor Activity of 2-Aryl-7-fluoro-6-(4-methyl-1-piperazinyl)-4(3*H*)-quinazolinones", *Heterocycles* 65(9):2061-2070 (2005).
Beugelmans et al., "One-pot Synthesis of 1-Oxi-1,2-dihydroisoquinolines (Isocarbostyrils) via SRN1 (Ar) Reactions," *Synthesis* 9:729-731 (1981).
Bisagni et al., "A Convenient Way to Dibenzo[c,h]-1,5-Naphthyridines (11-Aza-benzo[c]phenanthridines)," *Tetrahedron* 52:10427-10440 (1996).
Boyce et al., "Acylation and Alkylation of o-Toluinitrile. A New Route to 3-Substituted Isocarbostyrils," *J. Org. Chem.* 31:3807-3809 (1966).
Bradsher et al., "A New Isoquinoline Synthesis via o-Substituted Benzylamines," *Tetrahedron Lett.* 31:3149-3150 (1972).
Bradsher et al., "α-Acyl-o-toluinitriles as Intermediates in the Preparation of 3-Substituted Isoquinolines and 1-Amino-2-benzopyrylium Derivatives," *J. Org. Chem.* 43:3817-3820 (1978).
Cherubini et al., "Role of Antioxidants in Atherosclerosis: Epidemiological and Clinical Update," *Curr. Pharm. Des.* 11:2017-2032 (2005).
Cho et al., "Molecular Modeling of 3-Arylisoquinoline Antitumor Agents Active Against A-549. A Comparative Molecular Field Analysis Study," *Bioorg. & Med. Chem.* 10:2953-2961 (2002).

Cho et al., "Synthesis and Antitumor Activity of 3-Arylisoquinoline Derivatives," *Arch. Pharm. Res.* 20:264-268 (1997).

Cho et al., "Synthesis and Biological Evaluation of 3-Arylisoquinolines as Antitumor Agents," *Bioorg. & Med. Chem. Lett.* 8:41-46 (1998).

Cho et al., "Synthesis and Comparative Molecular Field Analysis (CoMFA) of Antitumor 3-Arylisoquinoline Derivatives," *Bioorg. & Med. Chem.* 6(12):2449-2458 (1998).

Co-pending U.S. Appl. No. 10/575,406, filed Nov. 1, 2006, Inventors: Norman C.W. Wong et al.

Barter et al., "Antiinflammatory Properties of HDL" *Circ. Res.* 95:764-772 (2004).

Clauson-Kaas et al., "Reactions of 3,4-dihydro-2H-pyrido[3,2-b]-1,4-oxazines" *Acta Chemica Scandinavica* 25(8):3135-3143 (1971). Retrieved from STN, file HCAPLUS, Accession No. 1972:34186 (Abstract).

Connolly et al., "Synthesis of quinazolinones and quinazolines" *Tetrahedron* 61(43):10153-10202 (2005).

Fisher Center for Alzheimer'S Research Foundation, "Alzheimer's Disease: 'Good' Cholesterol May Help Keep Alzheimer's at Bay" The Ninth International Conference on Alzheimer's Disease and Related Disorders, Philadelphia, PA, Jul. 22, 2004. Retrieved from the Internet: http://www.alzinfo.org/newsarticle/templates/archivenewstemplate.asp?articleid=156&zoneid=7 on Jul. 28, 2010 (3 pages).

Gaziano et al., "Relation Between Systemic Hypertension and Blood Lipids on the Risk of Myocardial Infarction" *Am. J. Cardiol.* 84(7):768-773 (1999).

Grundy et al., "Definition of Metabolic Syndrome: Report of the National Heart, Lung, and Blood Institute/American Heart Association Conference on Scientific Issues Related to Definition" *Circulation* 109:433-438 (2004).

Guillory, "Generation of Polymorphs, Hydrates, Solvates, and Amorphous Solids" in *Polymorphism in Pharmaceutical Solids*. Brittain, Harry G. (Ed.), Marcel Dekker, Inc., New York, 1999; vol. 95, pp. 202-208.

Hisano et al., "Studies on Organosulfur Compounds. XII. Syntheses and Pharmacological Activities of 2-Heterocyclic Substituted 4(3H)-Quinazolinones" *Chem. Pharm. Bull.* 23(9):1910-1916 (1975).

International Search Report and Written Opinion issued in International Application No. PCT/IB2010/000159; Date of Mailing: Aug. 5, 2010.

International Search Report and Written Opinion issued in International Application No. PCT/US2009/048457; Date of Mailing: Oct. 16, 2009.

Jensen et al., "Serum Lipids and Anthropometric Factors Related to the Prevalence of Intermittent Claudication" *Eur. J. Vasc. Endovasc. Surg.* 30:582-587 (2005).

Kalusa et al., "An efficient synthesis of 2,3-diaryl (3H)-quinazolin-4-ones via imidoyl chlorides" *Tetrahedron Letters* 49(41):5840-5842 (2008).

Koudinov et al., "Alzheimer's amyloid beta and lipid metabolism: a missing link?" *FASEB J.* 12:1097-1099 (1998).

Martin et al. "Modified Flavinoids As Strong Photoprotecting UV-Absorbers and Antioxidants" in *Strategies for Safe Food*. Eklund, T. et al. (Eds.) vol. 1, pp. 288-291 (2003).

Nigam et al., "Synthesis and Pharmacological Screening of Some New 2-(Phenyl/Chloromethyl)-3-[4 (N, N-Disubstituted Aminocarbonyl) Phenyl]-8-Substituted-4 (3H)-Quinazolones" *Indian Drugs* 27(4):238-243 (1990).

Nissen et al., "Effect of Recombinant ApoA-I Milano on Coronary Atherosclerosis in Patients With Acute Coronary Syndromes: A Randomized Controlled Trial" *JAMA* 290(17):2292-2300 (2003).

Office Action in U.S. Appl. No. 11/254,420, mailed Aug. 5, 2008.
Office Action in U.S. Appl. No. 11/254,420, mailed Sep. 28, 2009.
Office Action in U.S. Appl. No. 11/254,420, mailed Feb. 2, 2010.
Office Action in U.S. Appl. No. 11/254,420: Notice of Allowance, mailed Jul. 26, 2010.
Office Action in U.S. Appl. No. 11/255,103: Restriction Requirement, mailed Mar. 26, 2008.
Office Action in U.S. Appl. No. 11/255,103, mailed Mar. 31, 2010.
Office Action in U.S. Appl. No. 11/255,103, mailed Aug. 31, 2009.
Office Action in U.S. Appl. No. 11/255,103, mailed Sep. 24, 2008.
Office Action in U.S. Appl. No. 11/990,162: Restriction Requirement, mailed Jul. 10, 2009.
Office Action in U.S. Appl. No. 11/990,162, mailed Oct. 14, 2009.
Office Action in U.S. Appl. No. 11/990,162, mailed Apr. 1, 2010.

Patani et al., "Bioisosterism: A Rational Approach in Drug Design" *Chem. Rev.* 96(8):3147-3176 (1996).

Plump et al., "Human apolipoprotein A-I gene expression increases high density lipoprotein and suppresses atherosclerosis in the apolipoprotein E-deficient mouse" *Proc. Natl. Acad. Sci. USA* 91:9607-9611 (1994).

Raun et al., "Apolipoprotein A-I possesses an anti-obesity effect associated with increase of energy expenditure and upregulation of UCP1 in brown fat" *J. Cell. Mol. Med.* (2010). "Postprint"; 10.1111/j.1582.4934.2010.01045.x.

Rubins et al., "Reduction in Stroke With Gemfibrozil in Men With Coronary Heart Disease and Low HDL Cholesterol" *Circulation* 103:2828-2833 (2001).

Schork, "Genetics of Complex Disease" *Am. J. Respir. Crit. Care Med.* 156(4):S103-109 (1997).

Shah et al., "Effects of Recombinant Apolipoprotein A-$I_{Milano}$ on Aortic Atherosclerosis in Apolipoprotein E-Deficient Mice" *Circulation* 97(8):780-785 (1998).

Sharrett et al., "Associations of Lipoprotein Cholesterols, Apolipoproteins A-I and B, and Triglycerides with Carotid Atherosclerosis and Coronary Heart Disease" *Arterioscler. Thromb.* 14:1098-1104 (1994).

Tanne et al., "High-Density Lipoprotein Cholesterol and Risk of Ischemic Stroke Mortality" *Stroke* 28:83-87 (1997).

Wei et al., "Total Cholesterol and High Density Lipoprotein Cholesterol as Important Predictors of Erectile Dysfunction" *Am. J. Epidemiol.* 140(10):930-937 (1994).

Welsh et al., "Dyslipidemia In Diabetic Patients" *Perspectives in Cardiology*, Aug. 2002, pp. 40-48.

\* cited by examiner

COMPOUNDS FOR THE PREVENTION AND TREATMENT OF CARDIOVASCULAR DISEASES

TECHNICAL FIELD

The present disclosure relates to compounds, which are useful for regulating the expression of apolipoprotein A-I (ApoA-I), and their use for the treatment and prevention of cardiovascular disease and related disease states, including cholesterol- or lipid-related disorders, such as, for example, atherosclerosis.

BACKGROUND

Epidemiologic data demonstrate an inverse relationship between circulating levels of high density lipoprotein cholesterol (HDL-C) and the incidence of clinically significant atherosclerosis. Each 1 mg/dl increment in the HDL-C serum level is associated with a 2-3% decrement in cardiovascular risk; a 1% reduction in LDL-C reduces coronary heart disease (CHD) risk by 2% (Gordon et al. (1997) Am. J. Med. 62, 707-714). Experimental evidence further supports the protective effect of HDL-C against cardiovascular disease. For example, in subjects with low HDL-C, administration of gemfibrozil results in a 6% increase in the HDL-C level and a corresponding 22% reduction of the CHD risk (Rubins et al. (1999) N. Engl. J. Med. 341, 410-418). Observations in genetic disorders associated with low HDL-C due to reduced ApoA-I expression, also indicate the link between elevated risk of CHD and low HDL-C.

HDL-C appears to exert its anti-atherogenic effect by mediating reverse cholesterol transport (RCT), in which cholesterol is recruited from peripheral tissues and transported to the liver. In addition, HDL-C also exerts anti-inflammatory and anti-oxidant effects and promotes fibrinolysis. HDL-C particles protect against oxidation of LDL, an important initial step in promoting cholesterol uptake by arterial macrophages. HDL-C exists in two main forms, one containing both apolipoprotein A-I (ApoA-I) and apolipoprotein A-II (ApoA-II), and the other containing ApoA-I without ApoA-II (Schultz et al. (1993) Nature 365, 762-764). The cardioprotective effect of HDL-C is mostly, but not exclusively, attributable to ApoA-I.

Clinical and experimental data suggest that the production of ApoA-I is a critical determinant of circulating HDL-C. For example, persons with familial hyperalphalipoproteinemia (elevated ApoA-I) appear to be protected from atherosclerosis, while those deficient in ApoA-I (hypoalphalipoproteinemia) show accelerated cardiovascular disease. In addition, various experimental manipulations to increase production of ApoA-I are associated with reduced atherogenicity. For example, human ApoA-I is protective in transgenic animal models (Shah et al. (1998) Circulation 97, 780-785; Rubin et al. (1991) Nature 353, 265-267), and treatment with ApoA-$I_{Milano}$ prevents atherosclerotic lesions and leads to regression of atherosclerotic plaques in human patients (Nissen et al. (2003) JAMA 290, 2292-2300). Further lines of research demonstrate that ApoA-I plays a role in enhancing reverse cholesterol transport, attenuating oxidative stress, increasing paraoxonase activity, enhancing anticoagulant activity, and increasing anti-inflammatory activity (Andersson (1997) Curr. Opin. Lipidol. 8, 225-228). Accordingly, ApoA-I is an attractive target for therapeutic intervention.

Currently available therapeutic agents that increase the plasma concentration of ApoA-I, for example, recombinant ApoA-I or peptides that mimic ApoA-I, have potential drawbacks with respect to, e.g., stability during storage, delivery of active product, and in vivo half-life. Thus, small molecule compounds that up-regulate the production of endogenous ApoA-I, such as, for example, up-regulators of ApoA-I expression, would be very attractive as new therapeutic agents for cardiovascular disease.

One class of compounds that are thought to contribute to the prevention of various diseases, including cancer and cardiovascular disease, is polyphenols. Polyphenols are present in most food and beverages of plant origin and are the most abundant dietary antioxidants (Scalbert & Williamson (2000) J. Nutr. 130, 2073S-2085S). However, the protective properties of polyphenols have not been fully realized due to poor bioavailability (Manach et al. (2005) Am. J. Clin. Nutr. 81, 230S-242S), lack of clinical significance in various reported studies assessing them (Williamson & Manach (2005) Am. J. Clin. Nutr. 81, 243S-255S), and deleterious effects at higher dose concentrations. For example, an abundant and available source of resveratrol, a well known stilbene polyphenol, is red wine (Wu et. al. (2001) Int. J. Mol. Med. 8, 3-17). However, red wine cannot be consumed in therapeutically efficacious quantities on a daily basis due to the numerous well documented deleterious effects of excessive alcohol consumption. The effects of resveratrol may be better or safer in the absence of alcohol.

Several human clinical studies involving the anti-oxidant effect of various polyphenols in various foods or beverages, have failed to demonstrate an unequivocal benefit with respect to primary clinical endpoints, such as oxidative stress, lipemia, and inflammation (Williamson & Manach (2005) Am. J. Clin. Nutr. 81, 243S-255S). For example, out of twelve recent intervention studies with differing polyphenol sources, six showed no effect on lipid parameters and six showed an improvement in the lipid parameters (Manach (2005) Curr. Opin. Lipidol. 16, 77-84). Such inconclusive data has limited the potential use of polyphenols, despite their many beneficial properties.

The use of naturally occurring polyphenols as potential therapeutics has also been impeded by the inability to achieve efficacious levels in the body, partly due to poor bioavailability (Manach et al. (2005) Am. J. Clin. Nutr. 81, 230S-242S). The bioavailability of any given polyphenol varies widely (from 1-26%) in different individuals. This variability is also seen with administration of different polyphenols to the same individual due to differences in absorption, metabolism, and excretion rates. For example, polyphenol flavonoids, such as quercetin, have been reported to have less than 1% intestinal absorption following oral administration (Gugler et al. (1975) Eur. J. Clin. Pharm. 9, 229-234). In addition, some polyphenol metabolites are known to negatively influence the biological activity of the parent compounds (Manach et al. (2005) Am. J. Clin. Nutr. 81, 230S-242S). Such metabolites often differ from the parent compound in terms of toxicity, efficacy, and length of residence in the plasma. Another limiting factor is the poor solubility of many polyphenols that limits the potential routes of administration. These and other factors have made it difficult to determine appropriate dosages of the naturally occurring polyphenols, naringenin or resveratrol, for use in humans.

Thus, there exists a need for polyphenol-like compounds to be developed as therapeutic agents for the treatment and prevention of cardiovascular disease and related diseases, particularly, cholesterol- or lipid-related disorders, such as, for example, atherosclerosis. It is therefore one of the objects of the present invention to provide compounds that up-regulate the expression of ApoA-I. In addition, the compounds may have more favorable pharmacological properties than naturally occurring polyphenols.

SUMMARY

The present invention includes compounds that are useful for regulating the expression of apolipoprotein A-I (ApoA-I), and their use in the treatment and prevention of cardiovascular disease and related disease states, including cholesterol- and lipid-related disorders, such as, for example, atherosclerosis.

The methods of invention include administering to a mammal (e.g., a human) in need thereof a therapeutically effective amount of a compound of Formula I:

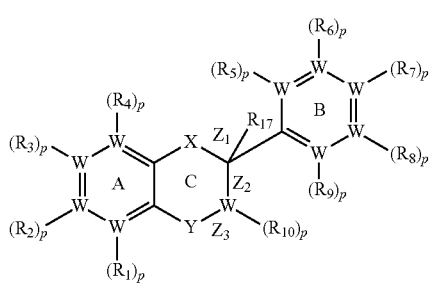

Formula I wherein:
X is selected from $CR_{11}$, $CR_{11}R_{13}$, CO, CS, O, S, SO, $SO_2$, N and $NR_{11}$, wherein $R_{11}$ may be the same or different than $R_{13}$;
Y is selected from $CR_{12}$, $CR_{12}R_{14}$, CO, CS, O, S, SO, $SO_2$, N and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{17}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl or bicyclic heteroaryl;
each W is independently selected from C and N, wherein if W is N, then p is 0 and if W is C, then p is 1;
$Z_1$, $Z_2$ and $Z_3$ are each independently selected from a single bond and a double bond;
wherein if Y is O, then X is not CO;
wherein if X is O, then $Z_1$ is a single bond;
wherein if X is O and $Z_2$ is a single bond, then $R_{10}$ is not hydroxyl or ester;
and pharmaceutically acceptable salts and hydrates thereof.

Also included are methods of administering alternative embodiments of Formula I as set forth on pp. 27-68 and 107-139 of co-pending patent application Ser. No. 11/255,103 incorporated by reference herein.

The invention further includes compounds of Formula II and methods of administering a therapeutically effective amount of those compounds to a mammal (e.g., a human) in need thereof:

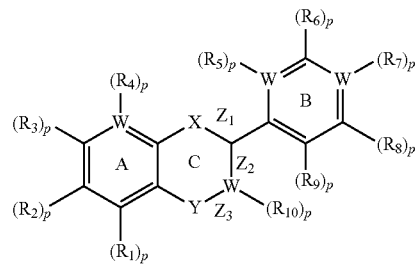

Formula II wherein:
X is selected from $CR_{11}$, $CR_{11}R_{13}$, N and $NR_{11}$, wherein $R_{11}$ may be the same or different than $R_{13}$;
Y is selected from $CR_{12}$, $CR_{12}R_{14}$, CO, $CHOR_{12}$, CS, S, SO, and $SO_2$, wherein $R_{12}$ may be the same or different than $R_{14}$;
$R_{11}$, $R_{12}$, $R_{13}$ and $R_{14}$ are each independently selected from hydrogen, unsubstituted alkyl, unsubstituted alkenyl, and unsubstituted alkynyl;
$R_1$ and $R_3$ are each independently selected from alkoxy, alkyl, alkenyl, alkynyl, amide, amino, halogen, hydroxyl, and hydrogen;
$R_2$ is selected from alkoxy, alkyl, alkenyl, alkynyl, amide, amino, halogen, and hydrogen;
$R_6$ and $R_8$ are each independently selected from alkoxy, alkyl, alkenyl, alkynyl, amide, amino, halogen, hydrogen, heterocyclyl, and cycloalkyl;
$R_5$ and $R_9$ are each independently selected from alkyl, alkenyl, alkynyl, halogen, and hydrogen;
$R_7$ is selected from alkoxy, alkyl, alkenyl, alkynyl, amide, amino, ether, hydrogen, and hydroxyl;
$R_{10}$ is selected from hydrogen and alkyl; or
two adjacent substituents selected from $R_1$, $R_2$, $R_3$, $R_5$, $R_6$, $R_7$, $R_8$, $R_9$, $R_{10}$, $R_{11}$, $R_{12}$, $R_{13}$, and $R_{14}$ are connected to form a group selected from aryl, heteroaryl, cycloalkyl, and heterocyclyl;
wherein each of $R_5$ and $R_9$ may independently be taken together with either $R_{10}$ or $R_{11}$ to form a group selected from aryl, heteroaryl, cycloalkyl, and heterocyclyl;
each W is independently selected from C and N, wherein if W is N, then p is 0 or 1, and if W is C, then p is 1 or 2;
wherein for W—$(R_4)_p$, W is C, p is 1 and $R_4$ is H, or W is N and p is 0;
$Z_1$, $Z_2$ and $Z_3$ are each independently selected from a single bond and a double bond, wherein at least one of $Z_1$ or $Z_2$ must be a double bond;
and pharmaceutically acceptable salts and hydrates thereof.

In certain embodiments, the methods, compounds, and compositions of the invention are useful for the prevention or treatment of diseases that benefit from raised ApoA-I or HDL, and diseases characterized by reduced ApoA-I and/or HDL-C, abnormal lipid parameters, or lipid parameters indicative of high cholesterol. The methods, compounds, and compositions of the invention can be used to increase expression of ApoA-I. Increasing expression of ApoA-I may refer to, but is not limited to, transcriptionally modulating the expression of the ApoA-I gene, thereby affecting the level of the ApoA-I protein produced (synthesized and secreted). An increase in ApoA-I levels may lead to an increase the levels of HDL-C and/or increase in the functionality of HDL-C particles. Thus, the methods, compounds, and compounds of the invention may further be used to reduce cholesterol levels. Accordingly, the methods, compounds, and compositions of the invention can be used for treatment and prevention of cardiovascular disease and related disease states, particularly, cholesterol- or lipid-related disorders, such as, for example, atherosclerosis.

DETAILED DESCRIPTION

Definitions

Figure 1:
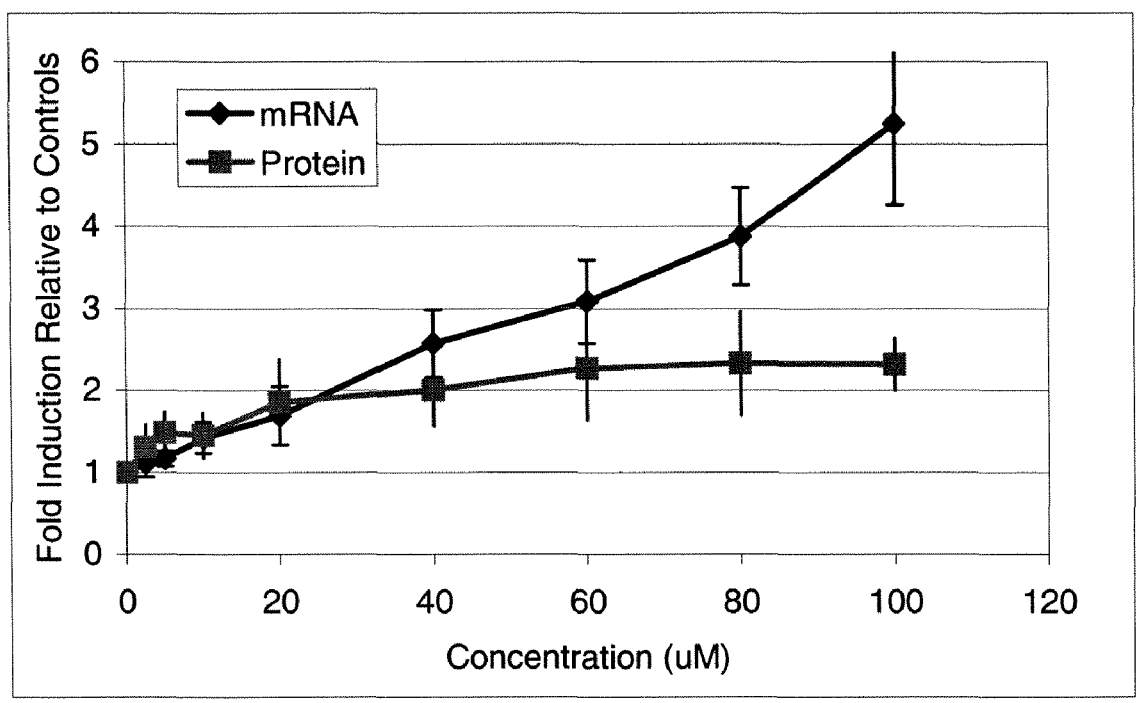
FIG. 1 depicts ApoA-I induction by 2-(4-(2-hydroxyethoxy)-3,5-dimethylphenyl)-5,7-dimethoxyquinazolin-4(3H)-one (Example 20) in HepG2 Cells (48 h).

The term "aldehyde" or "formyl" as used herein refers to —CHO.

The term "alkenyl" as used herein refers to an unsaturated straight or branched hydrocarbon having at least one carbon-carbon double bond, such as a straight or branched group of 2-22, 2-8, or 2-6 carbon atoms, referred to herein as ($C_2$-$C_{22}$) alkenyl, ($C_2$-$C_8$)alkenyl, and ($C_2$-$C_6$)alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as ($C_1$-$C_{22}$) alkoxy, ($C_1$-$C_8$)alkoxy, and ($C_1$-$C_6$)alkoxy, respectively. Exemplary alkoxy groups include, but are not limited to methoxy, ethoxy, etc.

The term "alkyl" as used herein refers to a saturated straight or branched hydrocarbon, such as a straight or branched group of 1-22, 1-8, or 1-6 carbon atoms, referred to herein as ($C_1$-$C_{22}$)alkyl, ($C_1$-$C_8$)alkyl, and ($C_1$-$C_6$)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkynyl" as used herein refers to an unsaturated straight or branched hydrocarbon having at least one carbon-carbon triple bond, such as a straight or branched group of 2-22, 2-8, or 2-6 carbon atoms, referred to herein as ($C_2$-$C_{22}$) alkynyl, ($C_2$-$C_8$)alkynyl, and ($C_2$-$C_6$)alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "amide" as used herein refers to the form —$NR_9C(O)R_b$, or —$C(O)NR_bR_c$, wherein $R_a$, $R_b$ and $R_c$ are each independently selected from alkyl, alkenyl, alkynyl, aryl, arylalkyl, cycloalkyl, haloalkyl, heteroaryl, heterocyclyl, and hydrogen. The amide can be attached to another group through $R_b$ or $R_c$. The amide also may be cyclic, for example $R_b$ and $R_c$ may be joined to form a 3- to 12-membered ring, such as a 3- to 10-membered ring or a 5- to 6-membered ring. The term "amide" encompasses groups such as sulfonamide, urea (ureido), carbamate, carbamic acid, and cyclic versions thereof. The term "amide" also encompasses an amide group attached to a carboxy group, e.g., -amide-COOH or salts such as -amide-COONa, etc, an amino group attached to a carboxy group, e.g., -amino-COOH or salts such as -amino-COONa, etc.

The term "amine" or "amino" as used herein refers to the form —$NR_dR_e$ or —$N(R_d)R_e$— where $R_d$ and $R_e$ are independently selected from alkyl, alkenyl, alkynyl, aryl, arylalkyl, carbamate, cycloalkyl, haloalkyl, heteroaryl, heterocyclyl, and hydrogen. The amino can be attached to the parent molecular group through the nitrogen. The amino also may be cyclic, for example, $R_d$ and $R_e$ may be joined together or with the N to form a 3- to 12-membered ring, e.g., morpholino or piperidinyl. The term amino also includes the corresponding quaternary ammonium salt of any amino group. Exemplary amino groups include alkyl amino groups, wherein at least one of $R_d$ and $R_e$ is an alkyl group.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this invention can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "($C_6$) aryl."

The term "arylalkyl" as used herein refers to an alkyl group having at least one aryl substituent, e.g. -aryl-alkyl-. Exemplary arylalkyl groups include, but are not limited to, arylalkyls having a monocyclic aromatic ring system, wherein the ring comprises 6 carbon atoms, referred to herein as "($C_6$) arylalkyl."

The term "aryloxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "($C_6$)aryloxy."

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "($C_6$)arylthio."

The term "arylsulfonyl" as used herein refers to an aryl group attached to a sulfonyl group, e.g., —S(O)$_2$-aryl-. Exemplary arylsulfonyl groups include, but are not limited to, arylsulfonyls having a monocyclic aromatic ring system, wherein the ring comprises 6 carbon atoms, referred to herein as "($C_6$)arylsulfonyl."

The term "benzyl" as used herein refers to the group —CH$_2$-phenyl.

The term "bicyclic aryl" as used herein refers to an aryl group fused to another aromatic or non-aromatic carbocyclic or heterocyclic ring. Exemplary bicyclic aryl groups include, but are not limited to, naphthyl or partly reduced forms thereof, such as di-, tetra-, or hexahydronaphthyl.

The term "bicyclic heteroaryl" as used herein refers to a heteroaryl group fused to another aromatic or non-aromatic carbocylic or heterocyclic ring. Exemplary bicyclic heteroaryls include, but are not limited to, 5,6 or 6,6-fused systems wherein one or both rings contain heteroatoms. The term "bicyclic heteroaryl" also encompasses reduced or partly reduced forms of fused aromatic system wherein one or both rings contain ring heteroatoms. The ring system may contain up to three heteroatoms, independently selected from oxygen, nitrogen, or sulfur. The bicyclic system may be optionally substituted with one or more groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary bicyclic heteroaryls include, but are not limited to, quinazolinyl, benzothiophenyl, benzoxazolyl, benzimidazolyl, benzothiazolyl, benzofuranyl, indolyl, quinolinyl, isoquinolinyl, phthalazinyl, benzotriazolyl, benzopyridinyl, and benzofuranyl.

The term "carbamate" as used herein refers to the form —R$_g$OC(O)N(R$_h$)—, —R$_g$OC(O)N(R$_h$)R$_i$—, or —OC(O)NR$_h$R$_i$, wherein R$_g$, R$_h$ and R$_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates, e.g., wherein at least one of R$_g$, R$_h$ and R$_i$ are independently selected from aryl or heteroaryl, such as pyridine, pyridazine, pyrimidine, and pyrazine.

The term "carbonyl" as used herein refers to —C(O)—.

The term "carboxy" as used herein refers to —COOH or its corresponding carboxylate salts, e.g. —COONa, etc. The term carboxy also includes "carboxycarbonyl," e.g., a carboxy group attached to a carbonyl group, e.g., —C(O)—COOH or salts such as —C(O)—COONa, etc.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides, etc., for example, succinic anhydride, succinimide, etc.

The term "ester" refers to the structure —C(O)O—, —C(O)O—R$_j$-, —R$_k$C(O)O—R$_j$-, or —R$_k$C(O)O—, where O is not bound to hydrogen, and R$_j$ and R$_k$ can independently be selected from alkoxy, aryloxy, alkyl, alkenyl, alkynyl, amide, amino, aryl, arylalkyl, cycloalkyl, ether, haloalkyl, heteroaryl, heterocyclyl. R$_k$ can be a hydrogen, but R$_j$ cannot be hydrogen. The ester may be cyclic, for example the carbon atom and R$_j$, the oxygen atom and R$_k$, or R$_j$ and R$_k$ may be joined to form a 3- to 12-membered ring. Exemplary esters include, but are not limited to, alkyl esters wherein at least one of Rj or Rk is alkyl, such as —O—C(O)-alkyl-, —C(O)—O-alkyl-, -alkyl-C(O)—O-alkyl-, etc. Exemplary esters also include aryl or heteoraryl esters, e.g. wherein at least one of Rj or Rk is a heteroaryl group such as pyridine, pyridazine, pyrmidine and pyrazine, such as a nicotinate ester. Exemplary esters also include reverse esters having the structure —R$_k$C(O)O—, where the oxygen is bound to the parent molecular group. Exemplary reverse esters include succinate, D-argininate, L-argininate, L-lysinate and D-lysinate. Esters also include carboxylic acid anhydrides and acid halides.

The term "ether" refers to the structure —R$_l$O—R$_m$-, where R$_l$ and R$_m$ can independently be alkyl, alkenyl, alkynyl, aryl, cycloalkyl, heterocyclyl, or ether. The ether can be attached to the parent molecular group through R$_l$ or R$_m$. Exemplary ethers include, but are not limited to, alkoxyalkyl and alkoxyaryl groups. Ethers also includes polyethers, e.g., where one or both of R$_l$ and R$_m$ are ethers.

The terms "halo" or "halogen" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example one to three heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2 to 5 carbon atoms and 1 to 3 heteroatoms, referred to herein as "$(C_2-C_5)$heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyi, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—$R_n$— (such as acetyl, —C(O)CH$_3$) or —$R_n$—C(O)—$R_o$—. The ketone can be attached to another group through $R_n$ or $R_o$. $R_n$ or $R_o$ can be alkyl, alkenyl, alkynyl, cycloalkyl, heterocyclyl or aryl, or $R_n$ or $R_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic acid and maleic acid.

The term "nitro" as used herein refers to the structure —NO$_2$.

The term "perfluoroalkoxy" as used herein refers to an alkoxy group in which all of the hydrogen atoms have been replaced by fluorine atoms.

The term "perfluoroalkyl" as used herein refers to an alkyl group in which all of the hydrogen atoms have been replaced by fluorine atoms. Exemplary perfluroalkyl groups include, but are not limited to, ($C_{1-5}$) perfluoroalkyl, such as trifluoromethyl, etc.

The term "perfluorocycloalkyl" as used herein refers to a cycloalkyl group in which all of the hydrogen atoms have been replaced by fluorine atoms.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone.

The term "phosphate" as used herein refers to the structure —OP(O)O$_2$—, —$R_x$OP(O)O$_2$—, —OP(O)O$_2$R$_y$—, or —$R_x$OP(O)O$_2$R$_y$—, wherein $R_x$ and $R_y$ can be selected from alkyl, alkenyl, alkynyl, aryl, cycloalkyl, heterocyclyl, and hydrogen.

The term "sulfide" as used herein refers to the structure —$R_z$S—, where $R_z$ can be selected from alkyl, alkenyl, alkynyl, aryl, arylalkyl, cycloalkyl, haloalkyl, heteroaryl, and heterocyclyl. The sulfide may be cyclic, forming a 3-12 membered ring. The term "alkylsulfide" as used herein refers to an alkyl group attached to a sulfur atom.

The term "sulfinyl" as used herein refers to the structure —S(O)O—, —$R_p$S(O)O—, —$R_p$S(O)OR$_q$—, or —S(O)OR$_q$—, wherein $R_p$ and $R_q$ can be selected from alkyl, alkenyl, aryl, arylalkyl, cycloalkyl, haloalkyl, heteroaryl, heterocyclyl, and hydroxyl. Exemplary sulfinyl groups include, but are not limited to, alkylsulfinyls wherein at least one of $R_p$ or $R_q$ is alkyl, alkenyl or alkynyl.

The term "sulfonamide" as used-herein refers to the structure —($R_r$)—N—S(O)$_2$—$R_s$— or —$R_t$($R_r$)—N—S(O)$_2$—$R_s$, where $R_t$, $R_r$, and $R_s$ can be, for example, hydrogen, alkyl, alkenyl, alkynyl, aryl, cycloalkyl, and heterocyclyl. Exemplary sulfonamides include alkylsulfonamides (e.g., where $R_s$ is alkyl), arylsulfonamides (e.g., where $R_s$ is aryl), cycloalkyl sulfonamides (e.g., where $R_s$ is cycloalkyl), and heterocyclyl sulfonamides (e.g., where $R_s$ is heterocyclyl), etc.

The term "sulfonate" as used herein refers to —OSO$_3^-$. Sulfonate includes salts such as —OSO$_3$Na, —OSO$_3$K, etc. and the acid —OSO$_3$H The term "sulfonic acid" refers to —SO$_3$H— and its corresponding salts, e.g. —SO$_3$K—, —SO$_3$Na—.

The term "sulfonyl" as used herein refers to the structure $R_u$SO$_2$—, where $R_u$ can be alkyl, alkenyl, alkynyl, aryl, cycloalkyl, and heterocyclyl, e.g., alkylsulfonyl. The term "alkylsulfonyl" as used herein refers to an alkyl group attached to a sulfonyl group. "Alkylsulfonyl" groups can optionally contain alkenyl or alkynyl groups.

The term "thioketone" refers to the structure —$R_V$—C(S)—$R_W$—. The ketone can be attached to another group through $R_V$ or $R_W$. $R_V$ or $R_W$ can be alkyl, alkenyl, alkynyl, cycloalkyl, heterocyclyl or aryl, or $R_V$ and $R_W$ can be joined to form a 3- to 12-membered ring.

"Alkyl," "alkenyl," "alkynyl," "alkoxy," "amino," and "amide" groups can be substituted with or interrupted by or branched with at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, ureido, and nitrogen. The substituents may be branched to form a substituted or unsubstituted heterocycle or cycloalkyl.

As used herein, a "suitable substituent" refers to a group that does not nullify the synthetic or pharmaceutical utility of the compounds of the invention or the intermediates useful for preparing them. Examples of suitable substituents include, but are not limited to: $C_{1-22}$, $C_{1-8}$, and $C_{1-6}$ alkyl, alkenyl or alkynyl; $C_{1-6}$ aryl, $C_{2-5}$ heteroaryl; $C_{3-7}$ cycloalkyl; $C_{1-22}$, $C_{1-8}$, and $C_{1-6}$ alkoxy; $C_6$ aryloxy; —CN; —OH; oxo; halo, carboxy; amino, such as —NH($C_{1-22}$, $C_{1-8}$, or $C_{1-6}$ alkyl), —N($C_{1-22}$, $C_{1-8}$, and $C_{1-6}$ alkyl)$_2$, —NH(($C_6$)aryl), or —N(($C_6$)aryl)$_2$; formyl; ketones, such as —CO($C_{1-22}$, $C_{1-8}$, and $C_{1-6}$ alkyl), —CO(($C_6$ aryl) esters, such as —CO$_2$($C_{1-22}$, $C_{1-8}$, and $C_{1-6}$ alkyl) and —CO$_2$ ($C_6$ aryl). One of skill in art can readily choose a suitable substituent based on the stability and pharmacological and synthetic activity of the compound of the invention.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present invention that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the invention. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

EMBODIMENTS OF THE INVENTION

One embodiment provides a method for increasing expression of ApoA-I in a mammal (e.g., a human) comprising administering a therapeutically effective amount of a compound of Formula I:

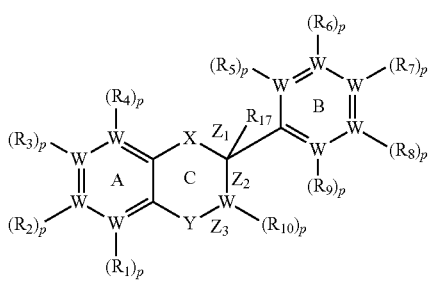

Formula I wherein:
X is selected from $CR_{11}$, $CR_{11}R_{13}$, CO, CS, O, S, SO, $SO_2$, N, and $NR_{11}$, wherein $R_{11}$ may be the same or different than $R_{13}$;
Y is selected from $CR_{12}$, $CR_{12}R_{14}$, CO, CS, O, S, SO, $SO_2$, N, and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{17}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl or bicyclic heteroaryl;
each W is independently selected from C and N, wherein if W is N, then p is 0 and if W is C, then p is 1;
$Z_1$, $Z_2$ and $Z_3$ are each independently selected from a single bond and a double bond;
wherein if Y is O, then X is not CO;
wherein if X is O, then $Z_1$ is a single bond;
wherein if X is O and $Z_2$ is a single bond, then $R_{10}$ is not hydroxyl or ester;
and pharmaceutically acceptable salts and hydrates thereof.

Another embodiment provides a method for increasing expression of ApoA-II in a mammal (e.g., a human) comprising administering a therapeutically effective amount of a compound of Formula II:

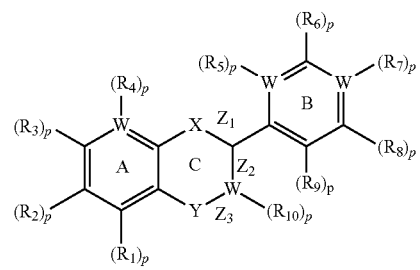

Formula II wherein:
X is selected from $CR_{11}$, $CR_{11}R_{13}$, N and $NR_{11}$, wherein $R_{11}$ may be the same or different than $R_{13}$;
Y is selected from $CR_{12}$, $CR_{12}R_{14}$, CO, $CHOR_{12}$, CS, S, SO, and $SO_2$, wherein $R_{12}$ may be the same or different than $R_{14}$;

$R_{11}$, $R_{12}$, $R_{13}$, and $R_{14}$ are each independently selected from hydrogen, unsubstituted alkyl (preferably $C_{1-3}$ alkyl), unsubstituted alkenyl (preferably $C_{1-3}$ alkenyl), and unsubstituted alkynyl (preferably $C_{1-3}$ alkynyl);
$R_1$ and $R_3$ are each independently selected from alkoxy (preferably methoxy), alkyl, alkenyl, alkynyl, amide, amino, halogen (preferably chloride), hydroxyl, and hydrogen;
$R_2$ is selected from alkoxy, alkyl, alkenyl, alkynyl, amide, amino, halogen (preferably bromide or chloride), and hydrogen;
$R_6$ and $R_8$ are each independently selected from alkoxy, alkyl (preferably methyl), alkenyl, alkynyl, amide, amino, halogen (preferably chloride or fluoride), hydrogen, heterocyclyl, and cycloalkyl;
$R_5$ and $R_9$ are each independently selected from alkyl, alkenyl, alkynyl, halogen (preferably chloride), and hydrogen;
$R_7$ is selected from alkoxy, alkyl, alkenyl, alkynyl, amide, amino, ether, ester, hydrogen, and hydroxyl;
$R_{10}$ is selected from hydrogen and alkyl (preferably methyl); or
two adjacent substituents selected from $R_1$, $R_2$, $R_3$, $R_5$, $R_6$, $R_7$, $R_8$, $R_9$, $R_{10}$, $R_{11}$, $R_{12}$, $R_{13}$ and $R_{14}$ are connected to form a group selected from aryl, heteroaryl, cycloalkyl, and heterocyclyl;
wherein each of $R_5$ and $R_9$ may independently be taken together with either $R_{10}$ or $R_{11}$ to form a group selected from aryl, heteroaryl, cycloalkyl, and heterocyclyl;
each W is independently selected from C and N, wherein if W is N, then p is 0 or 1, and if W is C, then p is 1;
wherein for W—$(R_4)_p$, W is C, p is 1 and $R_4$ is H, or W is N and p is 0;
$Z_1$, $Z_2$ and $Z_3$ are each independently selected from a single bond and a double bond, wherein at least one of $Z_1$ or $Z_2$ is a double bond;
and pharmaceutically acceptable salts and hydrates thereof.

Another embodiment provides a method for increasing expression of ApoA-I in a mammal (e.g., a human) comprising administering a therapeutically effective amount of a compound of Formula II:

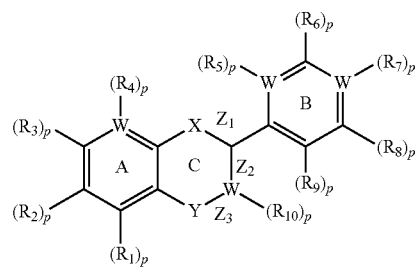

Formula II wherein:
X is selected from CH and N;
Y is selected from CO, CS, and $SO_2$;
$R_1$ and $R_3$ are each independently selected from alkoxy, alkyl, amino, halogen, and hydrogen;
$R_2$ is selected from alkoxy, alkyl, amino, and hydrogen;
$R_6$ and $R_8$ are each independently selected from alkoxy, amino, alkyl, hydrogen, and heterocyclyl;
$R_5$ and $R_9$ are each hydrogen;

$R_7$ is selected from alkoxy, alkyl, alkynyl, amide, amino, ether, hydrogen, and hydroxyl;

$R_{10}$ is hydrogen; or two adjacent substituents selected from $R_1$, $R_2$, $R_3$, $R_5$, $R_6$, $R_7$, $R_8$, $R_9$, and $R_{10}$ are connected to form group selected from aryl, heteroaryl, cycloalkyl and heterocyclyl;

wherein $R_5$ or $R_9$ may be taken together with $R_{10}$ to form a group selected from aryl, heteroaryl, cycloalkyl, and heterocyclyl;

each W is independently selected from C and N, wherein if W is N, then p is 0 or 1, and if W is C, then p is 1;

wherein for W—$(R_4)_p$, W is C, p is 1 and $R_4$ is H, or W is N and p is 0;

$Z_1$, $Z_2$, and $Z_3$ are each independently selected from a single bond and a double bond, wherein at least one of $Z_1$ or $Z_2$ is a double bond;

and pharmaceutically acceptable salts and hydrates thereof.

The following is a list of specific exemplary embodiments that are encompassed by the invention:

1. A method for increasing expression of ApoA-I in a mammal comprising administering a therapeutically effective amount of a compound of Formula II:

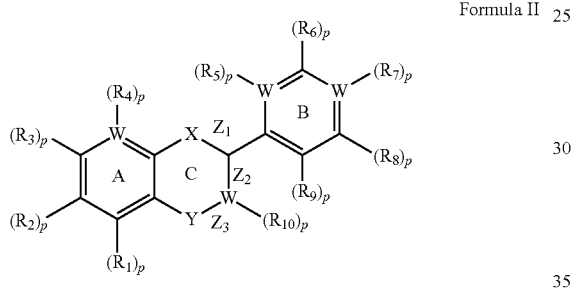

Formula II wherein:

X is selected from $CR_{11}$, $CR_{11}R_{13}$, N, and $NR_{11}$, wherein $R_{11}$ may be the same or different than $R_{13}$;

Y is selected from $CR_{12}$, $CR_{12}R_{14}$, CO, $CHOR_{12}$, CS, S, SO, and $SO_2$, wherein $R_{12}$ may be the same or different than $R_{14}$;

$R_{11}$, $R_{12}$, $R_{13}$ and $R_{14}$ are each independently selected from hydrogen, unsubstituted alkyl (preferably $C_{1-3}$ alkyl), unsubstituted alkenyl (preferably $C_{1-3}$ alkenyl), and unsubstituted alkynyl (preferably $C_{1-3}$ alkynyl);

$R_1$ and $R_3$ are each independently selected from alkoxy (preferably methoxy), alkyl, alkenyl, alkynyl, amide, amino, halogen (preferably chloride), hydroxyl, and hydrogen;

$R_2$ is selected from alkoxy, alkyl, alkenyl, alkynyl, amide, amino, halogen (preferably chloride and fluoride), and hydrogen;

$R_6$ and $R_8$ are each independently selected from alkoxy, alkyl (preferably methyl), alkenyl, alkynyl, amide, amino, halogen (preferably chloride), hydrogen, heterocyclyl, and cycloalkyl;

$R_5$ and $R_9$ are each independently selected from alkyl, alkenyl, alkynyl, halogen, and hydrogen;

$R_7$ is selected from alkoxy, alkyl, alkenyl, alkynyl, amide, amino, ether, ester, hydrogen, and hydroxyl;

$R_{10}$ is selected from hydrogen and alkyl (preferably methyl); or two adjacent substituents selected from $R_1$, $R_2$, $R_3$, $R_5$, $R_6$, $R_7$, $R_8$, $R_9$, $R_{10}$, $R_{11}$, $R_{12}$, $R_{13}$ and $R_{14}$ are connected to form a group selected from aryl, heteroaryl, cycloalkyl, and heterocyclyl;

wherein each of $R_5$ and $R_9$ may independently be taken together with $R_{10}$ or $R_{11}$ to form a group selected from aryl, heteroaryl, cycloalkyl, and heterocyclyl;

each W is independently selected from C and N, wherein if W is N, then p is 0 or 1, and if W is C, then p is 1;

wherein for W—$(R_4)_p$, W is C, p is 1 and $R_4$ is H, or W is N and p is 0;

$Z_1$, $Z_2$, and $Z_3$ are each independently selected from a single bond and a double bond, wherein at least one of $Z_1$ or $Z_2$ is a double bond;

and pharmaceutically acceptable salts and hydrates thereof.

In one embodiment, $R_7$ is not diethylamino or an alkoxy substituted with a carboxylate group.

In another embodiment, at least one of $R_{11}$, $R_{12}$, $R_{13}$, and $R_{14}$ is an unsubstituted ($C_{1-3}$) alkyl.

2. The method according to embodiment 1, wherein $Z_1$ is a double bond;

$Z_2$ and $Z_3$ are each a single bond;

X is selected from N and $CR_{11}$;

for W—$(R_{10})_p$, W is N and p is 1; and

Y is selected from CO, $SO_2$, SO, and CS.

3. The method according to embodiment 1, wherein $Z_2$ is a double bond;

X is $NR_{11}$;

for W—$(R_{10})_p$, W is N and p is 0; and

Y is selected from CO, $SO_2$, SO, and CS.

4. The method according to embodiment 1, wherein $Z_1$ and $Z_3$ are each a double bond;

X is selected from N and $CR_{11}$;

for W—$(R_{10})_p$, W is N, and p is 0; and

Y is selected from $CR_{12}$, $COR_{12}$, and SO.

5. The method according to embodiment 1, wherein $R_1$ and $R_3$ are each independently an alkoxy.

6. The method according to embodiment 5, wherein $R_6$ and $R_8$ are each independently selected from alkyl and hydrogen; and $R_7$ is selected from amino, hydroxyl, and alkoxy.

7. The method according to embodiment 6, wherein X is $CR_{11}$; for W—$(R_{10})_p$, W is N and $R_{10}$ is hydrogen; and Y is CO.

8. The method according to embodiment 6, wherein X is N; for W—$(R_{10})_p$, W is N and $R_{10}$ is hydrogen; and Y is CO.

9. The method according to embodiment 1, wherein $R_5$ and $R_9$ are each hydrogen.

10. The method according to embodiment 1, wherein at least one of $R_1$, $R_2$, and $R_3$ is not hydrogen.

11. The method according to embodiment 10, wherein $R_6$ and $R_8$ are each independently selected from alkyl and hydrogen; and $R_7$ is selected from amino, hydroxyl, and alkoxy.

12. The method according to embodiment 11, wherein X is $CR_{11}$; for W—$(R_{10})_p$, W is N and $R_{10}$ is hydrogen; and Y is CO.

13. The method according to embodiment 11, wherein X is N; for W—$(R_{10})_p$, W is N and $R_{10}$ is hydrogen; and Y is CO.

14. The method according to embodiment 1, wherein at least one of $R_6$, $R_7$, and $R_8$ is not hydrogen.

15. The method according to embodiment 14, wherein $R_6$ and $R_8$ are each independently selected from alkyl and hydrogen; and $R_7$ is selected from amino, hydroxyl, and alkoxy.

16. The method according to embodiment 15, wherein X is $CR_{11}$; for W—$(R_{10})_p$, W is N and $R_{10}$ is hydrogen; and Y is CO.

17. The method according to embodiment 16, wherein the compound of Formula II is selected from:

3-(4-hydroxy-3,5-dimethylphenyl)-6,8-dimethoxyisoquinolin-1(2H)-one (Example 7); and 7-(4-hydroxy-3,5-dimethylphenyl)-2,4-dimethoxy-1,6-naphthyridin-5(6H)-one (Example 16).

18. The method according to embodiment 15, wherein X is N; for W—$(R_{10})_p$, W is N and $R_{10}$ is hydrogen; and Y is CO.

19. The method according to embodiment 18, wherein the compound of Formula II is selected from:

2-(4-(2-hydroxyethoxy)-3,5-dimethylphenyl)-5,7-dimethoxyquinazolin-4(3H)-one (Example 20);

N-(2-(4-(5,7-dimethoxy-4-oxo-3,4-dihydroquinazolin-2-yl)-2,6-dimethylphenoxy)ethyl)methanesulfonamide (Example 102);

2-(4-hydroxy-3-methylphenyl)-5,7-dimethoxyquinazolin-4(3H)-one (Example 98);

2-(4-(2-hydroxyethoxy)-3-methylphenyl)-5,7-dimethoxyquinazolin-4(3H)-one (Example 97);

2-(4-(bis(2-hydroxyethyl)amino)phenyl)-5,7-dimethoxyquinazolin-4(3H)-one (Example 46);

2-(3,5-dimethyl-4-(2-morpholinoethoxy)phenyl)-5,7-dimethoxyquinazolin-4(3H)-one (Example 21); and 3-(4-hydroxy-3,5-dimethylphenyl)-6,8-dimethoxy-7-(morpholinomethyl)isoquinolin-1(2H)-one (Example 51).

20. The method according to embodiment 1, wherein X is selected from CH, N, and $NR_{11}$, and Y is selected from CH, CO, and $SO_2$.

21. The method according to embodiment 20, wherein $Z_1$ is a double bond;

$Z_2$ and $Z_3$ are each a single bond; and for W—$(R_{10})_p$, W is N and p is 1.

22. The method according to embodiment 20, wherein $Z_2$ is a double bond;

X is $NR_{11}$; and for W—$(R_{10})_p$, W is N and p is 0.

23. The method according to embodiment 20, wherein $Z_1$ and $Z_3$ are each a double bond;

X is selected from CH and N;

for W—$(R_{10})_p$, W is N and p is 0; and

Y is CH.

24. The method according to embodiment 1, wherein X is selected from CH and N, and Y is selected from CO and $SO_2$.

25. The method according to embodiment 24, wherein $Z_1$ is a double bond, $Z_2$ and $Z_3$ are each a single bond, and for W—$(R_{10})_p$, W is N and $R_{10}$ is hydrogen.

26. The method according to embodiment 24, wherein $Z_2$ is a double bond and for W—$(R_{10})_p$, W is N and p is 0.

27. The method according to embodiment 1, wherein $R_7$ is an amino or an alkoxy selected from the group represented by Formula III:

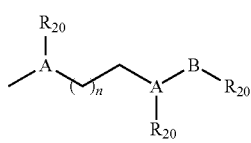

Formula III wherein:

A is selected from O and N;

n is selected from 0, 1, 2, 3, 4 and 5;

B is selected from —$C(O)N(R_h)_2$—, —$S(O)_2N(R_h)_2$—, —C(O)—, —$S(O)_2$—, and —C(O)O—, wherein each $R_h$ is independently selected from alkyl, alkenyl, alkynyl, aryl, arylalkyl, cycloalkyl, haloalkyl, heteroaryl, heterocyclyl, and hydrogen; and $R_{20}$ is selected from $C_1$-$C_6$ alkyl, $C_1$-$C_6$ alkenyl, $C_1$-$C_6$ alkynyl, aryl, arylalkyl, cycloalkyl, haloalkyl, heteroaryl, heterocyclyl, and hydrogen.

In another embodiment, if A is O and B is —$C(O)N(R_h)_2$—, then $R_{20}$ is not an unsaturated cycloalkyl.

28. The method according to embodiment 27, wherein the compound of Formula II is selected from:

2-(4-(5,7-dimethoxy-4-oxo-3,4-dihydroquinazolin-2-yl)-2,6-dimethylphenoxy)ethyl cyclohexylcarbamate (Example 108);

N-(2-(4-(5,7-dimethoxy-4-oxo-3,4-dihydroquinazolin-2-yl)-2,6-dimethylphenoxy)ethyl)acetamide (Example 112);

N-(2-(4-(5,7-dimethoxy-4-oxo-3,4-dihydroquinazolin-2-yl)-2,6-dimethylphenoxy)ethyl)isobutyramide (Example 114);

1-(2-(4-(5,7-dimethoxy-4-oxo-3,4-dihydroquinazolin-2-yl)-2,6-dimethylphenoxy)ethyl)-3-phenylurea (Example 117); and 3-(2-(4-(5,7-dimethoxy-4-oxo-3,4-dihydroquinazolin-2-yl)-2,6-dimethylphenoxy)ethyl)-1,1-dimethylurea (Example 118).

29. The method according to embodiment 1, wherein:

X is selected from $CR_{11}$, N, and $NR_{11}$,

Y is selected from CO, CS, and $SO_2$, $R_{11}$ is selected from hydrogen, unsubstituted alkyl (preferably $C_{1-3}$ alkyl), unsubstituted alkenyl (preferably $C_{1-3}$ alkenyl), and unsubstituted alkynyl (preferably $C_{1-3}$ alkynyl);

$R_1$ and $R_3$ are each independently selected from alkoxy (preferably methoxy), alkyl, amino, halogen (preferably chloride), and hydrogen;

$R_2$ is selected from alkoxy, alkyl, alkenyl, amide, amino, halogen (preferably bromide or chloride), and hydrogen;

$R_6$ and $R_8$ are each independently selected from alkoxy, alkyl (preferably methyl), amino, halogen (preferably chloride and fluoride), and hydrogen;

$R_5$ and $R_9$ are each independently selected from halogen (preferably chloride) and hydrogen;

$R_7$ is selected from alkoxy, alkyl, alkenyl, amide, amino, ether, hydrogen, and hydroxyl;

$R_{10}$ is selected from hydrogen and alkyl (preferably methyl); or two adjacent substituents selected from $R_1$, $R_2$, $R_3$, $R_6$, $R_7$, $R_8$, $R_{10}$, and $R_{11}$ are connected to form a group selected from aryl, heteroaryl, cycloalkyl, and heterocyclyl;

each W is independently selected from C and N, wherein if W is N, then p is 0 or 1, and if W is C, then p is 1;

wherein for W—$(R_4)_p$, W is C, p is 1 and $R_4$ is H, or W is N and p is 0;

$Z_1$, $Z_2$, and $Z_3$ are each independently selected from a single bond and a double bond, wherein at least one of $Z_1$ or $Z_2$ is a double bond;

and pharmaceutically acceptable salts and hydrates thereof.

30. The method according to embodiment 29, wherein:

X is selected from N and CH;

Y is CO;

$R_1$ and $R_3$ are each independently selected from alkoxy and hydrogen;

$R_2$ is selected from alkoxy, alkyl, and hydrogen;

$R_6$ and $R_8$ are each independently selected from alkyl, alkoxy, chloride, and hydrogen;

$R_5$ and $R_9$ are each hydrogen;

$R_7$ is selected from amino, hydroxyl, alkoxy (preferably a substituted ethoxy group), and alkyl substituted with a heterocyclyl;

$R_{10}$ is hydrogen; or two adjacent substituents selected from $R_6$, $R_7$, and $R_8$ are connected to form a heterocyclyl;

each W is independently selected from C and N, wherein if W is N, then p is 0 or 1, and if W is C, then p is 1;

for W—$(R_{10})_p$, W is N and p is 1;

for W—$(R_4)_p$, W is C, p is 1 and $R_4$ is H, or W is N and p is 0;

$Z_1$ is a double bond, and $Z_2$ and $Z_3$ are each a single bond;

with the proviso that at least one of $R_1$ and $R_3$ is alkoxy;

with the proviso that if $R_7$ is selected from hydroxyl and alkoxy, then at least one of $R_6$ and $R_8$ are independently selected from alkyl, alkoxy, and chloride;

with the proviso that if $R_7$ is an amino, then X is N;

with the proviso that if for W—$(R_7)_p$, W is N and p is 0, then at least one of $R_6$ and $R_8$ is selected from alkyl, alkoxy, and chloride;

and pharmaceutically acceptable salts and hydrates thereof.

31. The method according to embodiment 30, wherein the compound of Formula II is selected from:

3-(4-hydroxy-3,5-dimethylphenyl)-6,8-dimethoxyisoquinolin-1(2H)-one (Example 7);

3-(4-(2-hydroxyethoxy)-3,5-dimethylphenyl)-6,8-dimethoxyisoquinolin-1(2H)-one (Example 9);

3-(4-hydroxy-3,5-dimethylphenyl)-7-(morpholinomethyl) isoquinolin-1(2H)-one (Example 11);

2-(4-hydroxy-3,5-dimethylphenyl)-5,7-dimethoxyquinazolin-4(3H)-one (Example 13);

3-(4-(2-hydroxy-2-methylpropoxy)-3,5-dimethylphenyl)-6,8-dimethoxyisoquinolin-1(2H)-one (Example 14);

7-(4-hydroxy-3,5-dimethylphenyl)-2,4-dimethoxy-1,6-naphthyridin-5(6H)-one (Example 16);

2-(4-(2-hydroxyethoxy)-3,5-dimethylphenyl)-5,7-dimethoxyquinazolin-4(3H)-one (Example 20);

3-(3,5-dimethyl-4-(2-(4-methylpiperazin-1-yl)ethoxy)phenyl)-6,8-dimethoxyisoquinolin-1(2H)-one (Example 23);

2-(4-hydroxy-3-methoxyphenyl)-5,7-dimethoxyquinazolin-4(3H)-one (Example 31);

2-(4-(bis(2-hydroxyethyl)amino)phenyl)-5,7-dimethoxyquinazolin-4(3H)-one (Example 46);

2-(4-(bis(2-hydroxyethyl)amino)phenyl)-6,7-dimethoxyquinazolin-4(3H)-one (Example 47);

2-(2,3-dihydrobenzo[b][1,4]dioxin-6-yl)-6,7-dimethoxyquinazolin-4(3H)-one (Example 48);

2-(4-((4-ethylpiperazin-1-yl)methyl)phenyl)-5,7-dimethoxyquinazolin-4(3H)-one (Example 67);

2-(4-(2-hydroxyethoxy)-3,5-dimethylphenyl)-5,7-dimethoxypyrido[2,3-d]pyrimidin-4(3H)-one (Example 70);

2-(2-chloro-6-methylpyridin-4-yl)-5,7-dimethoxyquinazolin-4(3H)-one (Example 89);

5,7-dimethoxy-2-(4-methoxy-3,5-dimethylphenyl)quinazolin-4(3H)-one (Example 90);

2-(4-amino-3,5-dimethylphenyl)-5,7-dimethoxyquinazolin-4(3H)-one (Example 91);

N1-(2-(4-(5,7-dimethoxy-4-oxo-3,4-dihydroquinazolin-2-yl)-2,6-dimethylphenoxy)ethyl)-N2-methylphthalamide (Example 99);

2-(4-(2-aminoethoxy)-3,5-dimethylphenyl)-5,7-dimethoxyquinazolin-4(3H)-one (Example 99); and 4-chloro-N-(2-(4-(5,7-dimethoxy-4-oxo-3,4-dihydroquinazolin-2-yl)-2,6-dimethylphenoxy)ethyl)benzenesulfonamide (Example 101).

32. The method according to embodiment 1, wherein the compound of Formula II is selected from:

3-(4-Hydroxyphenyl)-2H-isoquinolin-1-one;

4-Isoquinolin-3-yl-phenol;

4-(Isoquinolin-3-yl)phenyl 2-amino-5-guanidinopentanoate tetrahydrochloride;

4-(1-Oxo-1,2-dihydroisoquinolin-3-yl)phenyl 2-amino-5-guanidinopentanoate trihydrochloride;

4-(1,6-naphthyridin-7-yl)phenol;

3-(4-hydroxyphenyl)-6,8-dimethoxyisoquinolin-1(2H)-one;

3-(4-hydroxy-3,5-dimethylphenyl)-6,8-dimethoxy-2-methylisoquinolin-1(2H)-one;

3-(4-hydroxy-3,5-dimethylphenyl)-6,8-dimethoxyisoquinolin-1(2H)-one;

7-(4-hydroxy-3,5-dimethylphenyl)-1,6-naphthyridin-5(6H)-one;

3-(4-(2-hydroxyethoxy)-3,5-dimethylphenyl)-6,8-dimethoxyisoquinolin-1(2H)-one;

3-(4-(2-(dimethylamino)ethoxy)-3,5-dimethylphenyl)-6,8-dimethoxyisoquinolin-1(2H)-one;

3-(4-hydroxy-3,5-dimethylphenyl)-7-(morpholinomethyl) isoquinolin-1(2H)-one;

2-hydroxy-7-(4-hydroxy-3,5-dimethylphenyl)-4-methoxy-1,6-naphthyridin-5(6H)-one;

2-(4-hydroxy-3,5-dimethylphenyl)-5,7-dimethoxyquinazolin-4(3H)-one;

3-(4-(2-hydroxy-2-methylpropoxy)-3,5-dimethylphenyl)-6,8-dimethoxyisoquinolin-1(2H)-one;

6,8-dimethoxy-3-(4-hydroxy-3,5-dimethylphenyl)-2H-1,2-benzothiazine-1,1-dioxide;

7-(4-hydroxy-3,5-dimethylphenyl)-2,4-dimethoxy-1,6-naphthyridin-5(6H)-one;

3-(4-hydroxy-3,5-dimethylphenyl)-6,8-dimethoxy-2,7-dimethylisoquinolin-1(2H)-one;

3-(4-hydroxy-3,5-dimethylphenyl)-6,8-dimethoxy-2-methyl-7-(morpholinomethyl) isoquinolin-1(2H)-one;

4-(6,8-dimethoxyisoquinolin-3-yl)-2,6-dimethylphenol;

3-(3,5-dimethyl-4-(2-morpholinoethoxy)phenyl)-6,8-dimethoxyisoquinolin-1(2H)-one;

2-(4-(2-hydroxyethoxy)-3,5-dimethylphenyl)-5,7-dimethoxyquinazolin-4(3H)-one;

2-(3,5-dimethyl-4-(2-morpholinoethoxy)phenyl)-5,7-dimethoxyquinazolin-4(3H)-one;

4-(2-(4-(6,8-dimethoxyisoquinolin-3-yl)-2,6-dimethylphenoxy)ethyl)morpholine;

3-(3,5-dimethyl-4-(2-(4-methylpiperazin-1-yl)ethoxy)phenyl)-6,8-dimethoxyisoquinolin-1(2H)-one;

2-(4-hydroxyphenyl)-5,7-dimethoxyquinazolin-4(3H)-one;

2-(4-(5,7-dimethoxy-4-oxo-3,4-dihydroquinazolin-2-yl)phenoxy)acetic acid;

5,7-dimethoxy-2-(pyridin-2-yl)quinazolin-4(3H)-one;

5,7-dimethoxy-2-(pyridin-3-yl)quinazolin-4(3H)-one;

2-(3,5-di-tert-butyl-4-hydroxyphenyl)-5,7-dimethoxyquinazolin-4(3H)-one;

2-(3,5-dimethoxyphenyl)-5,7-dimethoxyquinazolin-4(3H)-one;

5,7-dimethoxy-2-(4-methoxyphenyl)quinazolin-4(3H)-one;

2-(4-hydroxy-3-methoxyphenyl)-5,7-dimethoxyquinazolin-4(3H)-one;

2-(3-chloro-4-hydroxyphenyl)-5,7-dimethoxyquinazolin-4(3H)-one;

5,7-dimethoxy-2-(pyridin-4-yl)quinazolin-4(3H)-one;

2-(3,5-dimethyl-4-(2-morpholinoethoxy)phenyl)quinazolin-4(3H)-one;

2-(4-(2-hydroxyethoxy)-3,5-dimethylphenyl)quinazolin-4 (3H)-one;
2-(2,3-dihydrobenzo[b][1,4]dioxin-6-yl)quinazolin-4(3H)-one;
2-(4-(dimethylamino)naphthalen-1-yl)-5,7-dimethoxyquinazolin-4(3H)-one;
2-(4-(5,7-dimethoxy-4-oxo-3,4-dihydroquinazolin-2-yl) phenoxy)acetamide;
2-(4-(4-oxo-3,4-dihydroquinazolin-2-yl)phenoxy)acetic acid;
2-(4-(dimethylamino)pyridinon-1-yl)quinazolin-4(3H)-one;
2-(4-(4-oxo-3,4-dihydroquinazolin-2-yl)phenoxy)acetamide;
2-(2,3-dihydrobenzo[b][1,4]dioxin-6-yl)-5,7-dimethoxyquinazolin-4(3H)-one;
5,7-dimethoxy-2-(4-(4-methylpiperazin-1-yl)phenyl) quinazolin-4(3H)-one;
2-(4-(dimethylamino)pyridinon-1-yl)-6,7-dimethoxyquinazolin-4(3H)-one;
2-(4-(bis(2-hydroxyethyl)amino)phenyl)quinazolin-4(3H)-one;
2-(4-(bis(2-hydroxyethyl)amino)phenyl)-5,7-dimethoxyquinazolin-4(3H)-one;
2-(4-(bis(2-hydroxyethyl)amino)phenyl)-6,7-dimethoxyquinazolin-4(3H)-one;
2-(2,3-dihydrobenzo[b][1,4]dioxin-6-yl)-6,7-dimethoxyquinazolin-4(3H)-one;
5,7-dimethoxy-2-(4-morpholinophenyl)quinazolin-4(3H)-one;
7-(3,5-dimethyl-4-(2-morpholinoethoxy)phenyl)-2,4-dimethoxy-1,6-naphthyridin-5(6H)-one;
3-(4-hydroxy-3,5-dimethylphenyl)-6,8-dimethoxy-7-(morpholinomethyl)isoquinolin-1(2H)-one;
2-(4-hydroxy-3,5-dimethylphenyl)-6,7-dimethoxyquinazolin-4(3H)-one;
3-(4-(5,7-dimethoxy-4-oxo-3,4-dihydroquinazolin-2-yl) phenyl)propanoic acid;
N-(2-(4-hydroxy-3,5-dimethylphenyl)-4-oxo-3,4-dihydroquinazolin-6-yl)acetamide;
2-(4-(6,7-dimethoxy-4-oxo-3,4-dihydroquinazolin-2-yl)-2,6-dimethylphenoxy)acetamide;
2-(3-chloro-4-(2-hydroxyethoxy)phenyl)-5,7-dimethoxyquinazolin-4(3H)-one;
2-(4-(2-hydroxyethoxy)-3-methoxyphenyl)-5,7-dimethoxyquinazolin-4(3H)-one;
2-(4-(2-hydroxyethoxy)-3,5-dimethylphenyl)-6,7-dimethoxyquinazolin-4(3H)-one;
5,7-dimethoxy-2-(4-((4-methylpiperazin-1-yl)methyl)phenyl)quinazolin-4(3H)-one;
N-(4-(5,7-dimethoxy-4-oxo-3,4-dihydroquinazolin-2-yl)-2,6-dimethylphenyl)-2-hydroxyacetamide;
7-(4-(2-hydroxyethoxy)-3,5-dimethylphenyl)-2,4-dimethoxy-1,6-naphthyridin-5(6H)-one;
2-(4-hydroxy-3,5-dimethylphenyl)-6-(morpholinomethyl) quinazolin-4(3H)-one;
2,4-dimethoxy-7-(4-methoxy-3,5-dimethylphenyl)-1,6-naphthyridin-5(6H)-one;
2-(4-(5,7-dimethoxy-4-oxo-3,4-dihydroquinazolin-2-yl)-2,6-dimethylphenoxy)acetic acid;
N-(4-(5,7-dimethoxy-4-oxo-3,4-dihydroquinazolin-2-yl) phenyl)-2-hydroxyacetamide;
5,7-dimethoxy-2-(4-(morpholinomethyl)phenyl)quinazolin-4(3H)-one;
2-(4-((4-ethylpiperazin-1-yl)methyl)phenyl)-5,7-dimethoxyquinazolin-4(3H)-one;
2-(4-hydroxy-3,5-dimethylphenyl)-5,7-dimethoxypyrido[2,3-d]pyrimidin-4(3H)-one;
5,7-dimethoxy-2-(4-methoxy-3-(morpholinomethyl)phenyl) quinazolin-4(3H)-one;
2-(4-(2-hydroxyethoxy)-3,5-dimethylphenyl)-5,7-dimethoxypyrido[2,3-d]pyrimidin-4(3H)-one;
2-(4-hydroxy-3,5-dimethylphenyl)-5,7-dimethoxy-1-methylquinazolin-4(1H)-one;
2-(3,5-dimethyl-4-(2-(pyrrolidin-1-yl)ethoxy)phenyl)-5,7-dimethoxyquinazolin-4(3H)-one;
N-(2-(4-(2-hydroxyethoxy)-3,5-dimethylphenyl)-4-oxo-3,4-dihydroquinazolin-6-yl)acetamide;
7-(4-hydroxy-3,5-dimethylphenyl)-2,4-diisopropoxy-1,6-naphthyridin-5(6H)-one;
2-(4-hydroxy-3-(2-hydroxyethyl)phenyl)-5,7-dimethoxyquinazolin-4(3H)-one;
2-(4-(5,7-dimethoxyquinazolin-2-yl)-2,6-dimethylphenoxy) ethanol;
2-(4-(2-hydroxyethoxy)-3,5-dimethylphenyl)-5,7-dimethylquinazolin-4(3H)-one;
2-(4-(bis(2-hydroxyethyl)amino)phenyl)-5,7-dimethoxypyrido[2,3-d]pyrimidin-4(3H)-one;
5,7-dimethoxy-2-(4-(2-methoxyethoxy)-3,5-dimethylphenyl)quinazolin-4(3H)-one;
5,7-dichloro-2-(4-(2-hydroxyethoxy)-3,5-dimethylphenyl) quinazolin-4(3H)-one;
2-(4-hydroxy-3,5-dimethylphenyl)-5,7-dimethoxy-6-(morpholinomethyl)quinazolin-4(3H)-one;
2-(4-(2-hydroxyethoxy)-3,5-dimethylphenyl)-6-methoxyquinazolin-4(3H)-one;
2-(2-chlorophenyl)-5,7-dimethoxyquinazolin-4(3H)-one;
2-(4-(2-hydroxyethoxy)-3,5-dimethylphenyl)-5-methoxyquinazolin-4(3H)-one;
5,7-dimethoxy-2-o-tolylquinazolin-4(3H)-one;
5,7-dimethoxy-2-(6-(4-(methylsulfonyl)phenyl)pyridin-2-yl)quinazolin-4(3H)-one;
5,7-dimethoxy-2-(6-methylpyridin-2-yl)quinazolin-4(3H)-one;
5,7-dimethoxy-2-(6-(4-(methylthio)phenyl)pyridin-2-yl) quinazolin-4(3H)-one;
2-(2-chloro-6-methylpyridin-4-yl)-5,7-dimethoxyquinazolin-4(3H)-one;
5,7-dimethoxy-2-(4-methoxy-3,5-dimethylphenyl)quinazolin-4(3H)-one;
2-(4-amino-3,5-dimethylphenyl)-5,7-dimethoxyquinazolin-4(3H)-one;
5,7-dimethoxy-2-(1-phenyl-5-propyl-1H-pyrazol-4-yl) quinazolin-4(3H)-one;
2-(3,5-dimethylphenyl)-5,7-dimethoxyquinazolin-4(3H)-one;
2-(3-(2,6-dichlorophenyl)-5-methylisoxazol-4-yl)-5,7-dimethoxyquinazolin-4(3H)-one;
(E)-N'-(4-(5,7-dimethoxy-4-oxo-3,4-dihydroquinazolin-2-yl)-2,6-dimethylphenyl)-N,N-dimethylformimidamide;
6-bromo-2-(4-hydroxy-3,5-dimethylphenyl)quinazolin-4 (3H)-one;
6-bromo-2-(4-(2-hydroxyethoxy)-3,5-dimethylphenyl) quinazolin-4(3H)-one;
6-bromo-2-(4-(2-(tert-butyldimethylsilyloxy)ethoxy)-3,5-dimethylphenyl)quinazolin-4(3H)-one;
2-(4-(benzyloxy)-3,5-dimethylphenyl)-5,7-dimethoxyquinazolin-4(3H)-one;
2-(4-(2-hydroxyethoxy)-3-methylphenyl)-5,7-dimethoxyquinazolin-4(3H)-one;
2-(4-hydroxy-3-methylphenyl)-5,7-dimethoxyquinazolin-4 (3H)-one;
N1-(2-(4-(5,7-dimethoxy-4-oxo-3,4-dihydroquinazolin-2-yl)-2,6-dimethylphenoxy)ethyl)-N2-methylphthalamide;

2-(4-(2-aminoethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2,6-dimethylphenoxy)ethyl)-4-methoxybenzenesulfonamide;
4-chloro-N-(2-(4-(5,7-dimethoxy-4-oxo-3,4-dihydroquinazolin-2-yl)-2,6-dimethylphenoxy)ethyl)benzenesulfonamide;
N-(2-(4-(5,7-dimethoxy-4-oxo-3,4-dihydroquinazolin-2-yl)-2,6-dimethylphenoxy)ethyl)methanesulfonamide;
2-(4-(5,7-dimethoxy-4-oxo-3,4-dihydroquinazolin-2-yl)-2-methoxyphenoxy)acetic acid;
5-hydroxy-2-(4-hydroxy-3,5-dimethylphenyl)-7-methoxyquinazolin-4(3H)-one;
2-(4-(5,7-Dimethoxy-4-oxo-3,4-dihydroquinazolin-2-yl)-2,6-dimethyl-phenoxy)ethyl propylcarbamate;
2-(4-(5,7-Dimethoxy-4-oxo-3,4-dihydroquinazolin-2-yl)-2,6-dimethyl-phenoxy)ethyl methylcarbamate;
N-(2-(4-(5,7-Dimethoxy-4-oxo-3,4-dihydroquinazolin-2-yl)-2,6-dimethylphenoxy)ethyl)-4-methylbenzamide;
2-(4-(5,7-dimethoxy-4-oxo-3,4-dihydroquinazolin-2-yl)-2,6-dimethylphenoxy)ethyl cyclohexylcarbamate;
N-(2-(4-(5,7-dimethoxy-4-oxo-3,4-dihydroquinazolin-2-yl)-2,6-dimethylphenoxy)ethyl)benzenesulfonamide;
N-(2-(4-(5,7-dimethoxy-4-oxo-3,4-dihydroquinazolin-2-yl)-2,6-dimethylphenoxy)ethyl)-4-methylbenzenesulfonamide;
N-(2-(4-(5,7-dimethoxy-4-oxo-3,4-dihydroquinazolin-2-yl)-2,6-dimethylphenoxy)ethyl)-4-methoxybenzamide;
N-(2-(4-(5,7-dimethoxy-4-oxo-3,4-dihydroquinazolin-2-yl)-2,6-dimethylphenoxy)ethyl)acetamide;
N-(2-(4-(5,7-dimethoxy-4-oxo-3,4-dihydroquinazolin-2-yl)-2,6-dimethylphenoxy)ethyl)benzamide;
N-(2-(4-(5,7-dimethoxy-4-oxo-3,4-dihydroquinazolin-2-yl)-2,6-dimethylphenoxy)ethyl)isobutyramide;
1-(2-(4-(5,7-dimethoxy-4-oxo-3,4-dihydroquinazolin-2-yl)-2,6-dimethylphenoxy)ethyl)-3-methylurea;
1-(2-(4-(5,7-dimethoxy-4-oxo-3,4-dihydroquinazolin-2-yl)-2,6-dimethylphenoxy)ethyl)-3-(4-methoxyphenyl)urea;
1-(2-(4-(5,7-dimethoxy-4-oxo-3,4-dihydroquinazolin-2-yl)-2,6-dimethylphenoxy)ethyl)-3-phenylurea; and
3-(2-(4-(5,7-dimethoxy-4-oxo-3,4-dihydroquinazolin-2-yl)-2,6-dimethylphenoxy)ethyl)-1,1-dimethylurea.

33. The method of embodiment 1, wherein the therapeutically effective amount of the compound of Formula II is administered with a pharmaceutically acceptable carrier in a pharmaceutically acceptable composition.

34. The method of embodiment 1, further comprising treating or preventing a cardiovascular diseases, or cholesterol- or lipid-related disorder.

35. A compound of Formula II:

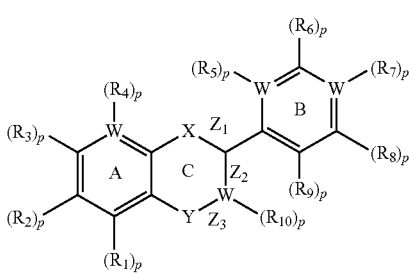

Formula II wherein:
X is selected from N and $CR_{11}$;
Y is selected from CO and $SO_2$;
$R_{11}$ is selected from hydrogen, unsubstituted alkyl (preferably $C_{1-3}$ alkyl), unsubstituted alkenyl (preferably $C_{1-3}$ alkenyl), and unsubstituted alkynyl (preferably $C_{1-3}$ alkynyl);
$R_1$ and $R_3$ are each independently selected from alkoxy (preferably methoxy), alkyl, amino, halogen (preferably chloride), and hydrogen;
$R_2$ is selected from alkoxy, alkyl, alkenyl, alkynyl, amide, amino, halogen (preferably bromide or chloride), and hydrogen;
$R_6$ and $R_8$ are each independently selected from alkyl (preferably methyl), alkoxy, amino, halogen (preferably chloride or fluoride), and hydrogen;
$R_5$ and $R_9$ are each hydrogen;
$R_7$ is selected from amino, amide, alkyl, hydroxyl, and alkoxy;
$R_{10}$ is selected from hydrogen and methyl;
each W is independently selected from C and N, wherein if W is N, then p is 0 or 1, and if W is C, then p is 1;
for W—$(R_{10})_p$, W is N and p is 1;
for W—$(R_7)_p$, W is C and p is 1;
for W—$(R_4)_p$, W is C, p is 1 and $R_4$ is H, or W is N and p is 0;
$Z_1$ is a double bond, and $Z_2$ and $Z_3$ are each a single bond;
with the proviso that if $R_1$ is hydrogen, then $R_3$ is alkoxy;
with the proviso that if $R_3$ is hydrogen, then $R_1$ is selected from amino and alkoxy;
with the proviso that if $R_7$ is selected from alkyl, hydroxyl, and alkoxy, then at least one of $R_6$ and $R_8$ is independently selected from alkyl, alkoxy, amino, and halogen;
with the proviso that if $R_7$ is amino, then X is N;
and pharmaceutically acceptable salts and hydrates thereof.

36. The compound according to embodiment 35, wherein X is N; for W—$(R_{10})_p$, W is N and $R_{10}$ is hydrogen; and $R_7$ is amino.

37. The compound according to embodiment 36, wherein the compound of Formula II is 2-(4-(bis(2-hydroxyethyl)amino)phenyl)-5,7-dimethoxyquinazolin-4(3H)-one (Example 46).

38. The compound according to embodiment 35, wherein for W—$(R_{10})_p$, W is N and $R_{10}$ is hydrogen; and $R_7$ is selected from hydroxyl and alkoxy.

39. The compound according to embodiment 38, wherein the compound of Formula II is selected from:
7-(4-hydroxy-3,5-dimethylphenyl)-2,4-dimethoxy-1,6-naphthyridin-5(6H)-one (Example 15);
N-(2-(4-(5,7-dimethoxy-4-oxo-3,4-dihydroquinazolin-2-yl)-2,6-dimethylphenoxy)ethyl)methanesulfonamide (Example 102);
2-(4-hydroxy-3-methylphenyl)-5,7-dimethoxyquinazolin-4(3H)-one (Example 98);
2-(4-(2-hydroxyethoxy)-3-methylphenyl)-5,7-dimethoxyquinazolin-4(3H)-one (Example 97);
2-(3,5-dimethyl-4-(2-morpholinoethoxy)phenyl)-5,7-dimethoxyquinazolin-4(3H)-one (Example 20); and
3-(4-hydroxy-3,5-dimethylphenyl)-6,8-dimethoxy-7-(morpholinomethyl)isoquinolin-1(2H)-one (Example 51).

40. The compound according to embodiment 38, wherein $R_6$ and $R_8$ are each independently alkyl;
$R_2$ is hydrogen; and
$R_7$ is selected from hydroxyl and alkoxy (preferably substituted with a hydroxyl.)

41. The compound according to embodiment 40, wherein the compound of Formula II is selected from:
3-(4-hydroxy-3,5-dimethylphenyl)-6,8-dimethoxyisoquinolin-1(2H)-one (Example 7); and
2-(4-(2-hydroxyethoxy)-3,5-dimethylphenyl)-5,7-dimethoxyquinazolin-4(3H)-one (Example 19).

42. The compound according to embodiment 35, wherein $R_7$ is selected from an amino or an alkoxy selected from the group represented by Formula III:

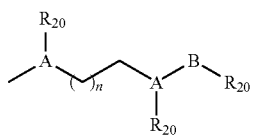

Formula III wherein:
A is selected from O and N;
n is selected from 0,1, 2, 3, 4 and 5;
B is selected from —C(O)N($R_h$)$_2$—, —S(O)$_2$N($R_h$)$_2$—, —C(O)—, —S(O)$_2$—, —C(O)O—, wherein each $R_h$ is selected from alkyl, alkenyl, alkynyl, aryl, arylalkyl, cycloalkyl, haloalkyl, heteroaryl, heterocyclyl, and hydrogen; and
$R_{20}$ is selected from ($C_1$-$C_6$) alkyl, ($C_1$-$C_6$) alkenyl, ($C_1$-$C_6$) alkynyl, aryl, arylalkyl, cycloalkyl, haloalkyl, heteroaryl, heterocyclyl, and hydrogen.

In another embodiment, if A is O and B is —C(O)NH—, then $R_{20}$ is not an unsaturated cycloalkyl.

43. The compound according to embodiment 42, wherein the compound of Formula II is selected from:
2-(4-(5,7-dimethoxy-4-oxo-3,4-dihydroquinazolin-2-yl)-2,6-dimethylphenoxy)ethyl cyclohexylcarbamate (Example 108);
N-(2-(4-(5,7-dimethoxy-4-oxo-3,4-dihydroquinazolin-2-yl)-2,6-dimethylphenoxy)ethyl)acetamide (Example 112);
N-(2-(4-(5,7-dimethoxy-4-oxo-3,4-dihydroquinazolin-2-yl)-2,6-dimethylphenoxy)ethyl)isobutyramide (Example 114);
1-(2-(4-(5,7-dimethoxy-4-oxo-3,4-dihydroquinazolin-2-yl)-2,6-dimethylphenoxy)ethyl)-3-phenylurea (Example 117); and
3-(2-(4-(5,7-dimethoxy-4-oxo-3,4-dihydroquinazolin-2-yl)-2,6-dimethylphenoxy)ethyl)-1,1-dimethylurea (Example 118).

44. The compound according to embodiment 35, wherein the compound of Formula II is selected from:
3-(4-(2-(dimethylamino)ethoxy)-3,5-dimethylphenyl)-6,8-dimethoxyisoquinolin-1(2H)-one (Example 10);
7-(4-hydroxy-3,5-dimethylphenyl)-2,4-dimethoxy-1,6-naphthyridin-5(6H)-one (Example 16);
3-(4-hydroxy-3,5-dimethylphenyl)-6,8-dimethoxy-2,7-dimethylisoquinolin-1(2H)-one (Example 17);
2-(3,5-dimethyl-4-(2-morpholinoethoxy)phenyl)-5,7-dimethoxyquinazolin-4(3H)-one (Example 21);
2-(3,5-di-tert-butyl-4-hydroxyphenyl)-5,7-dimethoxyquinazolin-4(3H)-one (Example 28);
2-(4-hydroxy-3-methoxyphenyl)-5,7-dimethoxyquinazolin-4(3H)-one (Example 31);
2-(3-chloro-4-hydroxyphenyl)-5,7-dimethoxyquinazolin-4(3H)-one (Example 32);
5,7-dimethoxy-2-(4-(4-methylpiperazin-1-yl)phenyl)quinazolin-4(3H)-one (Example 43);
7-(3,5-dimethyl-4-(2-morpholinoethoxy)phenyl)-2,4-dimethoxy-1,6-naphthyridin-5(6H)-one (Example 50);
2-(4-hydroxy-3,5-dimethylphenyl)-6,7-dimethoxyquinazolin-4(3H)-one (Example 52);
2-(4-(6,7-dimethoxy-4-oxo-3,4-dihydroquinazolin-2-yl)-2,6-dimethylphenoxy)acetamide (Example 55);
2-(3-chloro-4-(2-hydroxyethoxy)phenyl)-5,7-dimethoxyquinazolin-4(3H)-one (Example 56);
2-(4-(2-hydroxyethoxy)-3-methoxyphenyl)-5,7-dimethoxyquinazolin-4(3H)-one (Example 57);
2-(4-(2-hydroxyethoxy)-3,5-dimethylphenyl)-6,7-dimethoxyquinazolin-4(3H)-one (Example 58);
N-(4-(5,7-dimethoxy-4-oxo-3,4-dihydroquinazolin-2-yl)-2,6-dimethylphenyl)-2-hydroxyacetamide (Example 60);
7-(4-(2-hydroxyethoxy)-3,5-dimethylphenyl)-2,4-dimethoxy-1,6-naphthyridin-5(6H)-one (Example 61);
2,4-dimethoxy-7-(4-methoxy-3,5-dimethylphenyl)-1,6-naphthyridin-5(6H)-one (Example 63);
2-(4-(5,7-dimethoxy-4-oxo-3,4-dihydroquinazolin-2-yl)-2,6-dimethylphenoxy)acetic acid (Example 64);
N-(4-(5,7-dimethoxy-4-oxo-3,4-dihydroquinazolin-2-yl) phenyl)-2-hydroxyacetamide (Example 65);
2-(4-hydroxy-3,5-dimethylphenyl)-5,7-dimethoxypyrido[2,3-d]pyrimidin-4(3H)-one (Example 68);
5,7-dimethoxy-2-(4-methoxy-3-(morpholinomethyl)phenyl)quinazolin-4(3H)-one (Example 69);
2-(3,5-dimethyl-4-(2-(pyrrolidin-1-yl)ethoxy)phenyl)-5,7-dimethoxyquinazolin-4(3H)-one (Example 72);
2-(4-hydroxy-3-(2-hydroxyethyl)phenyl)-5,7-dimethoxyquinazolin-4(3H)-one (Example 75);
2-(4-(bis(2-hydroxyethyl)amino)phenyl)-5,7-dimethoxypyrido[2,3-d]pyrimidin-4(3H)one (Example 78);
5,7-dimethoxy-2-(4-(2-methoxyethoxy)-3,5-dimethylphenyl)quinazolin-4(3H)-one (Example 79);
2-(4-(2-hydroxyethoxy)-3,5-dimethylphenyl)-5-methoxyquinazolin-4(3H)-one (Example 84);
(E)-N'-(4-(5,7-dimethoxy-4-oxo-3,4-dihydroquinazolin-2-yl)-2,6-dimethylphenyl)-N,N-dimethylformimidamide (Example 93);
2-(4-(benzyloxy)-3,5-dimethylphenyl)-5,7-dimethoxyquinazolin-4(3H)-one (Example 96);
2-(4-(2-aminoethoxy)-3,5-dimethylphenyl)-5,7-dimethoxyquinazolin-4(3H)-one (Example 99);
2-(4-(5,7-dimethoxy-4-oxo-3,4-dihydroquinazolin-2-yl)-2-methoxyphenoxy)acetic acid (Example 103);
2-(4-(5,7-Dimethoxy-4-oxo-3,4-dihydroquinazolin-2-yl)-2,6-dimethyl-phenoxy)ethyl propylcarbamate (Example 105);
2-(4-(5,7-Dimethoxy-4-oxo-3,4-dihydroquinazolin-2-yl)-2,6-dimethyl-phenoxy)ethyl methylcarbamate (Example 106);
N-(2-(4-(5,7-Dimethoxy-4-oxo-3,4-dihydroquinazolin-2-yl)-2,6-dimethylphenoxy)ethyl)-4-methylbenzamide (Example 107);
N-(2-(4-(5,7-dimethoxy-4-oxo-3,4-dihydroquinazolin-2-yl)-2,6-dimethylphenoxy)ethyl)benzenesulfonamide (Example 109);
N-(2-(4-(5,7-dimethoxy-4-oxo-3,4-dihydroquinazolin-2-yl)-2,6-dimethylphenoxy)ethyl)-4-methylbenzenesulfonamide (Example 110);
N-(2-(4-(5,7-dimethoxy-4-oxo-3,4-dihydroquinazolin-2-yl)-2,6-dimethylphenoxy)ethyl)-4-methoxybenzamide (Example 111);
N-(2-(4-(5,7-dimethoxy-4-oxo-3,4-dihydroquinazolin-2-yl)-2,6-dimethylphenoxy)ethyl)benzamide (Example 113);

1-(2-(4-(5,7-dimethoxy-4-oxo-3,4-dihydroquinazolin-2-yl)-2,6-dimethylphenoxy)ethyl)-3-methylurea (Example 115); and
1-(2-(4-(5,7-dimethoxy-4-oxo-3,4-dihydroquinazolin-2-yl)-2,6-dimethylphenoxy)ethyl)-3-(4-methoxyphenyl)urea (Example 116).

45. A compound selected from:
3-(4-Hydroxyphenyl)-2H-isoquinolin-1-one (Example 1);
4-Isoquinolin-3-yl-phenol (Example 2);
4-(isoquinolin-3-yl)phenyl 2-amino-5-guanidinopentanoate tetrahydrochloride (Example 3);
4-(1-Oxo-1,2-dihydroisoquinolin-3-yl)phenyl 2-amino-5-guanidinopentanoate trihydrochloride (Example 4);
4-(1,6-naphthyridin-7-yl)phenol (Example 5);
7-(4-hydroxy-3,5-dimethylphenyl)-1,6-naphthyridin-5(6H)-one (Example 8);
2-hydroxy-7-(4-hydroxy-3,5-dimethylphenyl)-4-methoxy-1,6-naphthyridin-5(6H)-one (Example 12);
4-(6,8-dimethoxyisoquinolin-3-yl)-2,6-dimethylphenol (Example 18);
4-(2-(4-(6,8-dimethoxyisoquinolin-3-yl)-2,6-dimethylphenoxy)ethyl)morpholine (Example 22);
2-(3,5-dimethyl-4-(2-morpholinoethoxy)phenyl)quinazolin-4(3H)-one (Example 34);
2-(4-(2-hydroxyethoxy)-3,5-dimethylphenyl)quinazolin-4(3H)-one (Example 35);
2-(2,3-dihydrobenzo[b][1,4]dioxin-6-yl)quinazolin-4(3H)-one (Example 36);
2-(4-(4-oxo-3,4-dihydroquinazolin-2-yl)phenoxy)acetic acid (Example 39);
2-(4-(dimethylamino)naphthalen-1-yl)quinazolin-4(3H)-one (Example 40);
2-(4-(4-oxo-3,4-dihydroquinazolin-2-yl)phenoxy)acetamide (Example 41);
2-(4-(bis(2-hydroxyethyl)amino)phenyl)quinazolin-4(3H)-one (Example 45);
7-(4-hydroxy-3,5-dimethylphenyl)-2,4-diisopropoxy-1,6-naphthyridin-5(6H)-one (Example 74);
2-(4-(5,7-dimethoxyquinazolin-2-yl)-2,6-dimethylphenoxy) ethanol (Example 76);
2-(4-(2-hydroxyethoxy)-3,5-dimethylphenyl)-5,7-dimethylquinazolin-4(3H)-one (Example 77);
5,7-dichloro-2-(4-(2-hydroxyethoxy)-3,5-dimethylphenyl) quinazolin-4(3H)-one (Example 80);
6-bromo-2-(4-hydroxy-3,5-dimethylphenyl)quinazolin-4(3H)-one (Example 94);
6-bromo-2-(4-(2-hydroxyethoxy)-3,5-dimethylphenyl) quinazolin-4(3H)-one (Example 95);
6-bromo-2-(4-(2-(tert-butyldimethylsilyloxy)ethoxy)-3,5-dimethylphenyl)quinazolin-4(3H)-one (Example 95);
5,7-dimethoxy-2-(pyridin-2-yl)quinazolin-4(3H)-one (Example 26);
5,7-dimethoxy-2-(pyridin-3-yl)quinazolin-4(3H)-one (Example 27);
2-(3,5-dimethoxyphenyl)-5,7-dimethoxyquinazolin-4(3H)-one (Example 29);
5,7-dimethoxy-2-(pyridin-4-yl)quinazolin-4(3H)-one (Example 33);
2-(4-(dimethylamino)naphthalen-1-yl)-5,7-dimethoxyquinazolin-4(3H)-one (Example 37);
2-(4-(dimethylamino)pyridin-1-yl)-6,7-dimethoxyquinazolin-4(3H)-one (Example 44);
2-(4-hydroxy-3,5-dimethylphenyl)-5,7-dimethoxy-1-methylquinazolin-4(1H)-one (Example 71);
2-(4-(2-hydroxyethoxy)-3,5-dimethylphenyl)-6-methoxyquinazolin-4(3H)-one (Example 82);
2-(2-chlorophenyl)-5,7-dimethoxyquinazolin-4(3H)-one (Example 83);
5,7-dimethoxy-2-o-tolylquinazolin-4(3H)-one (Example 85);
5,7-dimethoxy-2-(6-(4-(methylsulfonyl)phenyl)pyridin-2-yl)quinazolin-4(3H)-one (Example 86);
5,7-dimethoxy-2-(6-methylpyridin-2-yl)quinazolin-4(3H)-one (Example 87);
5,7-dimethoxy-2-(6-(4-(methylthio)phenyl)pyridin-2-yl) quinazolin-4(3H)-one (Example 88);
2-(3,5-dimethylphenyl)-5,7-dimethoxyquinazolin-4(3H)-one (Example 92); and
5-hydroxy-2-(4-hydroxy-3,5-dimethylphenyl)-7-methoxyquinazolin-4(3H)-one (Example 104).

46. A pharmaceutical composition comprising a compound according to embodiment 35 and a pharmaceutically acceptable carrier.

47. A method of treating cardiovascular disease, or cholesterol- or lipid-related disorders comprising administering a therapeutically effective amount of a compound according to embodiment 35.

48. A method of increasing expression of ApoA-I in a mammal comprising administering a therapeutically effective amount of a compound according to embodiment 35.

49. A compound of Formula II:

Formula II wherein:
X is selected from N and CH;
Y is CO;
$R_1$ and $R_3$ are each independently selected from alkoxy and hydrogen;
$R_2$ is selected from alkoxy, alkyl, and hydrogen;
$R_6$ and $R_8$ are each independently selected from alkyl, alkoxy, halogen (preferably chloride), and hydrogen;
$R_5$ and $R_9$ are each hydrogen;
$R_7$ is selected from amino, hydroxyl, alkoxy (preferably a substituted ethoxy group), and alkyl substituted with a heterocyclyl;
$R_{10}$ is hydrogen; or
two adjacent substituents selected from $R_6$, $R_7$, and $R_8$ are connected to form a heterocyclyl;
each W is independently selected from C and N, wherein if W is N, then p is 0 or 1, and if W is C, then p is 1;
for W—$(R_{10})_p$, W is N and p is 1;
for W—$(R_4)_p$, W is C, p is 1 and $R_4$ is H, or W is N and p is 0;
$Z_1$ is a double bond, and $Z_2$ and $Z_3$ are each a single bond;
with the proviso that if $R_2$ is alkoxy or hydrogen, then least one of $R_1$ and $R_3$ is alkoxy;
with the proviso that if $R_7$ is selected from hydroxyl and alkoxy, then at least one of $R_6$ and $R_8$ are independently selected from alkyl, alkoxy, and chloride;

with the proviso that if $R_7$ is an amino, then X is N;

with the proviso that if for W—$(R_7)_p$, W is N and p is 0, then at least one of $R_6$ and $R_8$ is selected from alkyl, alkoxy, and chloride;

and pharmaceutically acceptable salts and hydrates thereof.

50. The compound according to embodiment 49, wherein the compound of Formula II is selected from:

3-(4-hydroxy-3,5-dimethylphenyl)-6,8-dimethoxyisoquinolin-1(2H)-one (Example 7);

3-(4-(2-hydroxyethoxy)-3,5-dimethylphenyl)-6,8-dimethoxyisoquinolin-1(2H)-one (Example 9);

2-(4-hydroxy-3,5-dimethylphenyl)-5,7-dimethoxyquinazolin-4(3H)-one (Example 13);

3-(4-(2-hydroxy-2-methylpropoxy)-3,5-dimethylphenyl)-6,8-dimethoxyisoquinolin-1(2H)-one (Example 14);

7-(4-hydroxy-3,5-dimethylphenyl)-2,4-dimethoxy-1,6-naphthyridin-5(6H)-one (Example 16);

2-(4-(2-hydroxyethoxy)-3,5-dimethylphenyl)-5,7-dimethoxyquinazolin-4(3H)-one (Example 20);

3-(3,5-dimethyl-4-(2-(4-methylpiperazin-1-yl)ethoxy)phenyl)-6,8-dimethoxyisoquinolin-1(2H)-one (Example 23);

2-(4-hydroxy-3-methoxyphenyl)-5,7-dimethoxyquinazolin-4(3H)-one (Example 31);

2-(2,3-dihydrobenzo[b][1,4]dioxin-6-yl)-5,7-dimethoxyquinazolin-4(3H)-one (Example 42);

2-(4-(bis(2-hydroxyethyl)amino)phenyl)-5,7-dimethoxyquinazolin-4(3H)-one (Example 46);

2-(4-(bis(2-hydroxyethyl)amino)phenyl)-6,7-dimethoxyquinazolin-4(3H)-one (Example 47);

2-(2,3-dihydrobenzo[b][1,4]dioxin-6-yl)-6,7-dimethoxyquinazolin-4(3H)-one (Example 48);

2-(4-((4-ethylpiperazin-1-yl)methyl)phenyl)-5,7-dimethoxyquinazolin-4(3H)-one (Example 67);

2-(4-(2-hydroxyethoxy)-3,5-dimethylphenyl)-5,7-dimethoxypyrido[2,3-d]pyrimidin-4(3H)-one (Example 70);

2-(2-chloro-6-methylpyridin-4-yl)-5,7-dimethoxyquinazolin-4(3H)-one (Example 89);

5,7-dimethoxy-2-(4-methoxy-3,5-dimethylphenyl)quinazolin-4(3H)-one (Example 90);

2-(4-amino-3,5-dimethylphenyl)-5,7-dimethoxyquinazolin-4(3H)-one (Example 91);

N1-(2-(4-(5,7-dimethoxy-4-oxo-3,4-dihydroquinazolin-2-yl)-2,6-dimethylphenoxy)ethyl)-N2-methylphthalamide (Example 99);

2-(4-(2-aminoethoxy)-3,5-dimethylphenyl)-5,7-dimethoxyquinazolin-4(3H)-one (Example 99);

and 4-chloro-N-(2-(4-(5,7-dimethoxy-4-oxo-3,4-dihydroquinazolin-2-yl)-2,6-dimethylphenoxy)ethyl)benzenesulfonamide (Example 101).

51. The compound according to embodiment 49, wherein $R_7$ is selected from an amino or an alkoxy selected from the group represented by Formula III:

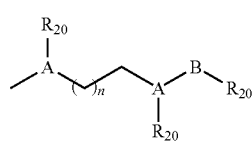

Formula III wherein:

A is selected from O and N;

n is selected from 0, 1, 2, 3, 4 and 5;

B is selected from —C(O)N$(R_h)_2$—, —S(O)$_2$N$(R_h)_2$—, —C(O)—, —S(O)$_2$—, and —C(O)O—, wherein each $R_h$ is independently selected from alkyl, alkenyl, alkynyl, aryl, arylalkyl, cycloalkyl, haloalkyl, heteroaryl, heterocyclyl, and hydrogen; and $R_{20}$ is selected from $(C_1$-$C_6)$ alkyl, $(C_1$-$C_6)$ alkenyl, $(C_1$-$C_6)$ alkynyl, aryl, arylalkyl, cycloalkyl, haloalkyl, heteroaryl, heterocyclyl, and hydrogen.

In another embodiment, if A is O and B is —C(O)NH—, then $R_{20}$ is not an unsaturated cycloalkyl.

52. The compound of embodiment 51, wherein the compound of Formula II is selected from:

N1-(2-(4-(5,7-dimethoxy-4-oxo-3,4-dihydroquinazolin-2-yl)-2,6-dimethylphenoxy)ethyl)-N2-methylphthalamide (Example 99);

2-(4-(2-aminoethoxy)-3,5-dimethylphenyl)-5,7-dimethoxyquinazolin-4(3H)-one (Example 99); and 4-chloro-N-(2-(4-(5,7-dimethoxy-4-oxo-3,4-dihydroquinazolin-2-yl)-2,6-dimethylphenoxy)ethyl)benzenesulfonamide (Example 101).

53. A pharmaceutical composition comprising a compound according to embodiment 49 and a pharmaceutically acceptable carrier.

54. A method of treating cardiovascular disease, or cholesterol- or lipid-related disorders comprising administering a therapeutically effective amount of a compound according to embodiment 49.

55. A method of increasing expression of ApoA-I in a mammal comprising administering a therapeutically effective amount of a compound according to embodiment 49.

56. A compound of Formula II:

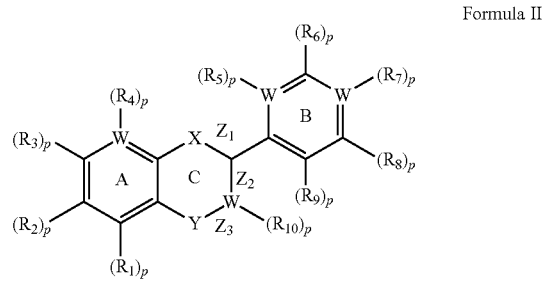

Formula II wherein:

X is selected from N and $CR_{11}$;

Y is selected from CO and $SO_2$;

$R_{11}$ is selected from hydrogen, unsubstituted alkyl, unsubstituted alkenyl, and unsubstituted alkynyl;

$R_1$ and $R_3$ are each independently selected from alkoxy (preferably methoxy), alkyl, amino, halogen (preferably chloride) and hydrogen;

$R_2$ is selected from —N—C(O)—$R_{18}$, —N—SO$_2$—$R_{18}$, —CH$_2$—C$(R_{18})_3$, —CH$_2$—N$(R_{18})_2$, and —CH$_2$—O—$R_{18}$, wherein each $R_{18}$ is independently selected from alkoxy, alkyl, alkenyl, amide, amino, aryl, arylalkyl, cycloalkyl, haloalkyl, halogen, heteroaryl, heterocyclyl, and hydrogen;

$R_6$ and $R_8$ are each independently selected from alkyl (preferably methyl), alkoxy, amino, halogen (preferably chloride or fluoride), and hydrogen;

$R_5$ and $R_9$ are each hydrogen;

$R_7$ is selected from amino, amide, alkyl, hydroxyl, and alkoxy;
$R_{10}$ is selected from hydrogen and methyl;
each W is independently selected from C and N, wherein if W is N, then p is 0 or 1, and if W is C, then p is 1;
for W—$(R_{10})_p$, W is N and p is 1;
for W—$(R_7)_p$, W is C and p is 1;
for W—$(R_4)_p$, W is C, p is 1 and $R_4$ is H, or W is N and p is 0;
$Z_1$ is a double bond, and $Z_2$ and $Z_3$ are each a single bond;
with the proviso that if $R_7$ is selected from alkyl, hydroxyl, and alkoxy, then at least one of $R_6$ and $R_8$ is independently selected from alkyl, alkoxy, amino, and halogen;
and pharmaceutically acceptable salts and hydrates thereof.

57. The compound according to embodiment 56, wherein X is N; for W—$(R_{10})_p$, W is N, and p is 1; and $R_{10}$ is hydrogen.

58. The compound according to embodiment 57, wherein the compound of Formula II is selected from:
N-(2-(4-hydroxy-3,5-dimethylphenyl)-4-oxo-3,4-dihydroquinazolin-6-yl)acetamide (Example 54);
2-(4-hydroxy-3,5-dimethylphenyl)-6-(morpholinomethyl)quinazolin-4(3H)-one (Example 62);
N-(2-(4-(2-hydroxyethoxy)-3,5-dimethylphenyl)-4-oxo-3,4-dihydroquinazolin-6-yl)acetamide (Example 73); and
2-(4-hydroxy-3,5-dimethylphenyl)-5,7-dimethoxy-6-(morphoinomethyl)quinazolin-4(3H)-one (Example 81).

59. The compound according to embodiment 56, wherein X is CH; for W—$(R_{10})_p$, W is N and $R_{10}$ is hydrogen; and $R_7$ is selected from hydroxyl and alkoxy.

60. The compound according to embodiment 59, wherein the compound of Formula II is selected from:
3-(4-hydroxy-3,5-dimethylphenyl)-7-(morpholinomethyl)isoquinolin-1(2H)-one (Example 11);
3-(4-hydroxy-3,5-dimethylphenyl)-6,8-dimethoxy-2-methyl-7-(morpholinomethyl)isoquinolin-1(2H)-one (Example 17); and
3-(4-hydroxy-3,5-dimethylphenyl)-6,8-dimethoxy-7-(morpholinomethyl)isoquinolin-1(2H)-one (Example 51).

61. The compound according to embodiment 56, wherein $R_6$ and $R_8$ are each independently alkyl; and $R_7$ is selected from hydroxyl and alkoxy (preferably substituted with a hydroxyl).

62. The compound according to embodiment 56, wherein $R_7$ is selected from an amino or an alkoxy selected from the group represented by Formula III:

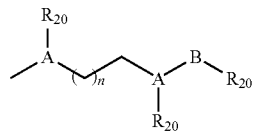

Formula III wherein:
A is selected from O and N;
n is selected from 0, 1, 2, 3, 4 and 5;
B is selected from —C(O)N($R_h$)$_2$—, —S(O)$_2$N($R_h$)$_2$—, —C(O)—, —S(O)$_2$—, —C(O)O—, wherein each $R_h$ is selected from alkyl, alkenyl, alkynyl, aryl, arylalkyl, cycloalkyl, haloalkyl, heteroaryl, heterocyclyl, and hydrogen; and
$R_{20}$ is selected from ($C_1$-$C_6$) alkyl, ($C_1$-$C_6$) alkenyl, ($C_1$-$C_6$) alkynyl, aryl, arylalkyl, cycloalkyl, haloalkyl, heteroaryl, heterocyclyl, and hydrogen.

In another embodiment, if A is O and B is —C(O)NH—, then $R_{20}$ is not an unsaturated cycloalkyl.

63. The compound according to embodiment 56, wherein $R_6$ and $R_8$ are each independently alkyl.

64. A pharmaceutical composition comprising a compound according to embodiment 56 and a pharmaceutically acceptable carrier.

65. A method of treating cardiovascular disease, or cholesterol- or lipid-related disorders comprising administering a therapeutically effective amount of a compound according to embodiment 56.

66. A method of increasing expression of ApoA-I in a mammal comprising administering a therapeutically effective amount of a compound according to embodiment 56.

67. A compound of Formula II:

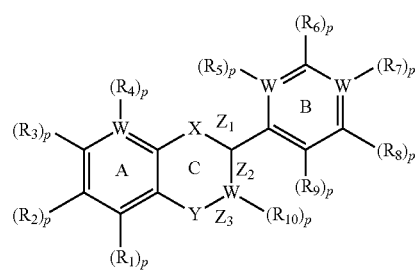

Formula II wherein:
X is selected from N and $CR_{11}$;
Y is selected from CO and $SO_2$;
$R_{11}$ is selected from hydrogen, unsubstituted alkyl, unsubstituted alkenyl, and unsubstituted alkynyl;
$R_1$ is selected from alkoxy (preferably methoxy) or amino;
$R_3$ is alkoxy (preferably methoxy);
$R_2$ is selected from alkoxy, alkyl, alkenyl, alkynyl, amide, amino, halogen (preferably bromide or chloride), and hydrogen;
$R_6$ and $R_8$ are each independently selected from alkyl, alkoxy, amino, halogen (preferably chloride or fluoride), and hydrogen;
$R_5$ and $R_9$ are each hydrogen;
$R_7$ is selected from amino, amide, alkyl, hydroxyl, and alkoxy;
$R_{10}$ is selected from hydrogen and methyl;
each W is independently selected from C and N, wherein if W is N, then p is 0 or 1, and if W is C, then p is 1;
for W—$(R_{10})_p$, W is N and p is 1;
for W—$(R_7)_p$, W is C and p is 1;
for W—$(R_4)_p$, W is C, p is 1 and $R_4$ is H, or W is N and p is 0;
$Z_1$ is a double bond, and $Z_2$ and $Z_3$ are each a single bond;
with the proviso that if $R_7$ is hydroxyl, then X is N;
and pharmaceutically acceptable salts and hydrates thereof.

68. The compound according to embodiment 67, wherein X is selected from N and CH;
$R_{10}$ is hydrogen; and
$R_7$ is selected from hydroxyl and alkoxy.

69. The compound according to embodiment 68, wherein the compound of Formula II is selected from:
2-(4-hydroxyphenyl)-5,7-dimethoxyquinazolin-4(3H)-one (Example 24);
2-(4-(5,7-dimethoxy-4-oxo-3,4-dihydroquinazolin-2-yl)phenoxy)acetic acid (Example 25);
5,7-dimethoxy-2-(4-methoxyphenyl)quinazolin-4(3H)-one (Example 30); and
2-(4-(5,7-dimethoxy-4-oxo-3,4-dihydroquinazolin-2-yl)phenoxy)acetamide (Example 38).

70. The compound according to embodiment 67, wherein
X is selected from N and CH;
$R_{10}$ is hydrogen; and
$R_7$ is selected from amide and amino.

71. The compound according to embodiment 70, wherein the compound of Formula II is selected from:
5,7-dimethoxy-2-(4-(4-methylpiperazin-1-yl)phenyl)quinazolin-4(3H)-one (Example 43);
2-(4-(bis(2-hydroxyethyl)amino)phenyl)-5,7-dimethoxyquinazolin-4(3H)-one (Example 46);
5,7-dimethoxy-2-(4-morpholinophenyl)quinazolin-4(3H)-one (Example 49);
N-(4-(5,7-dimethoxy-4-oxo-3,4-dihydroquinazolin-2-yl)phenyl)-2-hydroxyacetamide (Example 65); and
2-(4-(bis(2-hydroxyethyl)amino)phenyl)-5,7-dimethoxypyrido[2,3-d]pyrimidin-4(3H)one (Example 78).

72. The compound according to embodiment 67, wherein
X is selected from N and CH;
$R_{10}$ is hydrogen; and
$R_7$ is alkyl.

73. The compound according to embodiment 72, wherein the compound of Formula II is selected from:
3-(4-(5,7-dimethoxy-4-oxo-3,4-dihydroquinazolin-2-yl)phenyl)propanoic acid (Example 53);
5,7-dimethoxy-2-(4-((4-methylpiperazin-1-yl)methyl)phenyl)quinazolin-4(3H)-one (Example 59);
5,7-dimethoxy-2-(4-(morpholinomethyl)phenyl)quinazolin-4(3H)-one (Example 66); and
2-(4-((4-ethylpiperazin-1-yl)methyl)phenyl)-5,7-dimethoxyquinazolin-4(3H)-one (Example 67).

74. The compound according to embodiment 67, wherein $R_6$ and $R_8$ are each independently alkyl.

75. The compound according to embodiment 67, wherein $R_7$ is selected from an amino or an alkoxy selected from the group represented by Formula III:

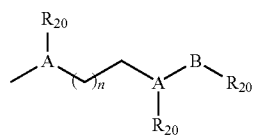

Formula III wherein:
A is selected from O and N;
n is selected from 0, 1, 2, 3, 4 and 5;
B is selected from —C(O)N($R_h$)$_2$—, —S(O)$_2$N($R_h$)$_2$—, —C(O)—, —S(O)$_2$—, —C(O)O—, wherein each $R_h$ is selected from alkyl, alkenyl, alkynyl, aryl, arylalkyl, cycloalkyl, haloalkyl, heteroaryl, heterocyclyl, and hydrogen; and
$R_{20}$ is selected from ($C_1$-$C_6$) alkyl, ($C_1$-$C_6$) alkenyl, ($C_1$-$C_6$) alkynyl, aryl, arylalkyl, cycloalkyl, haloalkyl, heteroaryl, heterocyclyl, and hydrogen.

In another embodiment, if A is O and B is —C(O)NH—, then $R_{20}$ is not an unsaturated cycloalkyl.

76. The compound according to embodiment 75, wherein $R_6$ and $R_8$ are each independently alkyl.

77. A pharmaceutical composition comprising a compound according to embodiment 67 and a pharmaceutically acceptable carrier.

78. A method of treating cardiovascular disease, or cholesterol- or lipid-related disorders comprising administering a therapeutically effective amount of a compound according to embodiment 67.

79. A method of increasing expression of ApoA-I in a mammal comprising administering a therapeutically effective amount of a compound according to embodiment 67.

Pharmaceutical Formulations and Methods of Treatment

The present disclosure also provides pharmaceutical compositions comprising compounds as disclosed herein, formulated together with one or more pharmaceutically acceptable carriers. These formulations include those suitable for oral, rectal, topical, buccal and parenteral (e.g. subcutaneous, intramuscular, intradermal, or intravenous) administration, although the most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of the compound as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association the active compound and the carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with the compound as a unit-dose formulation, for example, a tablet, which may contain from about 0.05% to about 95% by weight of the active compound. Other pharmacologically active substances may also be present including other compounds. The formulations of the invention may be prepared by any of the well known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the active compound with a liquid or finely divided solid carrier, or both, and then, if necessary, shaping the product. For example, a tablet may be prepared by compressing or molding a powder or granules of the compound, optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s).

Molded tablets may be made by molding, in a suitable machine, the powdered compound moistened with an inert liquid diluent.

Formulations suitable for buccal (sub-lingual) administration include lozenges comprising a compound in a flavored base, usually sucrose and acacia or tragacanth, and pastilles comprising the compound in an inert base such as gelatin and glycerin or sucrose and acacia.

Formulations of the present invention suitable for parenteral administration comprise sterile aqueous preparations of the compounds, which are approximately isotonic with the blood of the intended recipient. These preparations are administered intravenously, although administration may also be effected by means of subcutaneous, intramuscular, or intradermal injection. Such preparations may conveniently be prepared by admixing the compound with water and rendering the resulting solution sterile and isotonic with the blood. Injectable compositions according to the invention may contain from about 0.1 to about 5% w/w of the active compound.

Formulations suitable for rectal administration are presented as unit-dose suppositories. These may be prepared by admixing the compound with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound is generally present at a concentration of from about 0.1% to about 15% w/w of the composition, for example, from about 0.5% to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4): 219-244 (1966) and Table 1 for Equivalent Surface Area Dosage Factors).

TABLE 1

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The therapeutically effective dosage (i.e. $ED_{50}$) may vary with the dosage form, route of administration, the subject's age, condition, and sex, as well as the severity of the medical condition in the subject. The dosage may be determined by a physician and adjusted, as necessary, to suit observed effects of the treatment.

In one embodiment, a compound as disclosed herein, or a pharmaceutically acceptable salt or hydrate thereof, is administered in combination with another therapeutic agent. The other therapeutic agent can provide additive or synergistic value relative to the administration of a compound of the present invention alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; an ion-exchange resin; an antioxidant; an inhibitor of AcylCoA cholesterol acyltransferase (ACAT inhibitor); a tyrophostine; a sulfonylurea-based drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

In one embodiment, a method of treating or preventing cardiovascular disease, cholesterol- or lipid-related disorders, comprises administering to a mammal (e.g., human) a therapeutically effective amount of a disclosed compound. The disclosed compound may be administered as a pharmaceutically acceptable composition, comprising a disclosed compound and a pharmaceutically acceptable carrier.

As used herein, the term "cardiovascular disease" refers to diseases and disorders of the heart and circulatory system. Exemplary cardiovascular diseases, including cholesterol- or lipid-related disorders, include, but are not limited to acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholeasterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multiinfarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's diseases and inflammatory diseases.

One embodiment provides methods for altering lipid metabolism in a patient, e.g., increasing the ratio of HDL to LDL or ApoA-I to ApoB in the blood of a patient, comprising administering to the patient a composition of the invention in an amount effective to alter lipid metabolism.

One embodiment provides methods for elevating the levels of ApoA-I associated molecules, such as HDL, in the blood of a mammal, comprising administering to the mammal a composition comprising a disclosed compound or composition in an amount effective to elevate levels of ApoA-I and HDL associated proteins in the mammal.

In one embodiment, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

One embodiment provides a compound for administration to a patient, such as a human, as a preventative measure against cardiovascular diseases, including cholesterol- or lipid-related disorders. As used herein, "prevention" or "preventing" refers to a reduction of the risk of acquiring a given disease or disorder. An additional aspect of the invention provides a method for prevention of arteriosclerosis lesion development in a mammal, including the development of new arteriosclerotic lesions. In another aspect, the present invention provides a method for regressing arteriosclerosis lesions.

In another embodiment, the present compositions are administered as a preventative measure to a patient, such as a human having a genetic predisposition to a cardiovascular disease, including cholesterol- or lipid-related disorders, for example familial hypercholeasterolemia, familial combined hyperlipidemia, atherosclerosis, a dyslipidemia, a dyslipoproteinemia, or Alzheimer's disease.

In another embodiment, the compositions of the invention are administered as a preventative measure to a patient having a non-genetic predisposition to a cardiovascular disease, including cholesterol- or lipid-related disorders. Examples of such non-genetic predispositions include, but are not limited to, cardiac bypass surgery and percutaneous transiluminal coronary angioplasty, which often leads to restenosis, an accelerated form of atherosclerosis; diabetes in women, which often leads to polycystic ovarian disease; and cardiovascular disease, which often leads to impotence.

Angioplasty and open heart surgery, such as coronary bypass surgery, may be required to treat cardiovascular diseases, such as atherosclerosis. These surgical procedures entail using invasive surgical devices and/or implants, and are associated with a high risk of restenosis and thrombosis. Accordingly, the compounds of the invention may be used as coatings on surgical devices (e.g., catheters) and implants (e.g., stents) to reduce the risk of restenosis and thrombosis associated with invasive procedures used in the treatment of cardiovascular diseases.

In another embodiment, the present compositions may be used for the prevention of one disease or disorder and concurrently treating another (e.g., prevention of polycystic ovarian disease while treating diabetes; prevention of impotence while treating a cardiovascular disease).

Diseases and conditions associated with "diabetes mellitus" as defined herein refer to chronic metabolic disorder(s) caused by absolute or relative insulin deficiency including, but not limited to hyperglycemia, hyperinsulinemia, hyperlipidemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, skin and connective tissue disorders, foot ulcerations, metabolic acidosis, arthritis, osteoporosis and impaired glucose tolerance.

Preparation of Compounds

Exemplary compounds of the invention represented by the general formula A:

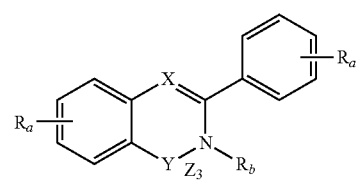

wherein:

$R_a$ may be selected from groups including, but not limited to, alkoxy, alkyl, alkenyl, alkynyl, amide, amino, aryl, arylalkyl, carbamate, cycloalkyl, ether, halogen, haloalkyl, heteroaryl, heterocyclyl, hydrogen and hydroxyl; $R_b$ may be selected from groups including, but not limited to, alkyl and hydrogen; X may be selected from, e.g., $CR_c$, N and $NR_c$, where $R_c$ represents substituents such as alkyl, alkenyl, alkynyl, and hydrogen; Y may be selected from, e.g., $CR_c$, CO, CS, and $SO_2$ where $R_c$ is as defined above; and $Z_3$ may be a single or double bond; may be synthesized from readily available starting materials as outlined in the exemplary schemes below. It should be appreciated that these designations are non-limiting examples.

Scheme 1

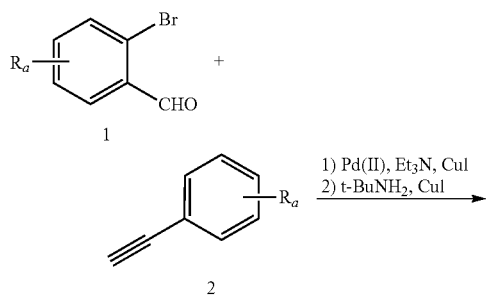

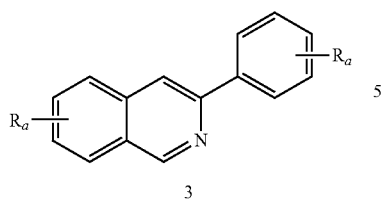

treatment with t-butylamine and CuI, can afford isoquinoline 3 as shown in Scheme 1.

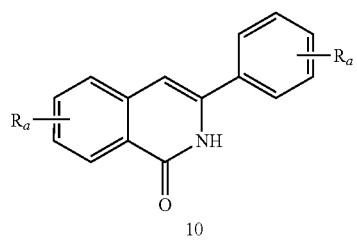

Condensation of amide 8 with nitrile 9 in the presence of n-BuLi can afford isoquinolinone 10, as shown in Scheme 3.

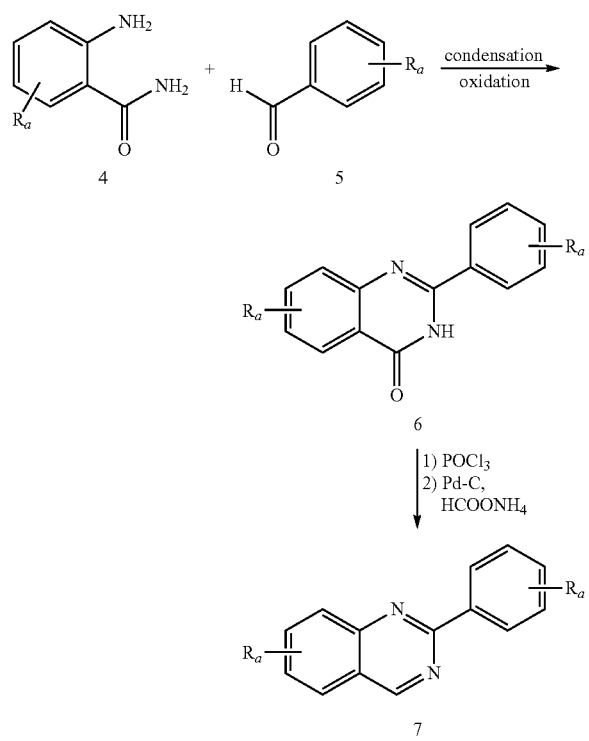

Scheme 2 illustrates that condensation followed by oxidation of amide 4 and aldehyde 5 can provide quinazolinone 6. Condensation can occur under a variety of conditions, such as NaHSO₃ and p-TsOH in dimethylacetamide, I₂ in the presence of K₂CO₃, and treatment with catalytic trifluoroacetic acid followed by DDQ oxidation. Conversion of quinazolinone 6 into quinazoline 7 can be achieved by treatment with POCl₃, followed by dehydration in the presence of a palladium catalyst.

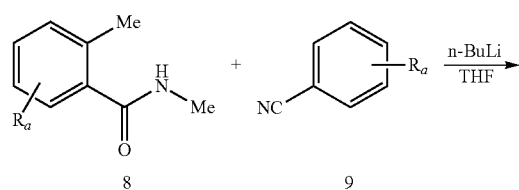

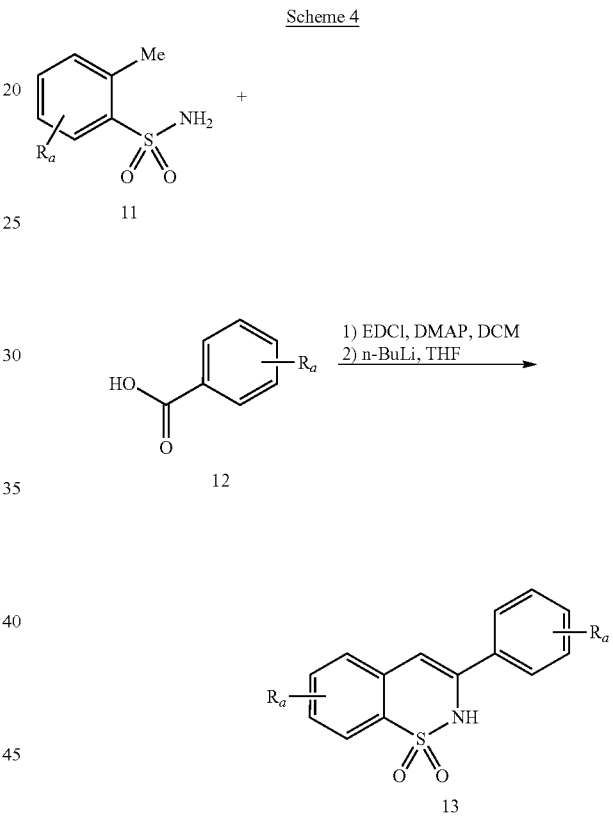

Scheme 4 provides a method for synthesizing benzothiazine-1,1-dioxide 13. Amide coupling of sulfonamide 11 with carboxylic acid 12 can be followed by treatment with n-BuLi to afford 13.

Abbreviations used herein denote the following compounds, reagents and substituents: acetic acid (AcOH); 2,2'-azobisisobutyronitrile (AIBN); N-bromosuccinimide (NBS); N-tert-butoxycarbonyl (Boc); t-butyldimethylsilyl (TBDMS); m-chloroperoxybenzoic acid (mCPBA); dimethylaminopyridine (DMAP); dichloromethane (DCM); dimethylformamide (DMF); dimethylsulfoxide (DMSO); ethanol (EtOH); ethyl acetate (EtOAc); 1-ethyl-3-(3-dimethylaminopropyl)carbodiimide (EDCl); 1-hydroxybenzotriazole (HOBt); iodomethane (MeI); lithium hexamethyldisilazide (LHMDS); methanol (MeOH); methoxymethyl (MOM); tetrahydrofuran (THF); triethylamine (Et₃N); lithium aluminum hydride (LAH); p-toluenesulfonic acid (p-TSA); tet-

EXAMPLE 1

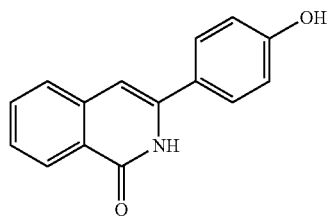

3-(4-Hydroxyphenyl)-2H-isoquinolin-1-one

To a solution of n-methyl-o-toluamide (2.0 g, 13.4 mmol) in THF (30 mL), n-butyl lithium (12.3 mL, 30.8 mmol, 2.5 M solution in hexane) was added slowly under nitrogen with cooling (ice-salt bath), maintaining the temperature below 20° C. After completion of addition, the mixture was stirred for 1 h at 0° C., then cooled to −50° C. and a solution of 4-methoxy benzonitrile (2.14 g, 16.08 mmol) in THF (5 mL) was added quickly. The cooling bath was removed and the solution was allowed to warm to room temperature. Saturated aqueous $NH_4Cl$ solution was added with cooling and the solid was isolated by filtration to give the methoxy compound (2.2 g, 65%). The methoxy compound (750 mg, 2.98 mmol) was added to a 50 mL flask and pyridinium hydrochloride (10 g) was added. The mixture was heated at 190° C. for 2 h, then cooled to room temperature, diluted with water, neutralized with $NaHCO_3$, and the solid was isolated by filtration to give 3-(4-hydroxyphenyl)-2H-isoquinolin-1-one (600 mg, 84%). Selected data: MS (ES) m/z: 238.92, 237.89; MP 239-241° C.

EXAMPLE 2

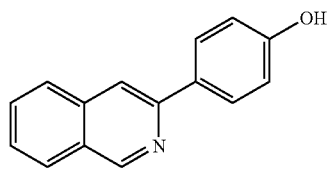

4-Isoquinolin-3-yl-phenol

To a solution of 2-bromobenzaldehyde (1.85 g, 10 mmol) and 4-methoxyphenyl acetylene (1.58 g, 12 mmol) in 40 mL of triethylamine were added dichlorobis(triphenylphosphine) palladium(II) (140 mg, 2 mol %) and copper (I) iodide (20 mg, 1 mol %). The reaction mixture was heated at 50° C. under nitrogen for 3 h. The reaction mixture was cooled to room temperature and the ammonium salt was removed by filtration. The filtrate was concentrated under reduced pressure. Purification of the crude compound by column chromatography (silica gel 230-400 mesh; 10% ethyl acetate in hexanes as eluent) afforded 2-(4-methoxyphenylethynyl) benzaldehyde (2.1 g, 89%). The above compound (2.06 g, 8.73 mmol) and t-butylamine (3.83 g, 52.4 mmol) were stirred under nitrogen for 24 h at room temperature. The resulting mixture was extracted with ether and the organic layer was dried over anhydrous $Na_2SO_4$, and concentrated to give the imine (2.4 g, 94%), which was used in the next step without further purification. To a solution of the above imine (2.39 g, 8.2 mmol) in 100 mL anhydrous DMF was added (0.156 g, 0.82 mmol) copper (I) iodide, and the solution was flushed with nitrogen. The reaction mixture was heated at 100° C. for 4 h. The mixture was cooled to room temperature, and diluted with ether (200 mL). The organic layer was washed with saturated aqueous ammonium chloride (3×100 mL). The organic layer was dried over anhydrous $Na_2SO_4$ and concentrated to give the crude compound as a dark colored solid. Purification by column chromatography (silica gel 230-400 mesh; 10% ethylacetate in hexanes as eluent) afforded 3-(4-methoxyphenyl)isoquinoline (1.064 g, 55%), as a white solid. The 3-(4-methoxyphenyl)isoquinoline (1.05 g, 4.47 mmol) was suspended in 30 mL hydroiodic acid and 12 mL of acetic acid was added. The reaction mixture was stirred at 110° C. for 2 h, then cooled to room temperature. The precipitate formed was filtered off, washed with acetic acid (2×5 mL) and dried under vacuum, to give a yellow solid. The crude compound was purified by triturating with 5% methanol in ether to give 4-isoquinolin-3-yl-phenol (0.83 g, 84%) as a white powder. Selected data: MS (ES) m/z: 222.89, 221.86; MP 218-219° C.

EXAMPLE 3

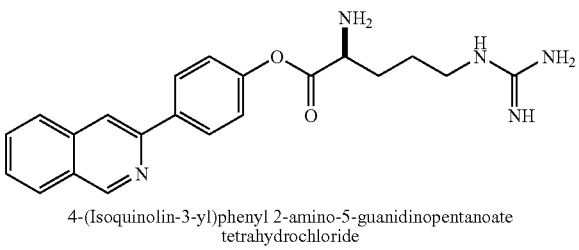

4-(Isoquinolin-3-yl)phenyl 2-amino-5-guanidinopentanoate tetrahydrochloride

To a solution of 4-isoquinolin-3-yl-phenol (0.133 g, 0.6 mmol) in anhydrous DMF (5 mL) were added HOBt (0.081 g, 0.6 mmol), Boc-Arg-(Boc)$_2$-OH (0.285 g, 0.6 mmol), and EDCl (0.115 g, 0.6 mmol). N,N-Diisopropyl ethyl amine (0.233 g, 1.8 mmol) was added and the mixture was stirred at room temperature for 24 h. Water (15 mL) was added and the white precipitate was filtered off, washed with water and dried under vacuum to give 0.3 g (74%) of the Boc-arginine derivative. The above compound (0.3 g) was dissolved in anhydrous dichloromethane (10 mL). HCl gas was bubbled into the solution at 0° C. for 4 h. A yellow precipitate was formed. The solvent was removed and the resulting solid was dried under vacuum. Triturating with ether gave 4-(isoquinolin-3-yl)phenyl 2-amino-5-guanidinopentanoate tetrahydrochloride (0.2 g, 86%). Selected data: MS (ES) m/z: 222.96 (M+1−Arg), 221.99 (M−Arg); MP 198-201° C.

EXAMPLE 4

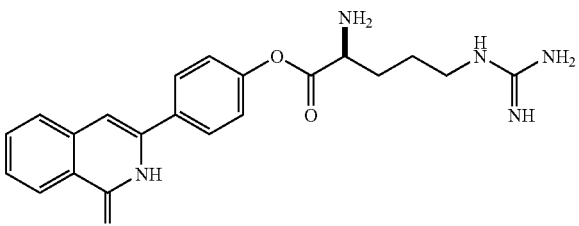

4-(1-Oxo-1,2-dihydroisoquinolin-3-yl)phenyl 2-amino-5-guanidinopentanoate trihydrochloride A mixture of 3-(4-hydroxyphenyl)-2H-isoquinolin-1-one (150 mg, 0.63 mmol) in DMF (5 mL), diisopropyl ethyl amine (245 mg, 1.89 mmol), EDCl (133 mg, 0.696 mmol), Boc-Arg (330 mg, 0.696 mmol) and HOBt (94 mg, 0.696 mmol) was stirred at room temperature for 24 h under nitrogen. The reaction mixture was diluted with water and the solid was collected by filtration. The crude product was purified by column chromatography using 5% MeOH in $CH_2Cl_2$, to give the tri-Boc ester product (375 mg 85%). HCl gas was bubbled through a solution of the tri-Boc ester (325 mg, 0.468 mmol) in $CH_2Cl_2$ (10 mL) for 6 h at 0° C. The solid was filtered off and washed with $CH_2Cl_2$ to give 4-(1-oxo-1,2-dihydroisoquinolin-3-yl)phenyl 2-amino-5-guanidinopentanoate trihydrochloride (170 mg, 72%). Selected data: MS (ES) m/z: 237.25 (M−Arg); $^{13}$C-NMR (DMSO-$d_6$): δ 168.8, 163.4, 157.7, 151.0, 139.8, 139.5, 133.4, 132.8, 128.9, 127.4, 127.3, 127.25, 125.6, 122.6, 104.2, 55.6, 52.5, 27.7, 25.0.

EXAMPLE 5

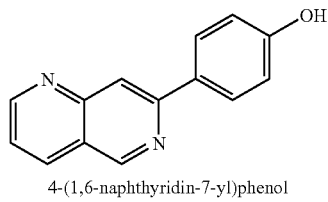

4-(1,6-naphthyridin-7-yl)phenol

To a solution of 2-bromo-3-pyridinecarboxaldehyde (1.86 g, 10 mmol) and 4'-methoxy phenylacetylene (1.58 g, 12 mmol) in triethylamine (40 mL) were added dichlorobis (triphenylphosphine)palladium (II) (140 mg, 2 mol %) and copper (I) iodide (20 mg, 1 mol %). The reaction mixture was heated at 50° C. under nitrogen for 3 h, then cooled to room temperature. The ammonium salt was removed by filtration. The filtrate was concentrated under reduced pressure leaving 2-(4-methoxy phenylethynyl)pyridine-3-carboxaldehyde (2.35 g, 99%) as a yellow solid. 2-(4-methoxy phenylethynyl) pyridine-3-carboxaldehyde (2.28 g, 9.60 mmol) and tert-butylamine (3.83 g, 60 mmol) were stirred under nitrogen for 24 h at room temperature. The resulting mixture was extracted with ether and dried over anhydrous $Na_2SO_4$. Removal of solvent gave the expected imine (2.72 g, 97%), which was used in next step without further purification. To a solution of the above imine (2.7 g, 9.23 mmol) in anhydrous DMF (50 mL) was added copper (I) iodide (0.190 g, 0.1 mmol). The reaction mixture was heated at 100° C. for 4 h, then cooled to room temperature and diluted with ether (200 mL). The organic layer was washed with a saturated aqueous ammonium chloride solution (3×100 mL). The organic layer was dried over anhydrous $Na_2SO_4$. Removal of solvent gave the crude compound as a dark-colored solid. Purification by column chromatography (silica gel 230-400 mesh; 30% ethyl acetate in hexanes as eluent) afforded 7-(4-methoxy phenyl) [1,6]naphthridine (0.730 g, 33%) as a brown solid. To a solution of 7-(4-methoxy phenyl)[1,6]naphthridine (0.485 g, 2.05 mmol) in anhydrous N-methyl-2-pyrrolidinone (5 mL) was added thiophenol (0.25 g, 2.26 mmol) and potassium carbonate (0.028 g, 0.205 mmol). The reaction mixture was stirred at 190° C. for 1 h under nitrogen. The reaction mixture was cooled to room temperature. The compound was purified by column chromatography to give 4-(1,6-naphthyridin-7-yl) phenol (0.33 g, 71%) as a pale yellow solid. Selected data: MS (ES) m/z: 223.95, 222.95; MP 219-221° C.

EXAMPLE 6

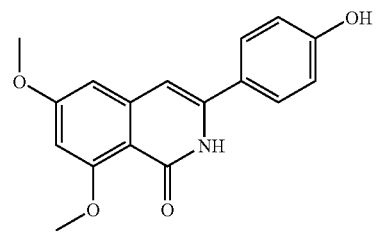

3-(4-hydroxyphenyl)-6,8-dimethoxyisoquinolin-1(2H)-one

To a suspension of 2-methyl-4,6-dimethoxy benzoic acid (2.8 g, 14.3 mmol) in $CH_2Cl_2$ (30 mL), oxalyl chloride (3.62 g, 28.5 mmol) was added and the mixture was stirred at room temperature for 16 h. The solvent and excess oxalyl chloride were removed at reduced pressure. The solid was dissolved in $CH_2Cl_2$ (10 mL) and methyl amine hydrochloride (1.33 g, 42.81 mmol) was added on cooling and the mixture was stirred at room temperature for 4 h. The solvent was removed and the crude product was purified by chromatography using 5% methanol in $CH_2Cl_2$, to give 1.3 g of the amide intermediate (43% yield). To a solution of the amide intermediate (1.29 g, 6.16 mmol) in THF (30 mL), n-butyl lithium (5.6 mL, 14.18 mmol, 2.5 M solution in hexane) was added slowly under nitrogen with cooling (ice-salt bath), maintaining the temperature below 20° C. The mixture was stirred for 1 h at 0° C., then cooled to −50° C. and a solution of 4-O-TBDMS-benzonitrile (1.58 g, 6.78 mmol) in THF (10 mL) was added quickly. The cooling bath was removed and the mixture was stirred at room temperature for 16 h. Saturated aqueous $NH_4Cl$ solution was added with cooling, and the layers were separated. The organic layer was washed with water, brine, dried over $Na_2SO_4$ and concentrated to give the crude intermediate, which was purified by chromatography using 5% methanol in $CH_2Cl_2$, to give two products (1) 678 mg of isoquinoline in 26% yield and (2) 780 mg of quinalone product in 27% yield. To a suspension of the above quinalone product (780 mg, 1.65 mmol) in ethanol (20 mL), conc. HCl (2 mL) was added and the mixture was heated at 70° C. for 2 h. The reaction mixture was cooled to room temperature and the solvent was removed and purified by chromatography to give 3-(4-hydroxyphenyl)-6,8-dimethoxyisoquinolin-1(2H)-one (215 mg, 44%). Selected data: MS (ES) m/z: 297.93; MP 245-247° C.

EXAMPLE 7

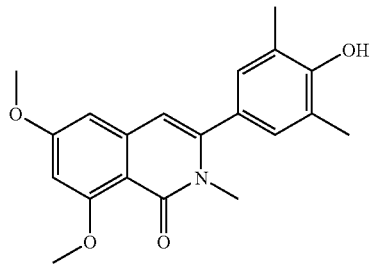

3-(4-hydroxy-3,5-dimethylphenyl)-6,8-dimethoxy-2-methylisoquinolin 1(2H)-one (left) and

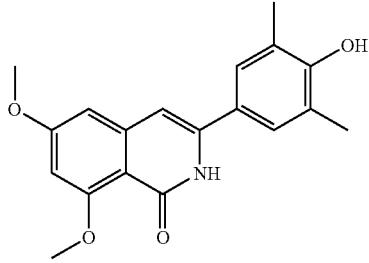

3-(4-hydroxy-3,5-dimethylphenyl)-6,8-dimethoxyisoquinolin-1(2H)-one (right)

To a suspension of 2-methyl-4,6-dimethoxy benzoic acid (2.61 g, 13.1 mmol) in CH$_2$Cl$_2$ (50 mL), oxalyl chloride (3.38 g, 26.6 mmol) was added and the mixture was stirred at room temperature for 16 h. The solvent and excess oxalyl chloride were removed at reduced pressure. The solid was dissolved in CH$_2$Cl$_2$ (10 mL) and methyl amine (1.24 g, 39.9 mmol) with cooling and was stirred at room temperature for 4 h. The solvent was removed and crude product was purified by chromatography by using 5% methanol in CH$_2$Cl$_2$ to give the amide (2.27 g, 82%). To a solution of the above amide (2.27 g, 10.9 mmol) in THF (50 mL), n-butyl lithium (9.98 mL, 25.0 mmol, 2.5 M solution in hexane) was added slowly under nitrogen with cooling, maintaining the temperature below 20° C. The mixture was stirred for 1 h at 0° C., then cooled to −50° C., and a solution of 4-O-TBDMS-3,5-dimethyl benzonitrile (2.97 g, 11.39 mmol) in THF (10 mL) was added quickly, the cooling bath was removed and the mixture was stirred for 16 h at room temperature. A saturated aqueous NH$_4$Cl solution was added with cooling, and the layers were separated. The organic layer was washed with water, brine, dried over Na$_2$SO$_4$ and concentrated to give 3.9 g of the crude product mixture. A suspension of the crude product mixture (3.9 g) in ethanol (20 mL) was heated with conc. HCl (2 mL) at 80° C. for 2 h. The reaction mixture was cooled to room temperature and the solvent was removed. The solid was dissolved in water and neutralized by NaHCO$_3$, followed by extraction with CH$_2$Cl$_2$. The product was purified by chromatography to give two products: 3-(4-hydroxy-3,5-dimethylphenyl)-6,8-dimethoxy-2-methylisoquinolin-1(2H)-one (128 mg, 5%) and 3-(4-hydroxy-3,5-dimethylphenyl)-6,8-dimethoxyisoquinolin-1(2H)-one (340 mg, 9%). Selected data for 3-(4-hydroxy-3,5-dimethylphenyl)-6,8-dimethoxy-2-methylisoquinolin-1(2H)-one: MS (ES) m/z: 340.01 (M); MP 253-254° C. Selected data for 3-(4-hydroxy-3,5-dimethylphenyl)-6,8-dimethoxyisoquinolin-1(2H)-one: MS (ES) m/z: 326.00; MP 226-227° C.

EXAMPLE 8

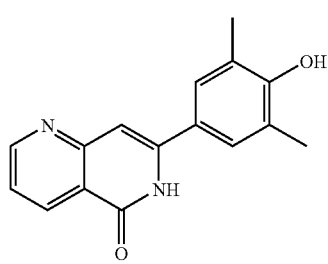

7-(4-hydroxy-3,5-dimethylphenyl)-1,6-naphthyridin-5(6H)-one

Oxalyl chloride (1.90 mL, 21.8 mmol) was added to 2-methyl nicotinic acid (1.50 g, 10.9 mmol) in anhydrous dichloromethane (20 mL) with triethylamine (1.6 mL, 11.5 mmol) and the reaction mixture was kept at room temperature overnight before the solvent was removed. THF was added to the residue and ammonia gas was bubbled through for 2 h. The THF was removed and the residue was dissolved into methanol and water and the pH was adjusted to 10.0 with potassium carbonate. The mixture was concentrated. After column chromatography the desired amide was isolated (1.10 g, 73.8%).

NaH (0.428 g, 10.7 mmol, 60% in mineral oil) was added to 4-hydroxy-3,5-dimethylbenzonitrile (1.50 g, 10 mmol) in anhydrous DMF (8 mL). Benzyl bromide (1.83 g, 10.7 mmol) was added and the reaction was kept at room temperature overnight. The reaction mixture was poured into water. The isolated solid was further washed with hexane to yield the desired ether building block (2.0 g, 84.3%). It was used in the next reaction without further purification. The above amide (0.65 g, 4.77 mmol) in anhydrous THF (15 mL) was added drop-wise to BuLi (7.5 mL, 1.60 M) at −20° C. The reaction mixture was kept at this temperature for 1 h and then the above ether building block (1.13 g, 4.77 mmol) in THF (20 mL) was added drop-wise at −20° C. and the reaction was stirred for 1.5 h. The reaction temperature was increased to room temperature and continued for a further 1 h. Water (20 mL) was added and the mixture was stirred for a while before the solvent was removed and the residue was purified by column chromatography to yield the desired intermediate (0.50 g, 29.4%). A 50 mL flask was charged with the above described intermediate (0.50 g, 0.0014 mol) and pyridine hydrogen chloride (2.4 g, 0.014 mol) and the mixture was heated to 180° C. for 1.5 h. The mixture was cooled and poured into methanol (4 mL), then filtered. The collected solid was further washed with ethyl acetate and dried to give 7-(4-hydroxy-3,5-dimethylphenyl)-1,6-naphthyridin-5(6H)-one (350 mg, 82.7%) as an HCl salt. Selected data: MS (ES) m/z: 266; MP>350° C.

EXAMPLE 9

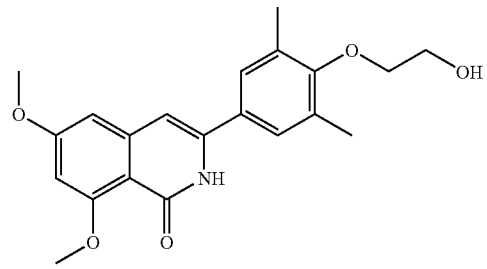

3-(4-(2-hydroxyethoxy)-3,5-dimethylphenyl)-6,8-dimethoxyisoquinolin-1(2H)-one

To a solution of 3,5-dimethyl-4-hydroxy benzonitrile (1.0 g, 6.79 mmol) in DMF (100 mL), were added a NaH (1.065 g, 26.63 mmol) and (2-bromoethoxy)-tert-butyl dimethyl silane (1.95 g, 8.15 mmol). The reaction mixture was stirred for 10 d at room temperature under nitrogen. The reaction mixture was poured into ice-water and the products were extracted with ethyl acetate. The organic layer was separated, washed with water, dried and concentrated to give crude product, which was purified by column chromatography to give 1.9 g of the B-ring building block in 92% yield.

n-Butyl lithium (2.84 mL, 7.1 mmol, 2.5 M solution in hexane) was added slowly to a solution of 2,4-dimethoxy-6-methyl benzamide (650 mg, 3.1 mmol) in THF (30 mL), under nitrogen with cooling (ice-salt bath), maintaining the temperature below 20° C. After completion of addition, the mixture was stirred for 1 h at 0° C., and then cooled to −50° C. and a solution of 4-(2-tert-butyldimethylsilanyloxy)ethoxy)-3,5-dimethyl benzonitrile (the B-ring building block, above) (996 mg, 3.26 mmol) in THF (10 mL) was added quickly. The cooling bath was removed and the reaction mixture was allowed to warm to room temperature and was stirred for 16 h at room temperature. A saturated $NH_4Cl$ solution was added with cooling, and the layers were separated. The organic layer was washed with water, brine, dried over $Na_2SO_4$ and concentrated to give 1.2 g of crude product.

The above crude product (1.2 g) was treated with ethanol (10 mL) and conc. HCl (2 mL) at 80° C. for 1 h. The solvent was removed and the residue was dissolved in methanol and neutralized by $NaHCO_3$. The solvent was evaporated and crude product was purified by column chromatography to give 3-(4-(2-hydroxyethoxy)-3,5-dimethylphenyl)-6,8-dimethoxyisoquinolin-1(2H)-one (100 mg, 11%). Selected data: MP 193-195° C.

EXAMPLE 10

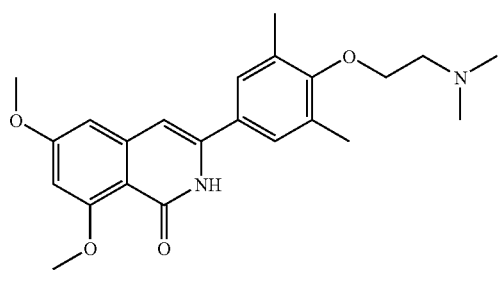

3-(4-(2-(dimethylamino)ethoxy)-3,5-dimethylphenyl)-6,8-dimethoxyisoquinolin-1(2H)-one In a 250 mL round-bottomed flask were placed 3,5-dimethyl-4-hydroxybenzonitrile (1.0 g, 6.79 mmol), $Ph_3P$ (1.96 g, 7.47 mmol), di-isopropylethylamine (1.75 g, 13.59 mmol) and 2-dimethylaminoethanol (660 mg, 7.47 mmol) in THF (30 mL). DEAD (1.42 g, 8.15 mmol) was added drop-wise at room temperature. The reaction mixture was stirred for 48 h at room temperature and water was added and the mixture was extracted with ethyl acetate. The combined organic layers were washed with water, brine and dried over $Na_2SO_4$ and concentrated to give crude product. The crude product was purified by column chromatography to give 1.17 g (79%) of the B-ring building block.

n-Butyl lithium (4.2 mL, 10.54 mmol, 2.5 M solution in hexane) was added slowly to a solution of 2,4-dimethoxy-6-methyl benzamide (958 mg, 4.58 mmol) in THF (30 mL) under nitrogen with cooling (ice-salt bath), maintaining the temperature below 20° C. After completion of the addition, the mixture was stirred for 1 h at 0° C., then cooled to −50° C. and a solution of 4-(2-dimethylaminoethoxy)-3,5-dimethyl benzonitrile (1.1 g, 5.04 mmol) (the B-ring building block) in THF (10 mL) was added quickly. The cooling bath was removed and the reaction mixture was allowed to warm to room temperature and stirred for 16 h at room temperature. A saturated $NH_4Cl$ solution was added with cooling and the layers were separated. The organic layer was washed with water, brine, dried over $Na_2SO_4$ and concentrated to give crude product. The crude product was purified by chromatography to give 3-(4-(2-(dimethylamino)ethoxy)-3,5-dimethylphenyl)-6,8-dimethoxyisoquinolin-1(2H)-one (162 mg, 8%) as a hydrochloride. Selected data: MS (ES) m/z: 397.06; MP 261-263° C. at decomposition (HCl).

EXAMPLE 11

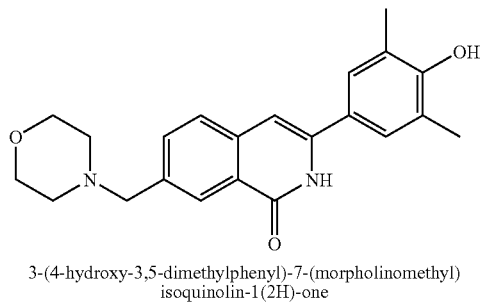

3-(4-hydroxy-3,5-dimethylphenyl)-7-(morpholinomethyl)isoquinolin-1(2H)-one

Hydrogen bromide in acetic acid (13 mL, 33 wt %) was added to a mixture of 2-methyl benzoic acid (4.08 g, 30 mmol), paraformaldehyde (2.50 g, 83.0 mmol), and o-phosphoric acid (7 mL, 85%). The reaction mixture was stirred at 115° C. for 15 h. It was cooled to room temperature and poured into ice-cold water. A white precipitate was formed. The mixture was extracted with ethyl acetate (300 mL). The organic layer was washed with water (100 mL), brine (100 mL) and dried over anhydrous $Na_2SO_4$. Removal of solvent gave 6.84 g of a white solid, which was used in the next step without further purification. The above compound (6.8 g) was dissolved in anhydrous dichloromethane (150 mL). Oxalyl chloride (7.8 mL) was added drop-wise. After the addition was complete, 3 drops of anhydrous DMF were added. A vigorous reaction occurred and the stirring was continued overnight. Solvent and excess oxalylchloride were removed under reduced pressure and the residue was dried under vacuum to give 7.02 g of brown liquid, which was used in the next step without further purification. The above compound (7.02 g, 28.36 mmol) was dissolved in anhydrous THF (60 mL) and cooled to 0° C. A solution of N-methylamine (2.0 M in THF, 19 mL, 38.03 mmol) was added drop-wise under nitrogen. The stirring was continued for 15 min at 0° C. The ice-bath was removed, and the stirring was continued at room temperature for 3 h. A white precipitate was formed. Water (100 mL) was added and the mixture was extracted with ethyl acetate (150 mL). The organic layer was separated, washed with water (50 mL), saturated $NaHCO_3$ solution (2×50 mL), water (50 mL), and brine (50 mL), and dried over anhydrous $Na_2SO_4$. Removal of solvent gave 5.64 g of 5-bromomethyl-2,N-dimethylbenzamide as a white solid which was used in the next step without further purification. To a solution of the above compound (2.42 g, 10 mmol) in anhydrous THF was added morpholine (1.92 g, 22 mmol) at room temperature under nitrogen. A white precipitate was formed. Stirring continued overnight. Water (100 mL) was added and the mixture was extracted with ethyl acetate (150 mL). The organic layer was separated, washed with water (50 mL) and brine (50 mL) and dried ($Na_2SO_4$). Removal of solvent gave a colorless oil, which was purified by column chromatography (silica gel 230-400 mesh; 0-5% methanol in $CH_2Cl_2$ as eluent) to give the desired benzamide intermediate (yield 0.50 g, 20%). N-Butyl lithium (1.6 M solution in hexanes, 4.1 mL, 6.6 mmol) was added drop-wise to a solution of the benzamide (0.5 g, 2.0 mmol) in anhydrous THF (4 mL) at −10° C. over a period of 10 min under nitrogen. Stirring was continued at 0°

C. for 1 h. The reaction mixture was cooled to −50° C. A solution of 4-(tert-butyidimethylsilanyloxy)-3,5-dimethyl-benzonitrile (0.653 g, 2.5 mmol) in anhydrous THF (3 mL) was quickly added. The cooling bath was removed and the reaction mixture was allowed to warm to room temperature. Stirring was continued at room temperature for 1 h. An aqueous ammonium chloride solution (5 mL) was added followed by ethyl acetate (50 mL). The organic layer was separated, washed with water (5 mL) and dried ($Na_2SO_4$). Removal of the solvent gave 1.23 g pale yellow gummy material, which was used in next step without further purification. The above compound (1.2 g) was dissolved in 10 mL anhydrous ethanol. Conc. HCl (1 mL) was added and the mixture was refluxed for 15 min, then cooled to room temperature. The solvent was removed under reduced pressure. The crude compound was basified with methanolic ammonia and purified by column chromatography (silica gel 230-400 mesh; 0-5% methanol in $CH_2Cl_2$ as eluent) to give 3-(4-hydroxy-3,5-dimethylphenyl)-7-morpholin-4-ylmethyl-2H-isoquinolin-1-one (35 mg) as a white solid (the free base). To a solution of the above compound (35 mg) in $CH_2Cl_2$ (5 mL) and MeOH (1 mL) was added drop-wise hydrogen chloride in ether (0.5 mL, 1.0 M) under nitrogen. The reaction mixture was stirred at room temperature for 1 h. The solvent was removed under reduced pressure and dried under vacuum to give the hydrochloride of 3-(4-hydroxy-3,5-dimethylphenyl)-7-(morpholinomethyl) isoquinolin-1(2H)-one (36 mg, 93%) as a yellow solid. Selected data: MP 281-283° C. (hydrochloride).

EXAMPLE 12

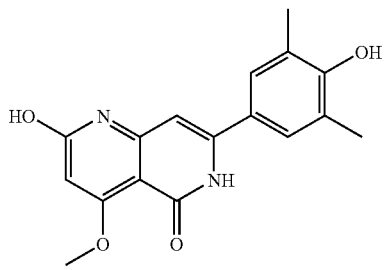

2-hydroxy-7-(4-hydroxy-3,5-dimethylphenyl)-4-methoxy-1,6-naphthyridin-5(6H)-one

A mixture of malonic acid (20 g, 192 mmol), 2,4,6-trichlorophenol (72 g, 365 mmol), and phosphorus oxychloride (38 mL, 403.2 mmol) was stirred at reflux for 12 h. The reaction mixture was cooled to 70° C. and poured into ice water. The solid was collected by filtration, washed with water, and air-dried to give malonic acid bis-(2,4,6-trichloro-phenyl) ester (85 g, 95%). A solution of malonic acid bis-(2,4,6-trichloro-phenyl)ester (85 g, 183.6 mmol) and ethyl 3-aminocrotonate (26.1 g, 202 mmol) in bromobenzene (100 mL) was stirred at reflux for 50 min. The reaction mixture was cooled to 50° C. and diluted with EtOAc (260 mL). The solid was collected by filtration, washed with water, and air-dried, to give 4,6-dihydroxy-2-methyl nicotinic acid ethyl ester (31 g, 86%).

A solution of 4,6-dihydroxy-2-methyl nicotinic acid ethyl ester (31 g, 157 mmol) in phosphorus oxychloride (60 mL, 629 mmol) was stirred at reflux for 1.5 h. The extra phosphorus oxychloride was removed and the reaction mixture was poured into ice water. The solid was removed by filtration. The filtrate was extracted with dichloromethane (3×100 mL) and concentrated. The residue was further purified by column chromatography to yield 4,6-dichloro-2-methyl nicotinic acid ethyl ester (16.9 g, 46%). A solution the ester (16.9 g, 71.3 mmol) in MeOH (60 mL) was mixed with sodium methoxide (58 mL, 257 mmol) and stirred at reflux for 12 h. The reaction was quenched by adding AcOH (50 mL), diluted with water (200 mL), extracted with dichloromethane (3×100 mL), and concentrated. The residue was purified by column chromatography to yield 4,6-dimethoxy-2-methyl nicotinic acid methyl ester (10 g, 67%). A solution of the ester (2.6 g, 12.3 mmol), lithium hydroxide (1.06 g, 44.1 mmol) in water (40 mL), MeOH (30 mL) and THF (20 mL) was stirred at reflux for 4 h. The reaction mixture was concentrated to dryness. The residue was mixed with HCl (conc., 20 mL) and was concentrated to dryness to yield crude 4,6-dimethoxy-2-methyl nicotinic acid (quantitative). To a solution of 4,6-dimethoxy-2-methyl nicotinic acid (2.5 g, 12.0 mmol) in dichloromethane (50 mL) and THF (50 mL) at room temperature was added oxalyl chloride (2.57 mL, 29.4 mmol) and DMF (3 drops). The reaction mixture was stirred at room temperature for 0.5 h, concentrated to afford 4,6-dimethoxy-2-methyl nicotinic acid chloride HCl salt (2.8 g). A solution of 4,6-dimethoxy-2-methyl nicotinic acid chloride HCl salt (8.5 g, 33.73 mmol) in dichloromethane (20 mL) and THF (20 mL) at room temperature was mixed with methylamine in THF (50 mL, 98 mmol) and stirred at 20° C. for 1 h. The reaction mixture was diluted with water (100 mL), extracted with dichloromethane (3×100 mL), and concentrated to yield 4,6-dimethoxy-2,N-dimethyl-nicotinamide (4.2 g, 66%) as a light yellow solid. A solution of 4-hydroxy-3,5-dimethylbenzonitrile (2 g, 13.6 mmol) in DMF (20 mL) at room temperature was mixed with sodium hydride (0.706 g, 17.6 mmol) and stirred for 0.5 h. Benzyl bromide (1.62 mL, 13.59 mmol) was then added and the reaction mixture was stirred at room temperature for 24 h. The reaction was quenched by adding water (200 mL), extracted with EtOAc (3×100 mL), and concentrated. The residue was purified by column chromatography to yield 4-benzyloxy-3,5-dimethylbenzonitrile (3.25 g, 100%), as a white solid. To a solution of 4,6-dimethoxy-2,N-dimethyl-nicotinamide (0.54 g, 2.57 mmol) in THF (50 mL) at −20° C. was added n-BuLi (3.54 mL, 5.67 mmol). The reaction was stirred at −20° C. to 0° C. for 2 h and then was cooled to −78° C. 4-Benzyloxy-3,5-dimethylbenzonitrile (0.49 g, 2.057 mmol) was added, the cooling bath was removed, and the reaction was allowed to warm to room temperature. After 14 h, the reaction was quenched by adding water (100 mL), extracted with dichloromethane (3×100 mL), and concentrated. The residue was purified by column chromatography to yield 7-(4-benzyloxy-3,5-dimethyl-phenyl)-2,4-dimethoxy-6H-[1,6]naphthyridin-5-one (0.32 g, 37%). A solution of 7-(4-benzyloxy-3,5-dimethyl-phenyl)-2,4-dimethoxy-6H-[1,6]naphthyridin-5-one (0.25 g, 0.6 mmol) in dichloromethane (100 mL) was mixed with $BBr_3$ (3 mL, 3 mmol) and stirred at room temperature for 16 h. The reaction was quenched by adding water (20 mL). The resulting solid was collected by filtration, washed with water and DCM, to yield a light yellow solid. This solid was mixed with HCl in ether (10 mL, 10 mmol), stirred for 1 h, and filtered to afford 2-hydroxy-7-(4-hydroxy-3,5-dimethylphenyl)-4-methoxy-1,6-naphthyridin-5(6H)-one hydrochloride (70 mg, 37%) as a light yellow solid. Selected data: MS (ES) m/z: 312; MP>330° C. (hydrochloride).

EXAMPLE 13

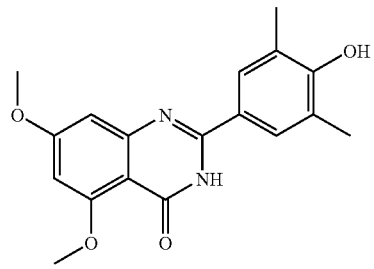

2-(4-hydroxy-3,5-dimethylphenyl)-5,7-dimethoxyquinazolin-4(3H)-one

A solution of 3,5-dimethoxyaniline (199 g, 1.30 mol) in ether (5.0 L) in a 5 L 3-necked flask was cooled to 0° C. HCl gas (227 g) was bubbled through the solution over 45 min. After 45 min at 10° C., the mixture was filtered, washed with isopropylacetate (4 L), and dried overnight on high vacuum at 45° C. to give the hydrochloride (242.3 g, 98%), as a white solid. A mixture of the hydrochloride above (20 g, 0.105 mol) and oxalyl chloride (33 mL) in a 3-necked flask equipped with a reflux condenser was heated for 2 h with stirring (170° C. external temperature), and the oxalyl chloride was distilled from the reaction mixture. The flask was cooled to 0° C. and methanol (40 mL) was added. The reaction mixture was heated to reflux for 45 min, filtered while hot, and washed with methanol (80 mL) to give the 4,6-dimethoxyisatin (17.2 g, 79%) as a yellow-green solid. To a heated solution (external temp 70° C.) of the isatin (162 g, 0.78 mol) in aqueous NaOH (40%, 1.5 L) was added $H_2O_2$ (35%, 405 mL) slowly over 2 h. After the addition of each portion of $H_2O_2$, the internal reaction temperature (initially 64° C.) increased (to a maximum temp of 80° C). After the addition was complete, the foaming reaction mixture was then stirred for an additional 2 h at 70° C., and the mixture was allowed to stir overnight while cooling to room temperature. The mixture was heated to 70° C. Additional $H_2O_2$ (75 mL) was added, and the mixture was stirred at 70° C. for a further 2 h until the reaction was complete. After cooling to 10° C. (bath temperature), aqueous $Na_2S_2O_3$ (150 mL, saturated) was added. The mixture was brought to pH 8 with HCl (37%, 1.6 L) and pH 6 with acetic acid (glacial, 75 mL), without allowing the reaction mixture to warm to greater than 40° C. Filtration of the reaction mixture and washing with water (4 L) gave the expected amino acid as a tan solid (83.7 g, 55%). To a solution of the amino acid (82.7 g, 0.42 mol) in anhydrous THF (4.2 L) was added EDCl (89.2 g, 0.48 mol), HOBT (65 g, 0.48 mol), and NMM (51.3 mL), and the mixture was allowed to stir at room temperature for 3 h. Aqueous $NH_3$ (83 mL, 50%) was added, and the mixture was stirred at room temperature for 16 h. Water (1.25 L) was added, and the mixture was extracted with DCM (2×250 mL). The combined extracts were then washed with water (2×500 mL). Concentration, formation of a slurry with ether (550 mL), filtration, and drying under high vacuum gave 2-amino-4,6-dimethoxybenzamide (46.7 g, 57%) as a brown solid.

2-Amino-4,6-dimethoxy-benzamide (1.06 g, 5.4 mmol), 3,5-dimethyl-4-hydroxybenzaldehyde (0.810 g, 5.4 mmol), $K_2CO_3$ (0.747 g, 5.4 mmol) and $I_2$ (1.645 g, 6.5 mmol) were mixed in DMF (20 mL) and the reaction mixture was heated at 80° C. for 12 h. It was cooled to room temperature and poured into crushed ice. The solid was collected and purified by column chromatography to give 2-(4-hydroxy-3,5-dimethylphenyl)-5,7-dimethoxyquinazolin-4(3H)-one (0.9 g, 51%) as a white solid. Selected data: MP 291-293° C.

EXAMPLE 14

To a solution of 4-hydroxy-3,5-dimethylbenzonitrile (2.00 g, 13.5 mmol) and 1-chloro-2-methyl propan-2-ol (8.85 g, 81.5 mmol) in ethanol (50 mL) was added potassium carbonate (7.5 g, 54 mmol) and water (5 mL). The reaction mixture was stirred at reflux for 24 h and cooled to room temperature. The precipitated solid was filtered off and washed with water. The solid was dissolved in ethyl acetate (100 mL), washed with water (50 mL), brine (50 mL), and dried over anhydrous $Na_2SO_4$. Removal of solvent gave 4-(2-hydroxy-2-methylpropoxy)-3,5-dimethyl benzonitrile (2.9 g, 97%) as a white solid.

To a solution of 4-(2-hydroxy-2-methylpropoxy)-3,5-dimethyl benzonitrile (2.90 g, 13.2 mmol) in anhydrous DMF (20 mL) was added imidazole (2.7 g, 40 mmol) and tert-butyidimethylsilylchloride (2.19 g, 14.6 mmol). The reaction mixture was stirred at room temperature under nitrogen for 3 d. Water (200 mL) was added and the mixture was extracted with ethyl acetate (200 mL). The organic layer was washed with water (2×100 mL) and brine (100 mL), and dried over anhydrous $Na_2SO_4$. The solvent was removed under reduced pressure and the crude compound was purified by column chromatography to give 4-[2-(tert-butyidimethylsilanyloxy)-2-methylpropoxy]-3,5-dimethylbenzonitrile (2.24 g, 54%). N-Butyl lithium (6.2 mL, 6.6 mmol, 1.6 M solution in hexanes) was added to a solution of 2,4-dimethoxy-6-N-dimethylbenzamide (0.9 g, 4.3 mmol) in anhydrous THF (10 mL) drop-wise at −10° C. over a period of 10 min under nitrogen. The stirring was continued at 0° C. for 1 h. The reaction mixture was cooled to −50° C. A solution of 4-[2-(tert-butyldimethylsilanyloxy)-2-methylpropoxy]-3,5-dimethylbenzonitrile (1.58 g, 4.73 mmol) in anhydrous THF (5 mL) was quickly added. The cooling bath was removed and the reaction mixture was allowed to warm to room temperature. The stirring was continued at room temperature for 1 h. An aqueous ammonium chloride solution (10 mL) was added followed by ethyl acetate (100 mL). The organic layer was separated, washed with water (10 mL) and dried ($Na_2SO_4$). The solvent was removed under reduced pressure and the crude compound was purified by column chromatography (silica gel 230-400 mesh; 0-5% methanol in $CH_2Cl_2$ as eluent) to give 3-{4-[2-(tert-butyidimethylsilanyloxy)-2-methylpropoxy]-3,5-dimethylphenyl}-6,8-dimethoxy-2H-isoquinolin-1-one (0.82 g, 37%), as a white solid.

The above compound (0.42 g, 0.82 mmol) was dissolved in anhydrous THF (20 mL). Tetrabutylammonium fluoride (4.1 mL, 1.0 M solution in THF) was added at 0° C. The reaction mixture was stirred at 0° C. for 10 min, then at room temperature for 2 h and then stirred at 70° C. for 24 h. The mixture was cooled to room temperature. Saturated aqueous ammonium chloride (30 mL) was added. The organic layer was separated, washed with water, brine, and dried over anhydrous $Na_2SO_4$. The solvent was removed under reduced pressure. The crude product was purified by column chromatography (silica gel 230-400 mesh; 0-4% methanol in $CH_2Cl_2$ as eluent) to give 3-(4-(2-hydroxy-2-methylpropoxy)-3,5-dimethylphenyl)-6,8-dimethoxyisoquinolin-1(2H)-one (0.15-g, 46%), as a white solid. Selected data: MS (ES) m/z: 397.98; MP 252-254° C. at decomposition.

EXAMPLE 15

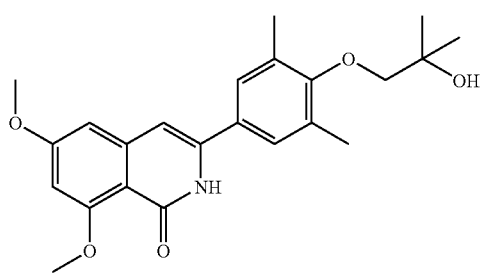

3-(4-(2-hydroxy-2-methylpropoxy)-3,5-dimethylphenyl)-6,8-dimethoxyisoquinolin-1(2H)-one

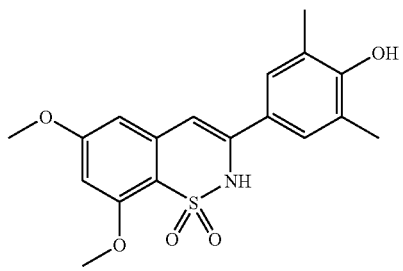

6,8-dimethoxy-3-(4-hydroxy-3,5-dimethylphenyl)-2H-1,2-benzothiazine-1,1-dioxide

To a 3-necked, round-bottomed flask was added 3,5-dimethoxytoluene (6.088 g, 40 mmol) and cyclohexane (28 mL) under nitrogen. Dimethyl carbonate (30.3 g, 336 mmol) was added and the reaction mixture was heated at 60° C. Excess chlorosulfonic acid was added over a period of 15 min. The liberated HCl gas was removed by inserting a tube into solid sodium hydroxide. On completion of the addition, the reaction mixture was heated to 70-72° C. for 1 h and then cooled to room temperature. The solid was filtered off and washed with dimethyl carbonate/cyclohexane (1:1, 20 mL). The solid was dried in vacuo to obtain pure material (6.13 g, 66%). To a mixture of the sulfonic acid (product from above, 4.65 g, 20 mmol) and triethyl amine (2.03 g, 2.79 mL) in acetone (40 mL) was added 2,4,6-trichloro-1,3,5-triazine (cyanuric chloride, 3.69 g, 20 mmol). The reaction mixture was heated under reflux for 20 h before being cooled to room temperature. The solution was passed through a Celite pad and evaporated in vacuo to leave a solid, which was filtered off and washed with hexane. The mixture of product and salt of cyanuric hydroxide and triethyl amine (7.58 g) was used for the next step without further purification.

To a 3-necked, round-bottomed flask, equipped with a condenser (acetone-dry ice cooling), was added the mixture from the step above (7.58 g) and acetone (100 mL). The reaction mixture was cooled to −78° C. and ammonia gas was bubbled through the solution for 0.5 h. The reaction mixture was kept standing overnight, allowing slow evaporation of ammonia gas, followed by the evaporation of solvent. Water was added and the product was extracted with DCM. The solvent was dried and evaporated to leave a mixture of solid and a dense liquid. The solid was filtered off and washed with hexane to leave pure sulfonamide (3.23 g, 70%).

To a round-bottomed flask was added 3,5-dimethyl-4-hydroxybenzoic acid (2.99 g, 18 mmol). Anhydrous DMF (20 mL) was added, followed by sodium hydride (1.8 g, 45 mmol). The reaction mixture was stirred at room temperature for 1 h. p-Methoxybenzyl chloride (6.20 g, 39.6 mmol) was added and the mixture was stirred at room temperature overnight (~20 h). The reaction mixture was poured into water, acidified with 1 N HCl and stirred for 1 h. The precipitated solid was filtered off, washed with water and hexane to obtain pure B-ring building block (6.93 g, 95%).

The B-ring building block (6.93 g, 17.1 mmol) was dissolved in a mixture of methanol (50 mL) and tetrahydrofuran (50 mL). Potassium hydroxide (1.25 g, 22.2 mmol) in water (20 mL) was added. The reaction mixture was refluxed at 70° C. for 24 h. The solvent was evaporated in vacuo. Water was added and the reaction mixture was acidified with 1 N HCl (pH 4-5). The solid was filtered off, washed with water and hexane. The yield was 4.61 g (94%). The product (1.932 g, 6.75 mmol) and the sulfonamide from above (1.04 g, 4.5 mmol) were taken in a 3-necked, round-bottomed flask under nitrogen. Dichloromethane (100 mL) was added with stirring. To this stirred mixture was added N-(3-dimethylaminopropyl)-N'-ethylcarbodiimide hydrochloride (EDCl.HCl, 1.36 g, 7.09 mmol), followed by N,N-dimethylaminopyridine (2.06 g, 16.9 mmol). The reaction mixture was stirred at room temperature for 24 h before being washed with 1 N HCl, 2.5% NaOH and saturated sodium bicarbonate solutions. The organic layers were dried and evaporated in vacuo to leave a residue, which was purified by silica gel (100 g) column chromatography, employing 20-50% ethyl acetate in hexane and 5% methanol in dichloromethane as eluents. Fractions 30-66 were combined to obtain pure materials (1.35 g, 60%). The compound from the step above (0.105 g, 0.21 mmol) was dissolved in tetrahydrofuran under nitrogen and cooled to −78° C. n-Butyllithium was added and the reaction mixture was allowed to warm to room temperature slowly and stirred overnight (~14 h). TLC showed incomplete conversion. The reaction mixture was quenched with saturated ammonium chloride solution and extracted with ethyl acetate. The solvent was evaporated in vacuo to leave a residue that was purified by silica gel (15 g) column chromatography, employing 20-50% ethyl acetate in hexane as eluents. The product was not pure enough, so another column was used, employing 0.5% methanol in hexane as eluent, and finally preparative TLC was employed to purify the material. The compound from the step above (0.277 g) was dissolved in trifluoroacetic acid (10 mL) under nitrogen and the reaction mixture was refluxed (bath temperature 80° C.) for 4 d. The solvent was evaporated in vacuo and the residue was dissolved in 0.25 N NaOH (20 mL), and acidified with acetic acid. The solid had precipitated out at this point. The solid was filtered off and washed with water, hexane and dried. From one batch, 0.005 g of pure material was isolated. From another batch, 0.060 g compound was isolated, which was not pure enough. This compound was further purified by preparative HPLC to give pure 6,8-dimethoxy-3-(4-hydroxy-3,5-dimethylphenyl)-2H-1,2-benzothiazine-1,1-dioxide (0.010 g). Selected data: MP 246.6-247.4° C.

EXAMPLE 16

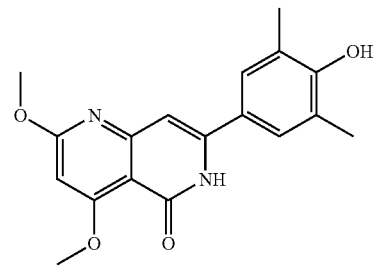

7-(4-hydroxy-3,5-dimethylphenyl)-2,4-dimethoxy-1,6-naphthyridin-5(6H)-one

A mixture of malonic acid (20 g, 192 mmol), 2,4,6-trichlorophenol (72 g, 365 mmol), and phosphorus oxychloride (38 mL, 403.2 mmol) was stirred at reflux for 12 h. The reaction mixture was cooled to 70° C. and poured into ice water. The solid was collected by filtration, washed with water, and dried to give malonic acid bis-(2,4,6-trichloro-phenyl)ester (85 g, 95%). A solution of malonic acid bis-(2,4,6-trichloro-phenyl) ester (85 g, 184 mmol) and ethyl 3-aminocrotonate (26.08 g, 201.9 mmol) in bromobenzene (100 mL) was stirred at reflux for 50 min. The reaction mixture was cooled to 50° C. and diluted with EtOAc (260 mL). The solid was collected by filtration, washed with water, and dried to give 4,6-dihydroxy-2-methyl nicotinic acid ethyl ester (31 g, 86%). A solution of 4,6-dihydroxy-2-methyl nicotinic acid ethyl ester (31 g, 157 mmol) in phosphorus oxychloride (60 mL, 629 mmol) was stirred at reflux for 1.5 h. The extra phosphorus oxychloride was removed and the reaction mixture was poured into ice water. The solid was removed by filtration. The filtrate was extracted with dichloromethane (3×100 mL) and concentrated. The residue was further purified by column chromatography, to yield 4,6-dichloro-2-methyl nicotinic acid ethyl ester (16.9 g, 46%). A solution of 4,6-dichloro-2-methyl nicotinic acid ethyl ester (16.9 g, 71.3 mmol) in MeOH (60 mL) was mixed with sodium methoxide (58 mL, 256.68 mmol) and stirred at reflux for 12 h. The reaction was quenched by adding HOAc (50 mL). The mixture was diluted with water (200 mL), extracted with dichloromethane (3×100 mL), and concentrated. The residue was purified by column chromatography (SiO$_2$, hexanes/EtOAc=6:1), to yield 4,6-dimethoxy-2-methyl nicotinic acid methyl ester (10 g, 67%). A solution of 4,6-dimethoxy-2-methyl nicotinic acid methyl ester (2.6 g, 12.3 mmol), lithium hydroxide (1.06 g, 44.08 mmol) in water (40 mL), MeOH (30 mL) and THF (20 mL) was stirred at reflux for 4 h. The reaction mixture was concentrated to dryness. The residue was mixed with HCl (conc., 20 mL) and was concentrated again on high vacuum to dryness to yield crude 4,6-dimethoxy-2-methyl nicotinic acid (quantitative yield). To a solution of 4,6-dimethoxy-2-methyl nicotinic acid (2.5 g, 12.0 mmol) in dichloromethane (50 mL) and THF (50 mL) at room temperature was added oxalyl chloride (2.57 mL, 29.4 mmol) and DMF (3 drops). The reaction mixture was stirred at room temperature for 0.5 h, concentrated to dryness using a rotary evaporator to afford crude 4,6-dimethoxy-2-methyl nicotinic acid chloride HCl salt (2.8 g, quantitative). A solution of 4,6-dimethoxy-2-methyl nicotinic acid chloride HCl salt (4.8 g, 23.5 mmol) in dichloromethane (100 mL) at room temperature was poured into a beaker of ammonium hydroxide (200 mL). The reaction mixture was stirred at room temperature for 1 h, extracted with dichloromethane (3×100 mL), and concentrated using a rotary evaporator to yield 4,6-dimethoxy-2-methyl-nicotinamide (2.4 g, 52%) as a light yellow solid. A solution of 4-hydroxy-3,5-dimethylbenzonitrile (2.00 g, 13.59 mmol) in DMF (20 mL) at room temperature was mixed with sodium hydride (0.706 g, 17.6 mmol) and stirred for 0.5 h. Benzyl bromide (1.62 mL, 13.59 mmol) was added and the reaction mixture was stirred at room temperature for 24 h. The reaction was quenched by adding water (200 mL), extracted with EtOAc (3×100 mL), and concentrated. The residue was purified by column chromatography to yield 4-benzyloxy-3,5-dimethylbenzonitrile (3.25 g, 100%) as a white solid. To a solution of 4,6-dimethoxy-2-methyl-nicotinamide (1 g, 5.1 mmol) in THF (120 mL) at −20° C. was added n-BuLi (9.6 mL, 15.3 mmol). The reaction was stirred at −20-0° C. for 2.5 h and then was cooled to −78° C. 4-Benzyloxy-3,5-dimethylbenzonitrile (1.21 g, 5.1 mmol) was added, the cooling bath was removed, and the reaction was allowed to warm up gradually to room temperature. After stirring at room temperature for 20 h the reaction was quenched by adding water (100 mL), extracted with dichloromethane (3×100 mL), and concentrated using a rotary evaporator. The residue was further purified by column (SiO$_2$, Hexanes/EtOAc/MeOH=3:2:1) to yield 7-(4-benzyloxy-3,5-dimethyl-phenyl)-2,4-dimethoxy-[1,6]naphthyridin-5-ylamine (0.4 g, 19%) and 7-(4-benzyloxy-3,5-dimethyl-phenyl)-2,4-dimethoxy-6H-[1,6]naphthyridin-5-one (0.34 g, 16%). A solution of 7-(4-benzyloxy-3,5-dimethyl-phenyl)-2,4-dimethoxy-6H-[1,6]naphthyridin-5-one (0.34 g, 0.82 mmol) in DMF (100 mL) and MeOH (100 mL) was mixed with palladium/carbon (0.1 g) and subjected to hydrogenation (50 psi) for 2 h. The mixture was filtered through a Celite-pad. The filtrate was concentrated on high vacuum to afford 7-(4-hydroxy-3,5-dimethyl-phenyl)-2,4-dimethoxy-6H-[1,6]naphthyridin-5-one (0.23 g, 88%). A solution of 7-(4-hydroxy-3,5-dimethyl-phenyl)-2,4-dimethoxy-6H-[1,6]naphthyridin-5-one (0.23 g, 0.7 mmol) in MeOH (20 mL) and DCM (20 mL) was mixed with HCl in ether (7 mL, 7 mmol) and stirred for 0.5 h. The reaction was concentrated using a rotary evaporator to get a solid residue. The solid was rinsed with DCM, collected by filtration, washed with DCM to yield the HCl salt of 7-(4-hydroxy-3,5-dimethylphenyl)-2,4-dimethoxy-1,6-naphthyridin-5(6H)-one (0.15 g, 59%) as a light yellow solid. Selected data: MS (ES) m/z: 327.06; MP>324° C. at decomposition (HCl salt).

EXAMPLE 17

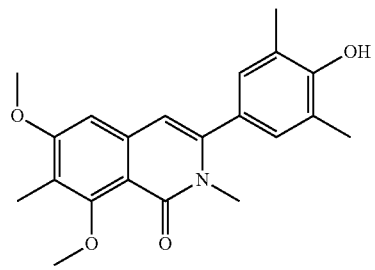

3-(4-hydroxy-3,5-dimethylphenyl)-6,8-dimethoxy-2,7-dimethylisoquinolin-1(2H)-one (left)
and

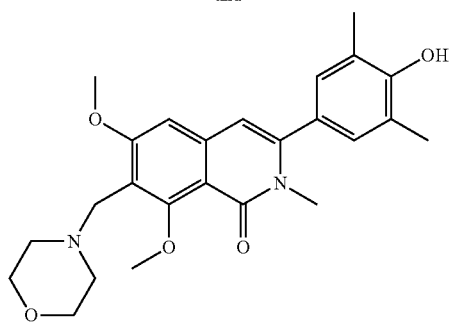

3-(4-hydroxy-3,5-dimethylphenyl)-6,8-dimethoxy-2-methyl-7-(morpholinomethyl) isoquinolin-1(2H)-one (right)

Methyl acetoacetate (69.67 g, 0.6 mol) in dry THF (350 mL) was cooled to −5° C. and sodium hydride (60% in mineral oil, 24.5 g) was added at −5 to 0° C. in 30 min. Diketene (50.4 g) in dry THF (80 mL) was then added drop-wise at 5° C. over 20 min. The resulting solution was allowed to stir for 1 h at −5° C., after which it was allowed to warm to room temperature and stirred overnight. Acetic acid (35 mL) was added and the THF solvent was removed. Water (200 mL) and ethyl acetate (300 mL) was added to the residue, pH was adjusted to 5.0 by adding HCl solution. The organic layer was separated and washed with brine and dried over sodium sulfate. After column purification and recrystalization, compound A (methyl 2,4-dihyroxy-6-methylbenzoate) was obtained (yield: 26.6 g, 24.3%). Sodium hydride (11.2 g, 0.279 mol, 60% in mineral oil) was added to compound A (24.8 g, 0.136 mol) in DMF (150 mL). The reaction temperature was cooled to −30° C. and methyl iodide (21.3 mL, 0.341 mol) was added and the reaction was kept at room temperature overnight. Sodium iodide was filtered off and DMF was removed. The residue was mixed with water (100 mL) and extracted with ethyl acetate. The organic layer was further washed with brine and dried over sodium sulfate. The crude mixture was purified by column chromatography to yield compound B (11.40 g, 39.9%). To a solution of compound B (11.4 g, 0.054 mol) in dry CCl$_4$ (90 mL) was added N-bromosuccinimide (10.6 g, 0.0596 mol). The mixture was refluxed overnight. CCl$_4$ was removed. Water (100 mL) was added to the residue and the solid was filtered off and washed with water and a mixture of ethyl acetate (10 mL) and hexane (30 mL) to yield compound C (13.1 g, 83.9%). Compound C (12.5 g, 0.043 mol), chloromethyl methyl ether (81.0 g) and anhydrous zinc chloride (7.0 g, 0.0513 mol) was kept at room temperature overnight. Chloromethyl methyl ether was removed and the residue was mixed with water and the pH was adjusted to 7 by adding sodium bicarbonate. The mixture was extracted with ethyl acetate and the organic layer was washed with brine and dried over sodium sulfate. Compound D (7.39 g, 50.6%) was obtained after column chromatography. Compound D (7.39 g, 0.0218 mol), morpholine (7.62 g, 0.0875 mol), and anhydrous THF (20 mL) were stirred at room temperature overnight. The solvent was evaporated. Water and ethyl acetate were added to the residue, pH was adjusted to 9.0 with sodium bicarbonate. The organic layer was washed with brine and dried with sodium sulfate. Compound E (5.4 g, 63.8%) was obtained after column chromatography. The hydrogenation reaction was carried out at 50 psi with compound E (5.4 g, 0.0139 mol) in THF (100 mL) and triethyl amine (3.9 mL) with Pd/C (10%, 2.6 g) as a catalyst for 2 d. After the catalyst was filtered off, the organic layer was purified by column chromatography to yield compound F (3.20 g, 74.4%) and 1.1 g starting material E. Compound F (3.20 g, 0.0103 mol) was dissolved in ethanol (30 mL) and potassium hydroxide (2.31 g, 0.041 mol) in water (20 mL) was added and the reaction mixture was heated to 100° C. overnight. The solvent was removed, the pH was adjusted to 6.0 and the water was removed. The residue was further dried under high vacuum and the compound was extracted with ethanol to yield compound G (2.95 g, 99%). Compound G (2.80 g, 0.0095 mol) was mixed with thionyl chloride (7.0 mL, 0.0108 mol) and heated to reflux for 1 h. Excess thionyl chloride was removed and the residue was further dried under high vacuum and anhydrous THF (20 mL) was added and methylamine in THF (2.0 M, 30 mL) was added and the reaction was stirred for overnight. THF was removed and pH was adjusted to 8.0-9.0, the mixture was extracted with dichloromethane and dried over sodium sulfate to give compound H (2.50 g, 85.4%).

NaH (1.14 g, 0.0285 mol, 60% in mineral oil) was added to 4-hydroxy-3,5-dimethylbenzonitrile (4.0 g, 0.027 mol) in anhydrous DMF (20 mL), followed by benzyl bromide (3.27 mL, 0.027 mol). The reaction was kept at room temperature overnight. The reaction mixture was poured into water and the solid was filtered off and washed with hexane to yield compound I (5.7 g, 89%). Compound I was used for the next step without further purification.

n-BuLi (1.60 M, 3.3 mL) was added drop-wise to compound H (0.25 g, 0.81 mmol) in anhydrous THF (25 mL) at −10° C. The reaction mixture was kept at 0° C. for 1 h then the cool bath was removed and the reaction mixture was further stirred for 45 min. Compound I (0.192 g, 0.81 mmol) in anhydrous THF (5 mL) was added drop-wise at −10° C. and the reaction was further kept for 30 min; the reaction temperature was increased to room temperature and the reaction mixture was stirred for a further 1 h. Water (20 mL) was added and the mixture was extracted with ethyl acetate. The solvent was removed and the residue was treated with acetic acid at 65° C. for 30 min then purified by column chromatography to yield compound J (0.110 g, 25.9%). Product J (300 mg) in methanol (80 mL) and 10% Pd/C (100 mg) as catalyst was stirred under H$_2$ (50 psi) for 1 h. The catalyst was filtered off and the solvent was removed. The residue was purified by column chromatography (10% methanol in ethyl acetate) to yield 3-(4-hydroxy-3,5-dimethylphenyl)-6,8-dimethoxy-2,7-dimethylisoquinolin-1(2H)-one (60 mg, 29.8%) and 3-(4-hydroxy-3,5-dimethylphenyl)-6,8-dimethoxy-2-methyl-7-(morpholinomethyl)isoquinolin-1(2H)-one (40 mg, 16.8%).

Selected data for 3-(4-hydroxy-3,5-dimethylphenyl)-6,8-dimethoxy-2,7-dimethylisoquinolin-1(2H)-one: MP 246-248° C. Selected data for 3-(4-hydroxy-3,5-dimethylphenyl)-6,8-dimethoxy-2-methyl-7-(morpholinomethyl)isoquinolin-1(2H)-one: MP 224-225° C.

EXAMPLE 18

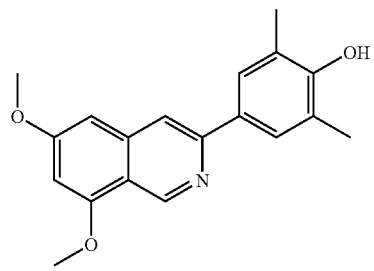

4-(6,8-dimethoxyisoquinolin-3-yl)-2,6-dimethylphenol

Phosphorousoxychloride (10 mL, 109.24 mmol) was added drop-wise at 0° C. to a stirred solution of 1-bromo-3,5-dimethoxy benzene (9.1 g, 41.9 mmol) in anhydrous DMF (40 mL). The reaction mixture was stirred at 0° C. for 10 min and then at room temperature for 30 min, then at 100° C. for 4 h. The reaction mixture was cooled to room temperature, poured into ice-cold water and kept overnight. A solid precipitated and was filtered off, washed with water and dried under vacuum to give 2-bromo-4,6-dimethoxy benzaldehyde (8.67 g, 84%) as a yellow solid. To a solution of 4-bromo-2,6-dimethylphenol (6.03 g, 30 mmol) in anhydrous DMF (100 mL) was added sodium hydride (60% suspension in mineral oil, 1.26 g, 31.5 mmol) in small portions under nitrogen at room temperature. The reaction mixture was stirred for 30 min. Benzyl bromide (5.39 g, 31.5 mmol) was added slowly and stirring was continued at room temperature for 2 h. Water (200 mL) was added and the mixture was extracted with hexanes (2×200 mL). The organic layer was washed with water (3×100 mL) and dried over anhydrous Na$_2$SO$_4$. Removal of solvent gave 2-benzyloxy-5-bromo-1,3-dimethylbenzene (9.59 g) as a white solid which was used in the next step without further purification. (Dichloro)bis(triphenylphosphene)palladium (0.239 g, 0.34 mmol) and copper (I) iodide (0.065 g, 0.34 mmol) were added to a solution of 2-benzyloxy-5-bromo-1,3-dimethylbenzene (4.96 g, 17.03 mmol) and trimethylsilyl acetylene (1.84 g, 18.74 mmol) in triethyl amine (70 mL). The reaction mixture was stirred at reflux under nitrogen for 4 h. The mixture was cooled to room temperature. The precipitated ammonium salt was filtered off. The filtrate was concentrated under reduced pressure. The residue was dissolved in hexanes (300 mL) and washed with 2 N aqueous HCl (2×50 mL), water (50 mL), brine (50 mL), and dried over anhydrous Na$_2$SO$_4$. Removal of solvent gave a dark brown liquid which was purified by column chromatography (silica gel 230-400 mesh; 0-5% ethyl acetate in hexanes as eluent) to give (4-benzyloxy-3,5-dimethylphenylethynyl)trimethylsilane (4.0 g, 76% yield) of as pale yellow oil. To a degassed solution of (4-benzyloxy-3,5-dimethylphenylethynyl)trimethylsilane (3.96 g, 12.83 mmol) in anhydrous THF (60 mL) was added tetrabutylammonium fluoride (38.5 mL, 1.0M solution in THF) at 0° C. under nitrogen. Stirring continued at 0° C. for 1 h. A saturated aqueous NH$_4$Cl solution (100 mL) was added. The reaction mixture was extracted with hexanes (300 mL). The organic layer was washed with saturated aqueous NH$_4$Cl solution and dried over anhydrous Na$_2$SO$_4$. The crude compound was purified by column chromatography to give 2-benzyloxy-5-ethynyl-1,3-dimethylbenzene (2.77 g, 91% yield) as a pale yellow oil. To a degassed solution of 2-bromo-4,6-dimethoxy benzaldehyde (2.37 g, 9.68 mmol) in DMF-triethylamine (5:1, 95 mL) were added dichlorobis(triphenylphosphine)-palladium(II) (0.34 g, 0.484 mmol) and copper(I) iodide (0.553 g, 2.90 mmol). The reaction mixture was degassed. To this stirred solution, a degassed solution of 2-benzyloxy-5-ethynyl-1,3-dimethylbenzene (2.86 g, 12.1 mmol) in DMF-triethylamine (5:1, 37 mL) was added at 75° C. under nitrogen over a period of 3 h. After the completion of the addition, stirring continued at 75° C. under nitrogen for 4 h. The reaction mixture was allowed to cool to room temperature. Water (200 mL) was added. The mixture was extracted with ethyl acetate (300 mL). The organic layer was washed with water (3×150 mL) and brine (150 mL), and dried over anhydrous $Na_2SO_4$. Removal of solvent gave a black gummy material, which was purified by column chromatography to give 2-(4-benzyloxy-3,5-dimethylphenylethynyl)-4,6-dimethoxybenzaldehyde (2.8 g, 72% yield) of as a brown solid. Tert-Butylamine (20 mL) was added to the above compound (2.63 g, 5.772 mmol). The reaction mixture was stirred under nitrogen for 16 h. Excess tert-butylamine was removed under reduced pressure. The mixture was dried under vacuum to give 3.11 g of imine as a brown solid. To a solution of above imine (3.07 g, 6.738 mmol) in anhydrous DMF (160 mL) was added copper (I) iodide (0.123 g, 0.674 mmol) and the reaction mixture was stirred at 100° C. for 5 h under nitrogen and cooled to room temperature. Water (200 mL) was added and the reaction mixture was extracted with ethyl acetate (2×200 mL). The organic layer was washed with water (2×100 mL), brine (150 mL), and dried over anhydrous $Na_2SO_4$. Removal of solvent gave a dark brown gummy material, which was purified by column chromatography (silica gel 230-400 mesh; 0-15% ethyl acetate in hexanes as eluent) to give 3-(4-benzyloxy-3,5-dimethylphenyl)-6,8-dimethoxy isoquinoline (0.689 g, 26%) as a brown solid. To a solution of 3-(4-benzyloxy-3,5-dimethylphenyl)-6,8-dimethoxy isoquinoline (0.68 g, 1.70 mmol) in 1:1 methanol-ethyl acetate (40 mL) was added Pd—C (10%, 200 mg) and the mixture was hydrogenated for 16 h. After reaction completion the mixture was filtered through Celite. The filtrate was concentrated and dried under vacuum to give 4-(6,8-Dimethoxyisoquinolin-3-yl)-2,6-dimethylphenol (0.51 g, 97%) as a yellow solid. To a solution of 4-(6,8-dimethoxyisoquinolin-3-yl)-2,6-dimethylphenol (25 mg, 0.081 mmol) in methanol/$CH_2Cl_2$ (1:1, 6 mL) was added a solution of hydrogen chloride in ether (1.0 M, 1 mL) and the reaction mixture was stirred at room temperature for 15 min. The solvent was removed under reduced pressure. The residue was triturated with ether to give the hydrochloride of 4-(6,8-dimethoxyisoquinolin-3-yl)-2,6-dimethylphenol (28 mg, 99%) as a yellow solid. Selected data: MP 255-256° C. (HCl salt).

EXAMPLE 19

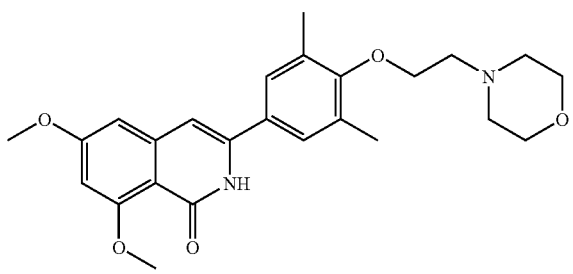

3-(3,5-dimethyl-4-(2-morpholinoethoxy)phenyl)-6,8-dimethoxyisoquinolin-1(2H)-one (3,5-Dimethoxy-phenyl)-acetic acid (10.0 g, 51 mmol) was dissolved in anhydrous methanol (100 mL) and $H_2SO_4$ (1 mL) was added drop-wise. The reaction mixture was refluxed overnight and cooled to room temperature. The solvent was removed and the residue was dissolved in ethyl acetate and washed with a $NaHCO_3$ solution, water and dried ($Na_2SO_4$). The solvent was evaporated in vacuo to obtain (3,5-dimethoxy-phenyl)-acetic acid methyl ester in 97% (10.4 g) yield. To a solution of (3,5-dimethoxy-phenyl)-acetic acid methyl ester (10.4 g, 49.5 mmol) in dimethyl formamide (40 mL), $POCl_3$ (5.4 mL, 59.37 mmol) was added at 55° C. After the addition, the reaction mixture was heated at 100° C. for 10 min and then stirred at room temperature overnight. The reaction mixture was poured into ice-water and extracted with ethyl acetate, washed with water, brine, dried over anhydrous $Na_2SO_4$ and evaporated in vacuo to obtain (2-formyl-3,5-dimethoxy-phenyl)-acetic acid methyl ester (10.0 g, 85%). (2-Formyl-3,5-dimethoxy-phenyl)-acetic acid methyl ester (5.0 g, 21 mmol) was dissolved in $CH_3CN$ (100 mL), $NaH_2PO_4$ (0.655 g, 5.46 mmol) in water (2 mL) and 30% $H_2O_2$ (2.3 mL, 21 mmol). The reaction mixture was cooled to 0° C. and a solution of $NaO_2Cl$ (2.65 g, 29.4 mmol) in water (5 mL) was added. The reaction mixture was stirred at room temperature for 4 h before being quenched by the addition of $Na_2SO_3$ solution. The mixture was acidified with 2 N HCl and extracted with ethyl acetate. The solvent was evaporated in vacuo to obtain 2,4-dimethoxy-6-methoxycarbonylmetyl-benzoic acid (5.25 g, 98%). To a solution of 2,4-dimethoxy-6-methoxycarbonylmetyl-benzoic acid (5.25 g, 20.6 mmol) in methanol (50 mL), a solution of NaOH (4.12 g, 103 mmol) in water (20 mL) was added and the reaction mixture was allowed to stir at room temperature for 3 h. The solvent was removed, diluted with water and acidified with 2 N HCl. The compound was extracted with ethyl acetate, washed with water, brine, dried over anhydrous $Na_2SO_4$ and evaporated in vacuo to obtain 2-carboxymethyl-4,6-dimethoxy-benzoic acid (4.65 g, 94%). To a suspension of 2-carboxymethyl-4,6-dimethoxy-benzoic acid (4.65 g, 19.4 mmol) in toluene (50 mL) was added acetic anhydride (2.01 mL, 21.3 mmol) and the reaction mixture was heated to reflux for 2 h. After cooling to 0° C., the precipitated solid was filtered off and washed with heptane and hexane to obtain 6,8-dimethoxy-isochroman-1,3-dione (3.56 g, 83%).

To a solution of 3,5-dimethyl-4-hydroxy-benzoic acid (3.0 g, 18.05 mmol) in pyridine (7 mL) was added acetic anhydride (2.05 mL, 21.66 mmol) and the reaction mixture was stirred at room temperature for 16 h. Water was added and the mixture was extracted with ethyl acetate, washed with water, brine and dried over anhydrous $Na_2SO_4$. The solvent was evaporated in vacuo to obtain 4-acetoxy-3,5-dimethyl-benzoic acid (3.52 g, 94%). To a solution of 4-acetoxy-3,5-dimethyl-benzoic acid (6.02 g, 28.91 mmol) in $CH_2Cl_2$ (80 mL), oxalyl chloride (5.04 mL, 57.83 mmol) was added slowly, followed by a drop of dimethyl formamide. The reaction mixture was stirred at room temperature for 2 h. The solvent was removed and acetic acid 4-chlorocarbonyl-2,6-dimethyl-phenyl ester was dried under vacuum (6.37 g, 97%). To a solution of N,N,N,N-tetramethyl guanidine (2.77 mL, 22.078 mmol) in $CH_3CN$ (50 mL), a solution of 6,8-dimethoxy-isochroman-1,3-dione (4.46 g, 20.07 mmol) in $CH_3CN$ (100 mL) was added slowly at <0° C. (bath temperature −20° C.) in 30 min. Then, $Et_3N$ was added in one portion, followed by a solution of acetic acid 4-chlorocarbonyl-2,6-dimethyl-phenyl ester (6.37 g, 28.1 mmol) in $CH_3CN$ (50 mL) and stirred for 30 min. at <0+ C. The reaction mixture was stirred at room temperature for 16 h, then heated to reflux for 3 h. After cooling to room temperature, the reaction mixture was quenched with 1 N HCl. The precipitated solid was filtered off to give a mixture of acetic acid 4-(6,8-dimethoxy-1,3-dioxo-isochroman-4-carbonyl)-2,6-dimethyl-phenyl ester and acetic acid 4-(6,8-dimethoxy-1-oxo-1H-isochromen-3-yl)-2,6-dimethyl-phenyl ester (6.0 g).

The above mixture (6.0 g) was dissolved in H$_2$SO$_4$ (30%, 30 mL) and heated at 100° C. for 2 h. The reaction mixture was cooled to room temperature and the precipitated solid was filtered off to obtain a mixture of acetic acid 4-(6,8-dimethoxy-1-oxo-1H-isochromen-3-yl)-2,6-dimethyl-phenyl ester and 3-(4-hydroxy-3,5-dimethyl-phenyl)-6,8-dimethoxy-isochromen-1-one (5.5 g). The above mixture (5.5 g) was dissolved in methanol (30 mL), K$_2$CO$_3$ (3.09 g, 22.4 mmol) and water (10 mL) were added and the reaction mixture was stirred at room temperature for 6 h. The solvent was removed and acidified with dilute HCl. The compound was extracted with ethyl acetate, washed with water, brine and dried over anhydrous Na$_2$SO$_4$. The solvent was evaporated in vacuo to leave a residue which was purified by chromatography (silica gel, 230-250 mesh; 2% methanol in dichloromethane) to obtain 3-(4-hydroxy-3,5-dimethyl-phenyl)-6,8-dimethoxy-isochromen-1-one. The yield was 1.462 g.

To a solution of 3-(4-hydroxy-3,5-dimethyl-phenyl)-6,8-dimethoxy-isochromen-1-one (0.875 g, 2.68 mmol) in DMF (5 mL), NaH (0.129 g, 3.22 mmol) was added and the mixture was stirred for 1 h. To the reaction mixture was added 1-chloro-2-iodo-ethane (1.23 mL, 13.4 mmol) and stirring was continued for 16 h. Then the reaction mixture was heated at 80° C. before being quenched with 1 N HCl at room temperature. The crude was purified by column chromatography (silica gel, 230-250 mesh; 2% methanol in dichloromethane). The yield was 0.36 g (35%). The compound 3-[4-(2-chloro-ethoxy)-3,5-dimethyl-phenyl]-6,8-dimethoxy-isochromen-1-one (0.36 g, 0.927 mmol) was dissolved in DMSO (5 mL), morpholine (0.4 mL, 4.63 mmol) and Et$_3$N (0.64 mL, 4.63 mmol) were added. The reaction mixture was heated at 110° C. for 16 h before being cooled to room temperature. Water was added and the compound was extracted with ethyl acetate. The solvent was evaporated in vacuo to leave a residue, which was purified by chromatography. The yield was 0.128 g (31%). The compound 3-[3,5-dimethyl-4-(2-morpholin-4-yl-ethoxy)-phenyl]-6,8-dimethoxy-isochromen-1-one (0.128 g, 0.29 mmol) and NH$_3$ (2.0 M solution in ethanol, 30 mL) were mixed in a steel bomb and heated at 130° C. for 16 h. The solvent was removed and the crude compound was purified by chromatography (silica gel, 230-250 mesh). The compound was then converted into the HCl salt of 3-(3,5-dimethyl-4-(2-morpholinoethoxy)phenyl)-6,8-dimethoxyisoquinolin-1(2H)-one (84 mg, 66%). Selected data: MP 196-198° C. (HCl salt).

EXAMPLE 20

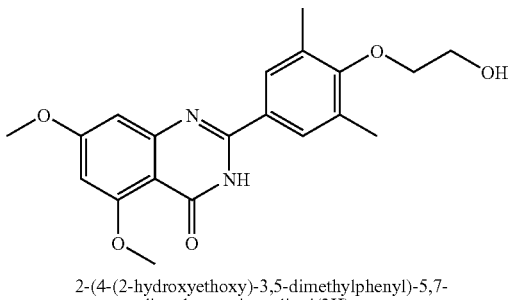

2-(4-(2-hydroxyethoxy)-3,5-dimethylphenyl)-5,7-dimethoxyquinazolin-4(3H)-one

A solution of 2-amino-4,6-dimethoxybenzamide (0.60 g, 3.06 mmol) and 4-[2-(tert-butyldimethylsilanoxy)ethoxy]-3,5-dimethylbenzaldehyde (0.856 g, 2.78 mmol) in N,N-dimethyl formamide (20 mL) was stirred at 70° C. for 1 h. Iodine (0.846 g, 3.33 mmol) and potassium carbonate (0.384 g, 2.78 mmol) were added and the reaction mixture was stirred at 70° C. for 16 h. The reaction mixture was poured into ice, and extracted with ethyl acetate. The organic layer was washed with water, brine, and dried over anhydrous Na$_2$SO$_4$. Removal of the solvent gave the crude product which was purified by column chromatography to give 2-(4-(2-hydroxyethoxy)-3,5-dimethylphenyl)-5,7-dimethoxyquinazolin-4(3H)-one (444 mg, 39%) as a white solid. Selected data: 229-231° C.

Alternatively, 2-(4-(2-hydroxyethoxy)-3,5-dimethylphenyl)-5,7-dimethoxyquinazolin-4(3H)-one can be synthesized by the following method. In a 2 L dry round-bottom flask with a reflux condenser and magnetic stirrer was placed 3,5-dimethyl-4-hydroxy benzaldehyde (26.9 g, 0.179 mol) in ethanol (350 mL). 2-chloroethanol (87.6 g, 1.074 mol) and K$_2$CO$_3$ (99 g, 0.716 mol) were added and the reaction mixture was heated to reflux for 24 h. The reaction mixture was cooled to room temperature and filtered. The solvent was removed under reduced pressure. The crude product was diluted with ethyl acetate and the organic layer was washed with water, brine, and dried over Na$_2$SO$_4$. Upon removal of solvent it gave 45 g of crude product. The crude product was purified by column chromatography (silica gel 230-400 mesh; 50% ethyl acetate in hexane as eluent) to give 33.3 g (95%) of product. To a solution of 2-amino-4,6-dimethoxy-benzamide (33.45 g, 0.170 mol) and 4-(2-hydroxy ethoxy)-3,5-dimethyl benzaldehyde (33.3 g, 0.170 mol) in N,N-dimethyl acetamide (300 mL), NaHSO$_3$ (33.3 g, 0.187 mol) and p-TSA (3.2 g, 17.1 mmol) were added and the reaction mixture was heated at 150° C. for 14 h. The reaction was cooled to room temperature. The solvent was removed under reduced pressure. The residue was diluted with water and stirred for 30 min at room temperature. The solids separated were filtered and dried to give crude product. The crude product was purified by column chromatography (silica gel 230-400 mesh; 5% methanol in CH$_2$Cl$_2$ as eluent) to give 2-(4-(2-hydroxyethoxy)-3,5-dimethylphenyl)-5,7-dimethoxyquinazolin-4(3H)-one (33 g, 52%).

EXAMPLE 21

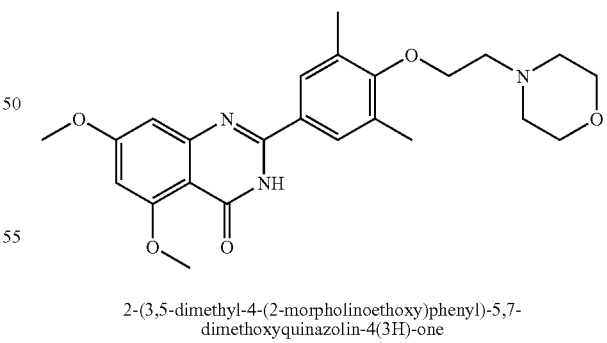

2-(3,5-dimethyl-4-(2-morpholinoethoxy)phenyl)-5,7-dimethoxyquinazolin-4(3H)-one

In a 250 mL round-bottomed flask were placed 3,5-dimethyl-4-hydroxy benzaldehyde (4.0 g, 26.7 mmol), Ph$_3$P (15.38 g, 58.66 mmol), di-isopropylethylamine (13.78 g, 106.7 mmol) and 2-morpholin-4-yl-ethanol (7.69, 58.7 mmol) in THF (100 mL), then DEAD (11.1 g, 64 mmol) was added drop-wise at room temperature. The reaction mixture was stirred for 3 d at room temperature and water was added and extracted with ethyl acetate. The combined organic layers were washed with water, brine and dried over Na$_2$SO$_4$ and concentrated to give crude product. The crude product was purified by column chromatography to give the B-ring building block (3.0 g, 43%).

To a solution of 2-amino-4,6-dimethoxybenzamide (451 mg, 2.3 mmol) and 3,5-dimethyl-4-(2-morpholin-4yl-ethoxy)-benzaldehyde (550 mg, 2.09 mmol) in N,N-dimethyl formamide (20 mL), iodine (636 mg, 2.5 mmol) and potassium carbonate (288 mg, 2.09 mmol) were added and the reaction mixture was stirred at 70° C. for 48 h. The reaction mixture was poured into ice. The mixture was extracted with ethyl acetate. The organic layer was washed with water, brine and dried over anhydrous Na$_2$SO$_4$. Removal of the solvent gave the crude product was purified by column chromatography and converted to the hydrochloride salt of 2-(3,5-dimethyl-4-(2-morpholinoethoxy)phenyl)-5,7-dimethoxyquinazolin-4(3H)-one (40 mg, 4%) as an off-white solid. Selected data: MS (ES) m/z: 440.1; MP 185-187° C. (HCl salt).

EXAMPLE 22

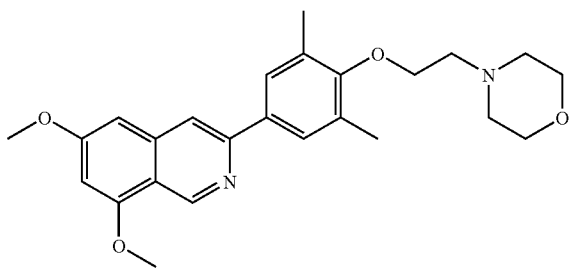

4-(2-(4-(6,8-dimethoxyisoquinolin-3-yl)-2,6-dimethylphenoxy) ethyl)morpholine

To a solution of 4-(6,8-dimethoxyisoquinolin-3-yl)-2,6-dimethylphenol (0.309 g, 1.0 mol) in anhydrous THF (20 mL), triphenyl phosphene (0.52 g, 2.0 mmol), 4-(2-hydroxyethyl)morpholine (0.262 g, 2.0 mmol) and N,N-diisopropylethylamine (0.387 g, 3.0 mmol) were added. To this stirred solution was added diethylazodicarboxylate (0.348 g, 2.0 mmol). The reaction mixture was stirred at room temperature overnight under nitrogen, then diluted with ethyl acetate (100 mL). The organic layer was washed with water and brine, and dried over anhydrous Na$_2$SO$_4$. The solvent was removed under reduced pressure. The crude material was purified by column chromatography to give 3-[3,5-dimethyl-4-(2-morpholin-4-ylethoxy)phenyl]-6,8-dimethoxyisoquinoline (0.54 g) as a white solid.

To a solution of the above compound (0.54 g, impure) in 1:1 ether-CH$_2$Cl$_2$ (10 mL), was added 1.0 M solution of hydrogen chloride in ether (2 mL) and the reaction mixture was stirred at room temperature for 30 min. Solvent was removed under reduced pressure. The residue was triturated with 10% methanol in ether to give 4-(2-(4-(6,8-dimethoxyisoquinolin-3-yl)-2,6-dimethylphenoxy)ethyl)morpholine (0.323 g, 70% over two steps) as a yellow solid. Selected data: MS (ES) m/z: 423.1; MP 239-240° C. (HCl salt).

EXAMPLE 23

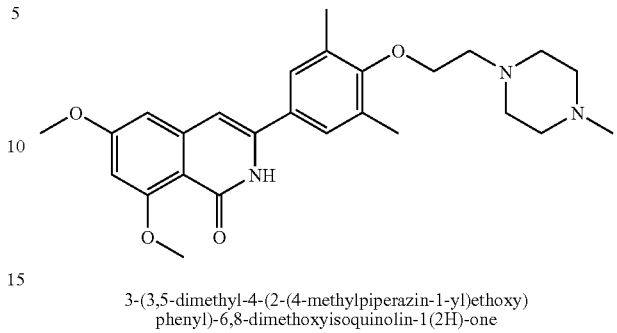

3-(3,5-dimethyl-4-(2-(4-methylpiperazin-1-yl)ethoxy) phenyl)-6,8-dimethoxyisoquinolin-1(2H)-one The compound 3-[4-(2-chloro-ethoxy)-3,5-dimethyl-phenyl]-6,8-dimethoxy-isochromen-1-one (298 mg, 0.767 mmol) was dissolved in DMSO (5 mL) and N-methyl piperazine (388 mg, 3.83 mmol) and Et$_3$N (392 mg, 3.83 mmol) were added. The reaction mixture was heated at 110° C. for 16 h before being cooled to room temperature. Water was added and the mixture was extracted with ethyl acetate. The solvent was evaporated in vacuo to leave a residue which was purified by column chromatography. The yield was 60 mg (17%). The compound 3-[3,5-dimethyl-4-(2-(4-methyl piperazin-1-yl-ethoxy)-phenyl]-6,8-dimethoxy-isochromen-1-one (60 mg, 0.13 mmol) and NH$_3$ (2.0 M solution in ethanol, 20 mL) were mixed in a steel bomb and heated at 130° C. for 16 h. The solvent was removed and the crude compound was purified by column chromatography. The compound was then converted to the hydrochloride salt of 3-(3,5-dimethyl-4-(2-(4-methylpiperazin-1-yl)ethoxy)phenyl)-6,8-dimethoxyisoquinolin-1(2H)-one (40 mg, 62%), an off-white solid. Selected data: MS (ES) m/z: 452.1; MP 195-198° C. (HCl salt).

EXAMPLE 24

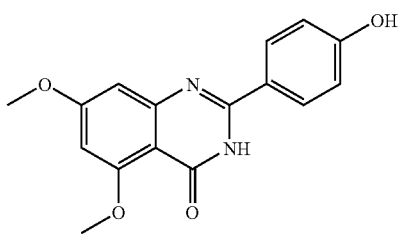

2-(4-hydroxyphenyl)-5,7-dimethoxyquinazolin-4(3H)-one

2-Amino-4,6-dimethoxy-benzamide (328 mg, 1.67 mmol), 4-hydroxybenzaldehyde (204 mg, 1.67 mmol), K$_2$CO$_3$ (231 mg, 1.67 mmol) and I$_2$ (508 mg, 2.0 mmol) were mixed in DMF (10 mL) and the reaction mixture was heated at 70° C. for 5 h. It was cooled to room temperature and poured into crushed ice. The solid was collected and purified by column chromatography (silica gel 230-400 mesh; 5% methanol in CH$_2$Cl$_2$ as eluent) to give 2-(4-hydroxyphenyl)-5,7-dimethoxyquinazolin-4(3H)-one (60 mg, 12%), as an off-white solid. Selected data: MS (m/z): 299.05; MP 303-305° C.

EXAMPLE 25

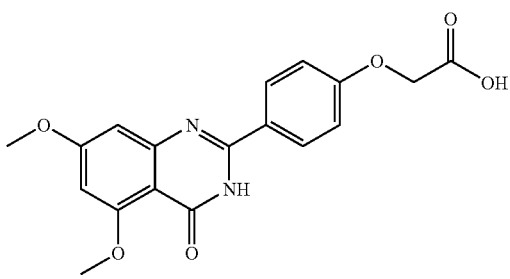

2-(4-(5,7-dimethoxy-4-oxo-3,4-dihydroquinazolin-2-yl)
phenoxy)acetic acid 2-(4-(5,7-Dimethoxy-4-oxo-3,4-dihydroquinazolin-2-yl) phenoxy)acetic acid was synthesized from 2-amino-4,6-dimethoxy-benzamide and (4-formyl phenoxy)acetic acid, using the method described for 2-(4-hydroxyphenyl)-5,7-dimethoxyquinazolin-4(3H)-one. 2-(4-(5,7-Dimethoxy-4-oxo-3,4-dihydroquinazolin-2-yl)phenoxy)acetic acid (135 mg, 21%) was isolated as an off-white solid. Selected data: MS (m/z): 357.04; MP 287-290° C.

EXAMPLE 26

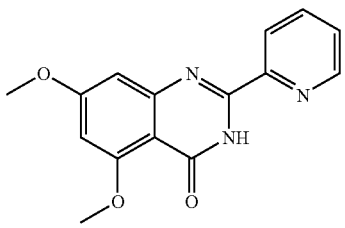

5,7-dimethoxy-2-(pyridin-2-yl)quinazolin-4(3H)-one

To a solution of 2-amino-4,6-dimethoxybenzamide (0.15 g, 0.764 mmol) in N,N-dimethyl acetamide (5 mL) were added 2-pyridine carboxaldehyde (0.082 g, 0.764 mmol), sodium hydrogen sulphite (58.5%, 0.15 g, 0.84 mmol), and p-toluenesulfonic acid (15 mg, 0.0764 mmol). The reaction mixture was stirred at 150° C. overnight. The mixture was cooled to room temperature. Water (40 mL) was added and the reaction mixture was extracted with dichloromethane (2×50 mL). The combined organic layers were washed with water and dried over anhydrous $Na_2SO_4$. The solvent was removed and the crude compound was purified by column chromatography (silica gel 230-400 mesh; 1% methanol in $CH_2Cl_2$ as eluent) to give 5,7-dimethoxy-2-(pyridin-2-yl) quinazolin-4(3H)-one (0.077 g, 36%) as a white solid. 5,7-dimethoxy-2-(pyridin-2-yl)quinazolin-4(3H)-one was converted to the corresponding hydrochloride. Selected data: MS (m/z): 284.0; MP 215-217° C. (hydrochloride).

EXAMPLE 27

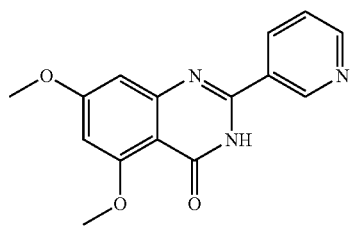

5,7-dimethoxy-2-(pyridin-3-yl)
quinazolin-4(3H)-one 5,7-Dimethoxy-2-(pyridin-3-quinazolin-4(3H)-one was synthesized from 2-amino-4,6-dimethoxybenzamide and 3-pyridine carboxaldehyde, using the method described for 5,7-dimethoxy-2-(pyridin-2-yl)quinazolin-4(3H)-one. 5,7-Dimethoxy-2-(pyridin-3-yl)quinazolin-4(3H)-one (105 mg, 48%) was isolated as a white solid. Selected data: MS (m/z): 284.0; MP 257-259° C. (hydrochloride).

EXAMPLE 28

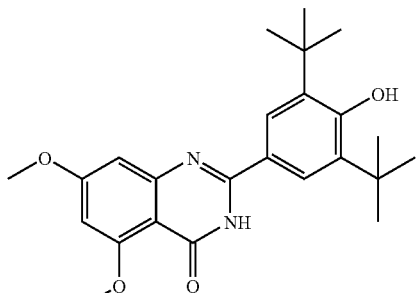

2-(3,5-di-tert-butyl-4-hydroxyphenyl)-5,7-
dimethoxyquinazolin-4(3H)-one 2-(3,5-di-tert-butyl-4-hydroxyphenyl)-5,7-dimethoxyquinazolin-4(3H)-one was synthesized from 2-amino-4,6-dimethoxybenzamide and 3,5-di-tert-butyl-4-hydroxybenzaldehyde, using the method described for 5,7-dimethoxy-2-(pyridin-2-yl)quinazolin-4(3H)-one. 2-(3,5-di-tert-butyl-4-hydroxyphenyl)-5,7-dimethoxyquinazolin-4(3H)-one (130 mg, 41%) was isolated as a light yellow solid. Selected data: MS (m/z): 411.17; MP 229.7-230.5° C.

EXAMPLE 29

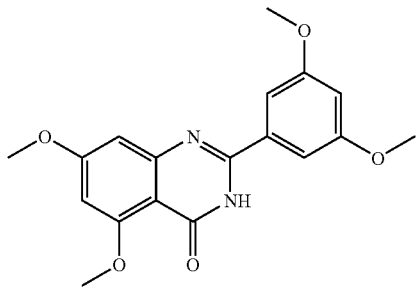

2-(3,5-dimethoxyphenyl)-5,7-
dimethoxyquinazolin-4(3H)-one 2-(3,5-dimethoxyphenyl)-5,7-dimethoxyquinazolin-4 (3H)-one was synthesized from 2-amino-4,6-dimethoxybenzamide and 3,5-dimethoxybenzaldehyde, using the method described for 5,7-dimethoxy-2-(pyridin-2-yl)quinazolin-4 (3H)-one. 2-(3,5-dimethoxyphenyl)-5,7-dimethoxyquinazolin-4(3H)-one (120 mg, 46%) was isolated as a yellow solid. Selected data: MS (m/z): 343.05; MP 270-272° C.

EXAMPLE 30

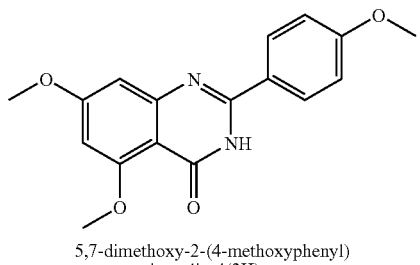

5,7-dimethoxy-2-(4-methoxyphenyl)
quinazolin-4(3H)-one 5,7-Dimethoxy-2-(4-methoxyphenyl)quinazolin-4(3H)-one was synthesized from 2-amino-4,6-dimethoxybenzamide and 4-methoxy benzaldehyde, using the method described for 5,7-dimethoxy-2-(pyridin-2-yl)quinazolin-4(3H)-one. 5,7-Dimethoxy-2-(4-methoxyphenyl)quinazolin-4(3H)-one (106 mg, 44%) was isolated as an off-white solid. Selected data: MS (m/z): 312.99; MP 276-277° C.

EXAMPLE 31

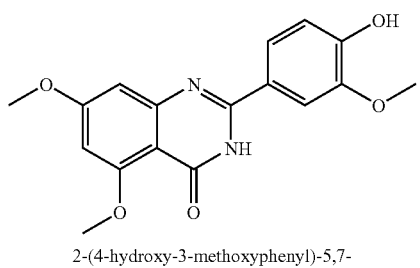

2-(4-hydroxy-3-methoxyphenyl)-5,7-
dimethoxyquinazolin-4(3H)-one 2-(4-Hydroxy-3-methoxyphenyl)-5,7-dimethoxyquinazolin-4(3H)-one was synthesized from 2-amino-4,6-dimethoxybenzamide and 4-hydroxy-3-methoxybenzaldehyde, using the method described for 5,7-dimethoxy-2-(pyridin-2-yl)quinazolin-4(3H)-one. 2-(4-Hydroxy-3-methoxyphenyl)-5,7-dimethoxyquinazolin-4(3H)-one (90 mg, 36%) was isolated as a white solid. Selected data: MS (m/z): 329.06; MP 294-296° C.

EXAMPLE 32

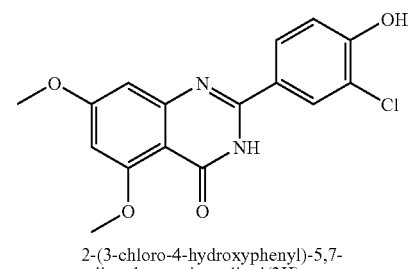

2-(3-chloro-4-hydroxyphenyl)-5,7-
dimethoxyquinazolin-4(3H)-one 2-(3-Chloro-4-hydroxyphenyl)-5,7-dimethoxyquinazolin-4(3H)-one was synthesized from 2-amino-4,6-dimethoxybenzamide and 3-chloro-4-hydroxybenzaldehyde, using the method described for 5,7-dimethoxy-2-(pyridin-2-yl)quinazolin-4(3H)-one. 2-(3-Chloro-4-hydroxyphenyl)-5,7-dimethoxyquinazolin-4(3H)-one (75 mg, 30%) was isolated as a yellow solid. Selected data: MS (m/z): 333.03; MP 279-281° C.

EXAMPLE 33

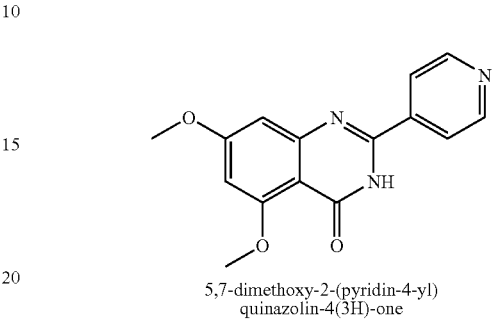

5,7-dimethoxy-2-(pyridin-4-yl)
quinazolin-4(3H)-one 5,7-Dimethoxy-2-(pyridin-4-yl)quinazolin-4(3H)-one was synthesized from 2-amino-4,6-dimethoxybenzamide and 4-pyridine carboxaldehyde, using the method described for 5,7-dimethoxy-2-(pyridin-2-yl)quinazolin-4(3H)-one. 5,7-Dimethoxy-2-(pyridin-4-yl)quinazolin-4(3H)-one (142 mg, 63%) was isolated as a pale brown solid and then converted to the corresponding hydrochloride (yellow solid). Selected data: MS (m/z): 284.06; MP 294-295° C. (hydrochloride).

EXAMPLE 34

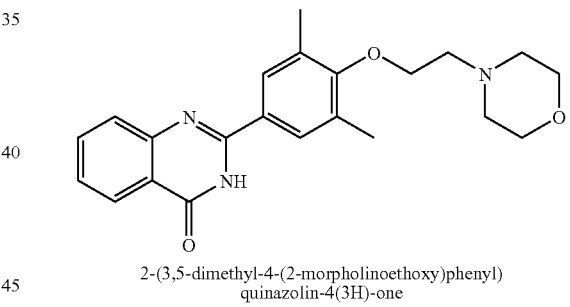

2-(3,5-dimethyl-4-(2-morpholinoethoxy)phenyl)
quinazolin-4(3H)-one

To a solution of 4-hydroxy-3,5-dimethyl benzaldehyde (3.0 g, 20 mmol) in anhydrous THF (100 mL), triphenyl phosphene (10.49 g, 40 mmol), 4-(2-hydroxyethyl)morpholine (5.25 g, 40 mmol) and N,N-diisopropylethylamine (7.76 g, 60 mmol) were added. To this stirred solution was added diethylazodicarboxylate (6.97 g, 40 mmol). The reaction mixture was stirred at room temperature overnight under nitrogen and diluted with ethyl acetate (200 mL). The organic layer was washed with water and brine and dried over anhydrous $Na_2SO_4$. The solvent was removed under reduced pressure. The crude material was purified by column chromatography (silica gel 230-400 mesh; 0-3% methanol in $CH_2Cl_2$ as eluent) to give 3,5-dimethyl-4-(2-morpholin-4-yl-ethoxy) benzaldehyde (1.66 g, 32%) as an oil.

To a solution of 2-amino benzamide (136 mg, 1.0 mmol) in N,N-dimethyl acetamide (5 mL) were added 3,5-dimethyl-4-(2-morpholin-4-yl-ethoxy)benzaldehyde (263 mg, 1.0 mmol), sodium hydrogen sulphite (58.5%) (196 mg, 1.1 mmol) and p-toluenesulfonic acid (19 mg, 0.1 mmol). The reaction mixture was stirred at 150° C. overnight. Water (40 mL) was added. The formed solid was filtered off, washed with water and a small amount of methanol and dried under vacuum to give the title compound (190 mg, 50%) as an off-white solid. To a solution of the above compound (174 mg, 0.458 mmol) in 2:1 anhydrous CH$_2$Cl$_2$-methanol (15 mL) was added 1.0 M solution of hydrogen chloride in ether (1.5 mL) and the reaction mixture was stirred at room temperature for 16 h. The solvent was removed under reduced pressure. The residue was triturated with 10% methanol in anhydrous ether to give the hydrochloride of 2-(3,5-dimethyl-4-(2-morpholinoethoxy)phenyl)quinazolin-4(3H)-one (187 mg, 98%), as an off-white solid. Selected data: MS (ES) m/z: 380.10; MP 300-302° C. (hydrochloride).

EXAMPLE 35

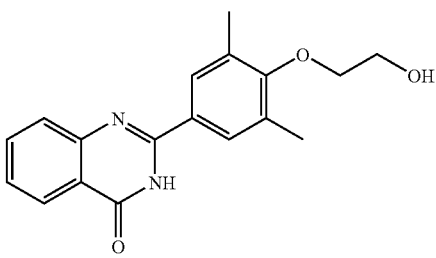

2-(4-(2-hydroxyethoxy)-3,5-dimethylphenyl)
quinazolin-4(3H)-one

A mixture of anthranilamide (0.15 g, 1.10 mmol), 4-[2(tert-butyl-dimethyl-silanyloxy)-ethoxy]-3,5-dimethyl-benzaldehyde (0.340 g, 1.101 mmol), sodium hydrogensulfite (0.126 g, 1.101 mmol) and p-toluenesulfonic acid (20 mg) in N,N-dimethyl acetamide (5 mL) was stirred at 150° C. for 3 h under nitrogen. The reaction mixture was cooled to room temperature and diluted with water (20 mL). The solid was collected by filtration, washed with water (10 mL×3) and dried under high vacuum to provide desired compound (328 mg, 70%), as a white solid. A solution of the above described compound (0.316 g, 0.745 mmol) in THF (3 mL) was cooled to 0° C. under nitrogen and TBAF (1.5 mL, 1.49 mmol) was added, followed by stirring at room temperature for 1 h. The reaction mixture was diluted with cold water (30 mL), the white precipitate was filtered off, washed with water (15 mL×3) and MeOH (20 mL×3) and dried under high vacuum, to afford 2-(4-(2-hydroxyethoxy)-3,5-dimethylphenyl) quinazolin-4(3H)-one (150 mg, 65%), as a white solid. Selected data: MS (ES) m/z: 311.04; MP 260-261° C.

EXAMPLE 36

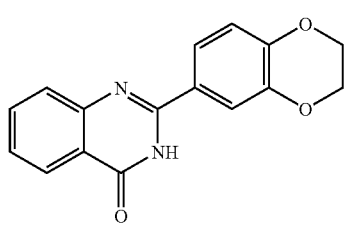

2-(2,3-dihydrobenzo[b][1,4]dioxin-6-yl)
quinazolin-4(3H)-one 2-(2,3-Dihydrobenzo[b][1,4]dioxin-6-yl)quinazolin-4 (3H)-one was synthesized from anthranilamide and 4-(pyrimidin-2-yloxy)-benzaldehyde, using the method described for 5,7-dimethoxy-2-(pyridin-2-yl)quinazolin-4(3H)-one. 2-(2,3-Dihydrobenzo[b][1,4]dioxin-6-yl)quinazolin-4(3H)-one (222 mg, 72%) was isolated as a light beige solid. Selected data: MS (m/z): 280.98; MP 267-268° C. (decomposed).

EXAMPLE 37

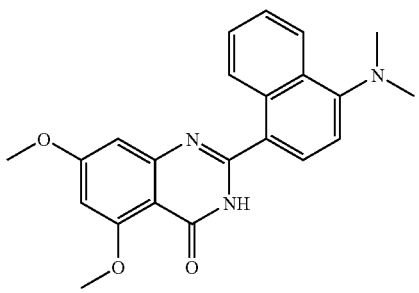

2-(4-(dimethylamino)naphthalen-1-yl)-5,7-
dimethoxyquinazolin-4(3H)-one 2-(4-(Dimethylamino)naphthalen-1-yl)-5,7-dimethoxyquinazolin-4(3H)-one was synthesized from 2-amino-4,6-dimethoxybenzamide and 4-dimethylamino-1-naphthaldehyde, using the method described for 5,7-dimethoxy-2-(pyridin-2-yl)quinazolin-4(3H)-one. 2-(4-(Dimethylamino) naphthalen-1-yl)-5,7-dimethoxyquinazolin-4(3H)-one (75 mg, 26%) was isolated as a yellow solid. Selected data: MS (m/z): 376.07; MP 269-271° C.

EXAMPLE 38

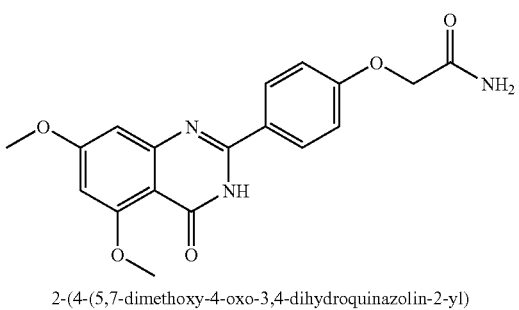

2-(4-(5,7-dimethoxy-4-oxo-3,4-dihydroquinazolin-2-yl)
phenoxy)acetamide

2-Amino-4,6-dimethoxy-benzamide (150 mg, 0.764 mmol), 2-(4-formyl-phenoxy)-acetamide (137 mg, 0.764 mmol), sodium hydrogen sulfite (150 mg, 58.5%) and p-toluenesulfonic acid monohydrate (15 mg) in N,N-dimethyl acetamide (15 mL) were heated to 150° C. overnight. N,N-dimethyl acetamide was removed under vacuum and the residue was poured into water (50 mL). The solid was filtered off and washed with methanol to yield 2-(4-(5,7-dimethoxy-4-oxo-3,4-dihydroquinazolin-2-yl)phenoxy)acetamide (74 mg, 27.2%). Selected data: MS (m/z): 356.09; MP 309-311° C. HPLC purity: 88.57%.

EXAMPLE 39

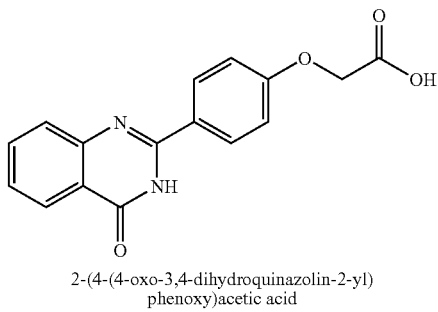

2-(4-(4-oxo-3,4-dihydroquinazolin-2-yl)
phenoxy)acetic acid 2-(4-(4-Oxo-3,4-dihydroquinazolin-2-yl)phenoxy)acetic acid was synthesized from anthranilamide and 4-formyl phenoxy acetic acid, using the method described for 5,7-dimethoxy-2-(pyridin-2-yl)quinazolin-4(3H)-one. 2-(4-(4-Oxo-3,4-dihydroquinazolin-2-yl)phenoxy)acetic acid (800 mg, 73%) was isolated as a white solid. Selected data: MS (m/z): 296.98; MP 285-287° C.

EXAMPLE 40

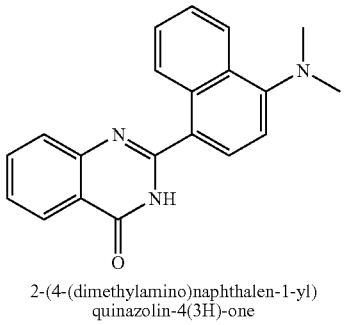

2-(4-(dimethylamino)naphthalen-1-yl)
quinazolin-4(3H)-one 2-(4-(Dimethylamino)naphthalen-1-yl)quinazolin-4(3H)-one was synthesized from anthranilamide and 4-dimethylamino-naphthalene-1-carbaldehyde, using the method described for 5,7-dimethoxy-2-(pyridin-2-yl)quinazolin-4(3H)-one. 2-(4-(Dimethylamino)naphthalen-1-yl)quinazolin-4(3H)-one (240 mg, 69%) was isolated as a pale yellow solid. Selected data: MS (m/z): 316.08; MP 224-226° C.

EXAMPLE 41

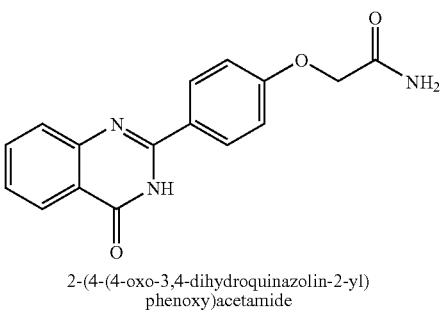

2-(4-(4-oxo-3,4-dihydroquinazolin-2-yl)
phenoxy)acetamide 2-(4-(4-Oxo-3,4-dihydroquinazolin-2-yl)phenoxy)acetamide was synthesized from anthranilamide and 2-(4-formyl-phenoxy)-acetamide, using the method described for 5,7-dimethoxy-2-(pyridin-2-yl)quinazolin-4(3H)-one. 2-(4-(4-Oxo-3,4-dihydroquinazolin-2-yl)phenoxy)acetamide (183 mg, 56%) was isolated as a light beige solid. Selected data: MS (m/z): 295.97; MP 277.5-278.5° C.

EXAMPLE 42

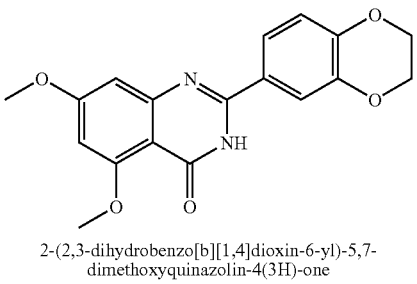

2-(2,3-dihydrobenzo[b][1,4]dioxin-6-yl)-5,7-
dimethoxyquinazolin-4(3H)-one 2-(2,3-Dihydrobenzo[b][1,4]dioxin-6-yl)-5,7-dimethoxyquinazolin-4(3H)-one was synthesized from 2-amino-4,6-dimethoxybenzamide and 2,3-dihydro-benzo[1,4]dioxine-6-carbaldehyde, using the method described for 5,7-dimethoxy-2-(pyridin-2-yl)quinazolin-4(3H)-one. 2-(2,3-Dihydrobenzo[b][1,4]dioxin-6-yl)-5,7-dimethoxyquinazolin-4(3H)-one (120 mg, 46%) was isolated as a yellow solid. Selected data: MS (m/z): 341.03; MP 307.5-309.6° C.

EXAMPLE 43

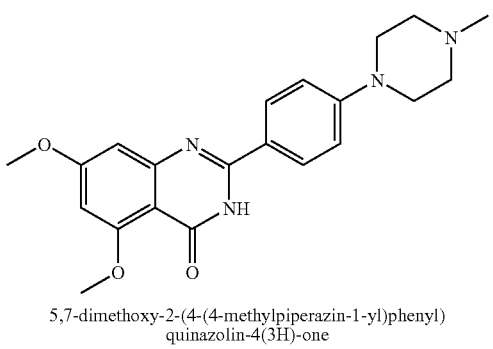

5,7-dimethoxy-2-(4-(4-methylpiperazin-1-yl)phenyl)
quinazolin-4(3H)-one

A solution of 4-(4-formyl-phenyl)-piperazine-1-carboxylic acid tert-butyl ester (1.3 g, 4.47 mmol) in THF (50 mL) was mixed with LAH (0.7 g, 17.87 mmol) and stirred at reflux for 14 h. The reaction was quenched at room temperature by adding KOH aqueous (14 N, 20 mL). The supernatant was decanted and combined with DCM washings, then diluted with water (50 mL). The mixture was extracted with DCM (3×50 mL) followed by concentration using a rotary evaporator to give [4-(4-methyl-piperazin-1-yl)-phenyl]-methanol (0.82 g, 89%). To a solution of DMSO (0.56 mL, 7.96 mmol) in DCM (50 mL) at −78° C. was added oxalyl chloride (0.7 mL, 7.96 mmol) and the resulting mixture was stirred at −78° C. for 0.5 h. A solution of [4-(4-methyl-piperazin-1-yl)-phenyl]-methanol (0.82 g, 3.98 mmol) in DCM (20 mL) was slowly added. The reaction was stirred at −78° C. for 1.5 h. Triethylamine (1.7 mL, 11.94 mmol) was added and the reaction was allowed to gradually warm up to room temperature. After stirring for 4 h the reaction was quenched by adding sodium bicarbonate aqueous (1 N, 50 mL). The mixture was extracted with DCM (3×50 mL) followed by concentration to afford a residue, which was further purified by column chromatography to yield 4-(4-methyl-piperazin-1-yl)-benzaldehyde (0.5 g, 61%).

5,7-Dimethoxy-2-(4-(4-methylpiperazin-1-yl)phenyl) quinazolin-4(3H)-one was synthesized from 2-amino-4,6-dimethoxybenzamide and 4-(4-methyl-piperazin-1-yl)-benzaldehyde, using the method described for 5,7-dimethoxy-2-(pyridin-2-yl)quinazolin-4(3H)-one. 5,7-Dimethoxy-2-(4-(4-methylpiperazin-1-yl)phenyl)quinazolin-4(3H)-one (120 mg, 41%) was converted to the corresponding hydrochloride (a yellow solid). Selected data: MS (m/z): 381.11; MP 252.4-254.2° C. (di-hydrochloride).

EXAMPLE 44

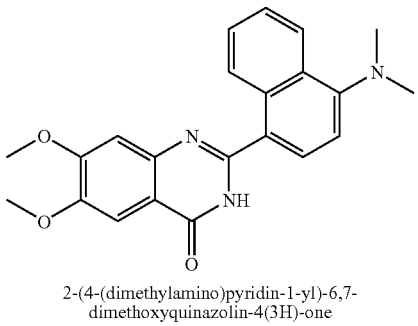

2-(4-(dimethylamino)pyridin-1-yl)-6,7-dimethoxyquinazolin-4(3H)-one

A solution of 4,5-dimethoxy-2-nitrobenzamide (10 g, 44.24 mmol) in MeOH (260 mL) was mixed with palladium/carbon (2 g) and subjected to hydrogenation (50 psi) for 20 h. The reaction mixture was filtered through a Celite pad, concentrated to yield 8.7 g of 2-amino-4,5-dimethoxybenzamide (100%).

2-(4-(Dimethylamino)naphthalen-1-yl)-6,7-dimethoxyquinazolin-4(3H)-one was synthesized from 2-amino-4,5-dimethoxy-benzamide and 4-Dimethylamino-naphthalene-1-carbaldehyde, using the method described for 5,7-dimethoxy-2-(pyridin-2-yl)quinazolin-4(3H)-one. 2-(4-(dimethylamino)naphthalen-1-yl)-6,7-dimethoxy-quinazolin-4(3H)-one (159 mg, 56%) was isolated as a white solid. Selected data: MS (m/z): 376.13; MP 235.5-236.5° C.

EXAMPLE 45

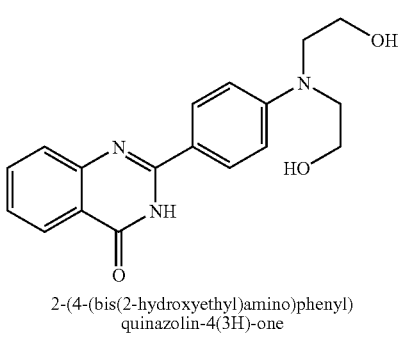

2-(4-(bis(2-hydroxyethyl)amino)phenyl)quinazolin-4(3H)-one 2-(4-(Bis(2-hydroxyethyl)amino)phenyl)quinazolin-4(3H)-one was synthesized from anthranilamide and 4-[bis-(2-hydroxy-ethyl)-amino]-benzaldehyde, using the method described for 5,7-dimethoxy-2-(pyridin-2-yl)quinazolin-4(3H)-one. 2-(4-(Bis(2-hydroxyethyl)amino)phenyl)quinazolin-4(3H)-one (150 mg, 42%) was isolated as a brown solid. Selected data: MS (m/z): 326.03; MP 228-230° C.

EXAMPLE 46

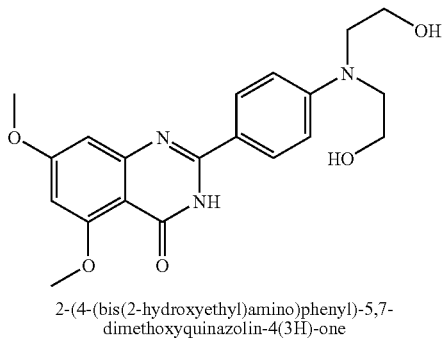

2-(4-(bis(2-hydroxyethyl)amino)phenyl)-5,7-dimethoxyquinazolin-4(3H)-one 2-(4-(Bis(2-hydroxyethyl)amino)phenyl)-5,7-dimethoxyquinazolin-4(3H)-one was synthesized from 2-amino-4,6-dimethoxybenzamide and 4-[bis-(2-hydroxy-ethyl)-amino]-benzaldehyde, using the method described for 5,7-dimethoxy-2-(pyridin-2-yl)quinazolin-4(3H)-one. 2-(4-(bis(2-hydroxyethyl)amino)phenyl)-5,7-dimethoxy-quinazolin-4(3H)-one (120 mg, 41%) was isolated as a yellow solid. Selected data: MS (m/z): 386.15; MP 249-251° C.

EXAMPLE 47

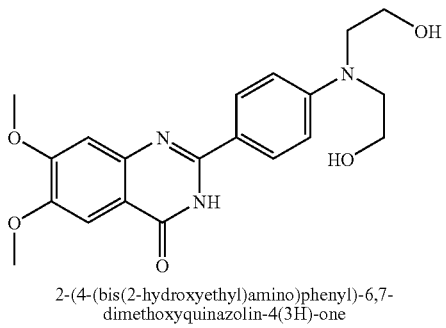

2-(4-(bis(2-hydroxyethyl)amino)phenyl)-6,7-dimethoxyquinazolin-4(3H)-one 2-(4-(Bis(2-hydroxyethyl)amino)phenyl)-6,7-dimethoxyquinazolin-4(3H)-one was synthesized from 2-amino-4,5-dimethoxy-benzamide and 4-(N,N-bis(2-hydroxyethyl) amino)benzaldehyde, using the method described for 5,7-dimethoxy-2-(pyridin-2-yl)quinazolin-4(3H)-one. 2-(4-(Bis (2-hydroxyethyl)amino)phenyl)-6,7-dimethoxyquinazolin-4 (3H)-one (72 mg, 24%) was isolated as a yellow solid. Selected data: MS (m/z): 386.15; MP 268-270° C.

EXAMPLE 48

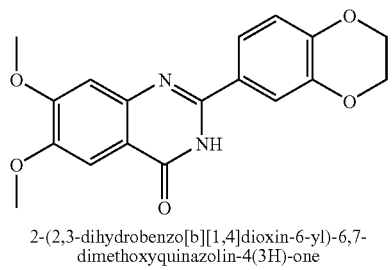

2-(2,3-dihydrobenzo[b][1,4]dioxin-6-yl)-6,7-dimethoxyquinazolin-4(3H)-one 2-(2,3-Dihydrobenzo[b][1,4]dioxin-6-yl)-6,7-dimethoxyquinazolin-4(3H)-one was synthesized from 2-amino-4,5-dimethoxybenzamide and 2,3-dihydro-benzo[1,4]dioxine-6-carbaldehyde, using the method described for 5,7-dimethoxy-2-(pyridin-2-yl)quinazolin-4(3H)-one. 2-(2,3-Dihydrobenzo[b][1,4]dioxin-6-yl)-6,7-dimethoxy-quinazolin-4(3H)-one (180 mg, 69%) was isolated as a light yellow solid. Selected data: MS (m/z): 341.03; MP 316.4-318.2° C.

EXAMPLE 49

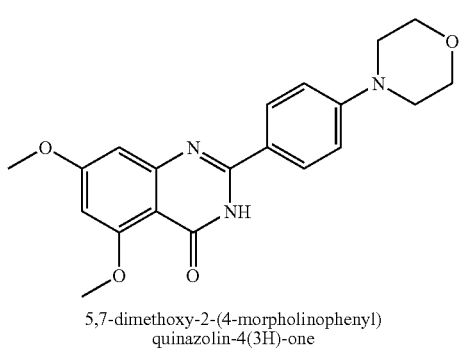

5,7-dimethoxy-2-(4-morpholinophenyl)quinazolin-4(3H)-one

A solution of 4-iodobenzaldehyde (1 g, 4.31 mmol) in MeOH (50 mL) was mixed with trimethyl orthoformate (4 mL, 36.10 mmol) and p-toluenesulfonic acid (5 mg). The reaction was stirred at room temperature for 3 h and then quenched by adding excess of sodium bicarbonate solid and stirred for 1 h. The solid was removed by filtration and the filtrate was concentrated to yield 1-dimethoxymethyl-4-iodobenzene (1.2 g, 100%). A mixture of 1-dimethoxymethyl-4-ido-benzene (1.2 g, 4.31 mmol), cesium carbonate (1.4 g, 4.31 mmol), morpholine (0.375 g, 4.31 mmol), and palladium tetrakis(triphenyl)phosphine (0.25 g, 0.216 mmol) in toluene (60 mL) and tert-butanol (10 mL) was thoroughly degassed and stirred at 110° C. for 28 h. The reaction was quenched by adding water (50 mL), extracted with DCM (3×100 mL), concentrated to afford a solid residue. Purification by column chromatography left 4-(4-dimethoxymethyl-phenyl)-morpholine (0.61 g, 60%). A solution of 4-(4-dimethoxymethyl-phenyl)-morpholine (0.61 g, 2.58 mmol) in THF (20 mL) was mixed with HCl in ether (10 mL, 10 mmol) and stirred at room temperature for 2 h. The reaction mixture was then neutralized with 1 N sodium bicarbonate aqueous to pH 9 and extracted with DCM (3×100 mL), to afford 4-morpholin-4-yl-benzaldehyde (0.37 g, 75%).

A mixture of 2-amino-4,6-dimethoxybenzamide (0.15 g, 0.765 mmol), 4-morpholin-4-yl-benzaldehyde (0.15 g, 0.765 mmol), sodium hydrogensulfite (0.136 g, 0.765 mmol) and p-toluenesulfonic acid (10 mg) in N,N-dimethyl acetamide (10 mL) was stirred at 155° C. for 14 h. The reaction mixture was cooled to room temperature and diluted with water (50 mL). The solid was collected by filtration, washed with water and MeOH to yield 5,7-dimethoxy-2-(4-morpholinophenyl)quinazolin-4(3H)-one (0.109 g, 39%).

A solution of 5,7-dimethoxy-2-(4-morpholinophenyl)quinazolin-4(3H)-one (0.109 g, 0.297 mmol) in DCM (5 mL) and MeOH (5 mL) was mixed with HCl in ether (3 mL, 3 mmol), stirred for 1.5 h, concentrated. The solid formed was rinsed with Hexanes, collected by filtration and washed with hexanes and DCM to yield the hydrochloride (0.115 g, 95%) as a brown solid. Selected data: MS (m/z): 368.13; MP 217.5-219.4° C. (hydrochloride).

EXAMPLE 50

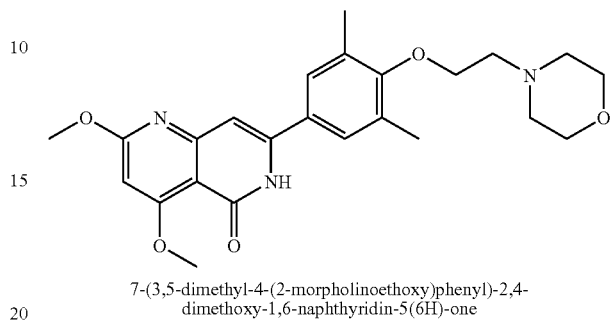

7-(3,5-dimethyl-4-(2-morpholinoethoxy)phenyl)-2,4-dimethoxy-1,6-naphthyridin-5(6H)-one Malonic acid (41.62 g, 0.4 mol), 2,4,6-trichlorophenol (157.96 g, 0.8 mol) and POCl$_3$ (134.9 g, 80.6 mL) were mixed in a flask and stirred under reflux overnight. The reaction mixture was cooled to 70° C. and poured into ice-water. The solid was filtered off, washed with water and dried (183.73 g, quantitative). The compound from above (183.73 g, 0.4 mol), ethyl 3-aminocrotonate (51.7 g, 0.4 mol) and bromobenzene (200 mL) were mixed. The reaction mixture was heated to reflux for 4 h and then stirred at room temperature overnight, diluted with ethyl acetate and filtered off. The solid was washed with ethyl acetate to obtain a light-yellow solid (107.7 g). The solid from above (107.7 g, 0.4 mol) was dissolved in POCl$_3$ (300 mL, 2.5 mol) and the reaction mixture was refluxed for 2 h. POCl$_3$ was removed and the residue was poured into water, and extracted with DCM. The solvent was removed to obtain a crude compound (73.02 g) which was used for the next step without further purification. The compound (73.02 g, 0.31 mol) was dissolved in methanol and sodium methoxide solution in methanol (25%) was added and the mixture was refluxed overnight (~14 h). The reaction mixture was quenched with acetic acid. DCM was added and the solvent was evaporated to leave a crude product (64.43 g), which was used for the next step without further purification. The compound (64.0 g) was dissolved in a mixture of methanol and THF. To this mixture was added lithium hydroxide (63.7 g, 1.52 mol) in water. The reaction mixture was refluxed for 3 d. The solvent was removed and conc. HCl (160 mL) was added and the mixture was concentrated. The residue was freeze dried. The crude salt (69.1 g) was used for the next step without further purification. The salt (34.6 g, 0.148 mol) was dissolved in DCM and oxalyl chloride (37.6 g, 25.8 mL) was added, followed by DMF (0.5 mL). The reaction mixture was stirred under nitrogen overnight. The solvent was evaporated in vacuo to obtain the crude acid chloride, which was used for the next step without further purification. The acid chloride was dissolved in DCM and ammonia gas was passed through the solution for 30 min. The reaction mixture was stirred overnight. Water was added and the solid was filtered off and washed with DCM. A small portion of pure A-ring building block (5 g) was isolated and crude materials (20 g) were saved.

To a solution of 4-hydroxy-3,5-dimethylbenzonitrile (5.04 g, 34.3 mmol) and PPh$_3$ (18.1 g, 68.6 mmol) in anhydrous THF (200 mL), were added 4-(2-hydroxyethyl)-morpholine (9.01 g, 68.6 mmol) and isopropylethylamine. To this stirred solution was added DEAD (11.95 g, 68.6 mmol) and the reaction mixture was stirred at room temperature overnight. THF was removed and ethyl acetate was added. The mixture was washed with water and brine. The crude was dissolved in DCM and washed with 1 N HCl. The aqueous layer was basified with 5% NaOH and saturated $NaHCO_3$ solution. The mixture was extracted with ethyl acetate and concentrated. The crude was dissolved in ether and hydrogen chloride in ether was added. The solvent was decanted off, dissolved in water, basified with solid $NaHCO_3$ and $NaHCO_3$ solution, extracted with ethyl acetate, and concentrated. The crude was purified by silica gel (100 g) column chromatography, employing 30-50% ethyl acetate in hexane as eluents to give the desired B-ring building block (0.455 g).

The A-ring building block (0.344 g, 1.75 mmol) was dissolved in anhydrous THF (50 mL) and cooled to −78° C. n-Butyllithium (3.3 mL, 5.25 mmol of 1.6 M in hexane) was added drop-wise and the temperature was increased to −20° C. for 40 min, to −10° C. for 1 h, and to −5 to −2° C. for 40 min, before the reaction mixture was cooled again to −78° C. and the B-ring building block (0.455 g, 1.75 mmol) in acetonitrile (10 mL) was added quickly. The reaction mixture was stirred at room temperature overnight (~20 h). The dark brown solution was quenched with acetic acid and refluxed for 1 h. Water was added and extracted with DCM. The crude was purified by silica gel (50 g) column chromatography, using hexane (500 mL), hexane:ethyl acetate (1:1, 750 mL), and then hexane:ethyl acetate:methanol (3:2:1) as eluents, to give 7-(3,5-dimethyl-4-(2-morpholinoethoxy)phenyl)-2,4-dimethoxy-1,6-naphthyridin-5(6H)-one (100 mg, 13%) as an off-white solid. Selected data: MS (m/z): 440.28; MP 212.5-212.9° C.

EXAMPLE 51

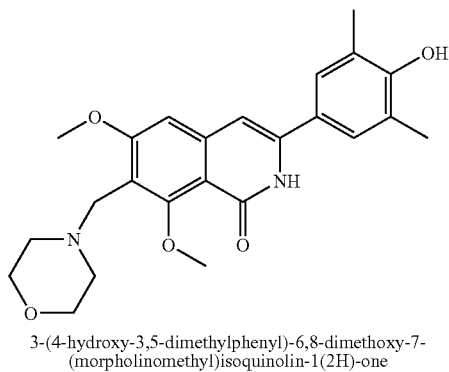

3-(4-hydroxy-3,5-dimethylphenyl)-6,8-dimethoxy-7-(morpholinomethyl)isoquinolin-1(2H)-one Methyl acetoacetate (69.67 g, 0.6 mol) in dry THF (350 mL) was cooled to −5° C. and sodium hydride in mineral oil (24.5 g, 60%) was added at −5 to 0° C. over 30 min. Diketene (50.4 g) in dry THF (80 mL) was added drop-wise at 5° C. over 20 min. The resulting solution was allowed to stir for 1.0 h at −5° C., after which it was allowed to warm to room temperature and stir overnight. Acetic acid (35 mL) was added and the THF solvent was removed. Water (200 mL) and ethyl acetate (300 mL) were added to the residue and the pH was adjusted to 5.0 by addition of HCl solution. The organic layer was separated and washed with brine and dried over sodium sulfate. After column purification and recrystalization, compound A (26.6 g, 24.3%) was obtained.

Sodium hydride in mineral oil (11.2 g, 0.279 mol, 60%) was added to compound A (24.8 g, 0.136 mol) in DMF (150 mL). The reaction was cooled to −30° C. and methyl iodide (21.3 mL, 0.341 mol) was added and the reaction was kept at room temperature overnight. Sodium iodide was filtered off and DMF was removed. The residue was mixed with water (100 mL) and extracted with ethyl acetate. The organic layer was washed with brine and dried over sodium sulfate. The crude mixture was purified by column chromatography to yield compound B (11.40 g, 39.9%). To a solution of compound B (11.4 g, 0.054 mole) in dry $CCl_4$ (90 mL) was added N-bromosuccinimide (10.6 g, 0.0596 mol). The mixture was refluxed overnight and $CCl_4$ solvent was removed. Water (100 mL) was added to the residue. After stirring for a while the solid was filtered off and washed with water, ethyl acetate (10 mL) and hexane (30 mL) to yield compound (13.1 g, 83.9%). Compound C (12.5 g, 0.043 mol), chloromethyl methyl ether (81.0 g) and anhydrous zinc chloride (7.0 g, 0.051 mol) were kept at room temperature overnight. Chloromethyl methyl ether was removed and the residue was mixed with water and the pH was adjusted to 7.0 using sodium bicarbonate. The mixture was extracted with ethyl acetate. The organic layer was washed with brine and dried over sodium sulfate. Compound D (7.39 g, 50.6%) was obtained after column chromatography. A solution of compound D (7.39 g, 0.022 mol), morpholine (7.62 g, 0.088 mol) and anhydrous THF (20 mL) was kept at room temperature overnight. The solvent was evaporated. Water and ethyl acetate were added to the residue, and pH was adjusted to 9.0 with sodium bicarbonate. The organic layer was washed with brine and dried over sodium sulfate, and concentrated. Compound E (5.4 g, 63.8%) was obtained after column chromatography. The hydrogenation reaction was carried out at 50 psi with compound E (5.4 g, 0.014 mol) in THF (100 mL) and triethyl amine (3.9 mL) with 10% Pd/C (2.6 g) as a catalyst for 2 d. After the catalyst was filtered off, the organic layer was purified by column chromatography to yield product F (3.20 g, 74.4%). Compound F (3.20 g, 0.0103 mol) was dissolved in ethanol (30 mL) and potassium hydroxide (2.31 g, 0.041 mol) in water (20 mL) was added and the reaction mixture was heated to 100° C. overnight. The solvent was removed, pH was adjusted to 6.0 and the water was removed. The residue was further dried under high vacuum and the compound was extracted with ethanol to yield compound G (2.95 g, 99%). Compound G (1.80 g, 6.1 mmol) with thionyl chloride (3 mL, 0.0411 mol) was refluxed for 1 h before the excess thionyl chloride was removed and the residue was dried under high vacuum. Anhydrous THF (20 mL) was added and ammonia gas was bubbled into the reaction mixture for 2 h. THF was removed and pH was adjusted to 8.0-9.0. The mixture was extracted with dichloromethane and dried over sodium sulfate to give compound H (1.30 g, 72.4%).

NaH in mineral oil (1.14 g, 0.0285 mol, 60%) was added to 4-hydroxy-3,5-dimethylbenzonitrile (4.0 g, 0.027 mol) in anhydrous DMF (20 mL) followed by benzyl bromide (3.27 mL, 0.027 mol). The reaction was kept at room temperature overnight. The reaction mixture was poured into water and the solid was filtered off and washed with hexane to yield Compound I (5.7 g, 89%). Compound I was used for the next step reaction without further purification. BuLi (1.60 M, 10.2 mL) was added drop-wise to compound H (0.8 g, 2.72 mmol) in anhydrous THF (25 mL) at −10° C. The reaction mixture was kept at 0° C. for one h before the cooling bath was removed. The reaction mixture was stirred for 45 minutes. Compound I (0.65 g, 2.72 mmol) in anhydrous THF (5 mL) was added drop-wise at −10° C. and the reaction was continued for a further 45 min. Water (20 mL) was added. The mixture was extracted with ethyl acetate. The solvent was removed and the residue was purified by column chromatography to yield compound J (0.180 g, 12.8%). Compound J (180 mg) in methanol (80 mL) was hydrogenated at 50 psi for 3 h, using 10% Pd/C as the catalyst. The catalyst and solvent were removed and the residue was purified by column chromatography to yield 3-(4-hydroxy-3,5-dimethylphenyl)-6,8-dimethoxy-7-(morpholinomethyl)isoquinolin-1(2H)-one (28 mg, 18.8%) as a white solid. Selected data: MS (m/z): 424.21; MP 158-161° C.

EXAMPLE 52

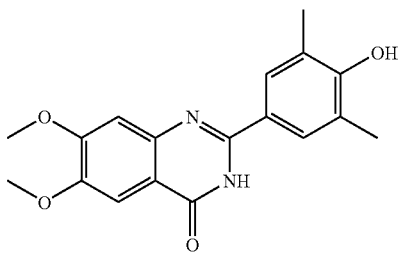

2-(4-hydroxy-3,5-dimethylphenyl)-6,7-dimethoxyquinazolin-4(3H)-one

To a solution of 2-amino-4,5-dimethoxybenzamide (0.157 g, 0.8 mmol) in N,N-dimethylacetamide (5 mL) were added 3,5-dimethyl-4-hydroxybenzaldehyde (0.120 g, 0.8 mmol), sodium hydrogen sulphite (58.5%, 0.156 g, 0.88 mmol) and p-toluenesulfonic acid (15 mg, 0.08 mmol). The reaction mixture was stirred at 150° C. for 3 h. The reaction mixture was cooled to room temperature and water (40 mL) was added. A white precipitate was formed and filtered off, washed with water and a small amount of methanol and dried under vacuum to give 2-(4-hydroxy-3,5-dimethylphenyl)-6,7-dimethoxyquinazolin-4(3H)-one (0.230 g, 88% yield) as an off-white solid. Selected data: MS (ES) m/z: 327.12; MP>300° C.

EXAMPLE 53

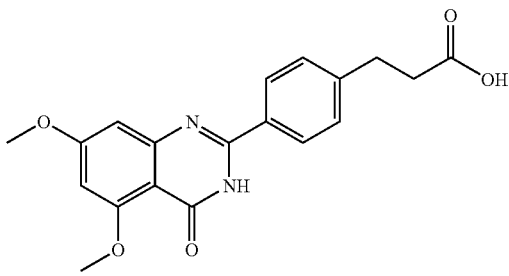

3-(4-(5,7-dimethoxy-4-oxo-3,4-dihydroquinazolin-2-yl)phenyl)propanoic acid

To a solution of 4-iodobenzaldehyde (0.116 g, 0.5 mmol), acrolein diethylacetal (0.3 mL, 1.5 mmol), tetra-n-butylammonium chloride (0.139 g, 0.5 mmol) and triethylamine in anhydrous dimethylformamide (2 mL), palladium acetate (0.003 g, 0.015 mmol) was added. The reaction mixture was heated at 90° C. and stirred for 16 h. The reaction mixture was diluted with 2 N hydrochloric acid and extracted with diethyl ether. The solvent was evaporated in vacuo to leave a residue which was purified by column chromatography (silica gel) employing 1-5% ethyl acetate in hexane as eluents to obtain 3-(4-formyl-phenyl)-propionic acid ethyl ester (0.734 g).

To a round-bottomed flask were added 2-amino-4,6-dimethoxy-benzamide (0.161 g, 0.82 mmol), 3-(4-formyl-phenyl)-propionic acid ethyl ester (0.170 g, 0.82 mmol), sodium bisulfite (0.160 g, 0.902 mmol), p-toluenesulfonic acid (0.016 g, 0.082 mmol) and N,N-dimethylacetamide (10 mL). The reaction mixture was refluxed at 155° C. for 16 h before being cooled to room temperature. Water was added and the precipitated solid was filtered off and washed with water and methanol to obtain 3-[4-(5,7-dimethoxy-4-oxo-3,4-dihydro-quinazolin-2-yl)-phenyl]-propionic acid ethyl ester (0.304 g, 97%). The compound 3-[4-(5,7-dimethoxy-4-oxo-3,4-dihydro-quinazolin-2-yl)-phenyl]-propionic acid ethyl ester (0.304 g, 0.795 mmol) was taken up in a 1:1 mixture of THF and methanol (6 mL). A solution of potassium hydroxide (0.089 g, 1.59 mmol) in water (6 mL) was added to the reaction mixture and stirred at room temperature for 16 h. The solvent was removed and the reaction mixture was acidified with 1 N hydrochloric acid. The precipitated solid was filtered off and washed with water and methanol. The solid was further washed with methanol to obtain 3-(4-(5,7-dimethoxy-4-oxo-3,4-dihydroquinazolin-2-yl)phenyl)propanoic acid (0.143 g, 51%). Selected data: MS (ES) m/z: 355.0; MP 250.6-251.1° C.

EXAMPLE 54

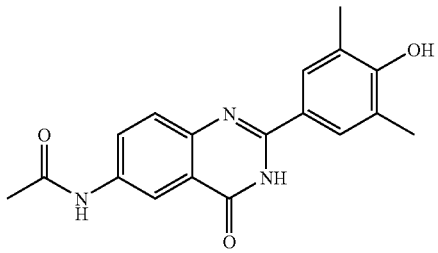

N-(2-(4-hydroxy-3,5-dimethylphenyl)-4-oxo-3,4-dihydroquinazolin-6-yl)acetamide

To a round-bottomed flask were added 2-amino-5-nitro-benzamide (0.681 g, 3.76 mmol), 4-hydroxy-3,5-dimethyl-benzaldehyde (0.565 g, 3.76 mmol), sodium bisulfite (0.747 g, 4.2 mmol), p-toluenesulfonic acid, monohydrate (0.072 g, 0.376 mmol) and N,N-dimethylacetamide (60 mL). The reaction mixture was refluxed at 155° C. for 16 h before being cooled to room temperature. Water was added and the precipitated solid was filtered off, washed with water and methanol to obtain a crude which was purified by column chromatography (silica gel (50 g) employing 1-20% methanol in dichloromethane as eluents, to obtain 2-(4-hydroxy-3,5-dimethyl-phenyl)-6-nitro-3H-quinazolin-4-one (0.220 g, 19%). The compound 2-(4-hydroxy-3,5-dimethyl-phenyl)-6-nitro-3H-quinazolin-4-one (0.220 g, 0.71 mmol) was hydrogenated in dimethyl formamide (20 mL) using palladium on activated carbon (0.076 g, 0.071 mmol) at room temperature for 14 h. The solvent was evaporated and the crude was purified by column chromatography (silica gel 25 g) employing 1-5% methanol in dichloromethane as eluents to obtain 6-amino-2-(4-hydroxy-3,5-dimethyl-phenyl)-3H-quinazolin-4-one (0.132 g). The compound 6-amino-2-(4-hydroxy-3,5-dimethyl-phenyl)-3H-quinazolin-4-one was dissolved in pyridine under nitrogen. Acetic anhydride was added at room temperature and stirred for 4 h. Pyridine was removed and the residue was dried. Methanol was added to the flask and a solution of potassium carbonate in water was added and stirred for 4 h. The solvent was removed, acidified with 1 N hydrochloric acid and the precipitated solid was filtered off and dried to obtain N-(2-(4-hydroxy-3,5-dimethylphenyl)-4-oxo-3,4-dihydroquinazolin-6-yl)acetamide (0.037 g, 17%). Selected data: MS (ES) m/z: 324.1; MP 336.5° C. (decomposed).

EXAMPLE 55

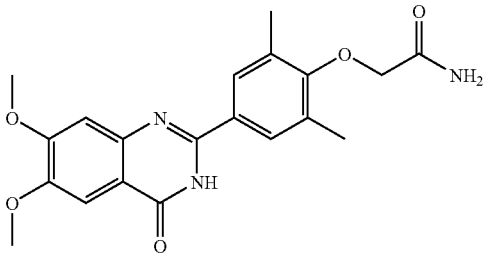

2-(4-(6,7-dimethoxy-4-oxo-3,4-dihydroquinazolin-2-yl)-
2,6-dimethylphenoxy)acetamide A solution of 4-hydroxy-3,5-dimethoxybenzaldehyde (1.0 g, 6.66 mmol) in DMF (10 mL) was cooled to 0° C. under nitrogen. NaH (0.4 g, 10 mmol, 60% in oil) was added portion-wise. The reaction was stirred for 30 min, then 2-bromoacetamide (0.918 g, 6.66 mmol) was added and stirring was continued for 36 h at room temperature. The DMF was removed under reduced pressure and water (50 mL) was added. The mixture was extracted with EtOAc (50 mL×3). The combined organic layers were washed with an aqueous solution of NaOH (50 mL, 10%), washed with water (50 mL) and brine solution (50 mL) and dried over $MgSO_4$ and concentrated to give 0.6 g of crude intermediate, which was purified by flash column chromatography to provide the desired intermediate (366 mg, 26%), as a white solid. A mixture of 2-amino-4,5-dimethoxybenzamide (0.2 g, 1.019 mmol), 2-(4-formyl-2,6-dimethyl-phenoxy acetamide (0.211 g, 1.019 mmol), sodium hydrogensulfite (0.116 g, 1.121 mmol) and p-toluenesulfonic acid (20 mg) in N,N-dimethyl acetamide (5 mL) was stirred at 150° C. for 16 h under nitrogen. The reaction mixture was cooled to room temperature and water (50 mL) was added. The white precipitate was filtered off and washed with cold water (30 mL×2) and dried under high vacuum to provide 2-(4-(6,7-dimethoxy-4-oxo-3,4-dihydroquinazolin-2-yl)-2,6-dimethylphenoxy)acetamide (300 mg, 76%) as a off white solid. Selected data: MS (ES) m/z: 384.1 (M+1); MP 354-356° C.

EXAMPLE 56

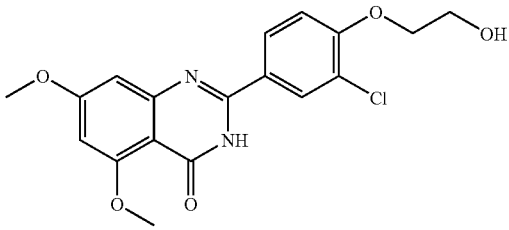

2-(3-chloro-4-(2-hydroxyethoxy)phenyl)-5,7-
dimethoxyquinazolin-4(3H)-one

A mixture of 3-chloro-4-hydroxy-benzaldehyde (227 mg, 1.45 mmol), (2-bromoethoxy)-tert-butyldimethylsilane (347 mg, 1.45 mmol), cesium carbonate (709 mg, 2.18 mmol) and DMSO (2 mL) was stirred at 80° C. for 17 h. The reaction mixture was cooled to room temperature and water (50 mL) was added. The resulting precipitate was filtered off, washed with water, air-dried, dissolved in a small amount of ethyl acetate and purified by column chromatography. 4-[2-(tert-Butyl-dimethyl-silanyloxy)-ethoxy]-3-chloro-benzaldehyde was obtained as a white solid (yield: 267 mg, 58%). To a 100 mL round-bottomed flask was added 2-amino-4,6-dimethoxy-benzamide (166 mg, 0.85 mmol), 4-[2-(tert-Butyl-dimethyl-silanyloxy)-ethoxy]-3-chloro-benzaldehyde (267 mg, 0.85 mmol), p-toluenesulfonic acid monohydrate (21 mg, 0.11 mmol), sodium hydrogensulfite (216 mg, 1.2 mmol) and dimethylacetamide (5 mL). The mixture was stirred in a 150° C. oil bath under nitrogen for 17 h. After cooling to room temperature, water (50 mL) was added. The precipitate was filtered off, washed with water and air-dried. The crude product was purified by column chromatography to give 2-(3-chloro-4-(2-hydroxyethoxy)phenyl)-5,7-dimethoxyquinazolin-4(3H)-one (45 mg, 23%). Selected data: MS (ES) m/z: 377.03; MP 287-288° C. (decomposed).

EXAMPLE 57

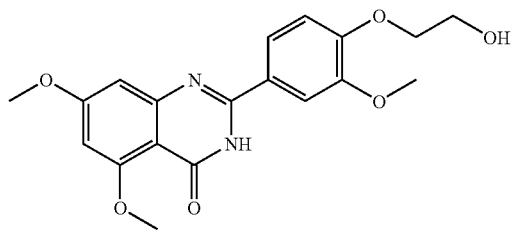

2-(4-(2-hydroxyethoxy)-3-methoxyphenyl)-5,7-
dimethoxyquinazolin-4(3H)-one

NaH (0.12 g, 0.0050 mol, 60% in mineral oil) was added to 4-hydroxy-3-methoxylbenzalde (0.636 g, 4.18 mmol) in anhydrous DMF (15 mL) and then (2-bromoethoxy)-tert-butyl-dimethylsilane (1.0 g, 4.18 mmol) was added and the reaction was kept at room temperature overnight. The reaction mixture was poured into water. The mixture was extracted with dichloromethane and the combined organic layers were passed through a column to yield 4-[2-(tert-butyl-dimethyl-silanyloxy)-ethoxy]-3-methoxybenzaldehyde (170 mg, 13%). 2-Amino-4,6-dimethoxy-benzamide (101 mg, 0.515 mmol), 4-[2-(tert-butyl-dimethyl-silanyloxy)-ethoxy]-3-methoxybenzaldehyde (160 mg, 0.515 mmol), sodium hydrogen sulfite (100 mg, 58.5%) and p-toluenesulfonic acid monohydrate (10 mg) were mixed with N,N-dimethyl acetamide (15 mL) and heated to 150° C. for 16 h. N,N-dimethyl acetamide was removed under vacuum and the residue was poured into water (50 mL). The solid was filtered off and further purified by column chromatography to yield 2-(4-(2-hydroxyethoxy)-3-methoxyphenyl)-5,7-dimethoxyquinazolin-4(3H)-one (15 mg, 7.8%). Selected data: MS (ES) m/z: 373.1; MP 246-248° C.

EXAMPLE 58

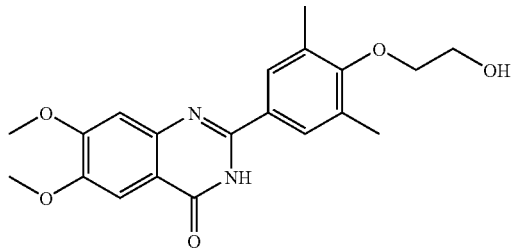

2-(4-(2-hydroxyethoxy)-3,5-dimethylphenyl)-6,7-
dimethoxyquinazolin-4(3H)-one

To a solution of 2-amino-5,6-dimethoxy-benzamide (200 mg, 1.01 mmol) and 4-[2-(tert-butyldimethylsilanoxy) ethoxy]-3,5-dimethylbenzaldehyde (314 mg, 1.01 mmol) in N,N-dimethyl acetamide (10 mL), NaHSO$_3$(199 mg, 1.12 mmol) and p-TSA (19 mg, 0.1 mmol) were added and the reaction mixture was heated at 150° C. for 3 h, cooled to room temperature and poured into water. The solid was collected and washed with methanol to give 280 mg of mixture products. To a solution of the above mixture (280 mg, 0.578 mmol) in THF (20 mL), TBAF (150 mg, 0.578 mmol) was added at 0° C. and allowed to stir at room temperature for 3 h. The reaction mixture was quenched by addition of water. The organic layer was separated and the aqueous layer was extracted with ethyl acetate. The combined organic layers were washed with water, brine and dried over Na$_2$SO$_4$. The solvent was removed to give crude product. The crude product was purified by column chromatography (silica gel 230-400 mesh; 2% methanol in CH$_2$Cl$_2$ as eluent) to give 2-(4-(2-hydroxyethoxy)-3,5-dimethylphenyl)-6,7-dimethoxyquinazolin-4(3H)-one (135 mg, 63%). Selected data: MS (ES) m/z: 371.1; MP>300° C.

EXAMPLE 59

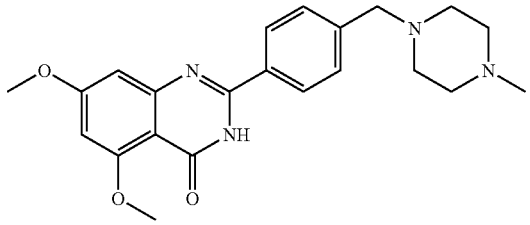

5,7-dimethoxy-2-(4-((4-methylpiperazin-1-yl) methyl)phenyl)quinazolin-4(3H)-one

To a solution of 4-bromomethyl-benzoic acid ethyl ester (4.0 g, 16.46 mmol) in THF (30 mL), N-methyl piperazine (3.29 g, 32.92 mmol) was added and the reaction mixture was stirred for 48 h at room temperature. Then, the reaction mixture was diluted with water and the mixture was extracted with ethyl acetate. The combined organic layers were washed well with water, brine, and dried over Na$_2$SO$_4$. The solvent was removed to give 4.0 g of crude product in 93% yield. Lithium aluminum hydride (0.771 g, 20.32 mmol) was taken in a 3-neck dry flask and THF was added on cooling. A solution of 4-(4-methylpiperazin-1-ylmethyl)-benzoic acid ethyl ester (4.0 g, 15.26 mmol) in THF (10 mL) was added slowly on cooling. After completion of addition, the reaction mixture was heated at reflux for 3 h. The reaction mixture was cooled to 0° C. and 10% NaOH solution was added, followed by water. The organic layer was separated and the aqueous layer was extracted with ethyl acetate. The combined organic layer was washed well with water, brine and dried over Na$_2$SO$_4$. The solvent was removed to give 2.4 g of crude product in 67% yield.

A 3-neck flask with anhydrous CH$_2$Cl$_2$ (100 mL) was cooled to the −78° C. Then, oxalyl chloride (1.66 g, 13.09 mmol) and DMSO (1.7 g, 21.8 mmol) were added at −78° C. and stirred for 15 min at −78° C. The solution of (4-(4-methylpiperazin-1-ylmethyl)phenyl)-methanol (2.4 g, 10.9 mmol) in CH$_2$Cl$_2$ (10 mL) was added at −78° C. and stirred at −78° C. for 1 h. Then Et$_3$N (4.41 g, 43.63 mmol) was added at −78° C. The reaction mixture was allowed to come to room temperature. Water was added and the organic layer was separated. The aqueous layer was extracted with CH$_2$Cl$_2$. The combined organic layer was washed with water, brine and dried over Na$_2$SO$_4$. Then, solvent was removed to give 2.23 g of crude product in 94% yield.

To a solution of 2-amino-4,6-dimethoxy-benzamide (150 mg, 0.76 mmol) and 4-(4-methyl piperazin-1-ylmethyl)ben-zaldehyde (166 mg, 0.76 mmol) in N,N-dimethyl acetamide (10 mL), NaHSO$_3$ (149 mg, 0.84 mmol) and p-TSA (319 mg, 1.68 mmol) were added and the reaction mixture was heated at 150° C. for 3 h. The mixture was cooled to room temperature and water was added and neutralized by addition of NaHCO$_3$. The solvent was removed under reduced pressure to give the crude product. The crude was purified by column chromatography (silica gel 230-400 mesh; 4% NH$_3$ in methanol/CH$_2$Cl$_2$ as eluent) to give the product 5,7-dimethoxy-2-(4-((4-methylpiperazin-1-yl)methyl)phenyl)quinazolin-4 (3H)-one as a free base, which was converted to the hydrochloride salt (115 mg, 35%). Selected data: MS (ES) m/z: 395.2; MP 275-277° C. (hydrochloride).

EXAMPLE 60

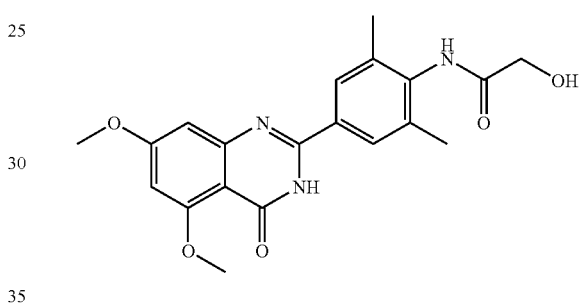

N-(4-(5,7-dimethoxy-4-oxo-3,4-dihydroquinazolin-2-yl)-2,6-dimethylphenyl)-2-hydroxyacetamide A mixture of 2,6-dimethyl-phenylamine (0.62 mL, 5.0 mmol), DMSO (100 mL), conc. Aqueous HCl (36.5-38%, 5.0 mL), and dried CuCl$_2$ was stirred at 90° C. under nitrogen for 5 h. The reaction was quenched with water. The pH of the mixture was adjusted to ~8 using a 10% sodium hydroxide solution. The mixture was extracted with ether (3×100 mL). The solution was dried over Na$_2$SO$_4$ and concentrated to dryness. The resulting brown oil was dissolved in dichloromethane (anhydrous, 20 mL) and N-ethyldiisopropylamine (DIPEA, 1.0 mL, 5.8 mmol) was added. The mixture was cooled to 0° C., acetoxyacetyl chloride (0.8 mL, 7.4 mmol) was added slowly. The mixture was stirred at room temperature under nitrogen for 17 h. The mixture was concentrated to dryness and purified by column chromatography. Acetic acid (4-formyl-2,6-dimethyl-phenylcarbamoyl)-methyl ester was obtained as yellow/beige solid (96 mg). A mixture of acetic acid (4-formyl-2,6-dimethyl-phenylcarbamoyl)-methyl ester (96 mg, 0.38 mmol), 2-amino-4,6-dimethoxy-benzamide (74 mg, 0.38 mmol), p-toluenesulfonic acid monohydrate (21 mg, 0.11 mmol), sodium hydrogensulfite (96 mg, 0.53 mmol) and dimethylacetamide (3 mL) was stirred in a 150° C. oil bath under nitrogen for 17 h. After cooling to room temperature, water (50 mL) was added. The precipitate was filtered off and washed with water. The filtrate was extracted with dichloromethane, dried over Na$_2$SO$_4$, purified by column chromatography, using (1) 5% methanol/dichloromethane, and (2) 10% methanol/dichloromethane as eluents. Acetic acid [4-(5,7-dimethoxy-4-oxo-3,4-dihydroquinazolin-2-yl)-2,6-dimethyl-phenylcarbamoyl]-methyl ester was obtained as a beige solid (70 mg, 43%). Acetic acid [4-(5,7-dimethoxy-4-oxo-3,4-dihydroquinazolin-2-yl)-2,6-dimethyl-phenylcarbamoyl]-methyl ester (70 mg, 0.16 mmol) was dissolved in methanol/dichloromethane (10 mL) and a solution of potassium carbonate (442 mg, 20 mmol) in water was added. The solution was stirred at room temperature for 17 h. 2 N HCl was added to adjust the reaction mixture pH to ~8. The mixture was then concentrated under reduced pressure. The resulting precipitate was filtered off, washed with water, air-dried, then washed with ether and dried, leaving N-(4-(5,7-dimethoxy-4-oxo-3,4-dihydroquinazolin-2-yl)-2,6-dimethylphenyl)-2-hydroxyacetamide (30 mg, 49%) as a light brown solid. Selected data: MS (ES) m/z: 384.1; MP 190-192° C.

EXAMPLE 61

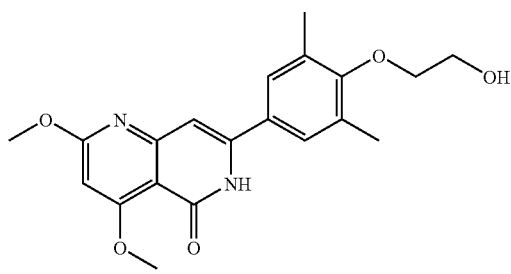

7-(4-(2-hydroxyethoxy)-3,5-dimethylphenyl)-2,4-dimethoxy-1,6-naphthyridin-5(6H)-one 2-[4-(5-amino-2,4-dimethoxy-[1,6]naphthyridin-7-yl)-2,6-dimethylphenoxyl]-ethanol (0.302 g, 0.82 mmol) in water (5 mL) and conc. Hydrochloric acid (3 mL) were mixed with stirring. The reaction mixture was cooled to 0° C. and a solution of sodium nitrite (0.305 g, 4.42 mmol) in water (3 mL) was added dropwise. The reaction mixture was stirred at 0° C. for 40 min. To the reaction mixture was added 1 N hydrochloric acid (10 mL) and heated at 55° C. for 50 min and then stirred at room temperature overnight. The reaction mixture was extracted with dichloromethane and the aqueous layer was basified with aqueous 5% NaOH and saturated NaHCO₃ solution. Water was evaporated and the organic compound was washed with a dichloromethane/methanol solution and concentrated to leave a crude which was purified by silica gel (50 g) column chromatography, employing 50% ethyl acetate in hexane and hexane/ethyl acetate/methanol (3:2:1) as eluent, to obtain 7-(4-(2-hydroxyethoxy)-3,5-dimethylphenyl)-2,4-dimethoxy-1,6-naphthyridin-5(6H)-one (0.080 g, 26%). Selected data: MS (ES) m/z: 371.1; MP 224.9-225.4° C.

EXAMPLE 62

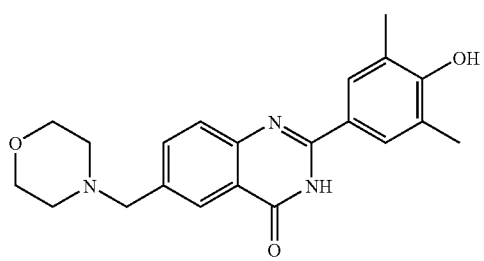

2-(4-hydroxy-3,5-dimethylphenyl)-6-(morpholinomethyl)quinazolin-4(3H)-one

2-Amino-5-morpholino-4-ylmethyl-benzamide hydrochloride salt (200 mg, 0.649 mmol), 4-hydroxy-3,5-dimethylbenzalde (97.4 mg, 0.649 mmol), sodium hydrogen sulfite (127 mg, 58.5%), and p-toluenesulfonic acid monohydrate (10 mg) in N,N-dimethyl acetamide (10 mL) were heated to 150° C. for 6 h. N,N-dimethyl acetamide was removed under vacuum. The residue was poured into water (50 mL) and dichloromethane was used to extract the compound, which was further purified by column chromatography to yield 30 mg free base of 2-(4-hydroxy-3,5-dimethylphenyl)-6-(morpholinomethyl) quinazolin-4(3H)-one. The base was treated with 1.0 M HCl to give the corresponding hydrochloride (36 mg, 11.68%). Selected data: MS (ES) m/z: 366.1; mp 284-286° C. (hydrochloride).

EXAMPLE 63

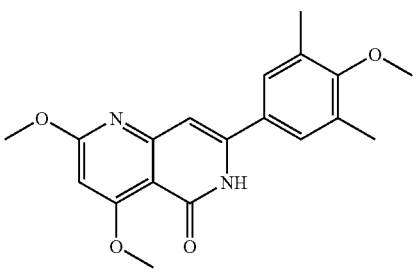

2,4-dimethoxy-7-(4-methoxy-3,5-dimethylphenyl)-1,6-naphthyridin-5(6H)-one

To a solution of 4,6-dimethoxy-2-methyl nicotinamide (2.0 g, 10.2 mmol) in THF (80 mL), n-butyl lithium (19.12 mL, 30.6 mmol, 1.6 M solution in hexane) was added slowly under nitrogen at −78° C. After completion of addition the mixture was stirred for 1 h at 0° C. Then cooled to −78° C. and a solution of 4-methoxy benzonitrile (1.65 g, 10.2 mmol) in THF (10 mL) was added quickly. The cooling bath was removed and the reaction mixture was allowed to warm to room temperature and stirred for 16 h at room temperature. Saturated NH₄Cl solution was added with cooling. The organic layer was washed with water, brine, dried over Na₂SO₄ and concentrated to give crude product. The crude product was purified by chromatography using 50% ethyl acetate in hexane and then 2% methanol in ethyl acetate to give 2,4-dimethoxy-7-(4-methoxy-3,5-dimethylphenyl)-1,6-naphthyridin-5(6H)-one (410 mg, 12%), as a yellow solid. Selected data: MS (ES) m/z: 341.1; mp 262-263° C. (at decomposition).

EXAMPLE 64

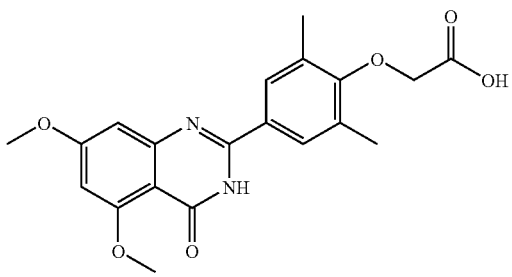

2-(4-(5,7-dimethoxy-4-oxo-3,4-dihydroquinazolin-2-yl)-2,6-dimethylphenoxy)acetic acid A solution of sodium hydroxide (2.53 g, 63.25 mmol) in water (65 mL) was added to a mixture of bromoacetic acid (5.27 g, 37.95 mmol) and 3,5-dimethyl-4-hydroxy-benzaldehyde (1.9 g, 12.65 mmol) in water (30 mL). The reaction mixture was stirred at 100° C. for 24 h. The solution was acidified to pH ~2 with conc. HCl. The brown solid was filtered off, washed with water, dried under vacuum, and purified by column chromatography to give (4-formyl-2,6-dimethylphenoxy)-acetic acid as a light brown solid (0.40 g). To a solution of 2-amino-4,6-dimethoxybenzamide (0.150 g, 0.764 mmol) in N,N-dimethyl acetamide (5 mL) were added (4-formyl-2,6-dimethyl-phenoxy)-acetic acid (0.159 g, 0.764 mmol), sodium hydrogen sulphite (58.5%, 0.150 g, 0.84 mmol) and prtoluenesulfonic acid (15 mg, 0.0764 mmol). The reaction mixture was stirred at 150° C. for 3 h. it was then cooled to room temperature and water (40 mL) was added. A yellow precipitate was formed and filtered off, washed with water and a small amount of methanol. Triturated with 10% methanol in ether to give 0.084 g of compound, which was further purified by preparative HPLC to give 2-(4-(5,7-dimethoxy-4-oxo-3,4-dihydroquinazolin-2-yl)-2,6-dimethylphenoxy)acetic acid (47 mg, 13%) as a white solid. Selected data: MS (ES) m/z: 384.0; MP 270-272° C.

EXAMPLE 65

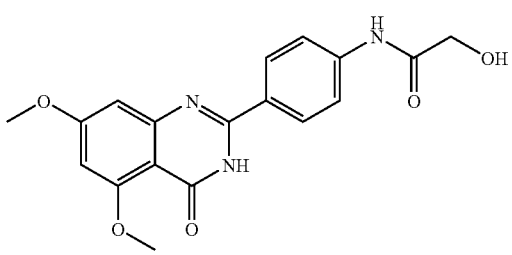

N-(4-(5,7-dimethoxy-4-oxo-3,4-dihydroquinazolin-2-yl)phenyl)-2-hydroxyacetamide

To a solution of 4-aminobenzaldehyde (1 g, 8.52 mmol) at 0° C. under nitrogen atmosphere were added triethylamine (2.3 mL, 16.5 mmol), 4-dimethylaminopyridine (0.1 g, 0.82 mmol) and acetoxyacetyl chloride (1.77 mL, 16.5 mmol). The reaction mixture was allowed to warm up to room temperature and was stirred for 2.5 h. Triethylamine (1.15 mL, 8.25 mmol) and acetoxyacetyl chloride (0.88 mL, 8.25 mmol) were added and the reaction mixture was stirred for 1 h more. The reaction mixture was poured into a 1 M hydrochloric acid solution (60 mL), then extracted with methylene chloride (20 mL×3) and the combined organic layers were washed with saturated aqueous sodium bicarbonate solution and dried over anhydrous sodium sulfate. The crude solid (3.17 g) was purified by flash column chromatography to provide pure acetic acid (4-formyl-phenylcarbamoyl)-methyl ester (1.14 g, 62% yield) as an orange solid. A mixture of 2-amino-4,6-dimethoxy-benzamide (0.15 g, 0.76 mmol), Acetic acid (4-formyl-phenylcarbamoyl)-methyl ester (0.169 g, 0.76 mmol), sodium hydrogensulfite (0.087 g, 0.84 mmol) and p-toluenesulfonic acid (15 mg, 0.076 mmol) in N,N-dimethyl acetamide (5 mL) was stirred at 150° C. for 4.5 h under nitrogen. The reaction mixture was cooled to room temperature and diluted with cold water (60 mL) to obtain a yellow solid. The yellow solid was filtered off, washed with cold water (20 mL×2), methanol and dried under vacuum to provide crude compound (230 mg, 75%).

The yellow solid was triturated with ether and methanol to provide acetic acid [4-(5,7-dimethoxy-4-oxo-3,4-dihydro-quinazolin-2-yl)-phenylcarbamoyl]-methyl ester (112 mg, 37%). To a solution of acetic acid [4-(5,7-dimethoxy-4-oxo-3,4-dihydro-quinazolin-2-yl)-phenylcarbamoyl]-methyl ester (0.23 g, 0.59 mmol) in THF/methanol mixture (3.5 mL/3.5 mL) was added potassium carbonate (0.41 g, 2.95 mmol). The reaction mixture was heated at reflux overnight and the solvent was concentrated under vacuum and diluted with water (60 mL) to obtain a precipitate. The yellow solid was filtered, washed with water (20 mL), methanol and dried under vacuum to provide crude compound. The yellow solid was triturated with ether and methanol to provide the desired compound N-(4-(5,7-dimethoxy-4-oxo-3,4-dihydroquinazolin-2-yl)phenyl)-2-hydroxyacetamide (55 mg, 55%). Selected data: MS (ES) m/z: 356.1; mp 318-319° C.

EXAMPLE 66

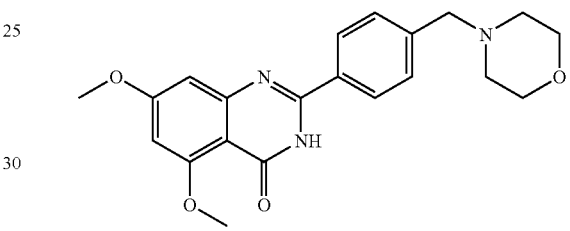

5,7-dimethoxy-2-(4-(morpholinomethyl)phenyl)quinazolin-4(3H)-one

To a solution of 4-bromoethyl-benzoic acid ethyl ester (4.0 g, 16.46 mmol) in THF (30 mL), morpholine (2.87 g, 32.92 mmol) was added and the reaction mixture was stirred for 48 h at room temperature. The reaction mixture was diluted with water and the product was extracted with ethyl acetate. The combined organic layers were washed with water, brine, and dried over $Na_2SO_4$. The solvent was removed to give 3.4 g of crude product in 83% yield.

LAH (0.571 g, 15.05 mmol) was added to a 3-neck dry flask and THF (50 mL) was added on cooling. A solution of 4-morpholin-4-ylmethyl)-benzoic acid ethyl ester (3.0 g, 12.04 mmol) in THF (10 mL) was added slowly on cooling. After completion of addition, the reaction mixture was heated at reflux for 3 h. The reaction mixture was cooled to 0° C. and a 10% NaOH solution was added carefully followed by water. The organic layer was separated and the aqueous layer was extracted with ethyl acetate. The combined organic layers were washed with water, brine and dried over $Na_2SO_4$. The solvent was removed to give (4-morpholin-4-ylmethyl phenyl)methanol (2.0 g, 80%). To the 3-flask anhydrous $CH_2Cl_2$ (100 mL) was added and cooled to −78° C. Oxalyl chloride (1.47 g, 11.59 mmol) and DMSO (1.5 g, 19.32 mmol) were added at −78° C. The reaction mixture was stirred for 15 min at −78° C. A solution of (4-morpholin-4-ylmethyl phenyl)methanol (2.0 g, 9.66 mmol) in $CH_2Cl_2$ (10 mL) was added at −78° C. and the mixture was stirred at −78° C. for 1 h. Then, $Et_3N$ (3.9 g, 38.64 mmol) was added. The reaction mixture was allowed to come at room temperature. Water was added and the organic layer was isolated. The aqueous layer was extracted with $CH_2Cl_2$. The combined organic layers were washed with water, brine and dried over Na₂SO₄. Then solvent was removed to give crude 4-morpholin-4-ylmethyl benzaldehyde (1.6 g, 81%).

To a solution of 2-amino-4,6-dimethoxy-benzamide (150 mg, 0.76 mmol) and 4-morpholin-4-ylmethyl benzaldehyde (156 mg, 0.76 mmol) in N,N-dimethyl acetamide (10 mL), NaHSO₃ (150 mg, 0.84 mmol) and p-TSA (174 mg, 0.91 mmol) were added and the reaction mixture was heated at 150° C. for 5 h. The reaction mixture was cooled to room temperature, water was added and the mixture was neutralized with NaHCO₃. The solvent was removed under reduced pressure to give the crude product, which was purified by column chromatography to give 5,7-dimethoxy-2-(4-(morpholinomethyl)phenyl)quinazolin-4(3H)-one, which was converted to the hydrochloride salt (165 mg, 51%). Selected data: MS (ES) m/z: 382.07; MP 206-208° C. (at decomposition).

EXAMPLE 67

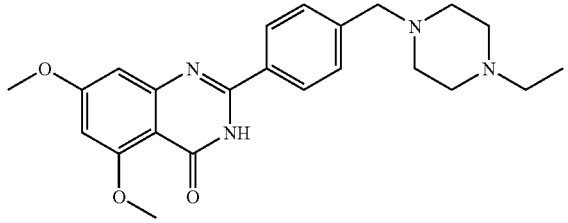

2-(4-((4-ethylpiperazin-1-yl)methyl)phenyl)-5,7-dimethoxyquinazolin-4(3H)-one

To a solution of 4-bromoethyl-benzoic acid ethyl ester (4.0 g, 16.46 mmol) in THF (30 mL), N-ethyl piperazine (3.76 g, 32.92 mmol) was added and the reaction mixture was stirred for 16 h at room temperature. The reaction mixture was diluted with water and the product was extracted with ethyl acetate. The combined organic layers were washed with water, brine, and dried over Na₂SO₄. The solvent was removed to give 4.61 g of crude 4-(4-ethyl piperazin-1-ylmethyl)-benzoic acid ethyl ester (100% yield). LAH (0.792 g, 20.86 mmol) was taken up in a 3-neck dry flask and THF (60 mL) was added on cooling. A solution of 4-(4-ethyl piperazin-1-ylmethyl)-benzoic acid ethyl ester (4.61 g, 16.69 mmol) in THF (10 mL) was added slowly on cooling. After completion of addition, the reaction mixture was heated at reflux for 2 h. The reaction mixture was cooled to 0° C., 10% NaOH solution was added, and then water was added. The organic layer was separated and the aqueous layer was extracted with ethyl acetate. The combined organic layers were washed with water, brine and dried over Na₂SO₄. The solvent was removed to give 2.78 g of crude (4-(4-ethyl piperazin-1-ylmethyl)phenyl)-methanol in 78% yield. To a 3-neck flask containing anhydrous CH₂Cl₂ (100 mL) cooled to the –78° C. oxalyl chloride (1.8 g, 14.25 mmol) and DMSO (1.85 g, 23.76 mmol) were added and the mixture was stirred for 15 min at –78° C. The solution of (4-(4-ethyl piperazin-1-ylmethyl)phenyl)-methanol (2.78 g, 11.88 mmol) in CH₂Cl₂ (10 mL) was added at –78° C. and stirred at –78° C. for 1 h. Then Et₃N (4.8 g, 47.52 mmol) was added at –78° C. The reaction mixture was allowed to come to room temperature. Water was added and the organic layer was separated. The aqueous layer was extracted with CH₂Cl₂. The combined organic layers were washed with water, brine and dried over Na₂SO₄. Then, solvent was removed to give crude 4-(4-ethyl piperazin-1-ylmethyl)benzaldehyde (2.5 g, 91%).

To a solution of 2-amino-4,6-dimethoxy-benzamide (150 mg, 0.76 mmol) and 4-(4-ethyl piperazin-1-ylmethyl)benzaldehyde (177 mg, 0.76 mmol) in N,N-dimethyl acetamide (10 mL), NaHSO₃ (150 mg, 0.84 mmol) and p-TSA (319 mg, 1.68 mmol) were added and the reaction mixture was heated at 150° C. for 5 h. The reaction mixture was cooled to room temperature, water was added and the mixture was neutralized with NaHCO₃. The solvent was removed under reduced pressure to give the crude product, which was purified by column chromatography to give 2-(4-((4-ethylpiperazin-1-yl)methyl)phenyl)-5,7-dimethoxyquinazolin-4(3H)-one (87 mg, 27%), which was converted to the hydrochloride salt. Selected data: MS (ES) m/z: 409.11; MP 278-280° C. (at decomposition).

EXAMPLE 68

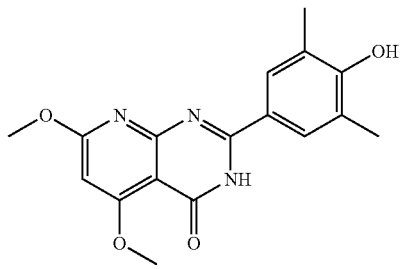

2-(4-hydroxy-3,5-dimethylphenyl)-5,7-dimethoxyprido[2,3-d]pyrimidin-4(3H)-one

A mixture of dimethyl acetone-1,3-dicarboxylate (200 g, 1.15 mol), cyanamide (48.3 g, 1.15 mol), and Ni(acac)₂ (14.75 g, 0.0574 mol) in dioxane (200 mL) was heated to reflux for 16 h and then cooled to room temperature. The precipitate was filtered off, and the solid was mixed with methanol (200 mL) and stirred for 30 min and filtered again to give 93 g product (44% yield). In a 1 L flask with a reflux condenser was added the product from step one (93.0 g, 0.505 mol) and POCl₃ (425 mL) and the reaction mixture was heated to reflux for 35 min. POCl₃ (300 mL) was evaporated under vacuum. The residue was poured into ice and water (400 mL), which was neutralized with KOH to pH 6-7. The precipitate was filtered off and extracted with ethyl acetate (2×300 mL). The organic solution was concentrated and purified by column chromatography to give methyl 2-amino-4,6-dichloropyridine-3-carboxylate (22.5 g, 20.1%). In a 500 mL flask with reflux condenser was added methyl 2-amino-4,6-dichloropyridine-3-carboxylate (22.5 g, 0.101 mol) and 25 wt % sodium methoxide in methanol (88 mL, 0.407 mol), together with methanol (20 mL). The mixture was heated to reflux for 5 h then cooled to room temperature. Acetic acid (15 mL) was added to the mixture and the pH was adjusted to ~7.0. Methanol was removed and the residue was poured into water (100 mL). The precipitated solid was filtered off and rinsed with water (3×200 mL) to give methyl 2-amino-4,6-dimethoxypyridine-3-carboxylate (18.5 g, 86.4%). In a 500 mL flask with a reflux condenser was added methyl 2-amino-4,6-dimethoxypyridine-3-carboxylate (18.5 g, 0.0872 mol), potassium hydroxide (19.5 g, 0.349 mol) in water (80 mL) and ethanol (100 mL). The mixture was heated to 80° C. for 16 h. The solvent was removed and aqueous HCl was used to adjust pH to 6.0. The water was removed by lyophilization. The obtained solid was extracted with methanol to yield 2-amino-4,6-dimethoxy-nicotinic acid in quantitative yield. 2-Amino-4,6-dimethoxy-nicotinic acid (17.2 g, 0.0872 mol) was added to THF (110 mL). 1-[3-(dimethylamino)propyl]-3-ethylcarbodiimide hydrochloride (21.73 g, 0.113 mol), 1-hydroxybenzotriazole hydrate (12.96 g, 0.0959 mol) and 4-methyl morpholine (9.7 g, 0.0959 mol) were then added to the suspension. After stirring for 10 min at room temperature, 50% v/v ammonium hydroxide (18.3 g, 0.262 mol) was added. The reaction mixture was kept at room temperature for 16 h. THF was removed and the residue was poured into cold water (100 mL). The precipitate was filtered off and further washed with cold water to yield 5.3 g of the pure desired compound. The aqueous solution was further extracted with dichloromethane (3×150 mL) to yield 8.4 g crude product, which was further purified by column chromatography to give a total of 10.8 g (62.8%) of 2-amino-4,6-dimethoxy-nicotinamide.

To a solution of 2-amino-4,6-dimethoxy-nicotinamide (1.40 g, 7.1 mmol) and 4-hydroxy-3,5-dimethylbenzaldehyde (1.07 g, 7.1 mmol) in N,N-dimethyl acetamide (20 mL), NaHSO$_3$ (1.39 g, 7.81 mmol) and p-TSA (0.675 g, 3.55 mmol) were added and the reaction mixture was heated at 150° C. overnight. The solvent was removed under reduced pressure. The residue was diluted with water and the solid was collected and further washed with methanol. The crude product was purified by column chromatography (silica gel 230-400 mesh; 2% methanol in CH$_2$Cl$_2$ as eluent) to give 2-(4-hydroxy-3,5-dimethylphenyl)-5,7-dimethoxypyrido[2,3-d]pyrimidin-4(3H)-one (0.92 g, 39.6%). Selected data: MS (ES) m/z: 328.07; MP 297-299° C.

EXAMPLE 69

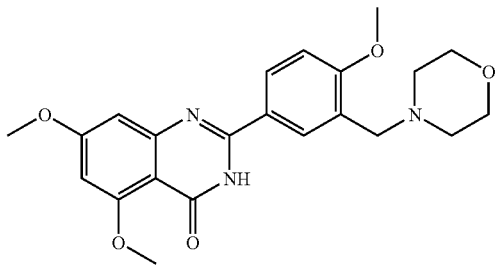

5,7-dimethoxy-2-(4-methoxy-3-(morpholinomethyl)phenyl)quinazolin-4(3H)-one 5,7-Dimethoxy-2-(4-methoxy-3-(morpholinomethyl)phenyl)quinazolin-4(3H)-one was synthesized from 2-amino-4,6-dimethoxybenzamide and 4-methoxy-3-morpholin-4-ylmethyl-benzaldehyde, using the method described for 5,7-dimethoxy-2-(pyridin-2-yl)quinazolin-4(3H)-one. 5,7-Dimethoxy-2-(4-methoxy-3-(morpholinomethyl)phenyl)quinazolin-4(3H)-one (65 mg, 28%) was isolated as a light yellow solid. Selected data: MS (m/z): 412.07; MP 282.7-284.5° C.

EXAMPLE 70

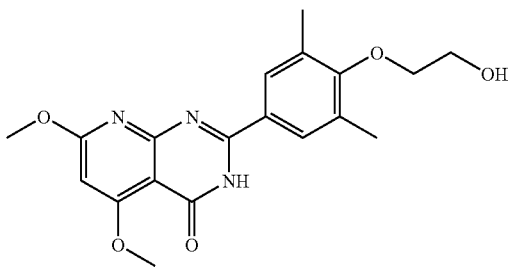

2-(4-(2-hydroxyethoxy)-3,5-dimethylphenyl)-5,7-dimethoxypyrido[2,3-d]pyrimidin-4(3H)-one To a solution of 2-amino-4,6-dimethoxy-nicotinamide (1.07 g, 5.42 mmol) and 4-[2-(tert-butyidimethylsilanoxy)ethoxy]-3,5-dimethylbenzaldehyde (1.67 g, 5.42 mmol) in N,N-dimethyl acetamide (25 mL), NaHSO$_3$ (1.06 g, 5.97 mmol) and p-TSA (1.14 g, 5.97 mmol) were added and the reaction mixture was heated at 150° C. for 16 h, cooled to room temperature and poured into water. The solid was collected to give 3.25 g of crude product. To a solution of the crude product (3.25 g, 6.70 mmol) in THF (50 mL), TBAF (3.5 g, 13.4 mmol) was added at 0° C. and the mixture was stirred at room temperature for 1 h. The reaction mixture was quenched with water. The organic layer was separated and the aqueous layer was extracted with ethyl acetate. The combined organic layers were washed with water, brine and dried over Na$_2$SO$_4$. The solvent was removed, and the crude was purified by column chromatography (silica gel 230-400 mesh; 2% methanol in CH$_2$Cl$_2$ as eluent) to give 2-(4-(2-hydroxyethoxy)-3,5-dimethylphenyl)-5,7-dimethoxypyrido[2,3-d]pyrimidin-4(3H)-one (132 mg, 6%). Selected data: MS (ES) m/z: 371.99; MP 255-256° C.

EXAMPLE 71

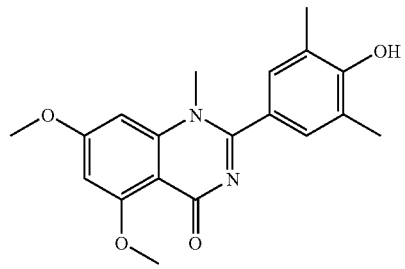

2-(4-hydroxy-3,5-dimethylphenyl)-5,7-dimethoxy-1-methylquinazolin-4(1H)-one

2-Amino-4,6-dimethoxybenzamide (0.5 g, 2.55 mmol) and methyl iodide (0.17 mL, 2.81 mmol) were mixed in a closed bomb and heated at 110° C. for 14 h. The compound was washed with a dichloromethane-methanol mixture. After removing the solvent, the crude was purified by silica gel column chromatography (40 g) employing 1-5% methanol in dichloromethane to give 2,4-dimethoxy-6-methylaminobenzamide (0.027 g, 50.4%).

The compound 3,5-dimethyl-4-hydroxybenzoic acid (5.04 g, 30.33 mmol) was mixed with pyridine (20 mL). Acetic anhydride (3.72 g, 36.4 mmol) was added and the mixture was stirred at room temperature for 4 h. The solvent was evaporated in vacuo to obtain 4-acetoxy-3,5-dimethyl-benzoic acid in quantitative yield (6.33 g). The compound 4-acetoxy-3,5-dimethyl-benzoic acid (0.36 g, 1.73 mmol)) was dissolved in dichloromethane (5 mL) and oxalyl chloride (0.3 mL, 3.46 mmol) was added dropwise, followed by 1 drop of DMF. The reaction mixture was stirred at room temperature under nitrogen for 2 h. The solvent was evaporated in vacuo to obtain acetic acid 4-chlorocarbonyl-2,6-dimethyl-phenyl ester in quantitative yield (0.392 g).

A solution of 2,4-dimethoxy-6-methylamino-benzamide (0.28 g, 1.33 mmol) in pyridine (10 mL) was added to acetic acid 4-chlorocarbonyl-2,6-dimethyl-phenyl ester (1.1 eq.) and stirred at room temperature for 14 h. The solvent was removed and the reaction mixture was acidified with 1 N HCl and extracted with ethyl acetate. The solvent was removed and the crude was purified by silica gel column chromatography (40 g) employing 1% methanol in dichloromethane to give acetic acid 4-(5,7-dimethoxy-1-methyl-4-oxo-1,4-dihydroquinazolin-2-yl)-2,6-dimethyl-phenyl ester (0.34 g, 67%). Acetic acid 4-(5,7-dimethoxy-1-methyl-4-oxo-1,4-dihydro-quinazolin-2-yl)-2,6-dimethyl-phenyl ester (0.34 g, 0.89 mmol) was dissolved in ethanol (5 mL), 5% aqueous NaOH solution (10 mL) was added dropwise and the mixture was stirred at room temperature for 1.5 h. The compound was extracted with ethyl acetate and washed with ether to give 2-(4-hydroxy-3,5-dimethylphenyl)-5,7-dimethoxy-1-methylquinazolin-4(1H)-one (0.13 g, 43%). Selected data: MS (ES) m/z: 340.17; MP 188.5-189.1° C.

EXAMPLE 72

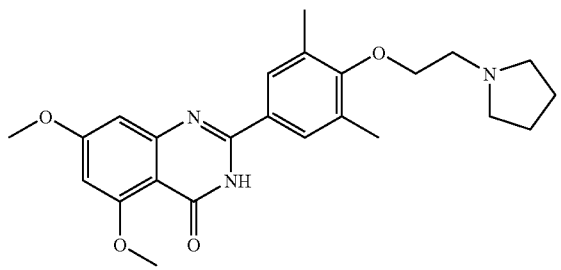

2-(3,5-dimethyl-4-(2-(pyrrolidin-1-yl)ethoxy)phenyl)-5,7-dimethoxyquinazolin-4(3H)-one A solution of 3,5-dimethoxy-4-hydroxybenzaldehyde (3 g, 20 mmol) and 1-(2-chloro-ethyl)-pyrrolidine hydrochloride (3.74 g, 22 mmol) in DMF (50 mL) was mixed with sodium hydride (2.24 g, 56 mmol) and potassium iodide (0.73 g, 4.4 mmol). The reaction mixture was stirred at room temperature for 2 h and then at 80° C. for an additional 2 h. The reaction was quenched with water (50 mL), extracted with EtOAc (3×100 mL), concentrated to afford an oily residue. Purification by column chromatography to yield 3.4 g of 3,5-dimethyl-4-(2-pyrrolidin-1-yl-ethoxy)-benzaldehyde (70%). A mixture of 2-amino-4,6-dimethoxybenzamide (0.2 g, 1.02 mmol), 3,5-dimethyl-4-(2-pyrrolidin-1-yl-ethoxy)-benzaldehyde (0.251 g, 1.02 mmol), sodium hydrogensulfite (0.181 g, 1.02 mmol) and p-toluenesulfonic acid (0.234 g, 1.224 mmol) in N,N-dimethyl acetamide (10 mL) was stirred at 155° C. for 2 h. The reaction mixture was cooled to room temperature, diluted with water (50 mL), extracted with EtOAc (3×50 mL), and concentrated to afford a solid residue. The solid was further purified by column chromatography to yield about 40 mg impure product. This same reaction was repeated three times on the same scale and the impure product after each column was combined and subjected to one final column to yield 2-(3,5-dimethyl-4-(2-(pyrrolidin-1-yl) ethoxy)phenyl)-5,7-dimethoxyquinazolin-4(3H)-one (76 mg, 4%) as a light yellow solid. Selected data: MS (ES) m/z: 424.04; MP 181.0-183.2° C.

EXAMPLE 73

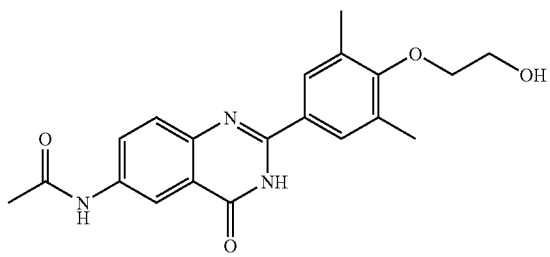

N-(2-(4-(2-hydroxyethoxy)-3,5-dimethylphenyl)-4-oxo-3,4-dihydroquinazolin-6-yl)acetamide To a solution of 2-amino-5-nitro-benzamide (680 mg, 3.75 mmol) and 4-[2-(tert-butyidimethylsilanoxy)ethoxy]-3,5-dimethylbenzaldehyde (1.16 g, 3.75 mmol) in N,N-dimethyl acetamide (35 mL), NaHSO₃ (736 mg, 4.14 mmol) and p-TSA (71 mg, 0.375 mmol) were added and the reaction mixture was heated at 150° C. for 5 h. The solvent was evaporated under reduced pressure. The residue was diluted with water and the solids were filtered off to give crude product (590 mg, 44%). To a solution of above crude product (490 mg, 1.38 mmol) in DMF (20 mL) and MeOH (20 mL), Pd—C (100 mg, 10%) was added and the reaction mixture was hydrogenated for 4 h at room temperature at 30 psi H₂. The reaction mixture was filtered and the solvent was evaporated to give crude product. The crude was purified by column chromatography (silica gel 230-400 mesh; 4% methanol in CH₂Cl₂ as eluent) to give 6-amino-2-(4-(2-hydroxy ethoxy)-3,5-dimethyl phenyl)-3H-quinazolin-4-one (190 mg, 42% yield). To a solution of 6-amino-2-(4-(2-hydroxy ethoxy)-3, 5-dimethyl phenyl)-3H-quinazolin-4-one (95 mg, 0.29 mmol) in pyridine (5 mL), acetic anhydride (108 mg, 0.73 mmol) was added and the mixture was stirred for 16 h at room temperature. The solvent was removed and the solids were dissolved in a mixture of MeOH (10 mL) and THF (10 mL) (compound was partially soluble). Then K₂CO₃ (100 mg, 0.73 mmol) was added and the reaction mixture was stirred for 3 h at room temperature. The solvent was removed and the crude was purified by column chromatography (silica gel 230-400 mesh; 5% methanol in CH₂Cl₂ as eluent) to give N-(2-(4-(2-hydroxyethoxy)-3,5-dimethylphenyl)-4-oxo-3, 4-dihydroquinazolin-6-yl)acetamide (65 mg, 60%). Selected data: MS (ES) m/z: 368.09; MP>300° C.

EXAMPLE 74

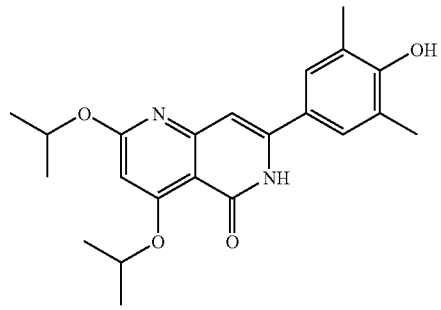

7-(4-hydroxy-3,5-dimethylphenyl)-2,4-diisopropoxy-1,6-naphthyridin-5(6H)-one

Malonic acid (5.27 g, 51 mmol), 2,4,6-trichlorophenol (20 g, 100 mmol) and phosphorus oxychloride (17.17 g, 112 mmol) were stirred under nitrogen atmosphere at reflux for 12 h. The reaction mixture was cooled to 70° C. and poured into ice water. The formed precipitate was collected, washed with water and dried under vacuum to provide the desired malonic acid bis-(2,4,6-trichloro-phenyl)ester as a white solid (23.37 g, quantitative yield). To a mixture of malonic acid bis-(2,4, 6-trichloro-phenyl)ester (23.37 g, 50.5 mmol) and ethyl-3-aminocrotonate (6.38 mL, 50.5 mmol) under nitrogen atmosphere was added bromobenzene (5 mL). The reaction mixture was heated under reflux for 2.5 h then cooled to room temperature and diluted with ethyl acetate. The formed precipitate was filtered off, washed several times with ethyl acetate and dried under vacuum to afford the desired 4,6- dihydroxy-2-methyl-nicotinic acid ethyl ester as a yellow solid (13.04 g, quantitative yield). To a mixture of 4,6-dihydroxy-2-methyl-nicotinic acid ethyl ester (12.93 g, 65.57 mmol) in N,N-dimethylformamide (550 mL) and potassium carbonate (27.18 g, 196.71 mmol) under nitrogen atmosphere was added dropwise isopropyl iodide (19.65 mL, 196.71 mmol). The resulting slurry was vigorously stirred at room temperature overnight and then filtered to remove insoluble salts. The filtrate was diluted with water (300 mL) and extracted with ethyl acetate (4×400 mL). The combined organic layers were washed with brine, dried over sodium sulfate and evaporated to afford the desired 4,6-diisopropoxy-2-methyl-nicotinic acid ethyl ester as an oil which solidified on standing (15.24 g, 82.6%). To a solution of 4,6-diisopropoxy-2-methyl-nicotinic acid ethyl ester (15.24 g, 54.2 mmol) in methanol (70 mL) was added sodium hydroxide in water (70 mL). The reaction mixture was heated under reflux for 48 h. The solvent was removed under reduced pressure and concentrated hydrochloric acid was added (20 mL). The solvent was evaporated to provide the desired 4,6-diisopropoxy-2-methyl-nicotinic acid as a white salt (26.91 g, theoretical mass: 13.73 g). To a solution of 4,6-diisopropoxy-2-methyl-nicotinic acid salt (13.73 g, 54.2 mmol) in methylene chloride (160 mL) under nitrogen atmosphere was added oxalyl chloride (9.46 mL, 108.4 mmol) followed by N,N-dimethylformamide (1 mL). The reaction mixture was stirred overnight then the solvent was evaporated to obtain the desired crude acid chloride, which was used for the next step without further purification. To 50% v/v ammonia hydroxide (500 mL) at room temperature was added dropwise a solution of the crude 4,6-diisopropoxy-2-methyl-nicotinoyl chloride in methylene chloride (400 mL). The reaction mixture was stirred for 3.5 h. The solution was separated and the aqueous layer was extracted with methylene chloride (100 mL×8). The combined organic layers were dried over sodium sulfate and evaporated to afford a crude solid (6.94 g). The crude was purified by flash column chromatography to provide pure 4,6-diisopropoxy-2-methyl-nicotinamide as an orange solid (3.0 g, 21.9%). To a solution of 4,6-diisopropoxy-2-methyl-nicotinamide (0.3 g, 1.18 mmol) in THF (5 mL) under nitrogen was added 1.6 M n-BuLi solution in hexanes (3 mL, 4.75 mmol) at −20° C. The reaction mixture was allowed to warm-up to room temperature and left to stir for 2 h. The reaction was then cooled to −20° C. and a solution of 4-benzyloxy-3,5-dimethyl-benzonitrile in THF (5 mL) was added dropwise. The reaction mixture was allowed to warm to room temperature and was left to stir for 20 h. Water and acetic acid were added until pH ~5. The solution was heated to 55° C. for 3 h then cooled to room temperature, diluted with ethyl acetate, separated and the aqueous layer was extracted with ethyl acetate. The combined organic layers were washed with brine, dried over sodium sulfate and evaporated under reduced pressure to provide crude orange oil (1.02 g). The crude was purified by flash column chromatography to provide pure 7-(4-benzyloxy-3,5-dimethyl-phenyl)-2,4-diisopropoxy-6H-[1,6]naphthyridin-5-one as a yellow solid (0.10 g, 17.9%). To a solution of 7-(4-benzyloxy-3,5-dimethylphenyl)-2,4-diisopropoxy-[1,6]naphthyridin-5-ylamine (0.10 g, 0.21 mmol) in methanol (4 mL) was added palladium on charcoal catalyst (0.06 g, 0.54 mmol). The reaction mixture was stirred under 1 atmosphere pressure of hydrogen for 20 h and diluted with methanol and filtered through a Celite pad. The solvent was evaporated under reduced pressure to provide a crude solid (0.077 g) which was triturated with ether followed by methanol to afford the desired compound 7-(4-hydroxy-3,5-dimethylphenyl)-2,4-diisopropoxy-1,6-naphthyridin-5(6H)-one (35 mg, 43.2%). Selected data: MS (ES) m/z: 383.08; MP 206-208° C.

EXAMPLE 75

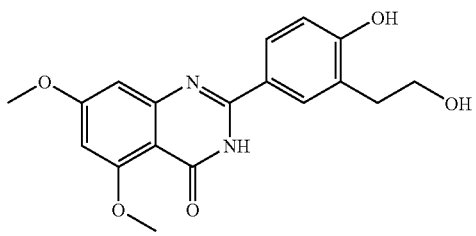

2-(4-hydroxy-3-(2-hydroxyethyl)phenyl)-5,7-dimethoxyquinazolin-4(3H)-one

To a solution of 3-bromo-4-hydroxybenzaldehyde (5 g, 2.44 mmol) in acetone (100 mL) under nitrogen atmosphere was added potassium carbonate (50 6 g, 36.6 mmol). The slurry mixture was cooled to 0° C. and chloromethyl ether (9.25 mL, 12.2 mmol) was added dropwise. The ice bath was removed and the mixture was heated at 70° C. for 2.5 h. After cooling to room temperature, excess potassium carbonate was filtered off and the acetone evaporated under reduced pressure. The residue was dissolved in ethyl acetate (300 mL) and water (100 mL) was added. The organic layer was separated, washed with 0.5 N sodium hydroxide solution (100 mL×2) followed by brine and dried over sodium sulfate and concentrated to give a crude oil (6.69 g), which was purified by Flash Column Chromatography on 230-400 mesh silica gel (40-63 μm particle size) eluted with EtOAc/hexane: ⅔ to provide pure 3-bromo-4-methoxymethoxy-benzaldehyde, as an oil (4.46 g, 73.2%). To a solution of 3-bromo-4-methoxymethoxy-benzaldehyde (4.4 g, 17.9 mmol) and vinyl-tributyl tin (5.8 mL, 19.7 mmol) in toluene (130 mL) under nitrogen atmosphere was added an catalytic amount of tetrakis(triphenylphosphine)palladium (0.79 mg, 0.68 mmol). The resulting mixture was heated at 100° C. overnight, cooled to room temperature and a saturated potassium fluoride solution (30 mL) was added. The solution was stirred for 30 min then diluted with ethyl acetate, separated, and the aqueous layer was extracted with ethyl acetate. The combined organic layers were washed with brine, dried over sodium sulfate and evaporated under reduced pressure to provide crude yellow oil (4.6 g). The crude was purified by flash column chromatography to give pure 4-methoxymethoxy-3-vinyl-benzaldehyde as a yellow oil (1.95 g, 56.5%). To a solution of 4-methoxymethoxy-3-vinyl-benzaldehyde (1.8 g, 9.46 mmol) in THF (25 mL) under nitrogen was added borane dimethyl sulfide complex at 0° C. The solution was allowed to warm to room temperature and was stirred for 18 h. The reaction mixture was quenched at 0° C. with methanol (12 mL), hydrogen peroxide solution (8 mL) and 4 N sodium hydroxide solution (12 mL). The mixture was vigorously stirred at room temperature for 12 h and was diluted with ethyl acetate. The aqueous layer was extracted with ethyl acetate. The combined organic layers were washed with brine, dried over sodium sulfate and evaporated under reduced pressure to provide crude oil (3.2 g). The crude was purified by flash column chromatography to give pure 2-(5-hydroxymethyl-2-methoxymethoxy-phenyl)-ethanol (1.19 g, 59.5%). The mixture of 2-(5-hydroxymethyl-2-methoxymethoxy-phenyl)-ethanol (0.78 g, 3.69 mmol) and magnesium dioxide (0.086 g, 0.99 mmol) in chloroform (12 mL) was heated at 80° C. for 3 h under nitrogen. The reaction mixture was cooled to room temperature and was diluted with chloroform and filtered through a Celite pad to give the desired 3-(2-hydroxy-ethyl)-4-methoxymethoxy-benzaldehyde (0.63 g, 81.3%), which was used without further purification.

A mixture of 2-amino-4,6-dimethoxy-benzamide (0.25 g, 1.27 mmol), 3-(2-hydroxy-ethyl)-4-methoxymethoxy-benzaldehyde (0.268 g, 1.27 mmol), sodium hydrogensulfite (0.146 g, 1.4 mmol) and p-toluenesulfonic acid (0.025 g, 0.127 mmol) in N,N-dimethyl acetamide (8 mL) was stirred at 150° C. overnight under nitrogen atmosphere. The reaction mixture was cooled to room temperature, the solvent evaporated under reduced pressure. Water (70 mL) was added to obtain a solid. The yellow solid was filtered off, washed with water and dried under vacuum to provide crude 2-[3-(2-hydroxy-ethyl)-4-methoxymethoxy-phenyl]-5,7-dimethoxy-3H-quinazolin-4-one (0.182 g, 36.7%) which was used as such in the next step. A solution of 2-[3-(2-hydroxy-ethyl)-4-methoxymethoxy-phenyl]-5,7-dimethoxy-3H-quinazolin-4-one (0.18 g), 50% acetic acid solution (4 mL) and catalytic amount of concentrated sulfuric acid (0.02 mL) was heated at 70° C. for 2.5 h. After cooling to room temperature the reaction mixture was diluted with water (30 mL) to obtain a solid. The solid was filtered off, washed with water and dried under high vacuum to provide crude solid (0.135 g, 85%). The crude was purified by flash column chromatography to give pure 2-(4-hydroxy-3-(2-hydroxyethyl)phenyl)-5,7-dimethoxyquinazolin-4(3H)-one (0.035 g. 8% over 2 steps). Selected data: MS (ES) m/z: 343.0; MP 249-250.3° C.

EXAMPLE 76

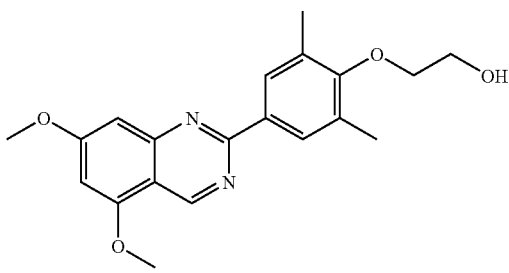

2-(4-(5,7-dimethoxyquinazolin-2-yl)-2,6-dimethylphenoxy)ethanol

To a 100 mL round bottom flask was added 2-amino-4,6-dimethoxy-benzamide (318 mg, 1.6 mmol), 4-(2-benzyloxy-ethoxy)-3,5-dimethyl-benzaldehyde (461 mg, 1.6 mmol), p-toluenesulfonic acid monohydrate (32 mg, 0.16 mmol), sodium hydrogensulfite (318 mg, 1.8 mmol) and dimethylacetamide (5 mL). The mixture was stirred in a 150° C. oil bath under nitrogen overnight. Water (40 mL) and ether (30 mL) were added. The precipitate was filtered off, washed with water then ether, and air-dried. The intermediate 2-[4-(2-benzyloxyethoxy)-3,5-dimethyl-phenyl]-5,7-dimethoxy-3H-quinazolin-4-one was obtained as light brown/beige solid. Yield 474 mg (64%). 2-[4-(2-Benzyloxy-ethoxy)-3,5-dimethyl-phenyl]-5,7-dimethoxy-3H-quinazolin-4-one (474 mg, 1.03 mmol) was stirred in phosphorus oxychloride (10 mL) at 100° C. for 4 h. Excess phosphorus oxychloride was removed under reduced pressure. Ice was added and the solid was collected. The solid was washed with water and ether, and air-dried. 2-[4-(2-benzyloxy-ethoxy)-3,5-dimethyl-phenyl]-4-chloro-5,7-dimethoxy-quinazoline was obtained as a light brown solid (yield: 356 mg, 72%). 2-[4-(2-Benzyloxy-ethoxy)-3,5-dimethyl-phenyl]-4-chloro-5,7-dimethoxy-quinazoline (192 mg, 0.4 mmol) was dissolved in a small amount of THF and 10% Pd/C (dry) (66 mg) was added. Anhydrous methanol (20 mL) and ammonium formate (955 mg) were added. The mixture was stirred in a 80° C. oil bath for 5 h. The mixture was filtered through Celite, washed with MeOH/DCM, purified by column chromatography to give 2-(4-(5,7-dimethoxyquinazolin-2-yl)-2,6-dimethylphenoxy) ethanol (36 mg, 25%) as an off-white solid. Selected data: MS (ES) m/z: 355.04; mp 169-170° C.

EXAMPLE 77

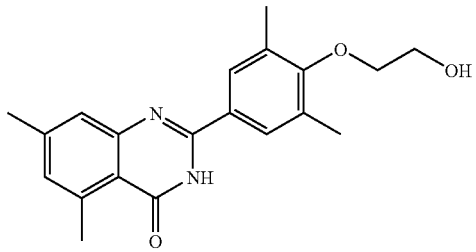

2-(4-(2-hydroxyethoxy)-3,5-dimethylphenyl)-5,7-dimethylquinazolin-4(3H)-one

To a solution of 4,6-dimethyl-2-nitroaniline (3 g, 18.07 mmol) in acetic acid (20 mL) and 6 N HCl (60 mL) at 0° C. was added a solution of sodium nitrite (2.18 g, 31.62 mmol) in water (5 mL). The reaction mixture was stirred at 0° C. for 30 min after completion of addition and copper (I) cyanide (3.24 g, 3 mmol) was added pinch by pinch. The resulting mixture was stirred at 0° C. for 5 h and at room temperature for an additional 2 h. The mixture was passed through a Celite pad, extracted with EtOAc (3×100 mL), and concentrated using a rotary evaporator to afford a solid residue. The solid was further purified by column (SiO$_2$, hexanes/EtOAc=7:1) to yield 2-chloro-1,5-dimethyl-3-nitro-benzene (2.6 g, 81%) as a light yellow solid. A solution of 2-chloro-1,5-dimethyl-3-nitro-benzene (2.6 g, 15.7 mmol) and copper (I) cyanide (7.05 g, 78.3 mmol) in DMAC (20 mL) was stirred at reflux for 14 h. The reaction mixture was cooled to room temperature, quenched by adding water (30 mL), filtered through a Celite pad, extracted with EtOAc (3×100 mL), and concentrated using a rotary evaporator to afford a solid residue. The solid was further purified by column (SiO$_2$, hexanes/EtOAc=6:1) to yield 0.64 g of 2,4-dimethyl-6-nitro-benzonitrile (23%). A solution of 2,4-dimethyl-6-nitro-benzonitrile (1.1 g, 6.24 mmol) in MeOH (20 mL) and water (10 mL) was mixed with hydrogen peroxide (10 mL), DMSO (10 mL) and potassium hydroxide (0.636 g, 11.36 mmol). The reaction mixture was stirred at 60° C. for 3 h, diluted with water (100 mL), extracted with EtOAc (3×100 mL), and concentrated using a rotary evaporator to afford 4,6-dimethyl-2-nitrobenzamide (0.52 g, 43%). A solution of 4,6-dimethyl-2-nitrobenzamide (0.52 g, 2.68 mmol) in MeOH (30 mL) was mixed with palladium carbon (0.25 g). The resulting suspension was stirred at room temperature under hydrogen for 14 h. The mixture was passed through a Celite pad, concentrated using a rotary evaporator to afford 2-amino-4,6-dimethyl benzamide (0.42 g, 95%).

A mixture of 2-amino-4,6-dimethyl benzamide (0.2 g, 1.22 mmol), 4-[2-(tert-butyl-dimethyl-silanyloxy)-ethoxy]-3,5-dimethyl-benzaldehyde (0.376 g, 1.22 mmol), sodium hydrogensulfite (0.22 g, 1.22 mmol) and prtoluenesulfonic acid (0.116 g, 0.61 mmol) in N,N-dimethyl acetamide (10 mL) was stirred at 155° C. for 14 h. The reaction mixture was cooled to room temperature and diluted with water (50 mL).

The solid crashed out and was collected by filtration to afford impure product. The solid was re-dissolved in THF (30 mL) and mixed with TBAF in THF (5 mL, 5 mmol). The reaction mixture was stirred at room temperature for 14 h and concentrated using a rotary evaporator to afford an oily residue. Further purification by column (SiO$_2$, EtOAc/DCM/MeOH=12:4:1) yielded an off-white solid. This solid was diluted with MeOH (10 mL) to make a slurry. The solid was collected by filtration and washed with MeOH to afford 2-(4-(2-hydroxyethoxy)-3,5-dimethylphenyl)-5,7-dimethylquinazolin-4(3H)-one (98 mg, 24%) as a white solid. Selected data: MS (ES) m/z: 339.10; MP 259.6-261.2° C.

EXAMPLE 78

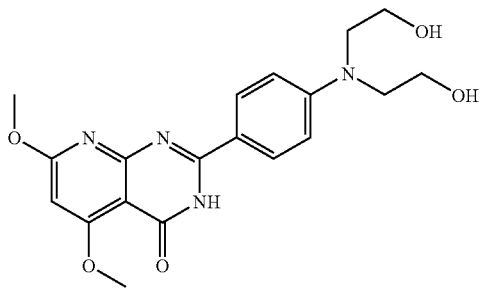

2-(4-(bis(2-hydroxyethyl)amino)phenyl)-5,7-dimethoxy-pyrido[2,3-d]pyrimidin-4(3H)one To a solution of 2-amino-4,6-dimethoxy-nicotinamide (300 mg, 1.52 mmol) and 4-(bis-(2-hydroxyethyl)amino)-benzaldehyde (318 mg, 1.52 mmol) in N,N-dimethylacetamide (10 mL) were added NaHSO$_3$ (297 mg, 1.67 mmol) and p-TSA (376 mg, 1.98 mmol) and the reaction mixture was heated at 150° C. for 4 h, cooled to room temperature, and concentrated under reduced pressure. The residue was diluted with water and the solid was filtered off to give the crude product. The crude product was purified by column chromatography to give 2-(4-(bis(2-hydroxyethyl)amino)phenyl)-5,7-dimethoxypyrido[2,3-d]pyrimidin-4(3H)-one (60 mg, 10%). Selected data: MS (ES) m/z: 387.05; MP 277-279° C.

EXAMPLE 79

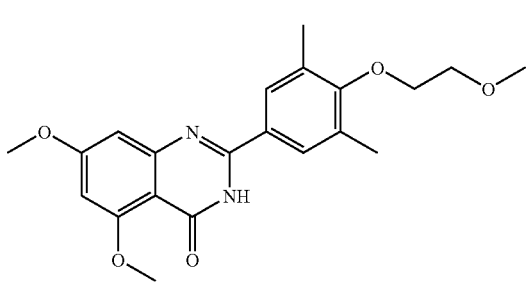

5,7-dimethoxy-2-(4-(2-methoxyethoxy)-3,5-dimethylphenyl)quinazolin-4(3H)-one

To a solution of 3,5-dimethyl-4-hydroxy benzaldehyde (2.0 g, 13.33 mmol) in DMF was added NaH (640 mg, 16.0 mmol, 60% in oil) and the mixture was stirred for 1 h at room temperature. A solution of 1-bromo-2-methoxy ethane (1.85 g, 13.33 mmol) was added and the mixture was stirred for 72 h at room temperature. The reaction mixture was quenched by addition of saturated NH$_4$Cl solution and diluted with water. The product was extracted with ethyl acetate. The combined organic layers were washed with water, brine and dried over Na$_2$SO$_4$. Upon removal of solvent, it gave 2.1 g of 4-(2-methoxy ethoxy)-3,5-dimethyl benzaldehyde (76 yield). To a solution of 2-amino-4,6-dimethoxybenzamide (200 mg, 1.02 mmol) and 4-(2-methoxy ethoxy)-3,5-dimethyl benzaldehyde (212 mg, 1.02 mmol) in N,N-dimethyl acetamide (10 mL), NaHSO$_3$ (199 mg, 1.12 mmol) and p-TSA (22 mg, 0.102 mmol) were added and the reaction mixture was heated at 150° C. for 3 h. Cooled to room temperature and the solvent was evaporated under reduced pressure. The residue was diluted with water and the solid was collected to give the crude product. The crude product was purified by chromatography using 2% MeOH in CH$_2$Cl$_2$ to give 5,7-dimethoxy-2-(4-(2-methoxyethoxy)-3,5-dimethylphenyl)quinazolin-4(3H)-one (170 mg, 43%). Selected data: MS (ES) m/z: 385.10; MP 201-202° C.

EXAMPLE 80

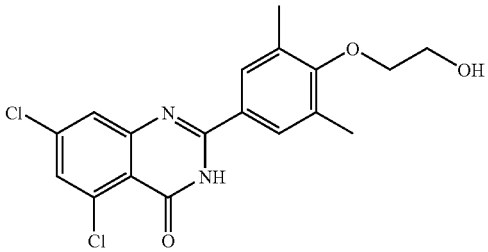

5,7-dichloro-2-(4-(2-hydroxyethoxy)-3,5-dimethylphenyl)quinazolin-4(3H)-one

To a solution of 2-amino-4,6-dichloro-benzoic acid (0.5 g, 2.43 mmol) in THF (22 mL) under nitrogen atmosphere was added successively N-(3-Dimehtylaminopropyl)-N'-ethyl-carbodiimide hydrochloride (0.51 g, 2.67 mmol), N-hydroxy-benzotriazole (0.36 g, 2.67 mmol) and N-methylmorpholine (0.3 mL, 2.67 mmol). The mixture was stirred for 1.5 h before a 50% ammonium hydroxide solution (1.03 mL, 14.58 mmol) was added. The mixture was stirred overnight. The solvent was evaporated under reduced pressure, water (20 mL) was added and the solution was extracted with EtOAc (50 mL×2). The combined organic layers were washed with water, brine, dried over sodium sulfate and evaporated under reduced pressure to provide crude yellow solid (0.45 g). The crude product was triturated with ether to give pure 2-amino-4,6-dichlorobenzamide (0.41 g, 82%). A mixture of 2-amino-4,6-dichloro-benzamide (0.2 g, 0.97 mmol), 4-[2-(tert-butyl-dimethyl-silanyloxy)-ethoxy]-3,5-dimethylbenzaldehyde (0.3 g, 0.97 mmol), sodium hydrogensulfite (0.11 g, 1.05 mmol) and p-toluenesulfonic acid (0.093 g, 0.48 mmol) in N,N-dimethyl acetamide (8 mL) was stirred at 150° C. overnight under nitrogen atmosphere. The reaction mixture was cooled to room temperature, the solvent was evaporated under reduced pressure, then water (70 mL) was added and the precipitate was collected, and washed with water, dried under vacuum and triturated with ether to provide the crude mixture of 2-[4-[2-(tert-butyl-dimethyl-silanyloxy)-ethoxy]-3,5-dimethyl-phenyl]-5,7-dichloro-3H-quinazolin-4-one and 5,7-dichloro-2-[4-(2-hydroxy-ethoxy)-3,5-dimethylphenyl]-3H- quinazolin-4-one (0.298 g), which was used as such in the next step. To the above described mixture (0.298 g, 0.59 mmol) in tetrahydrofurane (5 mL) was added tetrabutylammonium fluoride (2.35 mL, 2.35 mmol) under nitrogen atmosphere. The reaction mixture was stirred overnight before the solvent was evaporated under reduced pressure and water was added to obtain a precipitate. The solid was filtered off, washed with water, dried under vacuum and triturated with ether to provide crude yellow solid (0.226 g, 98%). The crude was purified twice by flash column chromatography to give pure 5,7-dichloro-2-(4-(2-hydroxyethoxy)-3,5-dimethylphenyl)quinazolin-4(3H)-one (0.069 g, 19%). Selected data: MS (ES) m/z: 378.92, 380.88, 382.89; MP 260.8-262.6° C.

EXAMPLE 81

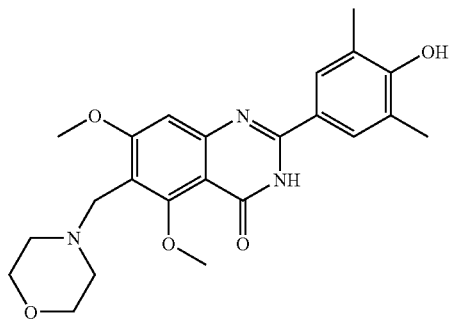

2-(4-hydroxy-3,5-dimethylphenyl)-5,7-dimethoxy-6-(morpholinomethyl)quinazolin-4(3H)-one To a solution of 2,6-dimethoxytoluene (50 g, 328.5 mmol) in ether (450 mL) was added freshly prepared dioxane dibromide in ether over 0.5 h. The mixture was stirred at room temperature for an additional 1.5 h and poured into a beaker containing water (500 mL). The aqueous layer was discarded and the ether layer was washed sequentially with water (2×500 mL), sodium bicarbonate (saturated aqueous) (2×500 mL), dried over sodium sulfate, and concentrated using a rotary evaporator to afford 76 g of 3-bromo-2,6-dimethoxytoluene as a colorless oil (100%). A cooling well was used to collect 300 mL of ammonia at −78° C., which was mixed with potassium (0.5 g) and ferric nitrate (0.5 g). Additional potassium (14.2 g, 364 mmol) was added at −78° C. portion-wise. The solution was stirred at −78° C. for 15 min. To this solution was slowly added 3-bromo-2,6-dimethoxytoluene (42 g, 182 mmol) in THF (100 mL). The resulting mixture was stirred at −78° C. for 3 h and then 0° C. for 1 h. The reaction was quenched by adding water (150 mL) and extracted with DCM (3×200 mL) to get a brown oil as the crude product. It was further purified by column chromatography to yield 22.1 g of 3,5-dimethoxy-4-methylaniline (73%). A solution of 3,5-dimethoxy-4-methylaniline (22.1 g, 132.3 mmol) in dioxane (380 mL) and water (380 mL) was mixed with potassium carbonate (45.6 g, 330.8 mmol) and (Boc)$_2$O (34.6 g 158.8 mmol) and stirred at room temperature for 14 h. The reaction mixture was then extracted with DCM (3×100 mL) and concentrated using a rotary evaporator. The resulting solid residue was purified by column chromatography. A mixture of DCM-hexanes (20 mL-300 mL) was used to make a slurry and the solid was collected by filtration and washed with hexanes to provide 28.6 g of (3,5-dimethoxy-4-methyl-phenyl)-carbamic acid tert-butyl ester (81%). A solution of (3,5-dimethoxy-4-methyl-phenyl)-carbamic acid tert-butyl ester (28.6 g, 107.1 mmol) in carbon tetrachloride (450 mL) was mixed with NBS (19.05 g, 107.1 mmol) and AIBN (1.55 g, 9.37 mmol) and the mixture was stirred at 80° C. with the light on for 2 h. The reaction was quenched by adding water (150 mL) and extracted with DCM (3×100 mL), and concentrated to afford a solid residue. Further purification by column chromatography yielded 34.9 g of (2-bromo-3,5-dimethoxy-4-methyl-phenyl)-carbamic acid tert-butyl ester (94%). A solution of (2-bromo-3,5-dimethoxy-4-methyl-phenyl)-carbamic acid tert-butyl ester (34.9 g, 100.9 mmol) in carbon tetrachloride (450 mL) was mixed with NBS (21.5 g, 121.0 mmol) and AIBN (1.55 g, 9.37 mmol) and was stirred at 80° C. with the light on for 4 h. The reaction was then quenched by adding water (150 mL) and extracted with DCM (3×100 mL), and concentrated to afford a solid residue. Further purification by column chromatography yielded 39 g of (2-bromo-4-bromomethyl-3,5-dimethoxy-phenyl)-carbamic acid tert-butyl ester (91%). A solution of (2-bromo-4-bromomethyl-3,5-dimethoxy-phenyl)-carbamic acid tert-butyl ester (39 g, 91.8 mmol) in THF (600 mL) was mixed with morpholine (45 mL, 515.0 mmol) and stirred at room temperature for 7 h. The reaction was diluted with water (300 mL), extracted with DCM (3×200 mL), and concentrated using a rotary evaporator. The residue was further purified by column (SiO$_2$, DCM/MeOH=20:1) to provide 35 g of (2-bromo-3,5-dimethoxy-4-morpholin-4-ylmethyl-phenyl)-carbamic acid tert-butyl ester (88%). A solution of (2-bromo-3,5-dimethoxy-4-morpholin-4-ylmethyl-phenyl)-carbamic acid tert-butyl ester (3 g, 6.94 mmol) in THF (150 mL) was mixed with NaH (0.333 g, 8.33 mmol) and stirred at room temperature for 1.5 h. The resulting mixture was cooled to −78° C. and mixed with nBuLi (3.33 mL, 8.33 mmol). The reaction was stirred for 1.5 h at −78° C. before addition of t-BuLi (8.16 mL, 13.88 mmol). The reaction was stirred at −78° C. for 1 h and carbon dioxide gas was then bubbled through for 8 h allowing the temperature to rise gradually to room temperature. The reaction was quenched by adding water (0.5 mL, 27.8 mmol) and concentrated using a rotary evaporator. The solid residue was made into slurry in minimal amount of MeOH and the solid was filtered off. The filtrate was then concentrated using a rotary evaporator and the solid was made into a slurry again in MeOH and filtered. After repeating two to three times, the filtrate was concentrated to yield 1.1 g of impure 6-tert-butoxycarbonylamino-2,4-dimethoxy-3-morpholin-4-ylmethyl-benzoic acid (40% crude yield).

A solution of 6-tert-butoxycarbonylamino-2,4-dimethoxy-3-morpholin-4-ylmethyl-benzoic acid (1.8 g, 4.54 mmol), EDCl.HCl (1.31 g, 6.82 mmol), HOBt (1.23 g, 9.09 mmol), and triethylamine (3.3 mL, 23.7 mmol) in THF (50 mL) was stirred at room temperature for 1 h. Ammonium hydroxide (50% aqueous, 10 mL) was then added to the reaction mixture. The resulting mixture was stirred at room temperature for 6 h. The reaction was quenched by adding water (50 mL), extracted with DCM (3×100 mL), and concentrated using a rotary evaporator. The residue was further purified by column (SiO$_2$, DCM/MeOH/EtOAc=2:1:4) to provide 0.9 g of (2-carbamoyl-3,5-dimethoxy-4-morpholin-4-ylmethyl-phenyl)-carbamic acid tert-butyl ester (50%). A solution of (2-carbamoyl-3,5-dimethoxy-4-morpholin-4-ylmethyl-phenyl)-carbamic acid tert-butyl ester (0.9 g, 2.74 mmol) in HOAc (20 mL) and 12 N HCl aqueous (20 mL) was stirred at 50° C. for 1 h and then concentrated to dryness using a rotary evaporator. The residue was mixed with saturated sodium bicarbonate aqueous (40 mL), extracted with DCM (3×100 mL), and concentrated. The residue was further purified by column (SiO$_2$, DCM/MeOH/EtOAc=3:2:3) to provide 0.6 g of 6-amino-2,4-dimethoxy-3-morpholin-4-ylmethyl-benzamide (89%). A mixture of 6-amino-2,4-dimethoxy-3-morpholin-4-ylmethyl-benzamide (0.6 g, 2.03 mmol), 3,5-dimethyl-4-hydroxy benzaldehyde (0.61 g, 4.06 mmol), sodium hydrogensulfite (1.24 g, 7.0 mmol) and p-toluenesulfonic acid (1.14 g, 6 mmol) in N,N-dimethyl acetamide (20 mL)

was stirred at 115° C. for 6 h. The reaction mixture was cooled to room temperature, diluted with water (50 mL), extracted with EtOAc, and concentrated. Purification by column chromatography afforded a solid residue, which was made into slurry in a mixed solvent of DCM-hexanes (3 mL-20 mL). The slurry was filtered and washed with hexanes to provide 2-(4-hydroxy-3,5-dimethylphenyl)-5,7-dimethoxy-6-(morpholinomethyl)quinazolin-4(3H)-one (56 mg, 6.6%) as a light yellow solid. Selected data: MS (ES) m/z: 426.0; MP 237.0-239.1° C.

EXAMPLE 82

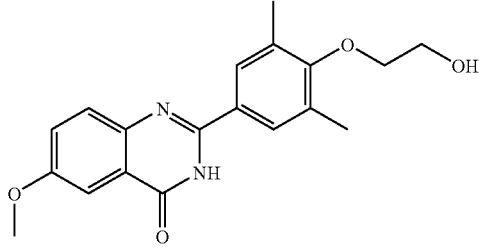

2-(4-(2-hydroxyethoxy)-3,5-dimethylphenyl)-6-methoxyquinazolin-4(3H)-one

Following the method described for 6-bromo-2-(4-(2-hydroxyethoxy)-3,5-dimethylphenyl)quinazolin-4(3H)-one, 2-(4-(2-hydroxyethoxy)-3,5-dimethylphenyl)-6-methoxyquinazolin-4(3H)-one was made from 2-amino-5-methoxybenzamide and 4-(2-(tert-butyldimethylsilyloxy)ethoxy)-3-methylbenzaldehyde in 4% yield and isolated as a white solid. Selected data: $^1$H NMR (300 MHz, DMSO-$d_6$) δ 12.28 (s, 1H), 7.88 (s, 2H), 7.68 (d, J=8.90 Hz, 1H), 7.53 (d, J=2.95 Hz, 1H), 7.43 (dd, J=8.90, 2.98 Hz, 1H), 4.89 (t, J=5.52 Hz, 1H), 3.92-3.80 (m, 5H), 3.73 (q, J=5.09, 5.09, 4.97 Hz, 2H), 2.32 (s, 6H); MS (APCI) m/z 341 [M+H]$^+$.

EXAMPLE 83

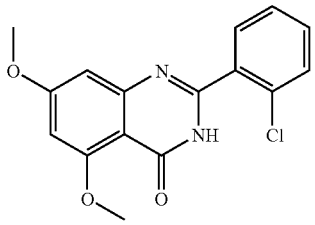

2-(2-chlorophenyl)-5,7-dimethoxyquinazolin-4(3H)-one

A mixture of 2-chlorobenzaldehyde (0.0430 g, 306 mmol), 2-amino-4,6-dimethoxybenzamide (0.0600 g, 0.306 mmol), NaHSO$_3$ (94%, 0.0474 g, 0.428 mmol), and p-TsOH.H$_2$O (0.0175 g, 0.0918 mmol) in DMA (3.06 mL) was heated at 140° C. for 16 h. The mixture was cooled and chromatographed on silica gel, fractions containing the product were combined, concentrated under vacuum, diluted with EtOAc (300 mL), washed with water (3×75 mL), brine (75 mL), dried over sodium sulfate, filtered and concentrated under vacuum to provide 2-(2-chlorophenyl)-5,7-dimethoxyquinazolin-4(3H)-one (0.0377 g, 39%) as a yellow solid. Selected data: $^1$H NMR (300 MHz, DMSO-$d_6$) δ 912.14 (s, 1H), 7.65-7.40 (m, 4H), 6.72 (d, J=2.29 Hz, 1H), 6.59 (d, J=2.30 Hz, 1H), 3.87 (s, 3H), 3.85 (s, 3H); MS (APCI) m/z 317 [M+H]$^+$.

EXAMPLE 84

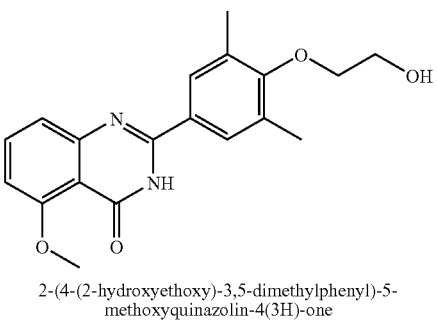

2-(4-(2-hydroxyethoxy)-3,5-dimethylphenyl)-5-methoxyquinazolin-4(3H)-one

Following the method described for 6-bromo-2-(4-(2-hydroxyethoxy)-3,5-dimethylphenyl)quinazolin-4(3H)-one, 2-(4-(2-Hydroxyethoxy)-3,5-dimethylphenyl)-5-methoxyquinazolin-4(3H)-one was made from 2-amino-6-methoxybenzamide (made from the corresponding amino acid in two steps) and 4-(2-(tert-butyldimethylsilyloxy)ethoxy)-3-methylbenzaldehyde in 77% yield and isolated as a white solid. Selected data: $^1$H NMR (300 MHz, DMSO-$d_6$) δ ppm 11.96 (s, 1H), 7.89 (s, 2H), 7.68 (t, J=8.20 Hz, 1H), 7.23 (d, J=7.89 Hz, 1H), 6.98 (d, J=8.19 Hz, 1H), 4.89 (t, J=5.53 Hz, 1H), 3.94-3.65 (m, 7H), 2.31 (s, 6H); MS (APCI) m/z 341 [M+H]$^+$.

EXAMPLE 85

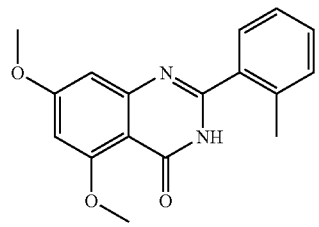

5,7-dimethoxy-2-o-tolylquinazolin-4(3H)-one

A mixture of 2-amino-4,6-dimethoxybenzamide (0.060 g, 0.306 mmol), 2-methylbenzaldehyde (0.037 g, 0.306 mmol), NaHSO$_3$ (0.032 g, 0.306 mmol), and p-TsOH.H$_2$O (0.00370 g, 0.021 mmol) in DMA (5.00 mL) was heated at 60° C. overnight. The mixture was cooled to room temperature, water (50.0 mL) and EtOAc (50.0 mL) was added. The layers were separated and the organic layer was washed with water (2×50 mL), brine (50 mL), dried and concentrated. The crude solid was purified via CombiFlash provide 5,7-dimethoxy-2-o-tolylquinazolin-4(3H)-one (0.025 g, 28%) as yellow solid. Selected data: $^1$H NMR (300 MHz, CDCl$_3$) δ 9.51 (s, 1H), 7.53 (dd, J=5.92, 3.07 Hz, 1H), 7.46-7.36(m, 1H), 7.32 (dd, J=9.04, 4.60 Hz, 2H), 6.81 (d, J=2.29 Hz, 1H), 6.49 (d, J=2.28 Hz, 1H), 3.95 (s, J=7.48 Hz, 3H), 3.94-3.88(s, 3H), 2.51 (s, 3H); MS (APCI) m/z 297 [M+H]$^+$.

EXAMPLE 86

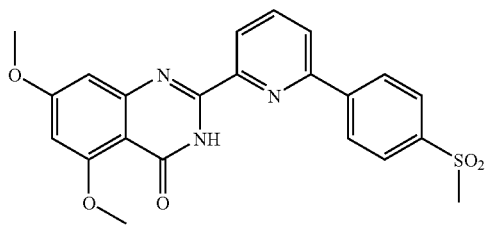

5,7-dimethoxy-2-(6-(4-(methylsulfonyl)phenyl)pyridin-2-yl)quinazolin-4(3H)-one

Following the procedure described above for 2-(2-chlorophenyl)-5,7-dimethoxyquinazolin-4(3H)-one, 5,7-dimethoxy-2-(6-(4-(methylsulfonyl)phenyl)pyridin-2-yl)quinazolin-4(3H)-one was made from 6-(4-(methylsulfonyl)phenyl)picolinaldehyde and 2-amino-4,6-dimethoxybenzamide in 38% as a yellow solid. Selected data: $^1$H NMR (300 MHz, DMSO-$d_6$) δ 11.75 (s, 1H), 8.69 (d, J=8.38 Hz, 2H), 8.46 (d, J=7.72 Hz, 1H), 8.33 (d, J=7.75 Hz, 1H), 8.22 (t, J=7.84 Hz, 1H), 8.08 (d, J=8.37 Hz, 2H), 6.85 (s, 1H), 6.63 (s, 1H), 3.95 (s, 3H), 3.90 (s, 3H), 3.4 (s, 3H); MS (APCI) m/z 438 [M+H]$^+$.

EXAMPLE 87

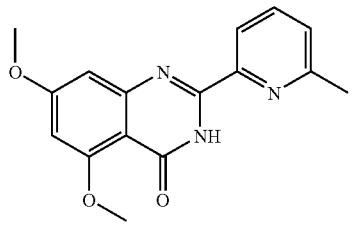

5,7-dimethoxy-2-(6-methylpyridin-2-yl)quinazolin-4(3H)-one

Following the method described for 2-(2-chlorophenyl)-5,7-dimethoxyquinazolin-4(3H)-one, 5,7-dimethoxy-2-(6-methylpyridin-2-yl)quinazolin-4(3H)-one was made from 6-methylpicolinaldehyde and 2-amino-4,6-dimethoxybenzamide in 33% yield and isolated as an off-white solid. Selected data: $^1$H NMR (300 MHz, DMSO-$d_6$) δ 11.00 (s, 1H), 8.21 (d, J=7.74 Hz, 1H), 7.95 (t, J=7.75 Hz, 1H), 7.52 (d, J=7.62 Hz, 1H), 6.82 (d, J=2.33 Hz, 1H), 6.60 (d, J=2.31 Hz, 1H), 3.92 (s, 3H), 3.87 (s, 3H), 2.62 (s, 3H); MS (APCI) m/z 298 [M+H]$^+$.

EXAMPLE 88

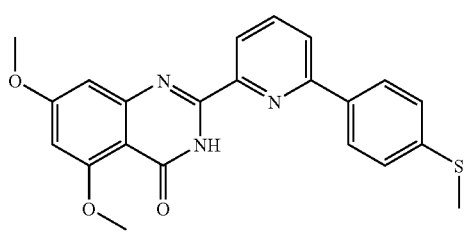

5,7-dimethoxy-2-(6-(4-(methylthio)phenyl)pyridin-2-yl)quinazolin-4(3H)-one

Following the procedure described above for 2-(2-chlorophenyl)-5,7-dimethoxyquinazolin-4(3H)-one, 5,7-dimethoxy-2-(6-(4-(methylthio)phenyl)pyridin-2-yl)quinazolin-4(3H)-one was made from 6-(4-(methylthio)phenyl)picolinaldehyde and 2-amino-4,6-dimethoxybenzamide in 39% as a white solid. Selected data: $^1$H NMR (300 MHz, DMSO-$d_6$) δ 11.51 (s, 1H), 8.39-8.30 (m, 3H), 8.23-8.05 (m, 2H), 7.46-7.37 (m, 2H), 6.84 (d, J=2.33 Hz, 1H), 6.62 (d, J=2.33 Hz, 1H), 3.92 (s, 3H), 3.88(s, 3H), 2.55 (s, 3H); MS (APCI) m/z 406[M+H]$^+$.

EXAMPLE 89

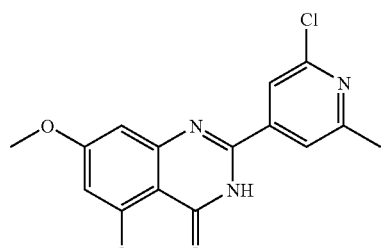

2-(2-chloro-6-methylpyridin-4-yl)-5,7-dimethoxyquinazolin-4(3H)-one

Following the method described for 5,7-dimethoxy-2-(4-methoxy-3,5-dimethylphenyl)quinazolin-4(3H)-one, 2-(2-chloro-6-methylpyridin-4-yl)-5,7-dimethoxyquinazolin-4(3H)-one was synthesized from 2-amino-4,6-dimethoxybenzamide and 2-chloro-6-methylisonicotinoyl chloride in 75% yield as a white solid. Selected data: $^1$H NMR (300 MHz, CDCl$_3$) δ 10.95 (s, 1H), 7.90 (s, 2H), 6.74 (d, J=2.33 Hz, 1H), 6.51(d, J=2.32 Hz, 1H), 3.88 (s, 3H), 3.86 (s, 3H), 2.29 (s, 3H); MS (APCI) m/z 332 [M+H]$^+$.

EXAMPLE 90

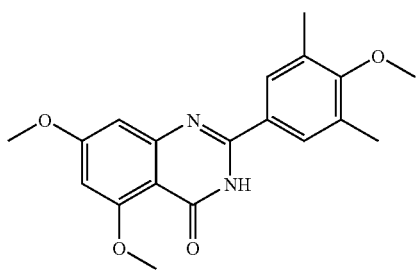

5,7-dimethoxy-2-(4-methoxy-3,5-dimethylphenyl)quinazolin-4(3H)-one

To a solution of 4-methoxy-3,5-dimethylbenzoic acid (0.100 g, 0.555 mmol) in CH$_2$Cl$_2$ (2.77 mL) cooled to 0-5° C. was added oxalyl chloride (67.8 μL, 0.777 mmol) followed by drop-wise addition of DMF (4.3 μL, 0.056 mmol). The mixture was stirred for 50 min, the volatiles were removed under vacuum, and the crude acid chloride was used immediately without further purification.

To a mixture of 2-amino-4,6-dimethoxybenzamide (0.0990 g, 0.555 mmol) and pyridine (44.9 μL, 0.555 mmol) in THF (2.02 mL) was added dropwise a solution of the acid chloride (crude residue described above) in THF (925 μL).

After 16 h, the mixture was diluted with EtOAc (300 mL), washed with saturated aqueous NH$_4$Cl (3×75 mL), saturated aqueous NaHCO$_3$ (3×75 mL), and brine (75 mL). The insoluble yellow solid was isolated by filtration to provide the amide (0.150 g, 83%). A mixture of the amide (0.148 g, 0.413 mmol) and 2 M NaOH (7.00 mL) was heated at 85° C. for 19 h, cooled to 5° C., and neutralized with 4 M HCl in dioxanes. The white solid was filtered and rinsed with acetone to provide 5,7-dimethoxy-2-(4-methoxy-3,5-dimethylphenyl)quinazolin-4(3H)-one (0.144 g, 100%). Selected data: $^1$H NMR (300 MHz, CDCl$_3$) δ 11.00 (s, 1H), 7.90 (s, 2H), 6.74 (d, J=2.33 Hz, 1H), 6.51 (d, J=2.32 Hz, 1H), 3.88 (s, 3H), 3.86 (s, 3H), 3.72 (s, 3H), 2.29 (s, 6H); MS (APCI) m/z 341 [M+H]$^+$.

EXAMPLE 91

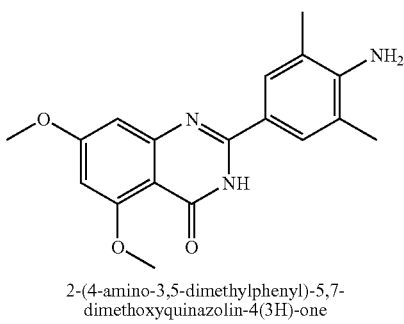

2-(4-amino-3,5-dimethylphenyl)-5,7-dimethoxyquinazolin-4(3H)-one

To a solution of 3,5-dimethyl-4-nitrobenzoic acid (1.00 g, 5.12 mmol) in CH$_2$Cl$_2$ (25.6 mL) cooled to 0-5° C. was added oxalyl chloride (0.626 mL, 7.17 mmol) followed by dropwise addition of DMF (39.8 µL). The mixture was stirred for 2 h, the volatiles were removed under vacuum, and the crude acid chloride was used immediately without further purification. To a mixture of 2-amino-4,6-dimethoxybenzamide (0.913 g, 4.65 mmol) and pyridine (414 µL, 5.12 mmol) in THF (18.6 mL) was added dropwise a solution of the acid chloride (crude residue described above) in THF (8.53 mL). After 16 h, the mixture was diluted with EtOAc (500 mL), washed with saturated aqueous NH$_4$Cl (3×100 mL), saturated aqueous NaHCO$_3$ (3×100 mL), and brine (100 mL). The insoluble yellow solid was isolated by filtration to provide the amide (1.51 g, 87%). A mixture of the amide (1.50 g, 4.03 mmol) and 2 M aqueous NaOH (25.0 mL) was heated at 85° C. for 17 h, then added THF (50 mL) and stirred at reflux for 25 h. The volatiles were removed under vacuum, the mixture was cooled to 5° C., and neutralized with 4 M HCl in dioxanes. After stirring for 30 min, the white solid was filtered and lyophilized from MeCN/H$_2$O to afford the cyclized compound (1.36 g, 95%). A mixture of the cyclized compound (0.200 g, 0.563 mmol), Na$_2$S$_2$O$_4$ (0.980 g, 5.63 mmol), water (5.00 mL) and MeOH (15.0 mL) was stirred at 70° C. for 2 h. The volatiles were removed under vacuum, then diluted with EtOAc (200 mL), washed with saturated NaHCO$_3$ (2×100 mL) and brine (75 mL). The organic layer was dried over sodium sulfate, filtered, and the volatiles were removed under vacuum to provide 2-(4-amino-3,5-dimethylphenyl)-5,7-dimethoxyquinazolin-4(3H)-one (0.062 g, 34%) as a yellow solid. Selected data: $^1$H NMR (300 MHz, DMSO-d$_6$) δ 11.45 (s, 1H), 7.78 (s, 2H), 6.66 (d, J=2.25 Hz, 1H), 6.42 (d, J=2.24 Hz, 1H), 5.26 (s, 2H), 3.88 (s, 3H), 3.86 (s, 3H), 2.14 (s, 6H); MS (APCI) m/z 326 [M+H]$^+$.

EXAMPLE 92

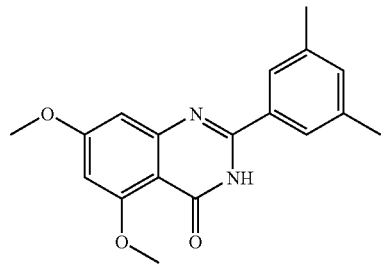

2-(3,5-dimethylphenyl)-5,7-dimethoxyquinazolin-4(3H)-one

A mixture of 2-amino-4,6-dimethoxybenzamide (0.0700 g, 0.36 mmol) and 3,5-dimethylbenzoyl chloride (0.112 g, 0.65 mmol) in THF (5.0 mL) was placed in a microwave reactor at 80° C. for 30 min. The THF was removed under reduced pressure, and the residue was purified via Combi-Flash chromatography to yield the expected amide. This material was used directly in the next step. A mixture of the amide and H$_2$O/MeCN (2:1, 5.00 mL) was basified to pH 12 with 2 N NaOH and stirred at 80° C. for 16 h. The mixture was cooled and neutralized with 1 N HCl. The resulting precipitate was collected on a frit, washed with water (5.00 mL) and lyophilized to yield 2-(3,5-dimethylphenyl)-5,7-dimethoxyquinazolin-4(3H)-one (0.0395 g, 31% over two steps) as a white solid. Selected data: $^1$H NMR (300 MHz, DMSO-d$_6$) δ 11.88 (s, 1H), 7.80 (s, 2H), 7.21 (s, 1H), 6.76 (d, J=2.24 Hz, 1H), 6.53 (d, J=2.21 Hz, 1H), 3.89 (s, 3H), 3.85 (s, 3H), 2.35 (s, 6H); MS (APCI) m/z 311 [M+H]$^+$.

EXAMPLE 93

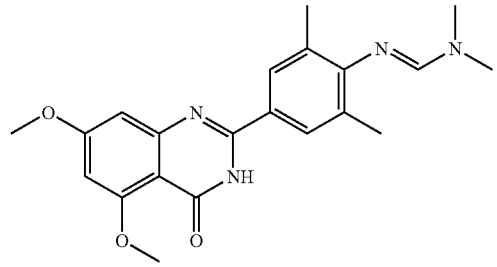

(E)-N'-(4-(5,7-dimethoxy-4-oxo-3,4-dihydroquinazolin-2-yl)-2,6-dimethylphenyl)-N,N-dimethylformimidamide To a solution of 2-(4-amino-3,5-dimethylphenyl)-5,7-dimethoxyquinazolin-4(3H)-one (0.096 g, 0.295 mmol) and diisopropylethylamine (61.7 µL, 0.354 mmol), in DMF (2.96 mL) was added dropwise methanesulfonyl chloride (25.2 µL, 0.325 mmol). After stirring at room temperature for 18 h, the mixture was diluted with EtOAc (300 mL), washed with saturated aqueous sodium bicarbonate (2×75 mL), saturated aqueous LiCl (2×75 mL), dried over sodium sulfate, filtered and concentrated under vacuum. The residue was purified over silica gel (12 g, CH$_2$Cl$_2$/CH$_3$OH) to provide (E)-N'-(4-

(5,7-dimethoxy-4-oxo-3,4-dihydroquinzolin-2-yl)-2,6-dimethylphenyl)-N,N-dimethylformimidamide (0.0502 g, 45%) as a white solid. Selected data: $^1$H NMR (300 MHz, DMSO-$d_6$) δ 11.68 (s, 1H), 7.87 (s, 2H), 7.40 (s, 1H), 6.72 (d, J=2.31 Hz, 1H), 6.48 (d, J=2.31 Hz, 1H), 3.88 (s, 3H), 3.86 (s, 3H), 2.97 (s, 6H), 2.12 (s, 6H); MS (APCI) m/z 381 [M+H]$^+$.

EXAMPLE 94

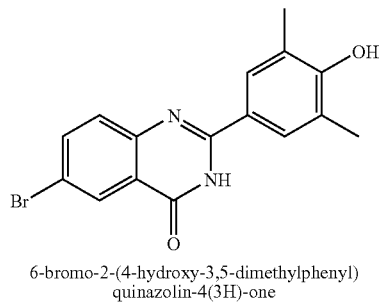

6-bromo-2-(4-hydroxy-3,5-dimethylphenyl)quinazolin-4(3H)-one

To a solution of 4-hydroxy-3,5-dimethylbenzoic acid (2.00 g, 12.0 mmol) in CH$_2$Cl$_2$ (60.2 mL) cooled to 0-5° C. was added oxalyl chloride (1.47 mL, 16.8 mmol) followed by dropwise addition of DMF (93.3 μL, 1.20 mmol). The mixture was stirred for 1.25 h, the volatiles were removed under vacuum to give crude acid chloride, which was used immediately without further purification. A mixture of 2-amino-5-bromobenzamide (1.99 g, 9.23 mmol) and the acid chloride (crude residue described above) in THF (92.3 mL) was stirred at room temperature for 17 h, then heated at reflux for 4 h. The volatiles were removed under vacuum, the residue was triturated with EtOAc, and filtered to afford the amide (3.02 g, 90%) as a yellow solid. A mixture of the amide (3.01 g, 8.29 mmol), 2 M NaOH (20.0 mL), water (40.0 mL), and MeCN (20.0 mL) was heated at reflux for 15 h, cooled to 5° C., and neutralized with 2 M aqueous HCl. After stirring for 30 min, the white solid was filtered, triturated with acetone, and filtered again to afford 6-bromo-2-(4-hydroxy-3,5-dimethylphenyl)quinazolin-4(3H)-one (2.28 g, 80%). Selected data: $^1$H NMR (300 MHz, DMSO-$d_6$) δ 8.18 (d, J=2.29 Hz, 1H), 7.93 (dd, J=8.72, 2.42 Hz, 1H), 7.86 (s, 2H), 7.63 (d, J=8.70 Hz, 1H), 5.75 (s, 1H), 2.24 (s, 6H); MS (APCI) m/z 346 [M+H]$^+$.

EXAMPLE 95

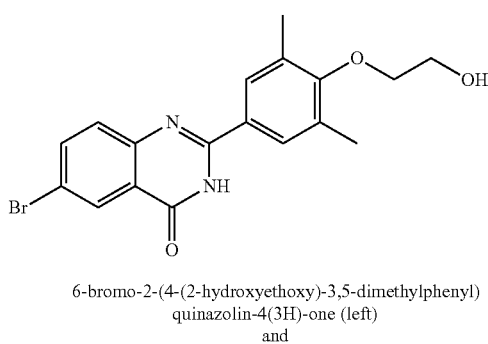

6-bromo-2-(4-(2-hydroxyethoxy)-3,5-dimethylphenyl)quinazolin-4(3H)-one (left)
and

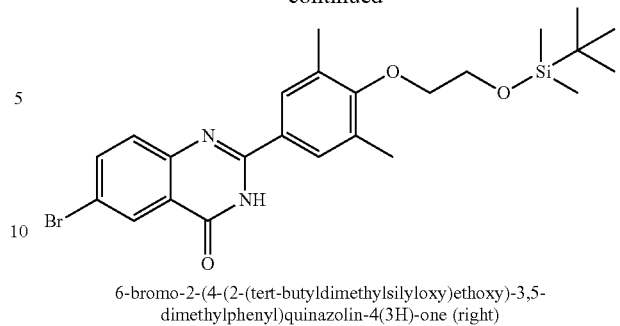

6-bromo-2-(4-(2-(tert-butyldimethylsilyloxy)ethoxy)-3,5-dimethylphenyl)quinazolin-4(3H)-one (right)

A mixture of 2-amino-5-bromobenzamide (0.100 g, 0.465 mmol), 4-(2-(tert-butyldimethylsilyloxy)ethoxy)-3-methylbenzaldehyde (0.143 g, 0.465 mmol), NaHSO$_3$ (94%, 0.0515 g, 0.465 mmol), and p-TsOH.H2O (0.00885 g, 0.0465 mmol) in DMA (5.81 mL) was heated at reflux for 15 min, cooled to room temperature, the water (20 mL) was added. The precipitate was filtered, washed with water, triturated with acetone and filtered again. The crude solid was chromatographed on silica gel (CH$_2$Cl$_2$/CH$_3$OH) to provide 6-bromo-2-(4-(2-hydroxyethoxy)-3,5-dimethylphenyl)quinazolin-4(3H)-one (0.0395 g, 22%) and 6-bromo-2-(4-(2-(tert-butyldimethylsilyloxy)ethoxy)-3,5-dimethylphenyl)quinazolin-4(3H)-one (0.0227 g, 10%) as white solids. Selected data for 6-bromo-2-(4-(2-hydroxyethoxy)-3,5-dimethylphenyl)quinazolin-4(3H)-one: $^1$H NMR (300 MHz, DMSO-$d_6$) δ 12.48 (s, 1H), 8.20 (d, J=2.34 Hz, 1H), 8.01-7.80 (m, 3H), 7.66 (d, J=8.72 Hz, 1H), 4.90 (t, J=5.46 Hz, 1H), 3.85 (t, J=4.87 Hz, 2H), 3.73 (dd, J=10.06, 5.11 Hz, 2H), 2.32 (s, 6H); MS (APCI) m/z 345 [M+H]$^+$. Selected data for 6-bromo-2-(4-(2-(tert-butyldimethylsilyloxy)ethoxy)-3,5-dimethylphenyl)quinazolin-4(3H)-one: $^1$H NMR (300 MHz, DMSO-$d_6$) δ 12.49 (s, 1H), 8.20 (d, J=2.34 Hz, 1H), 7.95 (dd, J=8.71, 2.41 Hz, 1H), 7.90 (s, 2H), 7.67 (d, J=8.72 Hz, 1H), 3.90 (m, 4H), 2.32 (s, 6H), 0.90 (s, 9H), 0.09 (s, 6H); MS (APCI) m/z 503 [M+H]$^+$.

EXAMPLE 96

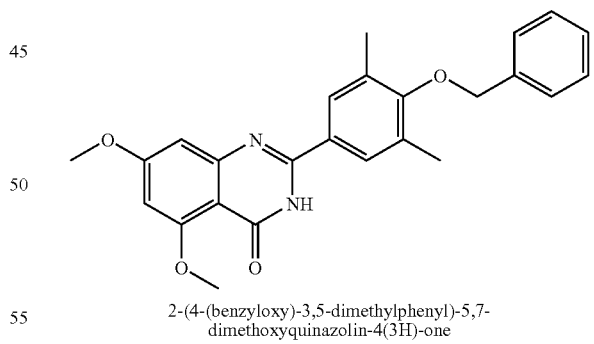

2-(4-(benzyloxy)-3,5-dimethylphenyl)-5,7-dimethoxyquinazolin-4(3H)-one

Following the method described for 2-(3-tert-butyl-1-methyl-1H-pyrazol-5-yl)-5,7-dimethoxyquinazolin-4(3H)-one, compound 2-(4-(benzyloxy)-3,5-dimethylphenyl)-5,7-dimethoxyquinazolin-4(3H)-one was synthesized from 2-amino-4,6-dimethoxybenzamide and 4-(benzyloxy)-3,5-dimethylbenzoyl chloride in 7% yield as a white solid. Selected data: $^1$H NMR (300 MHz, DMSO-$d_6$) δ 11.84 (s, 1H), 7.93 (s, 2H), 7.57-7.33 (m, 5H), 6.75 (d, J=2.28 Hz, 1H), 6.52 (d, J=2.27 Hz, 1H), 4.88 (s, 2H), 3.88 (s, 3H), 3.86 (s, 3H), 2.31 (s, 6H); MS (APCI) m/z 417 [M+H]$^+$.

EXAMPLE 97

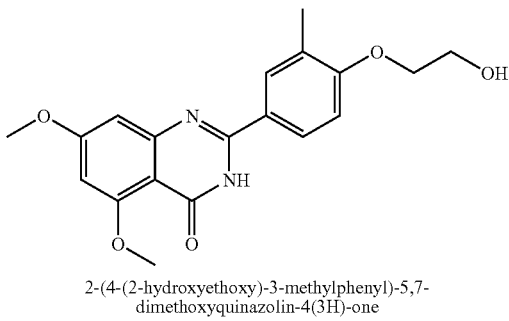

2-(4-(2-hydroxyethoxy)-3-methylphenyl)-5,7-dimethoxyquinazolin-4(3H)-one

A mixture of 3-methyl-4-hydroxybenzaldehyde (0.200 g, 1.5 mmol), (2-bromoethoxy)-tert-butyidimethylsilane (0.538 g, 2.25 mmol) and sodium hydride (0.061 g, 2.55 mmol) in DMF (5.00 mL) was stirred open at room temperature for 30 min in a microwave vial. The vial was then capped and heated in the microwave reactor for 1 h at 80° C. Water (55.0 mL) was added to quench. The solution was diluted with 1 N HCl (25.0 mL) and extracted with EtOAc (2×25.0 mL), dried and evaporated. The crude material was purified via CombiFlash to yield the alkylated aldehyde. A mixture of 2-amino-4,6-dimethoxybenzamide (0.167 g, 0.85 mmol), 4-(2-(tert-butyi-dimethylsilyloxy)ethoxy)-3-methylbenzaldehyde (0.250 g, 0.85 mmol), p-TsOH.H$_2$O (0.016 g, 0.085 mmol) and NaHSO$_3$ (0.088 g, 0.85 mmol) in DMA (5.00 mL) was stirred at 155° C. for 90 min. The solution was diluted with EtOAc (150 mL), washed with saturated NaHCO$_3$ (2×50 mL), 1 N HCl (2×75 mL), brine (50 mL), dried and the solvent was removed under reduced pressure to yield the TBS protected material (0.068 g, 17%) as a tan solid. The crude material was used directly in the next step. The TBS-protected material (0.068 g, 0.144 mmol) and 1 M TBAF in THF (1.00 mL, 7 mmol) was stirred at room temperature for 1 h. The volatiles were removed under vacuum, and the residue diluted with EtOAc (100 mL). The solution was washed with water (2×50.0 mL), brine (50.0 mL), dried and the solvent was removed. The residue was purified via CombiFlash to yield 2-(4-(2-hydroxyethoxy)-3-methylphenyl)-5,7-dimethoxyquinazolin-4(3H)-one (0.024 g, 47%) as an orange solid. Selected data: $^1$H NMR (300 MHz, DMSO-d$_6$) δ 11.81 (s, 1H), 8.05 (m, 2H), 7.05 (d, 1H, J=8.3 Hz), 6.72 (d, 1H, J=2.2 Hz), 6.50 (d, 1H, J=2.2 Hz), 4.87 (t, 1H, J=5.5 Hz), 4.09 (t, 2H, J=4.9 Hz), 3.89 (s, 3H), 3.84 (s, 3H), 3.76 (dd, 2H, J=5.1 Hz, J=10.0 Hz), 2.24 (s, 3H); MS (APCI) m/z 357 [M+H]$^+$.

EXAMPLE 98

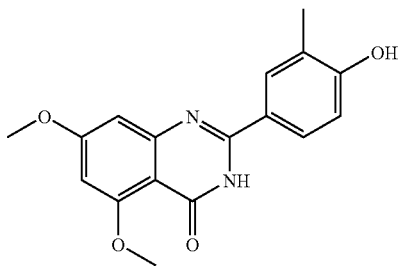

2-(4-hydroxy-3-methylphenyl)-5,7-dimethoxyquinazolin-4(3H)-one

A mixture of 4-hydroxy-3-methylbenzaldehyde (0.200 g, 1.47 mmol), 2-amino-4,6-dimethoxybenzamide (0.288 g, 1.47 mmol), NaHSO$_3$ (94%, 0.163 g, 1.47 mmol), and p-TsOH.H$_2$O (0.028 g, 0.147 mmol) in DMA (18.4 mL) was heated at reflux for 1 h. The mixture was diluted with EtOAc (300 mL), washed with saturated aqueous NH$_4$Cl (2×150 mL) and brine (75 mL), dried over sodium sulfate, filtered and concentrated under vacuum. The residue was triturated with MeOH and filtered off a yellow solid, which was freeze-dried from MeCN/H$_2$O to provide 2-(4-hydroxy-3-methylphenyl)-5,7-dimethoxyquinazolin-4(3H)-one (0.161 g, 35%). Selected data: $^1$H NMR (300 MHz, DMSO-d$_6$) δ 11.71 (s, 1H), 10.02 (s, 1H), 7.99 (d, J=1.88 Hz, 1H), 7.89 (dd, J=8.47, 2.29 Hz, 1H), 6.86 (d, J=8.50 Hz, 1H), 6.69 (d, J=2.31 Hz, 1H), 6.48 (d, J=2.31 Hz, 1H), 3.88 (s, 3H), 3.86 (s, 3H), 2.18 (s, 3H); MS (APCI) m/z 313 [M+H]$^+$.

EXAMPLE 99

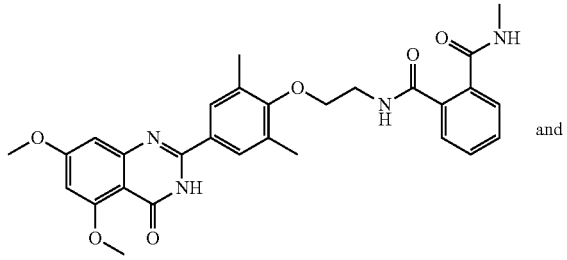

N1-(2-(4-(5,7-dimethoxy-4-oxo-3,4-dihydroquinazolin-2-yl)-2,6-dimethylphenoxy)ethyl)-N2-methylphthalamide (left)

2-(4-(2-aminoethoxy)-3,5-dimethylphenyl)-5,7-dimethoxyquinazolin-4(3H)-one (right)

A mixture of 3,5-dimethyl-4-hydroxybenzaldehyde (0.600 g, 4.00 mmol), N-(2-bromoethyl)-phthalimide (1.22 g, 4.80 mmol), K$_2$CO$_3$ (0.829 g, 6.00 mmol), NaI (3.00 g, 20.0 mmol) in DMF (40.0 mL) was heated at 80° C. for 2.5 h. The reaction was cooled to room temperature, diluted with EtOAc (200 mL), washed with 1 M NaOH (2×100 mL), 1 M HCl (2×100 mL), brine (75 mL), dried over sodium sulfate, filtered and concentrated under vacuum. The residue was chromatographed on silica gel (40 g, hexanes/EtOAc) to provide the expected ether (0.300 g, 23%) as a yellow solid. A mixture of the above ether (0.293 g, 0.907 mmol), 2-amino-4,6-dimethoxybenzamide (0.178 g, 0.907 mmol), NaHSO$_3$ (94%, 0.100 g, 0.907 mmol), and p-TsOH.H$_2$O (0.0173 g, 0.0907 mmol) in DMA (11.3 mL) was stirred at reflux for 1.5 h then cooled to room temperature. The mixture was diluted with EtOAc (250 mL), washed with saturated aqueous ammonium chloride (3×75 mL) and brine (75 mL), dried over sodium sulfate, filtered and concentrated under vacuum. The residue was chromatographed on silica gel (40 g, CH$_2$Cl$_2$/CH$_3$OH) to provide the expected product (0.075 g, 17%) as a light yellow solid. A mixture of the above compound (0.213 g, 0.426 mmol) and 2 M methylamine in THF (25.0 mL) was stirred at room temperature for 17 h. The volatiles were removed under vacuum and the residue was chromatographed on silica gel to provide compound N1-(2-(4-(5,7-dimethoxy-4-oxo-3,4-dihydroquinazolin-2-yl)-2,6-dimethylphenoxy)ethyl)-N2-methylphthalamide (0.0493 g, 22%) and compound 2-(4-(2-aminoethoxy)-3,5-dimethylphenyl)-5,7-dimethoxyquinazolin-4(3H)-one (0.0360 g, 23%) as white solids. Selected data for N1-(2-(4-(5,7-dimethoxy-4-oxo-3,4-dihydroquinazolin-2-yl)-2,6-dimethylphenoxy)ethyl)-N2-methylphthalamide: $^1$H NMR (300 MHz, DMSO-d$_6$) δ 11.80 (s, 1H), 8.51 (t, J=5.57 Hz, 1H), 8.18 (q, J=4.57 Hz, 1H), 7.89 (s, 2H), 7.53-7.42 (m, 4H), 6.74 (d, J=2.31 Hz, 1H), 6.52 (d, J=2.29 Hz, 1H), 3.96-3.80 (m, 8H), 3.61 (q, J=5.73 Hz, 2H), 2.71 (d, J=4.62 Hz, 3H), 2.32 (s, 6H); MS (APCI) m/z 531 [M+H]$^+$. Selected data for 2-(4-(2-aminoethoxy)-3,5-dimethylphenyl)-5,7-dimethoxyquinazolin-4(3H)-one: $^1$H NMR (300 MHz, DMSO-d$_6$) δ 7.90 (s, 2H), 6.74 (d, J=2.31 Hz, 1H), 6.51 (d, J=2.32 Hz, 1H), 3.88 (s, 3H), 3.85 (s, 3H), 3.77 (t, J=5.76 Hz, 2H), 2.91 (t, J=5.75 Hz, 2H), 2.30 (s, 6H); MS (APCI) m/z 370 [M+H]$^+$.

EXAMPLE 100

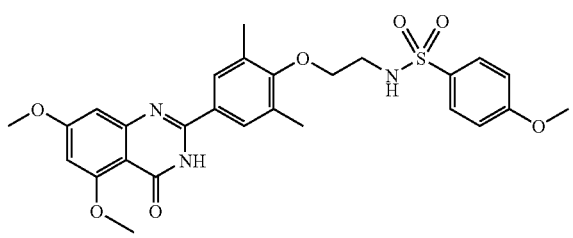

N-(2-(4-(5,7-dimethoxy-4-oxo-3,4-dihydroquinazolin-2-yl)-2,6-dimethylphenoxy)ethyl)-4-methoxybenzenesulfonamide A mixture of 2-(4-(2-aminoethoxy)-3,5-dimethylphenyl)-5,7-dimethoxyquinazolin-4(3H)-one (0.060 g, 0.162 mmol), 4-methoxybenzenesulfonyl chloride (0.044 mg, 0.211 mmol), and triethylamine (29.4 µL, 0.211 mmol) in CH$_2$Cl$_2$ (812 µL) was stirred at room temperature for 3 h. The mixture was chromatographed directly on silica gel to yield N-(2-(4-(5,7-dimethoxy-4-oxo-3,4-dihydroquinazolin-2-yl)-2,6-dimethylphenoxy)ethyl)-4-methoxybenzenesulfonamide (0.046 g, 53%) as a white solid after lyophilization from MeCN/H$_2$O. Selected data: $^1$H NMR (300 MHz, DMSO-d$_6$) δ ppm 11.81 (s, 1H), 7.88 (s, 2H), 7.83-7.73 (m, 3H), 7.17-7.07 (m, 2H), 6.73 (d, J=2.31 Hz, 1H), 6.52 (d, J=2.29 Hz, 1H), 3.91-3.75 (m, 11H), 3.12 (q, J=5.75 Hz, 2H), 2.24 (s, 6H); MS (APCI) m/z 540 [M+H]$^+$.

EXAMPLE 101

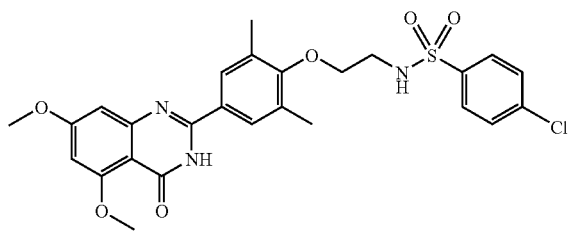

4-chloro-N-(2-(4-(5,7-dimethoxy-4-oxo-3,4-dihydroquinazolin-2-yl)-2,6-dimethylphenoxy)ethyl)benzenesulfonamide Following the method described for N-(2-(4-(5,7-dimethoxy-4-oxo-3,4-dihydroquinazolin-2-yl)-2,6-dimethylphenoxy)ethyl)-4-methoxybenzenesulfonamide, compound 4-chloro-N-(2-(4-(5,7-dimethoxy-4-oxo-3,4-dihydroquinazolin-2-yl)-2,6-dimethylphenoxy)ethyl)benzene-sulfonamide was made from 2-(4-(2-aminoethoxy)-3,5-dimethylphenyl)-5,7-dimethoxyquinazolin-4(3H)-one in 51% yield and isolated as a white solid after lyophilization from MeCN/H$_2$O. Selected data: $^1$H NMR (300 MHz, DMSO-d$_6$) δ ppm 11.8 (s, 1H), 8.1 (s, 1H), 7.9-7.6 (m, 6H), 6.75 (1H), 6.5 (1H), 3.9-3.7 (m, 8H), 3.15 (m, 2H), 2.2 (s, 6H); MS (APCI) m/z 544 [M+H]$^+$.

EXAMPLE 102

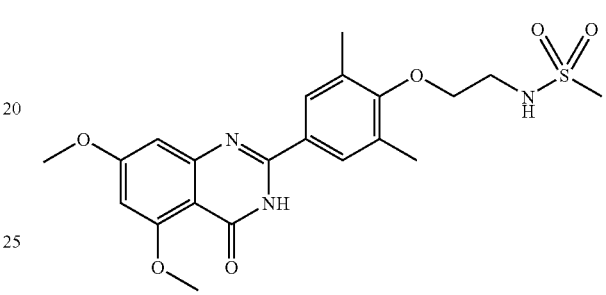

N-(2-(4-(5,7-dimethoxy-4-oxo-3,4-dihydroquinazolin-2-yl)-2,6-dimethylphenoxy)ethyl)methanesulfonamide Following the method described for N-(2-(4-(5,7-dimethoxy-4-oxo-3,4-dihydroquinazolin-2-yl)-2,6-dimethylphenoxy)ethyl)-4-methoxybenzenesulfonamide, compound N-(2-(4-(5,7-dimethoxy-4-oxo-3,4-dihydroquinazolin-2-yl)-2,6-dimethylphenoxy)ethyl)methanesulfonamide was made from 2-(4-(2-aminoethoxy)-3,5-dimethylphenyl)-5,7-dimethoxyquinazolin-4(3H)-one in 42% yield and isolated as a white solid after lyophilization from MeCN/H$_2$O. Selected data: $^1$H NMR (300 MHz, DMSO-d$_6$) δ ppm 11.82 (s, 1H), 7.90 (s, 2H), 7.33 (t, J=5.94 Hz, 1H), 6.74 (d, J=2.31 Hz, 1H), 6.52 (d, J=2.30 Hz, 1H), 3.92-3.81 (m, 8H), 3.41-3.34 (m, 2H), 2.97 (s, 3H), 2.32 (s, 6H); MS (APCI) m/z 448 [M+H]$^+$.

EXAMPLE 103

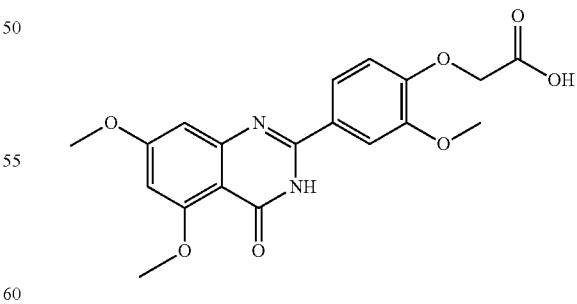

2-(4-(5,7-dimethoxy-4-oxo-3,4-dihydroquinazolin-2-yl)-2-methoxyphenoxy)acetic acid A mixture of NaOH (1.8 g, 0.045 mol) and 4-hydroxy-3-methoxylbenzalde (3.10 g, 0.0203 mol) in water (20 mL) was mixed with bromoacetic acid (2.82 g, 0.0203 mol) and heated to reflux for 6 h. The reaction mixture was adjusted to pH 3.0 by adding a HCl solution. The solid was filtered off and further washed with cold water and ethyl acetate (2×30 mL) to yield (4-formyl-2-methyl-phenoxy)-acetic acid (2.89 g, 67.7%). 2-Amino-4,6-dimethoxybenzamide (150 mg, 0.764 mmol) with (4-formyl-2-methyl-phenoxy)-acetic acid (160 mg, 0.764 mmol), sodium hydrogen sulfite (150 mg, 58.5%) and p-toluenesulfonic acid monohydrate (15 mg) in N,N-dimethyl acetamide (10 mL) were heated to 150° C. for 16 h. N,N-dimethyl acetamide was removed under vacuum and the residue was poured into water (50 mL). The solid was filtered off and further purified by base/acid extractions/washes to yield 2-(4-(5,7-dimethoxy-4-oxo-3,4-dihydroquinazolin-2-yl)-2-methoxyphenoxy)acetic acid (25 mg, 8.1%). Selected data: MS (ES) m/z: 387.1; MP 275-277° C.

EXAMPLE 104

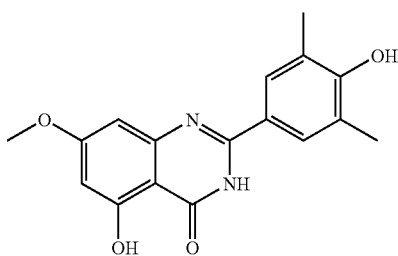

5-hydroxy-2-(4-hydroxy-3,5-dimethylphenyl)-7-methoxyquinazolin-4(3H)-one

A mixture of 2-amino-4,6-dimethoxy-benzamide (0.71 g, 3.71 mmol), 3,5-dimethyl-4-benzyloxy benzaldehyde (0.94 g, 3.90 mmol), sodium hydrogensulfite (0.68 g, 3.90 mmol) and p-toluenesulfonic acid (70 mg, 0.37 mmol) in N,N-dimethylacetamide (25 mL) was stirred at 150° C. for 16 h. The reaction mixture was cooled to room temperature and diluted with water (200 mL). The resulting solid was collected by filtration and washed with hexanes to afford 2-(4-benzyloxy-3,5-dimethyl-phenyl)-5,7-dimethoxy-3H-quinazolin-4-one as a white solid (1.2 g, 79%).

A mixture of 2-(4-benzyloxy-3,5-dimethyl-phenyl)-5,7-dimethoxy-3H-quinazolin-4-one (1.2 g, 2.92 mmol) and magnesium bromide (0.644 g, 3.5 mmol) in pyridine (50 mL) was stirred at reflux for 12 h. The mixture was concentrated and the solid residue was made into slurry with HCl (2 N, 100 mL). The solid was collected by filtration, washed with water and hexanes to yield 2-(4-benzyloxy-3,5-dimethyl-phenyl)-5-hydroxy-7-methoxy-3H-quinazolin-4-one as a white solid (0.76 g, 65%). A solution of ammonium formate (0.945 g, 15 mmol) and 2-(4-benzyloxy-3,5-dimethyl-phenyl)-5-hydroxy-7-methoxy-3H-quinazolin-4-one (0.1 g, 0.25 mmol) in DMF (50 mL) was mixed with palladium carbon (0.1 g) and stirred at 85° C. for 14 h. The resulting suspension was cooled to room temperature, passed through a Celite pad, and washed with DCM. The filtrate was concentrated and the residue was diluted with water (20 mL). The resulting solid was collected by filtration and washed with hexanes to afford 5-hydroxy-2-(4-hydroxy-3,5-dimethylphenyl)-7-methoxyquinazolin-4(3H)-one (57 mg, 74%) as light yellow solid. Selected data: MS (ES) m/z: 312.94; MP 291.3-293° C.

EXAMPLE 105

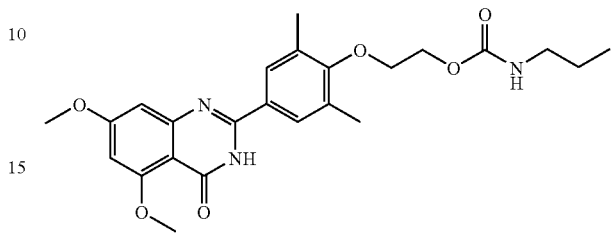

2-(4-(5,7-Dimethoxy-4-oxo-3,4-dihydroquinazolin-2-yl)-2,6-dimethyl-phenoxy)ethylpropylcarbamate A mixture of the compound of Example 20 (0.070 g, 0.19 mmol), propyl isocyanate (0.088 mL, 0.94 mmol), and TEA (0.14 g, 1.1 mmol) in THF (4.0 mL) was stirred at 70° C. for 16 h. The mixture was filtered, washed with THF, and the solvent was removed under reduced pressure. The residue was dissolved in EtOAc (50 mL) and washed with saturated aqueous sodium bicarbonate (50 mL), dried and the solvent was removed under reduced pressure. The resulting solid was chromatographed on silica gel to yield 2-(4-(5,7-Dimethoxy-4-oxo-3,4-dihydroquinazolin-2-yl)-2,6-dimethyl-phenoxy) ethyl propylcarbamate (0.035 g, 41%) as an off-white solid: Selected data: $^1$H NMR (300 MHz, DMSO-$d_6$) δ 11.82 (s, 1H), 7.90 (s, 2H), 7.23 (t, J=5.27 Hz, 1H), 6.74 (d, J=2.32 Hz, 1H), 6.52 (d, J=2.31 Hz, 1H), 4.27 (t, J=4.29 Hz, 2H), 3.99 (t, J=4.29 Hz, 2H), 3.89 (s, 3H), 3.84 (s, 3H), 3.02-2.86 (m, 2H), 2.29 (s, 6H), 1.50-1.30 (m, 2H), 0.84 (t, J=7.33 Hz, 3H); MS (APCI) m/z 456 [M+H]$^+$.

EXAMPLE 106

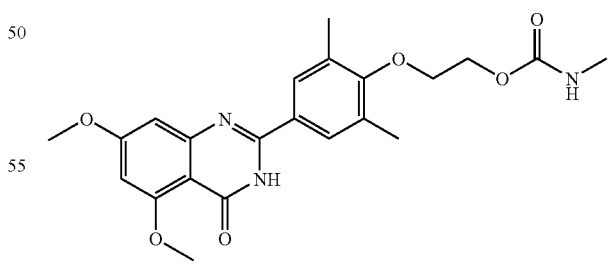

2-(4-(5,7-Dimethoxy-4-oxo-3,4-dihydroquinazolin-2-yl)-2,6-dimethyl-phenoxy)ethylmethylcarbamate Following the method described for 2-(4-(5,7-Dimethoxy-4-oxo-3,4-dihydroquinazolin-2-yl)-2,6-dimethyl-phenoxy) ethyl propylcarbamate, compound 2-(4-(5,7-Dimethoxy-4- oxo-3,4-dihydroquinazolin-2-yl)-2,6-dimethyl-phenoxy) ethyl methylcarbamate was made from 2-(4-(2-hydroxyethoxy)-3,5-dimethylphenyl)-5,7-dimethoxyquinazolin-4(3H)-one in 11% yield and isolated as an off-white solid: $^1$H NMR (300 MHz, DMSO-$d_6$) δ 11.82 (s, 1H), 7.90 (s, 2H), 7.08 (m, 1H), 6.74 (d, J=2.29 Hz, 1H), 6.52 (d, J=2.27 Hz, 1H), 4.27 (t, J=4.55 Hz, 2H), 3.99 (t, J=4.55 Hz, 2H), 3.89 (s, 3H), 3.84 (s, 3H), 2.60 (d, J=4.57 Hz, 3H), 2.29 (s, 6H); MS (APCI) m/z 428 [M+H]$^+$.

EXAMPLE 107

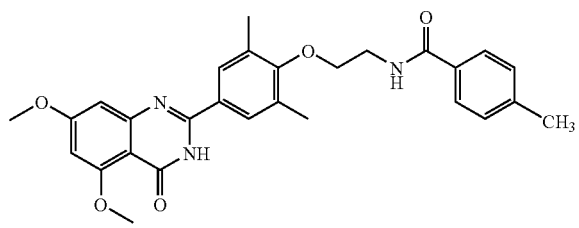

N-(2-(4-(5,7-Dimethoxy-4-oxo-3,4-dihydroquinazolin-2-yl)-2,6-dimethylphenoxy)ethyl)-4-methhylbenzamide A mixture of compound 2-(4-(2-aminoethoxy)-3,5-dimethylphenyl)-5,7-dimethoxyquinazolin-4(3H)-one (0.060 g, 0.16 mmol), p-toluoyl chloride (0.028 mL, 0.21 mmol), and PS-DIEA (0.057 g, 0.21 mmol) in CH$_2$Cl$_2$ (4.0 mL) was stirred at room temperature for 16 h. The mixture was filtered, washed with CH$_2$Cl$_2$ and the solvent was removed under reduced pressure. The resulting residue was chromatographed on silica gel to yield N-(2-(4-(5,7-Dimethoxy-4-oxo-3,4-dihydroquinazolin-2-yl)-2,6-dimethylphenoxy)ethyl)-4-methylbenzamide (0.037 g, 51%) as an off-white solid: $^1$H NMR (300 MHz, DMSO-$d_6$) δ 11.80-11.00 (s, 1H), 8.69 (t, J=5.43 Hz, 1H), 7.88 (s, 2H), 7.79 (d, J=8.19 Hz, 2H), 7.28 (d, J=8.00 Hz, 2H), 6.73 (d, J=2.31 Hz, 1H), 6.51 (d, J=2.31 Hz, 1H), 3.94 (t, J=5.59 Hz, 2H), 3.88 (s, 3H), 3.84 (s, 3H), 3.72-3.60 (m, 2H), 2.36 (s, 3H), 2.27 (s, 6H); MS (APCI) m/z 488 [M+H]$^+$.

EXAMPLE 108

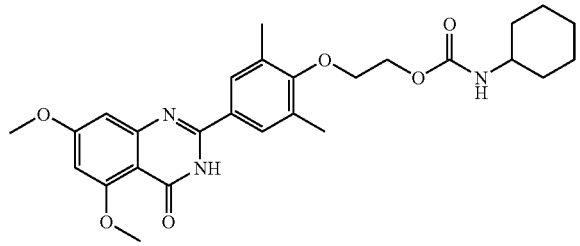

2-(4-(5,7-dimethoxy-4-oxo-3,4-dihydroquinazolin-2-yl)-2,6-dimethylphenoxy)ethylcyclohexylcarbamate A mixture of Example 18 (0.100 g, 0.270 mmol), cyclohexylisocyanate (172 µL, 1.35 mmol), and Et$_3$N (263 µL, 1.89 mmol) in THF (1.00 mL) was stirred at reflux for 4 h then diluted with EtOAc (200 mL) and washed with saturated aqueous ammonium chloride (3×75 mL) and brine (75 mL). The organic layer was dried over sodium sulfate, filtered and concentrated under vacuum. The residue was chromatographed on silica gel (12 g, CH$_2$Cl$_2$/CH$_3$OH) and the product freeze dried from MeCN/H$_2$O to provide 2-(4-(5,7-dimethoxy-4-oxo-3,4-dihydroquinazolin-2-yl)-2,6-dimethylphenoxy)ethyl cyclohexylcarbamate (0.0981 g, 73%) as a white solid. $^1$H NMR (300 MHz, DMSO-$d_6$δ) 11.82 (s, 1H), 7.90 (s, 2H), 7.24-7.05 (m, 1H), 6.73 (d, J=2.30 Hz, 1H), 6.52 (d, J=2.31 Hz, 1H), 4.30-4.22 (m, 1H), 4.03-3.95 (m, 1H), 3.88 (s, 3H), 3.85 (s, 3H), 2.29 (s, 6H), 1.82-1.46 (m, 5H), 1.18 (m, 5H); MS (APCI) m/z 496 [M+H]$^+$.

EXAMPLE 109

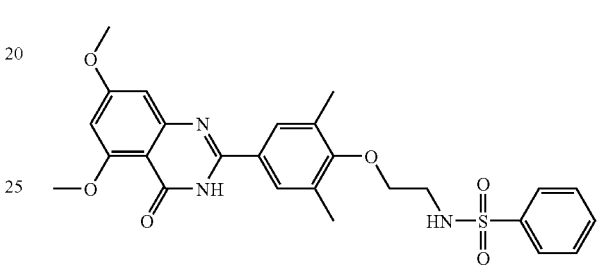

N-(2-(4-(5,7-dimethoxy-4-oxo-3,4-dihydroquinazolin-2-yl)-2,6-dimethylphenoxy)ethyl)benzenesulfonamide Following the methodology described for Example 100, the title compound was made from 2-(4-(2-aminoethoxy)-3,5-dimethylphenyl)-5,7-dimethoxyquinazolin-4(3H)-one in 41% yield and isolated as an off-white solid: MS (APCI) m/z 510 [M+H]$^+$.

EXAMPLE 110

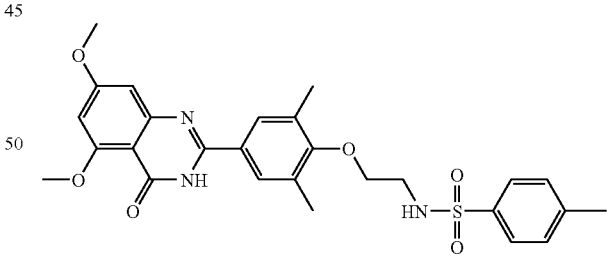

N-(2-(4-(5,7-dimethoxy-4-oxo-3,4-dihydroquinazolin-2-yl)-2,6-dimethylphenoxy)ethyl)-4-methhylbenzenesulfonamide Following the methodology described for Example 100, the title compound was made from 2-(4-(2-aminoethoxy)-3,5-dimethylphenyl)-5,7-dimethoxyquinazolin-4(3H)-one in 50% yield and isolated as an off-white solid: MS (APCI) m/z 524 [M+H]$^+$.

EXAMPLE 111

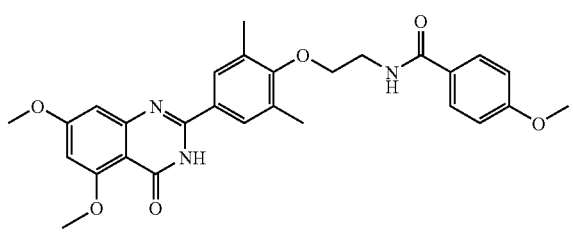

N(2-(4-(5,7-dimethoxy-4-oxo-3,4-dihydroquinazolin-2-yl)-2,6-dimethylphenoxy)ethyl)-4-methoxybenzamide Following the methodology described for Example 107, the title compound was made from 2-(4-(2-aminoethoxy)-3,5-dimethylphenyl)-5,7-dimethoxyquinazolin-4(3H)-one in 46% yield and isolated as a white solid: MS (APCI) m/z 526 [M+Na]$^+$.

EXAMPLE 112

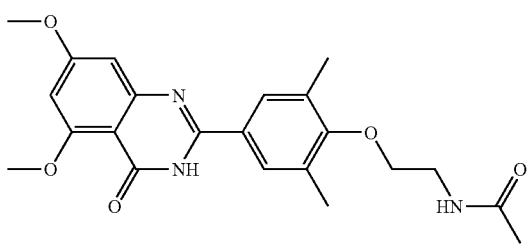

N-(2-(4-(5,7-dimethoxy-4-oxo-3,4-dihydroquinazolin-2-yl)-2,6-dimethylphenoxy)ethyl)acetamide Following the methodology described for Example 107, the title compound was made from 2-(4-(2-aminoethoxy)-3,5-dimethylphenyl)-5,7-dimethoxyquinazolin-4(3H)-one in 40% yield and isolated as a white solid: MS (APCI) m/z 412 [M+H]$^+$.

EXAMPLE 113

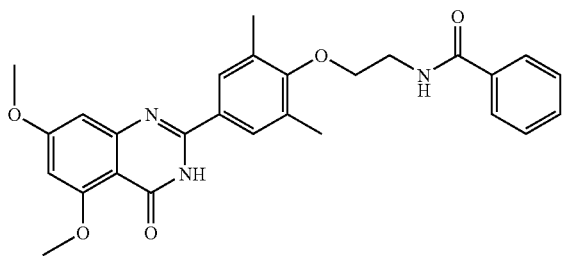

N-(2-(4-(5,7-dimethoxy-4-oxo-3,4-dihydroquinazolin-2-yl)-2,6-dimethylphenoxy)ethyl)benzamide Following the methodology described for Example 107, the title compound was made from 2-(4-(2-aminoethoxy)-3,5-dimethylphenyl)-5,7-dimethoxyquinazolin-4(3H)-one in 66% yield and isolated as a white solid: MS (APCI) m/z 474 [M+H]$^+$.

EXAMPLE 114

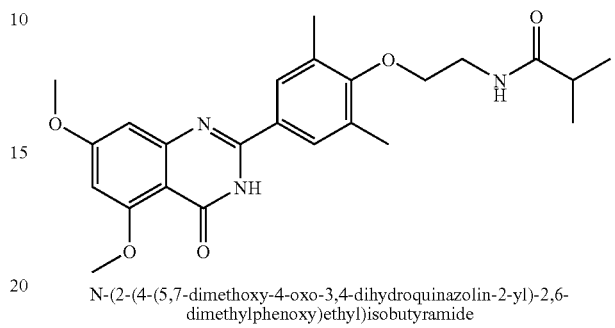

N-(2-(4-(5,7-dimethoxy-4-oxo-3,4-dihydroquinazolin-2-yl)-2,6-dimethylphenoxy)ethyl)isobutyramide Following the methodology described for Example 107, the title compound was made from 2-(4-(2-aminoethoxy)-3,5-dimethylphenyl)-5,7-dimethoxyquinazolin-4(3H)-one in 59% yield and isolated as a white solid: MS (APCI) m/z 440 [M+H]$^+$.

EXAMPLE 115

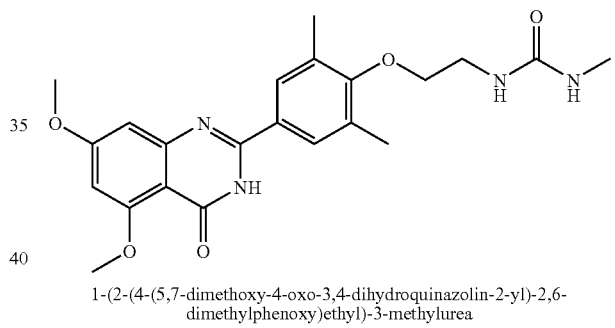

1-(2-(4-(5,7-dimethoxy-4-oxo-3,4-dihydroquinazolin-2-yl)-2,6-dimethylphenoxy)ethyl)-3-methylurea A mixture of compound 2-(4-(2-aminoethoxy)-3,5-dimethylphenyl)-5,7-dimethoxyquinazolin-4(3H)-one (0.10 g, 0.27 mmol), methylisocyanate (0.020 g, 0.35 mmol), and Et$_3$N (0.034 g, 0.35 mmol) in THF (4.0 mL) was stirred at room temperature for 16 hours. The mixture was filtered, washed with CH$_2$Cl$_2$ and the solvent was removed under reduced pressure. The resulting residue was chromatographed on silica gel to yield the title compound (0.082 g, 71%) as a white solid: MS (APCI) m/z 449 [M+Na]$^+$.

EXAMPLE 116

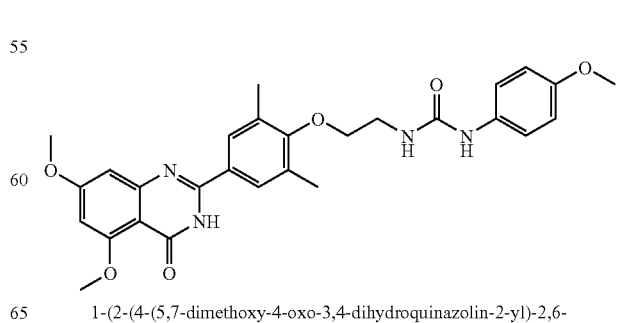

1-(2-(4-(5,7-dimethoxy-4-oxo-3,4-dihydroquinazolin-2-yl)-2,6-dimethylphenoxy)ethyl)-3-(4-methoxyphenyl)urea Following the methodology described for Example 115, the title compound was made from 2-(4-(2-aminoethoxy)-3,5-dimethylphenyl)-5,7-dimethoxyquinazolin-4(3H)-one in 57% yield and isolated as a white solid: MS (APCI) m/z 541 [M+Na]+.

EXAMPLE 117

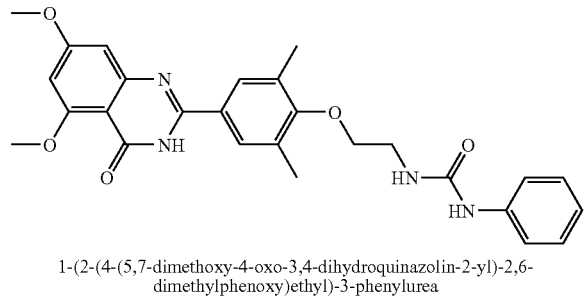

1-(2-(4-(5,7-dimethoxy-4-oxo-3,4-dihydroquinazolin-2-yl)-2,6-dimethylphenoxy)ethyl)-3-phenylurea Following the methodology described for Example 115, the title compound was made from 2-(4-(2-aminoethoxy)-3,5-dimethylphenyl)-5,7-dimethoxyquinazolin-4(3H)-one in 59% yield and isolated as a light yellow solid: MS (APCI) m/z 489 [M+H]+.

EXAMPLE 118

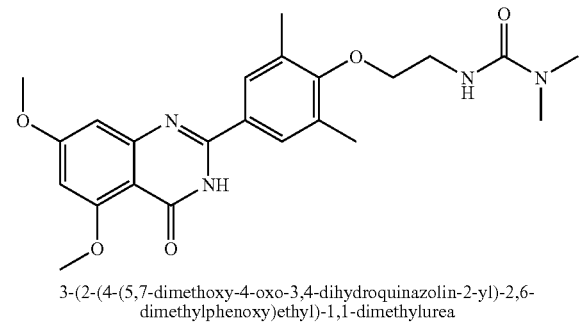

3-(2-(4-(5,7-dimethoxy-4-oxo-3,4-dihydroquinazolin-2-yl)-2,6-dimethylphenoxy)ethyl)-1,1-dimethylurea Following the methodology described for Example 115, the title compound was made from 2-(4-(2-aminoethoxy)-3,5-dimethylphenyl)-5,7-dimethoxyquinazolin-4(3H)-one in 59% yield and isolated as a white solid: MS (APCI) m/z 441 [M+H]+.

EXAMPLE 119

Quantification of ApoA-I mRNA

In this example, ApoA-I mRNA in tissue culture cells was quantitated to measure the transcriptional up-regulation of ApoA-I when treated with a compound of the invention.

HepG2 cells (~2×10⁵ per well) were placed in a 24-well plate in ~400 μL MEM, supplemented with 0.5% (v/v) FBS, 24 h before addition of the compound of interest. At time of harvesting, the spent media was removed from the HepG2 cells and immediately placed on ice (for immediate use) or at −80° C. (for future use) in ApoA-I and albumin ELISAs. The cells remaining in the plate wells were rinsed in 200 μL PBS. PBS was carefully removed to avoid removing any loosely attached cells.

Once the PBS was removed, 85 μL cell lysis solution was added the cells in each well and incubated for 5-10 min at room temperature, to allow for complete cell lysis and detachment. mRNA was then prepared using the "mRNA Catcher PLUS plate" from Invitrogen, according to the protocol supplied. After the last wash, as much wash buffer as possible was aspirated without allowing the wells to dry. Elution Buffer (E3, 80 μL) was then added to each well. mRNA was then eluted by incubating the mRNA Catcher PLUS plate with Elution Buffer for 5 min at 68° C. and then immediately placing the plate on ice.

The eluted mRNA isolated was then used in a one-step real-time room temperature-PCR reaction, using components of the Ultra Sense Kit together with Applied Biosystems primer-probe mixes. Real-time PCR data was analyzed, using the Ct values, to determine the fold induction of each unknown sample, relative to the control (that is, relative to the control for each independent DMSO concentration).

An active compound is one that causes a >15% increase in ApoA-I mRNA at a concentration less than or equal to 100 uM.

| Example # | Compound Name | Effect on ApoA-I mRNA levels |
|---|---|---|
| 107 | N-(2-(4-(5,7-Dimethoxy-4-oxo-3,4-dihydroquinazolin-2-yl)-2,6-dimethylphenoxy)ethyl)-4-methylbenzamide | Active |
| 106 | 2-(4-(5,7-Dimethoxy-4-oxo-3,4-dihydroquinazolin-2-yl)-2,6-dimethyl-phenoxy)ethyl methylcarbamate | Active |
| 105 | 2-(4-(5,7-Dimethoxy-4-oxo-3,4-dihydroquinazolin-2-yl)-2,6-dimethyl-phenoxy)ethyl propylcarbamate | Active |
| 102 | N-(2-(4-(5,7-dimethoxy-4-oxo-3,4-dihydroquinazolin-2-yl)-2,6-dimethylphenoxy)ethyl)methanesulfonamide | Active |
| 101 | 4-chloro-N-(2-(4-(5,7-dimethoxy-4-oxo-3,4-dihydroquinazolin-2-yl)-2,6-dimethylphenoxy)ethyl)benzenesulfonamide | Active |
| 100 | N-(2-(4-(5,7-dimethoxy-4-oxo-3,4-dihydroquinazolin-2-yl)-2,6-dimethylphenoxy)ethyl)-4-methoxybenzenesulfonamide | Active |
| 99 | 2-(4-(2-aminoethoxy)-3,5-dimethylphenyl)-5,7-dimethoxyquinazolin-4(3H)-one | Active |
| 99 | N1-(2-(4-(5,7-dimethoxy-4-oxo-3,4-dihydroquinazolin-2-yl)-2,6-dimethylphenoxy)ethyl)-N2-methylphthalamide | Active |
|  | 2-(2-(4-(5,7-dimethoxy-4-oxo-3,4-dihydroquinazolin-2-yl)-2,6-dimethylphenoxy)ethyl)isoindoline-1,3-dione | Inactive |
| 98 | 2-(4-hydroxy-3-methylphenyl)-5,7-dimethoxyquinazolin-4(3H)-one | Active |
| 97 | 2-(4-(2-hydroxyethoxy)-3-methylphenyl)-5,7-dimethoxyquinazolin-4(3H)-one | Active |
| 96 | 2-(4-(benzyloxy)-3,5-dimethylphenyl)-5,7-dimethoxyquinazolin-4(3H)-one | Active |
| 95 | 6-bromo-2-(4-(2-(tert-butyldimethylsilyloxy)ethoxy)-3,5-dimethylphenyl)quinazolin-4(3H)-one | Active |
| 95 | 6-bromo-2-(4-(2-hydroxyethoxy)-3,5-dimethylphenyl)quinazolin-4(3H)-one | Active |
| 94 | 6-bromo-2-(4-hydroxy-3,5-dimethylphenyl)quinazolin-4(3H)-one | Active |
| 93 | (E)-N'-(4-(5,7-dimethoxy-4-oxo-3,4-dihydroquinazolin-2-yl)-2,6-dimethylphenyl)-N,N-dimethylformimidamide | Active |
| 92 | 2-(3,5-dimethylphenyl)-5,7-dimethoxyquinazolin-4(3H)-one | Active |
|  | 5,7-dimethoxy-2-(3-nitrophenyl)quinazolin-4(3H)-one | Inactive |
| 91 | 2-(4-amino-3,5-dimethylphenyl)-5,7-dimethoxyquinazolin-4(3H)-one | Active |

| Example # | Compound Name | Effect on ApoA-I mRNA levels |
|---|---|---|
| 90 | 5,7-dimethoxy-2-(4-methoxy-3,5-dimethylphenyl)quinazolin-4(3H)-one | Active |
| 89 | 2-(2-chloro-6-methylpyridin-4-yl)-5,7-dimethoxyquinazolin-4(3H)-one | Active |
| 88 | 5,7-dimethoxy-2-(6-(4-(methylthio)phenyl)pyridin-2-yl)quinazolin-4(3H)-one | Active |
| 87 | 5,7-dimethoxy-2-(6-methylpyridin-2-yl)quinazolin-4(3H)-one | Active |
| 86 | 5,7-dimethoxy-2-(6-(4-(methylsulfonyl)phenyl)pyridin-2-yl)quinazolin-4(3H)-one | Active |
| 85 | 5,7-dimethoxy-2-o-tolylquinazolin-4(3H)-One | Active |
| 84 | 2-(4-(2-hydroxyethoxy)-3,5-dimethylphenyl)-5-methoxyquinazolin-4(3H)-one | Active |
| 83 | 2-(2-chlorophenyl)-5,7-dimethoxyquinazolin-4(3H)-one | Active |
| 82 | 2-(4-(2-hydroxyethoxy)-3,5-dimethylphenyl)-6-methoxyquinazolin-4(3H)-one | Active |
|  | 4-(4-ethoxy-5,7-dimethoxyquinazolin-2-yl)-2,6-dimethylphenol | Inactive |
| 81 | 2-(4-hydroxy-3,5-dimethylphenyl)-5,7-dimethoxy-6-(morpholinomethyl)quinazolin-4(3H)-one | Active |
| 80 | 5,7-dichloro-2-(4-(2-hydroxyethoxy)-3,5-dimethylphenyl)quinazolin-4(3H)-one | Active |
| 79 | 5,7-dimethoxy-2-(4-(2-methoxyethoxy)-3,5-dimethylphenyl)quinazolin-4(3H)-one | Active |
| 78 | 2-(4-(bis(2-hydroxyethyl)amino)phenyl)-5,7-dimethoxypyrido[2,3-d]pyrimidin-4(3H)-one | Active |
| 77 | 2-(4-(2-hydroxyethoxy)-3,5-dimethylphenyl)-5,7-dimethylquinazolin-4(3H)-one | Active |
| 76 | 2-(4-(5,7-dimethoxyquinazolin-2-yl)-2,6-dimethylphenoxy)ethanol | Active |
| 75 | 2-(4-hydroxy-3-(2-hydroxyethyl)phenyl)-5,7-dimethoxyquinazolin-4(3H)-one | Active |
| 104 | 5-hydroxy-2-(4-hydroxy-3,5-dimethylphenyl)-7-methoxyquinazolin-4(3H)-one | Active |
| 74 | 7-(4-hydroxy-3,5-dimethylphenyl)-2,4-diisopropoxy-1,6-naphthyridin-5(6H)-one | Active |
|  | 2-(4-(2-(benzyloxy)ethoxy)-3,5-dimethylphenyl)-5,7-dimethoxypyrido[2,3-d]pyrimidin-4(3H)-one | Inactive |
| 73 | N-(2-(4-(2-hydroxyethoxy)-3,5-dimethylphenyl)-4-oxo-3,4-dihydroquinazolin-6-yl)acetamide | Active |
| 72 | 2-(3,5-dimethyl-4-(2-(pyrrolidin-1-yl)ethoxy)phenyl)-5,7-dimethoxyquinazolin-4(3H)-one | Active |
| 71 | 2-(4-hydroxy-3,5-dimethylphenyl)-5,7-dimethoxy-1-methylquinazolin-4(1H)-one | Active |
| 70 | 2-(4-(2-hydroxyethoxy)-3,5-dimethylphenyl)-5,7-dimethoxypyrido[2,3-d]pyrimidin-4(3H)-one | Active |
| 69 | 5,7-dimethoxy-2-(4-methoxy-3-(morpholinomethyl)phenyl)quinazolin-4(3H)-one | Active |
| 68 | 2-(4-hydroxy-3,5-dimethylphenyl)-5,7-dimethoxypyrido[2,3-d]pyrimidin-4(3H)-one | Active |
| 67 | 2-(4-((4-ethylpiperazin-1-yl)methyl)phenyl)-5,7-dimethoxyquinazolin-4(3H)-one | Active |
| 66 | 5,7-dimethoxy-2-(4-(morpholinomethyl)phenyl)quinazolin-4(3H)-one | Active |
| 65 | N-(4-(5,7-dimethoxy-4-oxo-3,4-dihydroquinazolin-2-yl)phenyl)-2-hydroxyacetamide | Active |
| 64 | 2-(4-(5,7-dimethoxy-4-oxo-3,4-dihydroquinazolin-2-yl)-2,6-dimethylphenoxy)acetic acid | Active |
| 63 | 2,4-dimethoxy-7-(4-methoxy-3,5-dimethylphenyl)-1,6-naphthyridin-5(6H)-one | Active |
| 62 | 2-(4-hydroxy-3,5-dimethylphenyl)-6-(morpholinomethyl)quinazolin-4(3H)-one | Active |
| 61 | 7-(4-(2-hydroxyethoxy)-3,5-dimethylphenyl)-2,4-dimethoxy-1,6-naphthyridin-5(6H)-one | Active |
| 60 | N-(4-(5,7-dimethoxy-4-oxo-3,4-dihydroquinazolin-2-yl)-2,6-dimethylphenyl)-2-hydroxyacetamide | Active |
| 59 | 5,7-dimethoxy-2-(4-((4-methylpiperazin-1-yl)methyl)phenyl)quinazolin-4(3H)-one | Active |
| 58 | 2-(4-(2-hydroxyethoxy)-3,5-dimethylphenyl)-6,7-dimethoxyquinazolin-4(3H)-one | Active |
| 103 | 2-(4-(5,7-dimethoxy-4-oxo-3,4-dihydroquinazolin-2-yl)-2-methoxyphenoxy)acetic acid | Active |
| 57 | 2-(4-(2-hydroxyethoxy)-3-methoxyphenyl)-5,7-dimethoxyquinazolin-4(3H)-one | Active |
| 56 | 2-(3-chloro-4-(2-hydroxyethoxy)phenyl)-5,7-dimethoxyquinazolin-4(3H)-one | Active |
| 55 | 2-(4-(6,7-dimethoxy-4-oxo-3,4-dihydroquinazolin-2-yl)-2,6-dimethylphenoxy)acetamide | Active |
| 54 | N-(2-(4-hydroxy-3,5-dimethylphenyl)-4-oxo-3,4-dihydroquinazolin-6-yl)acetamide | Active |
| 53 | 3-(4-(5,7-dimethoxy-4-oxo-3,4-dihydroquinazolin-2-yl)phenyl)propanoic acid | Active |
|  | 2-(4-(4-chlorophenoxy)pyridin-3-yl)-5,7-dimethoxyquinazolin-4(3H)-one | Inactive |
| 51 | 3-(4-hydroxy-3,5-dimethylphenyl)-6,8-dimethoxy-7-(morpholinomethyl)isoquinolin-1(2H)-one | Active |
| 50 | 7-(4-hydroxy-3-(4-morpholinoethoxy)-2,4-dimethoxy-1,6-naphthyridin-5(6H)-one | Active |
| 49 | 5,7-dimethoxy-2-(4-morpholinophenyl)quinazolin-4(3H)-one | Active |
| 48 | 2-(2,3-dihydrobenzo[b][1,4]dioxin-6-yl)-6,7-dimethoxyquinazolin-4(3H)-one | Active |
| 47 | 2-(4-(bis(2-hydroxyethyl)amino)phenyl)-6,7-dimethoxyquinazolin-4(3H)-one | Active |
| 46 | 2-(4-(bis(2-hydroxyethyl)amino)phenyl)-5,7-dimethoxyquinazolin-4(3H)-one | Active |
| 45 | 2-(4-(bis(2-hydroxyethyl)amino)phenyl)quinazolin-4(3H)-one | Active |
| 44 | 2-(4-(dimethylamino)pyridin-1-yl)-6,7-dimethoxyquinazolin-4(3H)-one | Active |
| 43 | 5,7-dimethoxy-2-(4-(4-methylpiperazin-1-yl)phenyl)quinazolin-4(3H)-one | Active |
| 42 | 2-(2,3-dihydrobenzo[b][1,4]dioxin-6-yl)-5,7-dimethoxyquinazolin-4(3H)-one | Active |
| 41 | 2-(4-(4-oxo-3,4-dihydroquinazolin-2-yl)phenoxy)acetamide | Active |
| 40 | 2-(4-(dimethylamino)naphthalene-1-yl)quinazolin-4(3H)-one | Active |
| 39 | 2-(4-(4-oxo-3,4-dihydroquinazolin-2-yl)phenoxy)acetic acid | Active |
| 38 | 2-(4-(5,7-dimethoxy-4-oxo-3,4-dihydroquinazolin-2-yl)phenoxy)acetamide | Active |
| 37 | 2-(4-(dimethylamino)naphthalene-1-yl)-5,7-dimethoxyquinazolin-4(3H)-one | Active |
| 36 | 2-(2,3-dihydrobenzo[b][1,4]dioxin-6-yl)quinazolin-4(3H)-one | Active |
| 35 | 2-(4-(2-hydroxyethoxy)-3,5-dimethylphenyl)quinazolin-4(3H)-one | Active |
| 34 | 2-(3,5-dimethyl-4-(2-morpholinoethoxy)phenyl)quinazolin-4(3H)-one | Active |
| 33 | 5,7-dimethoxy-2-(pyridin-4-yl)quinazolin-4(3H)-one | Active |
| 32 | 2-(3-chloro-4-hydroxyphenyl)-5,7-dimethoxyquinazolin-4(3H)-one | Active |
| 31 | 2-(4-hydroxy-3-methoxyphenyl)-5,7-dimethoxyquinazolin-4(3H)-one | Active |
| 30 | 5,7-dimethoxy-2-(4-methoxyphenyl)quinazolin-4(3H)-one | Active |
| 29 | 2-(3,5-dimethoxyphenyl)-5,7-dimethoxyquinazolin-4(3H)-one | Active |
| 28 | 2-(3,5-di-tert-butyl-4-hydroxyphenyl)-5,7-dimethoxyquinazolin-4(3H)-one | Active |
| 26 | 5,7-dimethoxy-2-(pyridin-2-yl)quinazolin-4(3H)-one | Active |
| 24 | 2-(4-hydroxyphenyl)-5,7-dimethoxyquinazolin-4(3H)-one | Active |
| 23 | 3-(3,5-dimethyl-4-(2-(4-methylpiperazin-1-yl)ethoxy)phenyl)-6,8-dimethoxyisoquinolin-1(2H)-one | Active |
| 22 | 4-(2-(4-(6,8-dimethoxyisoquinolin-3-yl)-2,6-dimethylphenoxy)ethyl)morpholine | Active |
| 21 | 2-(3,5-dimethyl-4-(2-morpholinoethoxy)phenyl)-5,7-dimethoxyquinazolin-4(3H)-one | Active |
|  | 5,7-dimethoxy-2-p-tolylquinazolin-4(3H)-one | Inactive |
| 20 | 2-(4-(2-hydroxyethoxy)-3,5-dimethylphenyl)-5,7-dimethoxyquinazolin-4(3H)-one | Active |
| 19 | 3-(3,5-dimethyl-4-(2-morpholinoethoxy)phenyl)-6,8-dimethoxyisoquinolin-1(2H)-one | Active |

-continued

| Example # | Compound Name | Effect on ApoA-I mRNA levels |
|---|---|---|
| 18 | 4-(6,8-dimethoxyisoquinolin-3-yl)-2,6-dimethylphenol | Active |
| 17 | 3-(4-hydroxy-3,5-dimethylphenyl)-6,8-dimethoxy-2-methyl-7-(morpholinomethyl) isoquinolin-1(2H)-one | Active |
| 17 | 3-(4-hydroxy-3,5-dimethylphenyl)-6,8-dimethoxy-2,7-dimethylisoquinolin-1(2H)-one | Active |
| 16 | 7-(4-hydroxy-3,5-dimethylphenyl)-2,4-dimethoxy-1,6-naphthyridin-5(6H)-one | Active |
| 15 | 6,8-dimethoxy-3-(4-hydroxy-3,5-dimethylphenyl)-2H-1,2-benzothiazine-1,1-dioxide | Active |
| 14 | 3-(4-(2-hydroxy-2-methylpropoxy)-3,5-dimethylphenyl)-6,8-dimethoxyisoquinolin-1(2H)-one | Active |
| 13 | 2-(4-hydroxy-3,5-dimethylphenyl)-5,7-dimethoxyquinazolin-4(3H)-one | Active |
| 12 | 2-hydroxy-7-(4-hydroxy-3,5-dimethylphenyl)-4-methoxy-1,6-naphthyridin-5(6H)-one | Active |
| 11 | 3-(4-hydroxy-3,5-dimethypheny)-7-(morpholinomethyl)isoquinolin-1(2H)-one | Active |
| 10 | 3-(4-(2-(dimethylamino)ethoxy)-3,5-dimethylphenyl)-6,8-dimethoxyisoquinolin-1(2H)-one | Active |
| 9 | 3-(4-(2-hydroxyethoxy)-3,5-dimethylphenyl)-6,8-dimethoxyisoquinolin-1(2H)-one | Active |
| 8 | 7-(4-hydroxy-3,5-dimethylphenyl)-1,6-naphthyridin-5(6H)-one | Active |
| 7 | 3-(4-hydroxy-3,5-dimethylphenyl)-6,8-dimethoxyisoquinolin-1(2H)-one | Active |
| 7 | 3-(4-hydroxy-3,5-dimethylphenyl)-6,8-dimethoxy-2-methylisoquinolin-1(2H)-one | Active |
| 6 | 3-(4-hydroxyphenyl)-6,8-dimethoxyisoquinolin-1(2H)-one | Active |
|  | 3-(3-fluoro-4-hydroxyphenyl)-5-methoxyisoquinolin-1(2H)-one | Inactive |
| 5 | 4-(1,6-naphthyridin-7-yl)phenol | Active |
| 4 | 4-(1-Oxo-1,2-dihydroisoquinolin-3-yl)phenyl 2-amino-5-guanidinopentanoate | Active |
| 3 | 4-(Isoquinolin-3-yl)phenyl 2-amino-5-guanidinopentanoate tetrahydrochloride | Active |
| 2 | 4-Isoquinolin-3-yl-phenol | Active |
| 1 | 3-(4-Hydroxyphenyl)-2H-isoquinolin-1-one | Active |
| 108 | 2-(4-(5,7-dimethoxy-4-oxo-3,4-dihydroquinazolin-2-yl)-2,6-dimethylphenoxy)ethyl cyclohexylcarbamate | Active |
| 109 | N-(2-(4-(5,7-dimethoxy-4-oxo-3,4-dihydroquinazolin-2-yl)-2,6-dimethylphenoxy)ethyl)benzenesulfonamide | Active |
| 110 | N-(2-(4-(5,7-dimethoxy-4-oxo-3,4-dihydroquinazolin-2-yl)-2,6-dimethylphenoxy)ethyl)-4-methylbenzenesulfonamide | Active |
| 111 | N-(2-(4-(5,7-dimethoxy-4-oxo-3,4-dihydroquinazolin-2-yl)-2,6-dimethylphenoxy)ethyl)-4-methoxybenzamide | Active |
| 112 | N-(2-(4-(5,7-dimethoxy-4-oxo-3,4-dihydroquinazolin-2-yl)-2,6-dimethylphenoxy)ethyl)acetamide | Active |
| 113 | N-(2-(4-(5,7-dimethoxy-4-oxo-3,4-dihydroquinazolin-2-yl)-2,6-dimethylphenoxy)ethyl)benzamide | Active |
| 114 | N-(2-(4-(5,7-dimethoxy-4-oxo-3,4-dihydroquinazolin-2-yl)-2,6-dimethylphenoxy)ethyl)isobutyramide | Active |
| 115 | 1-(2-(4-(5,7-dimethoxy-4-oxo-3,4-dihydroquinazolin-2-yl)-2,6-dimethylphenoxy)ethyl)-3-methylurea | Active |
| 116 | 1-(2-(4-(5,7-dimethoxy-4-oxo-3,4-dihydroquinazolin-2-yl)-2,6-dimethylphenoxy)ethyl)-3-(4-methoxyphenyl)urea | Active |
| 117 | 1-(2-(4-(5,7-dimethoxy-4-oxo-3,4-dihydroquinazolin-2-yl)-2,6-dimethylphenoxy)ethyl)-3-phenylurea | Active |
| 118 | 3-(2-(4-(5,7-dimethoxy-4-oxo-3,4-dihydroquinazolin-2-yl)-2,6-dimethylphenoxy)ethyl)-1,1-dimethylurea | Active |

EXAMPLE 120

ApoA-I mRNA and Protein Induction

In this example, ApoA-I mRNA and secreted protein from tissue culture cells were quantitated. The assay can be used to determine the potency for compounds of interest, including those of the present invention.

HepG2 cells or primary human hepatocytes (BD Gentest, lot 107) (~2×10$^5$ per well) were placed in a 24-well plate in ~400 µL MEM, supplemented with 0.5% (v/v) FBS, 24 h before addition of the compound of interest. The compounds of interest were dissolved in DMSO at 0.05% (v/v). Appropriate volumes of the stock solutions of the compounds in DMSO were then added to appropriate volumes of MEM, supplemented with 0.5% (v/v) FBS, to achieve the desired concentration (for example, 1 µL of a compound stock into 1 mL of MEM, supplemented with 0.5% (v/v) FBS).

Just prior to compound addition to the cells, the growth media was aspirated and replaced with 300 µL of fresh MEM, supplemented with 0.5% (v/v) FBS, followed by addition of 300 µL of the compound of interest in MEM, supplemented with 0.5% (v/v) FBS, to achieve the desired final compound concentration in a total volume of 600 µL. The final concentration of diluent (DMSO) was 0.05% (v/v).

Cells were incubated for the desired time. The cell media was then harvested, as were the cells. ApoA-I mRNA was measured as described in Example 119. Secreted ApoA-I was measured using an ApoA-I ELISA, as described below:

ApoA-I ELISA

In this example, the ApoA-I secreted into the media from tissue culture cells was quantitated to assess induction of endogenous ApoA-I protein secretion from cells treated with various small molecule compounds, such as those of the present invention.

At time of harvesting, spent media from the HepG2 cell cultures or primary cell culture was removed and stored at −80° C. in 1.5 mL microfuge tubes.

For the human ApoA-I ELISA, an ELISA plate was coated with ~100 µL/well human ApoA-I capture antibody diluted to ~2 µg/mL in coating buffer for ~1 h at room temperature. The plate was then washed three times in wash buffer. The plate was then blocked with ~200 µL/well human ApoA-I blocking buffer for at least ~30 min at room temperature.

Samples for use in generating a standard curve were prepared from spent media (MEM, supplemented with 0.5% (v/v) FBS) from HepG2 or primary cells treated with DMSO for 48 h. Serial 2 fold dilutions of the media were prepared in MEM, supplemented with 0.5% (v/v) FBS. The unknown samples—from the cultures treated with the compounds of interest—were also diluted in MEM, supplemented with 0.5% (v/v) FBS. The plate was washed three times in wash buffer. The standard curve and unknown samples (100 µL/well), in triplicate, were added to the plate and it was incubated for 1.5 h at room temperature.

The plate was washed three times in wash buffer. Human ApoA-I detection antibody, diluted 1:1000 in PBS, was added (100 µL/well) and the plate was incubated for 1 h at room temperature. The plate was washed three times in wash buffer.

Goat anti-rabbit IgG H & L chain specific peroxidase conjugate, diluted 1:2000 in PBS, was added (100 µL/well) and the plate was incubated for 40 min at room temperature in the dark. The plate was washed six times in wash buffer.

TMB liquid substrate was added (100 µL/well) and the plate was incubated on a shaker underneath tin foil during development. Once a sufficient "blue" color had been achieved, stop solution (50 µL/well, 1 M H$_2$SO4) was added and mixed thoroughly on the plate shaker. Air bubbles were removed and the absorbance at 450 nm was determined, using a Molecular Devices SpectraMax 190 Plate Reader and the human ApoA-I ELISA Softmax software.

Experiment A 2-(4-(2-hydroxyethoxy)-3,5-dimethylphenyl)-5,7-dimethoxyquinazolin-4(3H)-one at 0, 2.5, 5, 10, 20, 40, 60, 80 and 100 μM in HepG2 cell culture (48 h) and assayed for ApoA-I mRNA and secreted protein (FIG. 1).

Figure 2:
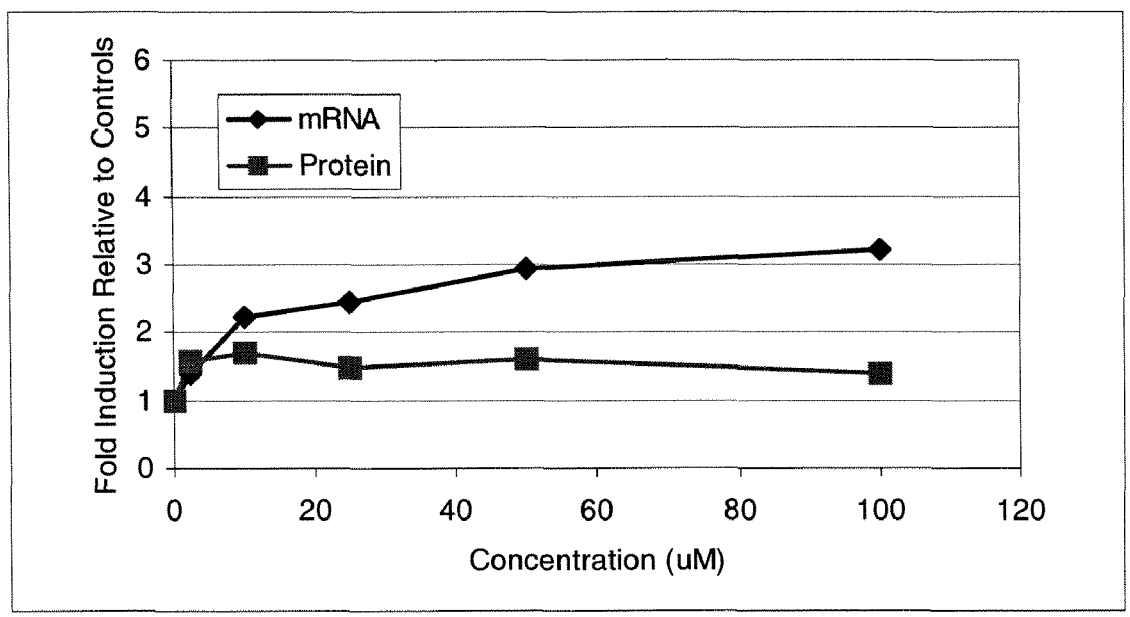
FIG. 2 depicts ApoA-I induction by 2-(4-(2-hydroxyethoxy)-3,5-dimethylphenyl)-5,7-dimethoxyquinazolin-4(3H)-one (Example 20) in primary human hepatocytes (48 h).

Experiment B 2-(4-(2-hydroxyethoxy)-3,5-dimethylphenyl)-5,7-dimethoxyquinazolin-4(3H)-one at 0, 2.5, 5, 10, 20, 40, 60, 80 and 100 μM in primary human hepatocytes (48 h) and assayed for ApoA-I mRNA and secreted protein (FIG. 2).

EXAMPLE 121

In Vivo Efficacy

To test whether the efficacy of compounds of the invention observed in vitro extended to an in vivo model, transgenic mice carrying multiple copies of the human ApoA-I gene (Bisaha et al. (1995) *J. Biol. Chem.* 34, 19979-88) or wild-type mice (C57BL/6 (Stock Number 000664) Jackson Laboratory (Bar Harbor, Me.)) were exposed to compounds of the invention. In the transgenic mice, the exogenous human ApoA-I gene in these mice enables them to express the human ApoA-I protein under the control of its own promoter.

Seven to eight week old male mice were housed five per cage (10"×20"×8" with aspen chip bedding) with pelleted Rodent chow [Purina 5001] and water available at all times. After an acclimation period of 1 week, animals were individually identified by numbering on tail and weighed. Mice were pre bled via the retro-orbital plexus, and 100 μL of blood was collected in 1.5 mL Eppendorf tube containing 5 μL of 0.5 mM EDTA and chilled on ice. Plasma was collected after centrifuging the whole blood at 14000 rpm [TOMY high speed micro-refrigerated centrifuge NTX-150] for 10 min at 4° C. and frozen at −80° C. Mice were grouped based on having an average body weight of 25 g.

A day following pre-bleed, mice were dosed by oral gavage or i.p. daily using a 20 gauge, 1½" curved disposable feeding needle (Popper & Sons); when B.I.D., mice were gavaged morning and afternoon (8 am and 5 pm); when Q.D. mice were gavaged in morning (8 am). Compounds were prepared each day in vehicle. One day prior to necropsy mice were weighed and fasted overnight. On final day of dosing, mice were sacrificed post 2 h of dosing by inhalation of $CO_2$ and blood was obtained via cardiac puncture (0.7-1.0 mL). Plasma was collected and frozen at −80° C. Samples were assayed for ApoA-I by ELISA, and HDL-C by HPLC (Polaris 200 with an auto sampler Prostar 410 from Varian on a Superose 6 10/30 column from Amersham). During necropsy, liver and enterocytes from the duodenum and jejunum of the small intestine were collected, cleaned with cold PBS and frozen at −80° C. for further analysis of compound and mRNA levels by Q-PCR.

Figure 3:
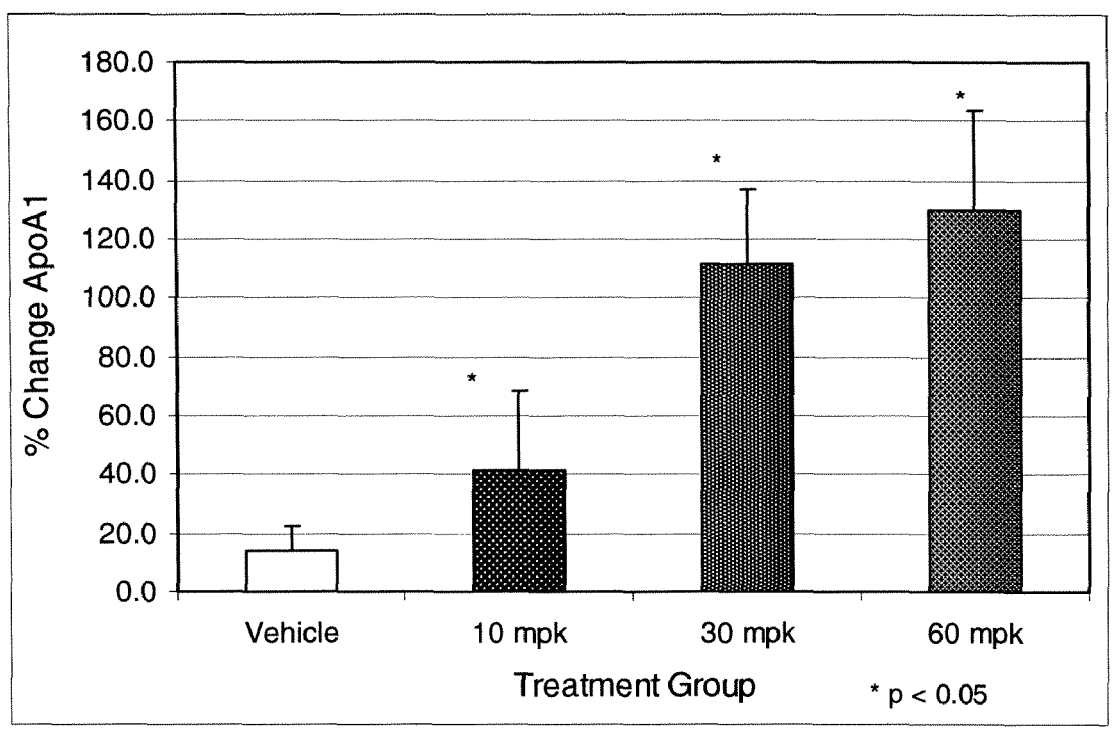
FIG. 3 depicts plasma levels of ApoA-I in hApoA-I transgenic mice receiving 2-(4-(2-hydroxyethoxy)-3,5-dimethylphenyl)-5,7-dimethoxyquinazolin-4(3H)-one (Example 20) (10, 30, and 60 mg/kg body weight) twice daily for 7 days by oral gavage.
Figure 4:
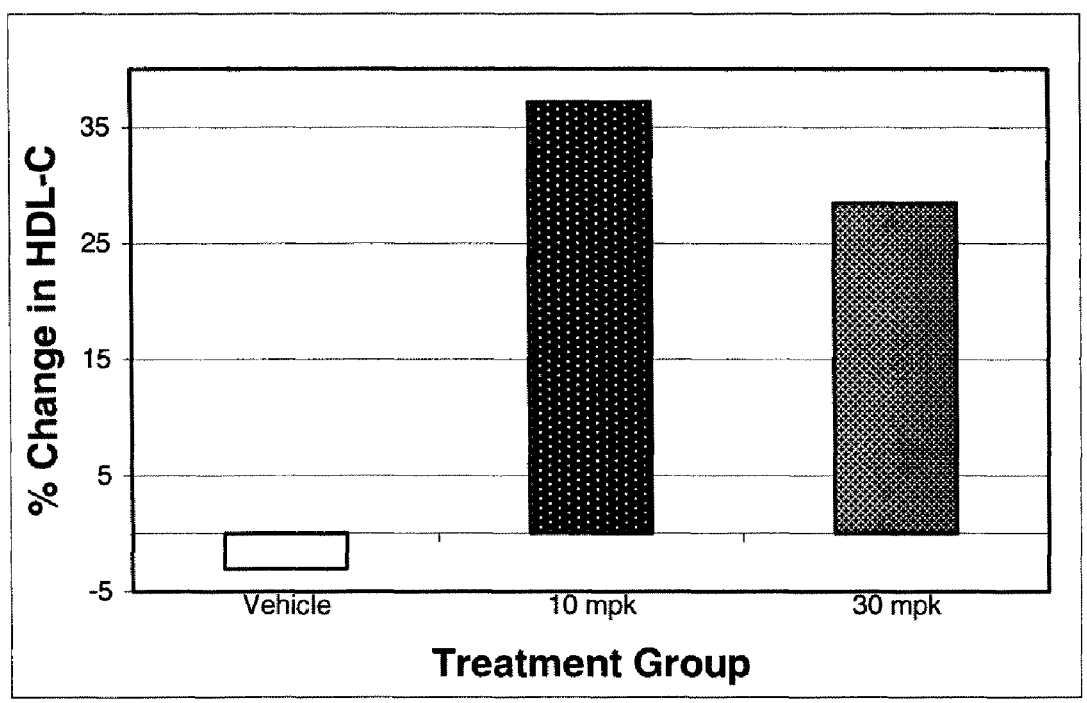
FIG. 4 depicts plasma levels of HDL cholesterol in hApoA-I transgenic mice receiving 2-(4-(2-hydroxyethoxy)-3,5-dimethylphenyl)-5,7-dimethoxyquinazolin-4(3H)-one (Example 20) (10 and 30 mg/kg body weight) twice daily for 7 days by oral gavage.

Experiment A 2-(4-(2-hydroxyethoxy)-3,5-dimethylphenyl)-5,7-dimethoxyquinazolin-4(3H)-one (10, 30 and 60 mg/kg of body weight, mpk) were BID administered to hApoA-I transgenic mice daily for seven days by oral gavage in 1% DMSO, 2.5% Tween-80, 10% PEG-300 QS to water. Plasma was assayed for ApoA-I (FIG. 3), and HDL cholesterol (FIG. 4).

Figure 5:
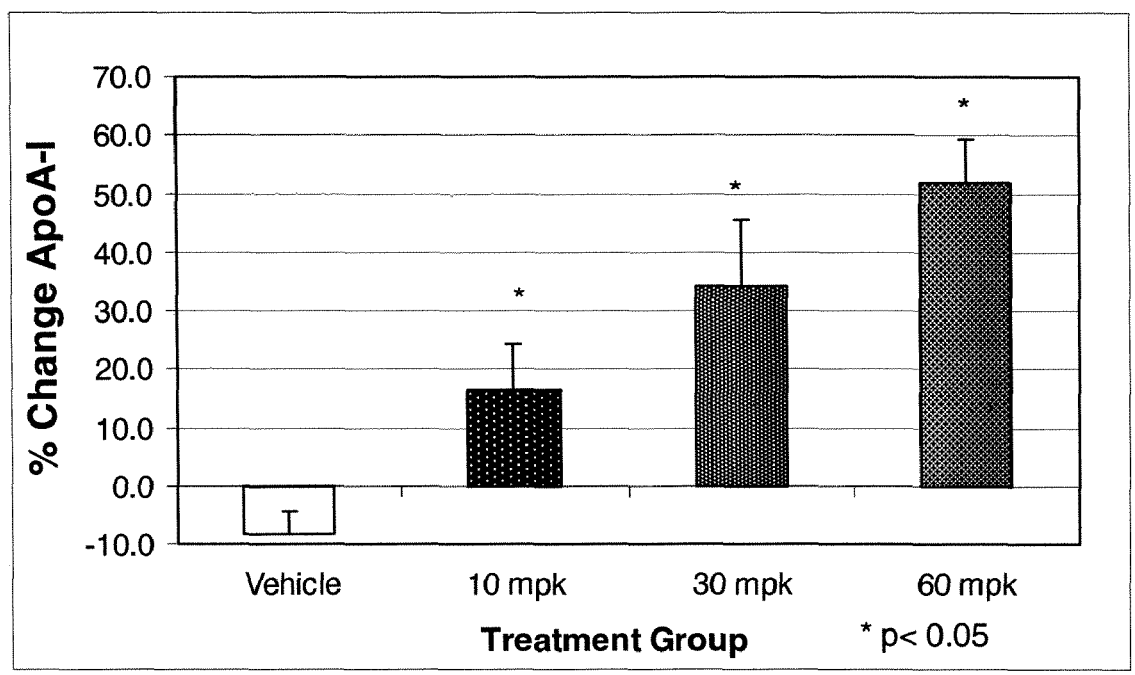
FIG. 5 depicts plasma levels of ApoA-I in wild-type C57BL/6 mice receiving 2-(4-(2-hydroxyethoxy)-3,5-dimethylphenyl)-5,7-dimethoxyquinazolin-4(3H)-one (Example 20) (10, 30 and 60 mg/kg of body weight) twice daily for 3 days by intraperitoneal administration.
Figure 6:
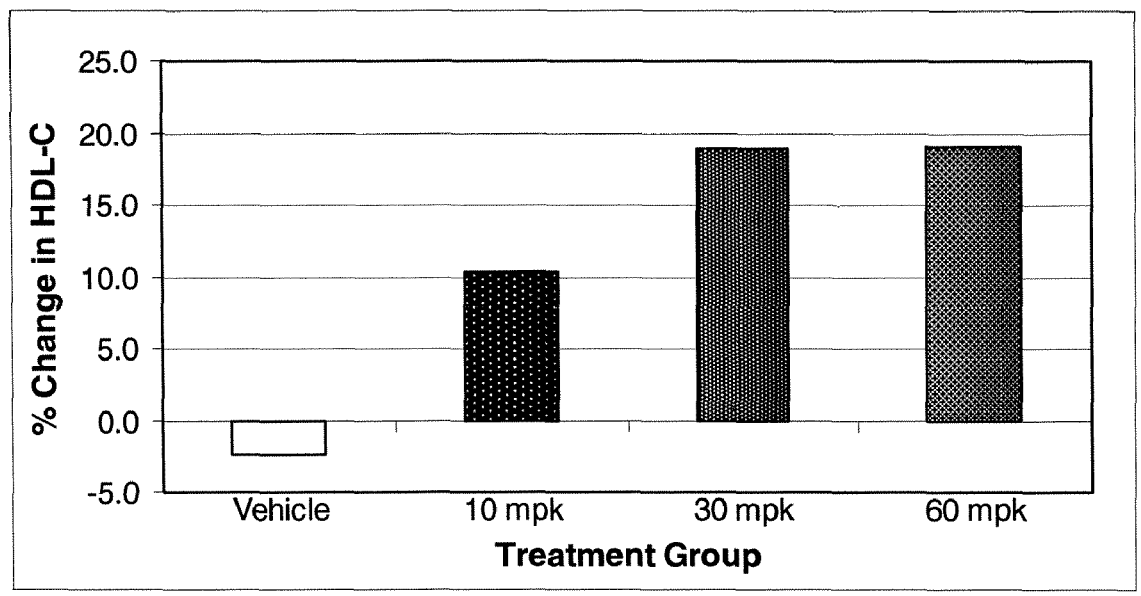
FIG. 6 depicts plasma levels of HDL cholesterol in wild-type C57BL/6 mice receiving 2-(4-(2-hydroxyethoxy)-3,5-dimethylphenyl)-5,7-dimethoxyquinazolin-4(3H)-one (Example 20) (10, 30 and 60 mg/kg of body weight) twice daily for 3 days by intraperitoneal administration.

Experiment B 2-(4-(2-hydroxyethoxy)-3,5-dimethylphenyl)-5,7-dimethoxyquinazolin-4(3H)-one (10, 30 and 60 mg/kg of body weight) were BID administered to wild type C57BL/6 mice daily for three days by intraperitoneal administration in 1% DMSO, 2.5% Tween-80, 10% PEG-300 QS to water. Plasma was assayed for ApoA-I (FIG. 5), and HDL cholesterol (FIG. 6).

Figure 7:
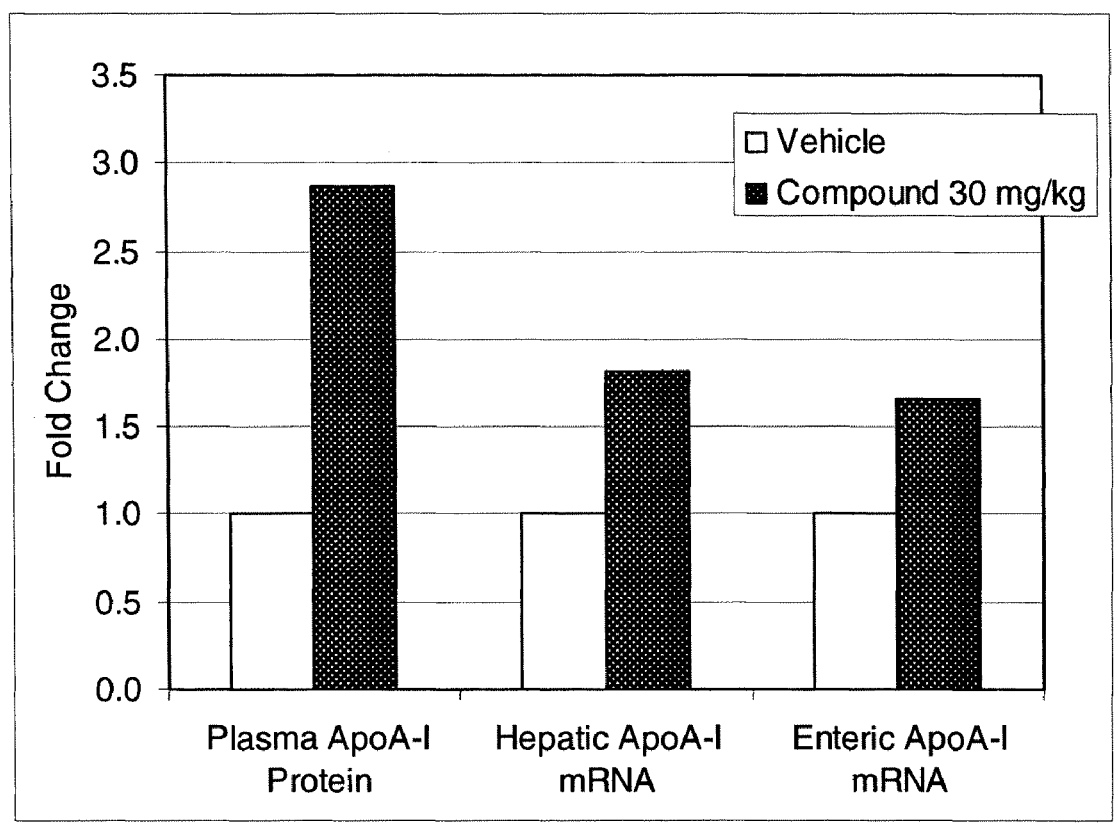
FIG. 7 depicts plasma levels of ApoA-I and tissue levels of ApoA-I mRNA in hApoA-I transgenic mice administered 2-(4-(2-hydroxyethoxy)-3,5-dimethylphenyl)-5,7-dimethoxyquinazolin-4(3H)-one (Example 20) (30 mg/kg body weight) twice daily for 7 days by oral gavage.

Experiment C 2-(4-(2-hydroxyethoxy)-3,5-dimethylphenyl)-5,7-dimethoxyquinazolin-4(3H)-one (30 mg/kg of body weight) were BID administered to hApoA-I transgenic mice daily for seven days by oral gavage in 1% DMSO, 2.5% Tween-80, 10% PEG-300 QS to water. Plasma was assayed for ApoA-I and tissues were assayed for mRNA (FIG. 7).

These results indicate that the compounds of the invention are useful for increasing the transcription of ApoA-I in vivo, and elevating plasma levels of ApoA-I and circulating levels of HDL-C in wild type and hApoA-I transgenic mice. These results demonstrate that compounds of the invention activate the human ApoA-I transgene in mice, leading to an increase in circulating ApoA-I.

All references referred to herein are incorporated by reference in their entirety. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A compound of Formula II:

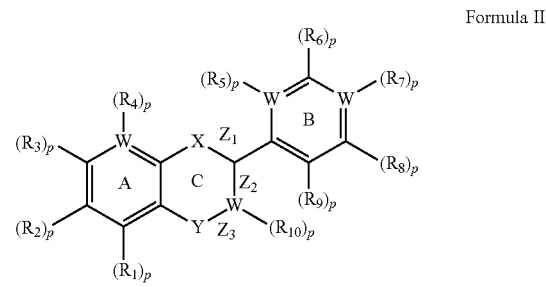

Formula II wherein:
X is N;
Y is CO;
$R_1$ and $R_3$ are each independently selected from alkoxy, alkyl, amino, halogen, and hydrogen;
$R_2$ is selected from alkoxy, alkyl, alkenyl, alkynyl, amide, amino, halogen, and hydrogen;
$R_6$ and $R_8$ are each independently selected from alkyl, alkoxy, amino, halogen, and hydrogen;
$R_5$ and $R_9$ are each hydrogen;
$R_7$ is selected from amino, amide, alkyl, hydroxyl, and alkoxy;
$R_{10}$ is hydrogen;
each W is independently selected from C and N, wherein if W is N, then p is 0 or 1, and if W is C, then p is 1;
for W—$(R_{10})_p$, W is N and p is 1;
for W—$(R_7)_p$, W is C and p is 1;
for W—$(R_4)_p$, W is C, p is 1 and $R_4$ is H, or W is N and p is 0;
$Z_1$ is a double bond, and $Z_2$ and $Z_3$ are each a single bond;
with the proviso that if $R_1$ is hydrogen, then $R_3$ is alkoxy;
with the proviso that if $R_3$ is hydrogen, then $R_1$ is selected from amino and alkoxy;
with the proviso that if $R_7$ is selected from alkyl, hydroxyl, and alkoxy, then at least one of $R_6$ and $R_8$ is independently selected from alkyl, alkoxy, amino, and halogen;
and pharmaceutically acceptable salts thereof.

2. The compound according to claim 1, wherein $R_7$ is amino.

3. The compound according to claim 2, wherein the compound of Formula II is 2-(4-(bis(2-hydroxyethyl)amino)phenyl)-5,7-dimethoxyquinazolin-4(3H)-one.

4. The compound according to claim 1, wherein $R_7$ is selected from hydroxyl and alkoxy.

5. The compound according to claim 4, wherein the compound of Formula II is selected from:
N-(2-(4-(5,7-dimethoxy-4-oxo-3,4-dihydroquinazolin-2-yl)-2,6-dimethylphenoxy)ethyl)methanesulfonamide;
2-(4-hydroxy-3-methylphenyl)-5,7-dimethoxyquinazolin-4(3H)-one;
2-(4-(2-hydroxyethoxy)-3-methylphenyl)-5,7-dimethoxyquinazolin-4(3H)-one; and
2-(3,5-dimethyl-4-(2-morpholinoethoxy)phenyl)-5,7-dimethoxyquinazolin-4(3H)-one.

6. The compound according to claim 4, wherein $R_6$ and $R_8$ are each independently alkyl;
$R_2$ is hydrogen; and
$R_7$ is selected from hydroxyl and alkoxy substituted with a hydroxyl.

7. The compound according to claim 6, wherein the compound of Formula II is 2-(4-(2-hydroxyethoxy)-3,5-dimethylphenyl)-5,7-dimethoxyquinazolin-4(3H)-one.

8. The compound according to claim 1, wherein $R_7$ is an amino or an alkoxy selected from the group represented by Formula III:

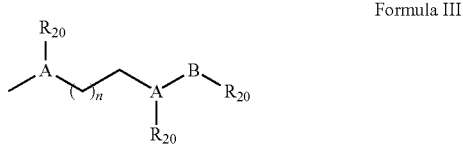

Formula III wherein:
A is selected from O and N;
n is selected from 0, 1, 2, 3, 4 and 5;
B is selected from —C(O)N($R_h$)$_2$—, —S(O)$_2$N($R_h$)$_2$—, —C(O)—, S(O)$_2$—, —C(O)O—, wherein each $R_h$ is selected from alkyl, alkenyl, alkynyl, aryl, arylalkyl, cycloalkyl, haloalkyl, heteroaryl, heterocyclyl, and hydrogen; and
$R_{20}$ is selected from ($C_1$-$C_6$) alkyl, ($C_1$-$C_6$) alkenyl, ($C_1$-$C_6$) alkynyl, aryl, arylalkyl, cycloalkyl, haloalkyl, heteroaryl, heterocyclyl, and hydrogen.

9. The compound according to claim 8, wherein the compound of Formula II is selected from:
2-(4-(5,7-dimethoxy-4-oxo-3,4-dihydroquinazolin-2-yl)-2,6-dimethylphenoxy)ethyl cyclohexylcarbamate;
N-(2-(4-(5,7-dimethoxy-4-oxo-3,4-dihydroquinazolin-2-yl)-2,6-dimethylphenoxy)ethyl)acetamide;
N-(2-(4-(5,7-dimethoxy-4-oxo-3,4-dihydroquinazolin-2-yl)-2,6-dimethylphenoxy)ethyl)isobutyramide;
1-(2-(4-(5,7-dimethoxy-4-oxo-3,4-dihydroquinazolin-2-yl)-2,6-dimethylphenoxy)ethyl)-3-phenylurea; and
3-(2-(4-(5,7-dimethoxy-4-oxo-3,4-dihydroquinazolin-2-yl)-2,6-dimethylphenoxy)ethyl)-1,1-dimethylurea.

10. The compound according to claim 1, wherein the compound of Formula II is selected from:
2-(3,5-dimethyl-4-(2-morpholinoethoxy)phenyl)-5,7-dimethoxyquinazolin-4(3H)-one;
2-(3,5-di-tert-butyl-4-hydroxyphenyl)-5,7-dimethoxyquinazolin-4(3H)-one;
2-(4-hydroxy-3-methoxyphenyl)-5,7-dimethoxyquinazolin-4(3H)-one;
2-(3-chloro-4-hydroxyphenyl)-5,7-dimethoxyquinazolin-4(3H)-one;
5,7-dimethoxy-2-(4-(4-methylpiperazin-1-yl)phenyl)quinazolin-4(3H)-one;
2-(4-hydroxy-3,5-dimethylphenyl)-6,7-dimethoxyquinazolin-4(3H)-one;
2-(4-(6,7-dimethoxy-4-oxo-3,4-dihydroquinazolin-2-yl)-2,6-dimethylphenoxy)acetamide;
2-(3-chloro-4-(2-hydroxyethoxy)phenyl)-5,7-dimethoxyquinazolin-4(3H)-one;
2-(4-(2-hydroxyethoxy)-3-methoxyphenyl)-5,7-dimethoxyquinazolin-4(3H)-one;
2-(4-(2-hydroxyethoxy)-3,5-dimethylphenyl)-6,7-dimethoxyquinazolin-4(3H)-one;
N-(4-(5,7-dimethoxy-4-oxo-3,4-dihydroquinazolin-2-yl)-2,6-dimethylphenyl)-2-hydroxyacetamide;
2-(4-(5,7-dimethoxy-4-oxo-3,4-dihydroquinazolin-2-yl)-2,6-dimethylphenoxy)acetic acid;
N-(4-(5,7-dimethoxy-4-oxo-3,4-dihydroquinazolin-2-yl)phenyl)-2-hydroxyacetamide;
2-(4-hydroxy-3,5-dimethylphenyl)-5,7-dimethoxypyrido[2,3-d]pyrimidin-4(3H)-one;
5,7-dimethoxy-2-(4-methoxy-3-(morpholinomethyl)phenyl)quinazolin-4(3H)-one;
2-(3,5-dimethyl-4-(2-(pyrrolidin-1-yl)ethoxy)phenyl)-5,7-dimethoxyquinazolin-4(3H)-one;
2-(4-hydroxy-3-(2-hydroxyethyl)phenyl)-5,7-dimethoxyquinazolin-4(3H)-one;
2-(4-(bis(2-hydroxyethyl)amino)phenyl)-5,7-dimethoxypyrido[2,3-d]pyrimidin-4(3H)one;
5,7-dimethoxy-2-(4-(2-methoxyethoxy)-3,5-dimethylphenyl)quinazolin-4(3H)-one;
2-(4-(2-hydroxyethoxy)-3,5-dimethylphenyl)-5-methoxyquinazolin-4(3H)-one;
(E)-N'-(4-(5,7-dimethoxy-4-oxo-3,4-dihydroquinazolin-2-yl)-2,6-dimethylphenyl)-N,N-dimethylformimidamide;
2-(4-(benzyloxy)-3,5-dimethylphenyl)-5,7-dimethoxyquinazolin-4(3H)-one;
2-(4-(2-aminoethoxy)-3,5-dimethylphenyl)-5,7-dimethoxyquinazolin-4(3H)-one;
2-(4-(5,7-dimethoxy-4-oxo-3,4-dihydroquinazolin-2-yl)-2-methoxyphenoxy)acetic acid;
2-(4-(5,7-Dimethoxy-4-oxo-3,4-dihydroquinazolin-2-yl)-2,6-dimethyl-phenoxy)ethyl propylcarbamate;
2-(4-(5,7-Dimethoxy-4-oxo-3,4-dihydroquinazolin-2-yl)-2,6-dimethyl-phenoxy)ethyl methylcarbamate;
N-(2-(4-(5,7-Dimethoxy-4-oxo-3,4-dihydroquinazolin-2-yl)-2,6-dimethylphenoxy)ethyl)-4-methylbenzamide;
N-(2-(4-(5,7-dimethoxy-4-oxo-3,4-dihydroquinazolin-2-yl)-2,6-dimethylphenoxy)ethyl)benzenesulfonamide;
N-(2-(4-(5,7-dimethoxy-4-oxo-3,4-dihydroquinazolin-2-yl)-2,6-dimethylphenoxy)ethyl-4-methylbenzenesulfonamide;
N-(2-(4-(5,7-dimethoxy-4-oxo-3,4-dihydroquinazolin-2-yl)-2,6-dimethylphenoxy)ethyl)-4-methoxybenzamide;
N-(2-(4-(5,7-dimethoxy-4-oxo-3,4-dihydroquinazolin-2-yl)-2,6-dimethylphenoxy)ethyl)benzamide;
1-(2-(4-(5,7-dimethoxy-4-oxo-3,4-dihydroquinazolin-2-yl)-2,6-dimethylphenoxy)ethyl)-3-methylurea; and
1-(2-(4-(5,7-dimethoxy-4-oxo-3,4-dihydroquinazolin-2-yl)-2,6-dimethylphenoxy)ethyl)-3-(4-methoxyphenyl)urea.

11. A compound selected from:
2-(3,5-dimethyl-4-(2-morpholinoethoxy)phenyl)quinazolin-4(3H)-one;
2-(4-(2-hydroxyethoxy)-3,5-dimethylphenyl)quinazolin-4(3H)-one;
2-(2,3-dihydrobenzo[b][1,4]dioxin-6-yl)quinazolin-4(3H)-one;
2-(4-(4-oxo-3,4-dihydroquinazolin-2-yl)phenoxy)acetic acid;
2-(4-(dimethylamino)naphthalen-1-yl)quinazolin-4(3H)-one;
2-(4-(4-oxo-3,4-dihydroquinazolin-2-yl)phenoxy)acetamide;
2-(4-(bis(2-hydroxyethyl)amino)phenyl)quinazolin-4(3H)-one;
2-(4-(5,7-dimethoxyquinazolin-2-yl)-2,6-dimethylphenoxy)ethanol;
2-(4-(2-hydroxyethoxy)-3,5-dimethylphenyl)-5,7-dimethylquinazolin-4(3H)-one;
5,7-dichloro-2-(4-(2-hydroxyethoxy)-3,5-dimethylphenyl)quinazolin-4(3H)-one;
6-bromo-2-(4-hydroxy-3,5-dimethylphenyl)quinazolin-4(3H)-one;
6-bromo-2-(4-(2-hydroxyethoxy)-3,5-dimethylphenyl)quinazolin-4(3H)-one;
6-bromo-2-(4-(2-(tert-butyldimethylsilyloxy)ethoxy)-3,5-dimethylphenyl)quinazolin-4(3H)-one;
5,7-dimethoxy-2-(pyridin-4-yl)quinazolin-4(3H)-one;
2-(4-(dimethylamino)naphthalen-1-yl)-5,7-dimethoxyquinazolin-4(3H)-one;
2-(4-(dimethylamino)pyridin-1-yl)-6,7-dimethoxyquinazolin-4(3H)-one;
2-(4-hydroxy-3,5-dimethylphenyl)-5,7-dimethoxy-1-methylquinazolin-4(1H)-one;
2-(4-hydroxy-3,5-dimethylphenyl)-5,7-dimethoxy-6-(morphoinomethyl)quinazolin-4(3H)-one;
2-(4-(2-hydroxyethoxy)-3,5-dimethylphenyl)-6-methoxyquinazolin-4(3H)-one; and
5-hydroxy-2-(4-hydroxy-3,5-dimethylphenyl)-7-methoxyquinazolin-4(3H)-one.

12. A pharmaceutical composition comprising a compound according to any one of claims 1-11 and a pharmaceutically acceptable carrier.

13. A compound of Formula II:

Formula II wherein:
X is N;
Y is CO;
$R_1$ and $R_3$ are each independently selected from alkoxy and hydrogen;
$R_2$ is selected from alkoxy, alkyl, and hydrogen;
$R_6$ and $R_8$ are each independently selected from alkyl, alkoxy, chloride, and hydrogen;
$R_5$ and $R_9$ are each hydrogen;
$R_7$ is selected from amino, hydroxyl, alkoxy, and alkyl substituted with a heterocyclyl;
$R_{10}$ is hydrogen; or
two adjacent substituents selected from $R_6$, $R_7$, and $R_8$ are connected to form a heterocyclyl;
each W is independently selected from C and N, wherein if W is N, then p is 0 or 1, and if W is C, then p is 1;
for W—$(R_{10})_p$, W is N and p is 1;
for W—$(R_4)_p$, W is C, p is 1 and $R_4$ is H, or W is N and p is 0;
$Z_1$ is a double bond, and $Z_2$ and $Z_3$ are each a single bond;
with the proviso that if $R_2$ is alkoxy or hydrogen, then least one of $R_1$ and $R_3$ is alkoxy;
with the proviso that if $R_7$ is selected from hydroxyl and alkoxy, then at least one of $R_6$ and $R_8$ are independently selected from alkyl, alkoxy, and chloride;
with the proviso that if for W—$(R_7)_p$, W is N and p is 0, then at least one of $R_6$ and $R_8$ is selected from alkyl, alkoxy, and chloride;
and pharmaceutically acceptable salts thereof.

14. The compound according to claim 13, wherein the compound of Formula II is selected from:
3-(4-hydroxy-3,5-dimethylphenyl)-6,8-dimethoxyisoquinolin-1(2H)-one;
3-(4-(2-hydroxyethoxy)-3,5-dimethylphenyl)-6,8-dimethoxyisoquinolin-1(2H)-one;
2-(4-hydroxy-3,5-dimethylphenyl)-5,7-dimethoxyquinazolin-4(3H)-one;
2-(4-(2-hydroxyethoxy)-3,5-dimethylphenyl)-5,7-dimethoxyquinazolin-4(3H)-one);
2-(4-hydroxy-3-methoxyphenyl)-5,7-dimethoxyquinazolin-4(3H)-one;
2-(2,3-dihydrobenzo[b][1,4]dioxin-6-yl)-5,7-dimethoxyquinazolin-4(3H)one;
2-(4-(bis(2-hydroxyethyl)amino)phenyl)-5,7-dimethoxyquinazolin-4(3H)-one;
2-(4-(bis(2-hydroxyethyl)amino)phenyl)-6,7-dimethoxyquinazolin-4(3H)-one;
2-(2,3-dihydrobenzo[b][1,4]dioxin-6-yl)-6,7-dimethoxyquinazolin-4(3H)-one;
2-(4-((4-ethylpiperazin-1-yl)methyl)phenyl)-5,7-dimethoxyquinazolin-4(3H)-one;
2-(4-(2-hydroxyethoxy)-3,5-dimethylphenyl)-5,7-dimethoxypyrido[2,3-d]pyrimidin-4(3H)-one;
2-(2-chloro-6-methylpyridin-4-yl)-5,7-dimethoxyquinazolin-4(3H)-one;
5,7-dimethoxy-2-(4-methoxy-3,5-dimethylphenyl)quinazolin-4(3H)-one;
2-(4-amino-3,5-dimethylphenyl)-5,7-dimethoxyquinazolin-4(3H)-one;
N1-(2-(4-(5,7-dimethoxy-4-oxo-3,4-dihydroquinazolin-2-yl)-2,6-dimethylphenoxy)ethyl)-N2-methylphthalamide;
2-(4-(2-aminoethoxy)-3,5-dimethylphenyl)-5,7-dimethoxyquinazolin-4(3H)-one;
and 4-chloro-N-(2-(4-(5,7-dimethoxy-4-oxo-3,4-dihydroquinazolin-2-yl)-2,6-dimethylphenoxy)ethyl)benzenesulfonamide.

15. The compound according to claim 13, wherein $R_7$ is selected from an amino or an alkoxy selected from the group represented by Formula III:

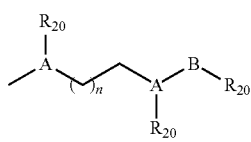

Formula III wherein:
A is selected from O and N;
n is selected from 0, 1, 2, 3, 4 and 5;
B is selected from —C(O)N($R_h$)$_2$—, —S(O)$_2$N($R_h$)$_2$—, —C(O)—, —S(O)$_2$—, and —C(O)O—, wherein each $R_h$ is independently selected from alkyl, alkenyl, alkynyl, aryl, arylalkyl, cycloalkyl, haloalkyl, heteroaryl, heterocyclyl, and hydrogen; and
$R_{20}$ is selected from ($C_1$-$C_6$) alkyl, ($C_1$-$C_6$) alkenyl, ($C_1$-$C_6$) alkynyl, aryl, arylalkyl, cycloalkyl, haloalkyl, heteroaryl, heterocyclyl, and hydrogen.

16. The compound of claim 15, wherein the compound of Formula II is selected from:
N1-(2-(4-(5,7-dimethoxy-4-oxo-3,4-dihydroquinazolin-2-yl)-2,6-dimethylphenoxy)ethyl)-N2-methylphthalamide;
2-(4-(2-aminoethoxy)-3,5-dimethylphenyl)-5,7-dimethoxyquinazolin-4(3H)-one; and
4-chloro-N-(2-(4-(5,7-dimethoxy-4-oxo-3,4-dihydroquinazolin-2-yl)-2,6-dimethylphenoxy)ethyl)benzenesulfonamide.

17. A pharmaceutical composition comprising a compound according to any one of claims 13-16 and a pharmaceutically acceptable carrier.

18. A compound of Formula II:

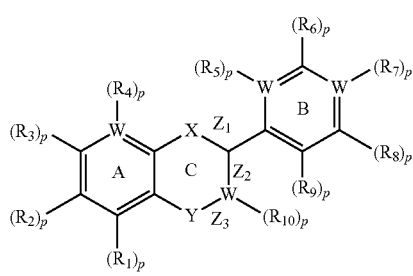

Formula II wherein:
X is N;
Y is CO;
$R_1$ and $R_3$ are each independently selected from alkoxy, alkyl, amino, halogen, and hydrogen;
$R_2$ is selected from —N—C(O)—$R_{18}$, —N—SO$_2$—$R_{18}$, —CH$_2$—C($R_{18}$)$_3$, —CH$_2$—N($R_{18}$)$_2$, and —CH$_2$—O—$R_{18}$, wherein each $R_{18}$ is independently selected from alkoxy, alkyl, alkenyl, amide, amino, aryl, arylalkyl, cycloalkyl, haloalkyl, halogen, heteroaryl, heterocyclyl, and hydrogen;
$R_6$ and $R_8$ are each independently selected from alkyl, alkoxy, amino, halogen, and hydrogen;
$R_6$ and $R_9$ are each hydrogen;
$R_7$ is selected from amino, amide, alkyl, hydroxyl, and alkoxy;
$R_{10}$ is hydrogen;
each W is independently selected from C and N, wherein if W is N, then p is 0 or 1, and if W is C, then p is 1;
for W—($R_{10}$)$_p$, W is N and p is 1;
for W—($R_7$)$_p$, W is C and p is 1;
for W—($R_4$)$_p$, W is C, p is 1 and $R_4$ is H, or W is N and p is 0;
$Z_1$ is a double bond, and $Z_2$ and $Z_3$ are each a single bond; with the proviso that if $R_7$ is selected from alkyl, hydroxyl, and alkoxy, then at least one of $R_6$ and $R_8$ is independently selected from alkyl, alkoxy, amino, and halogen;
and pharmaceutically acceptable salts thereof.

19. The compound according to claim 18, wherein the compound of Formula II is selected from:
N-(2-(4-hydroxy-3,5-dimethylphenyl)-4-oxo-3,4-dihydroquinazolin-6-yl)acetamide;
2-(4-hydroxy-3,5-dimethylphenyl)-6-(morpholinomethyl)quinazolin-4(3H)-one;
N-(2-(4-(2-hydroxyethoxy)-3,5-dimethylphenyl)-4-oxo-3,4-dihydroquinazolin-6-yl)acetamide; and
2-(4-hydroxy-3,5-dimethylphenyl)-5,7-dimethoxy-6-(morphoinomethyl)quinazolin-4(3H)-one.

20. The compound according to claim 18, wherein $R_6$ and $R_8$ are each independently alkyl; and $R_7$ is selected from hydroxyl and alkoxy.

21. The compound according to claim 18, wherein $R_7$ is selected from an amino or an alkoxy selected from the group represented by Formula III:

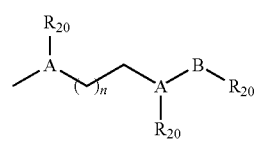

Formula III wherein:
A is selected from O and N;
n is selected from 0, 1, 2, 3, 4 and 5;
B is selected from —C(O)N($R_h$)$_2$—, —S(O)$_2$N($R_h$)$_2$—, —C(O)—, —S(O)$_2$—, —C(O)O—, wherein each $R_h$ is selected from alkyl, alkenyl, alkynyl, aryl, arylalkyl, cycloalkyl, haloalkyl, heteroaryl, heterocyclyl, and hydrogen; and
$R_{20}$ is selected from ($C_1$-$C_6$) alkyl, ($C_1$-$C_6$) alkenyl, ($C_1$-$C_6$) alkynyl, aryl, arylalkyl, cycloalkyl, haloalkyl, heteroaryl, heterocyclyl, and hydrogen.

22. The compound according to claim 18, wherein $R_6$ and $R_8$ are each independently alkyl.

23. A pharmaceutical composition comprising a compound according to any one of claim 18, 19, or 20-22 and a pharmaceutically acceptable carrier.

24. A compound of Formula II:

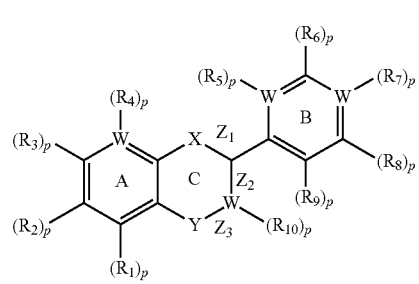

Formula II wherein:

X is N;

Y is CO;

$R_1$ is selected from alkoxy or amino;

$R_3$ is alkoxy;

$R_2$ is selected from alkoxy, alkyl, alkenyl, alkynyl, amide, amino, halogen, and hydrogen;

$R_6$ and $R_8$ are each independently selected from alkyl, alkoxy, amino, halogen, and hydrogen;

$R_5$ and $R_9$ are each hydrogen;

$R_7$ is selected from amino, amide, alkyl, hydroxyl, and alkoxy;

$R_{10}$ is hydrogen;

each W is independently selected from C and N, wherein if W is N, then p is 0 or 1, and if W is C, then p is 1;

for W—$(R_{10})_p$, W is N and p is 1;

for W—$(R_7)_p$, W is C and p is 1;

for W—$(R_4)_p$, W is C, p is 1 and $R_4$ is H, or W is N and p is 0;

$Z_1$ is a double bond, and $Z_2$ and $Z_3$ are each a single bond; and pharmaceutically acceptable salts thereof.

25. The compound according to claim 24, wherein $R_7$ is selected from hydroxyl and alkoxy.

26. The compound according to claim 25, wherein the compound of Formula II is selected from:
- 2-(4-hydroxyphenyl)-5,7-dimethoxyquinazolin-4(3H)-one;
- 2-(4-(5,7-dimethoxy-4-oxo-3,4-dihydroquinazolin-2-yl)phenoxy)acetic acid;
- 5,7-dimethoxy-2-(4-methoxyphenyl)quinazolin-4(3H)-one; and
- 2-(4-(5,7-dimethoxy-4-oxo-3,4-dihydroquinazolin-2-yl)phenoxy)acetamide.

27. The compound according to claim 24, wherein $R_7$ is selected from amide and amino.

28. The compound according to claim 27, wherein the compound of Formula II is selected from:
- 5,7-dimethoxy-2-(4-(4-methylpiperazin-1-yl)phenyl)quinazolin-4(3H)-one;
- 2-(4-(bis(2-hydroxyethyl)amino)phenyl)-5,7-dimethoxyquinazolin-4(3H)-one;
- 5,7-dimethoxy-2-(4-morpholinophenyl)quinazolin-4(3H)-one;
- N-(4-(5,7-dimethoxy-4-oxo-3,4-dihydroquinazolin-2-yl)phenyl)-2-hydroxyacetamide; and
- 2-(4-(bis(2-hydroxyethyl)amino)phenyl)-5,7-dimethoxy-pyrido[2,3-d]pyrimidin-4(3H)one.

29. The compound according to claim 24, wherein $R_7$ is alkyl.

30. The compound according to claim 29, wherein the compound of Formula II is selected from:
- 3-(4-(5,7-dimethoxy-4-oxo-3,4-dihydroquinazolin-2-yl)phenyl)propanoic acid;
- 5,7-dimethoxy-2-(4-((4-methylpiperazin-1-yl)methyl)phenyl)quinazolin-4(3H)-one;
- 5,7-dimethoxy-2-(4-(morpholinomethyl)phenyl)quinazolin-4(3H)-one; and
- 2-(4-((4-ethylpiperazin-1-yl)methyl)phenyl)-5,7-dimethoxyquinazolin-4(3H)-one.

31. The compound according to claim 24, wherein $R_6$ and $R_8$ are each independently alkyl.

32. The compound according to claim 24, wherein $R_7$ is selected from an amino or an alkoxy selected from the group represented by Formula III:

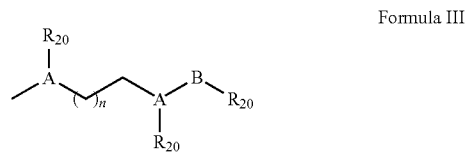

Formula III wherein:

A is selected from O and N;

n is selected from 0, 1, 2, 3, 4 and 5;

B is selected from —C(O)N($R_h$)$_2$—, —S(O)$_2$N($R_h$)$_2$—, —C(O)—, —S(O)$_2$—, —C(O)O—, wherein each $R_h$ is selected from alkyl, alkenyl, alkynyl, aryl, arylalkyl, cycloalkyl, haloalkyl, heteroaryl, heterocyclyl, and hydrogen; and $R_{20}$ is selected from ($C_1$-$C_6$) alkyl, ($C_1$-$C_6$) alkenyl, ($C_1$-$C_6$) alkynyl, aryl, arylalkyl, cycloalkyl, haloalkyl, heteroaryl, heterocyclyl, and hydrogen.

33. The compound according to claim 32, wherein $R_6$ and $R_8$ are each independently alkyl.

34. A pharmaceutical composition comprising a compound according to any one of claims 24-33 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,053,440 B2 | Page 1 of 1 |
| APPLICATION NO. | : 11/670238 | |
| DATED | : November 8, 2011 | |
| INVENTOR(S) | : Henrik C. Hansen | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1288 days.

Claim 11, col. 131, lines 36-37,
"2-(4-hydroxy-3,5-dimethylphenyl)-5,7-dimethoxy-6-(morphoinomethyl)quinazolin-4(3H)-one" should read
--2-(4-hydroxy-3,5-dimethylphenyl)-5,7-dimethoxy-6-(morpholinomethyl)quinazolin-4(3H)-one--.

Claim 18, col. 133, line 62, "$R_6$ and $R_9$" should read --$R_5$ and $R_9$--.

Claim 19, col. 134, lines 20-21,
"2-(4-hydroxy-3,5-dimethylphenyl)-5,7-dimethoxy-6-(morphoinomethyl)quinazolin-4(3H)-one" should read
--2-(4-hydroxy-3,5-dimethylphenyl)-5,7-dimethoxy-6-(morpholinomethyl)quinazolin-4(3H)-one--.

Claim 24, col. 135, line 13, "$R_{10}$is" should read --$R_{10}$ is--.

Signed and Sealed this
Twenty-first Day of February, 2012

David J. Kappos
*Director of the United States Patent and Trademark Office*